(12) United States Patent
Grillitsch et al.

(10) Patent No.: US 11,479,798 B2
(45) Date of Patent: Oct. 25, 2022

(54) RECOMBINANT HOST CELL WITH ALTERED MEMBRANE LIPID COMPOSITION

(71) Applicants: Boehringer Ingelheim RCV GmbH & Co KG, Vienna (AT); Validogen GmbH, Grambach (AT); Lonza Ltd, Visp (CH)

(72) Inventors: Karlheinz Grillitsch, St. Paul/Lav (AT); Guenther Daum, Graz (AT); Andreas Grutsch, Stattegg (AT)

(73) Assignees: BOEHRINGER INGELHEIM RCV GMBH & CO KG, Vienna (AT); SANDOZ AG, Basel (CH); VALIDOGEN GMBH, Grambach (AT); BIOMIN HOLDING GMBH, Herzogenburg (AT); LONZA LTD., Visp (CH)

(*) Notice: Subject to any disclaimer, the term of this patent is extended or adjusted under 35 U.S.C. 154(b) by 0 days.

(21) Appl. No.: 16/499,072

(22) PCT Filed: Mar. 28, 2018

(86) PCT No.: PCT/EP2018/057853
§ 371 (c)(1),
(2) Date: Sep. 27, 2019

(87) PCT Pub. No.: WO2018/178126
PCT Pub. Date: Oct. 4, 2018

(65) Prior Publication Data
US 2021/0301313 A1 Sep. 30, 2021

(30) Foreign Application Priority Data
Mar. 29, 2017 (EP) .................................. 17163588

(51) Int. Cl.
C12N 9/10 (2006.01)
C12N 15/81 (2006.01)
C12P 21/02 (2006.01)
C07K 16/00 (2006.01)
C12N 15/67 (2006.01)

(52) U.S. Cl.
CPC ............. *C12P 21/02* (2013.01); *C07K 16/00* (2013.01); *C12N 15/67* (2013.01); *C12N 15/815* (2013.01); *C07K 2317/55* (2013.01)

(58) Field of Classification Search
CPC .................................................... C12N 15/67
See application file for complete search history.

(56) References Cited

U.S. PATENT DOCUMENTS

| 7,893,320 B2* | 2/2011 | Cirpus | C12P 7/6472 800/281 |
| 2013/0137140 A1* | 5/2013 | Callewaert | C12P 21/00 435/69.1 |
| 2017/0029853 A1 | 2/2017 | Chu et al. | |

FOREIGN PATENT DOCUMENTS

| JP | 2002-514077 A | 5/2002 |
| JP | 2002514077 A5 | 11/2005 |
| JP | 2010519917 A | 6/2010 |
| JP | 2013535185 A | 10/2013 |
| WO | WO 2011/157761 A1 | 12/2011 |
| WO | 2015158800 A1 | 10/2015 |

OTHER PUBLICATIONS

Massart et al., 30(9), 603-617, 2019.*
Choudhary et al., "The Caveolin-Binding Motif of the Pathogen-Related Yeast protein Pry1, a Member of the CAP Protein Superfamily, is Required for in vivo Export of Cholesteryl Acetate," *J. Lipid Res.* (2014), 55(5):883-894, American Society for Biochemistry and Molecular Biology.
Dragosits et al., "The Response to Unfolded Protein is Involved in Osmotolerance of *Pichia pastoris*," *BMC Genomics* (2010), 11(1):16 pages, BioMed Central Ltd.
Horikawa et al., "Elongation and Desaturation of Fatty Acids are Critical in Growth, Lipid Metabolism and Ontogeny of *Caenorhabditis elegans*," *J. Biochem.* (2008), 144(2):149-158, The Japanese Biochemical Society.
Jazwinski and Conzelmann, "LAG1 Puts the Focus on Ceramide Signaling," *Int. J. Biochem. Cell Biol.* (2002), 30(11):1491-1495, Elsevier Science Ltd.
Opekarova and Tanner, "Specific Lipid Requirements of Membrane Proteins—A Putative Bottleneck in Heterologous Expression," Biochim. Biophys. Acta (2003) 1610(1):11-22, Elsevier Science B.V.
Database UniProt [Online], RecName: Full=Elongation of Fatty Acids Protein {ECO:0000256 RuleBase: RU361115}, EC=2.3.1.199, AltName: Full=Very-Long-Chain 3-Oxoacyl-CoA Synthase, XP002770361, Retrieved from EBI Accession No. UNIPROT: C4R3Y7, Database Accession No. C4R3Y7, Jul. 7, 2009.
Database UniProt [Online], RecName: Full-Elongation of Fatty Acids Proteins {ECO:0000256 RuleBase: RU361115}, DE, EC=2.3.1.199, XP002773118, Retrieved from EBI Accession No. UNIPROT: C4R513, Database Accession No. C4R513, Jul. 7, 2009.

(Continued)

*Primary Examiner* — Maryam Monshipouri
(74) *Attorney, Agent, or Firm* — Seyfarth Shaw; Jamaica Szeliga

(57) ABSTRACT

The present invention is in the field of recombinant biotechnology, in particular in the field of protein expression. The invention generally relates to a method of expressing a protein of interest (POI) from a host cell. The invention relates particularly to improving a host cell's capacity to express and/or secrete a protein of interest and use of the host cell for protein expression. The invention also relates to cell culture technology, and more specifically to culturing cells to produce desired molecules for medical purposes or food products.

6 Claims, 18 Drawing Sheets

Specification includes a Sequence Listing.

(56) References Cited

OTHER PUBLICATIONS

Database UniProt [Online], "SubName: Full-Ceramide Synthase Component, Involved in Synthesis of Ceramide {ECO:0000313 EMBL: CAY67734.1;" XP002773119, Retrieved from EBI Accession No. UNIPROT:C4QWW1, Database Accession No. C4QWW1, Jul. 7, 2009.

Database UniProt [Online], SubName: Full=Uncharacterized Protein {ECO:0000313 EMBL:CAY70008.1}, XP002773120, Retrieved from EBI Accession No. UNIPROT:C4R3H3, Database Accession No. C4R3H3, Jul. 7, 2009.

Japanese Patent Office Notification of Reasons for Rejection, JP-2019-553357, dated Apr. 20, 2022. (Parallel action to U.S. Appl. No. 16/499,072).

* cited by examiner

Figure 1

ELO3 amino acid sequence (SEQ ID NO: 1)

```
MSDINTLSQK IPSYVQYGIP SIDHPFGIRL WPIFSHFFEA VVGYPAEDFR FIQGLTTMAN
LKDALGVIAV YYFVIFGGQW LMRTLNARPF KLNFLFQLHN LVLTGASFTL LILIVEQLIP
GIYRHGIFWA ICHKDSFTNE LVTLYYLNYL IKYVELIDTV FLVLKRKKLL FLHTYHHGAT
ALLCYTQLLG HTAVEWVPIA LNLAVHVVLY WYYFLSARGI RVWWKQWVTR FQIIQFLIDL
GFVYFATYTF YADKYFPELP NMGTCYGTEE AAAFGYLILT SYLVLFILFY IRVYKSGPTT
SKGKSKAAAT TGQKTETASP SGKSTSVRRA
```

ELO2 amino acid sequence (SEQ ID NO: 2)

```
MSILSFDKPF GIELWPIFDT FASKATHGAF VPSEFEFVAG KLPLSTLEPV LYSIAAYYFI
VFGGYYFIKK LELKPLVLNA LFSAHNLFLT TASLVLLTLM VEQLVPIIYH HGLFYAICNT
RAWTQELVTL YYLNYLIKFV EFIDTFFLVV KQKKLTFLHT YHHGATALLC YTQLVGVTSI
SWVPISLNLG VHVVMYWYYF LASRGIRVWW KEWVTRFQIM QFILDLGFVY FASYQKFAYT
YFKDVLPYCG DCAGTMVAAV SGCAILSSYL VLFIAFYIEV YRKQGKKSRY VKKVRGGVAA
KVNEYVLLED KQLASGASSR SSSPVTRNLR SRKA
```

LAG1 amino acid sequence (SEQ ID NO: 3)

```
MSKEEKTRRR RASSIGNINL GDNAVPSLTT RKSNAQQRKS SSARINLINK KGSSDWGLVK
KIGLSLVELS SRHTWLPFLV SLVAIHGSYL LSNNHTPSNP LHKFVDLSYK IEGTNPPMYG
KGWKDFCFVF YFMIFFSFYR EFLMQALLKP LASKLGITRE SKVRRFMEQS YSMCYYGFSG
PLGLYIMAGM PLWYFNTTEF YITYPHKSHE YLFKYYYLGQ AAFWSQQAVV LMLQLEKPRK
DFKELVIHHI ITIALIYCSY RFHFTWMGLA VYITMDISDF FLALSKTLNY VDSAYTGPAF
MFFVGVWFYL RHWLNVKILW SVLTEFRTVG PFELNWITQQ YKCWISQPIV FSLIFALQLV
NLYWFVLILR  ILYRHIFLDV  TKDERSDDES  EEEAQVEPSK KEE
```

LAC1 amino acid sequence (SEQ ID NO: 4)

```
MGVETSSSGT QHFSDDGCVS SRKPNATVSF EKPERANELK NHKIYKKSKA SWLQRNQILL
ASSLLNALFI LKQIPSFQSL VNKFFHLQYK NLDGTYDIGK DDYFFVIYWI INLTIIRSVL
MDWVLEPLAI KIVGINNRKA LTRFKEQGWS LFYYTTSWTV GFYLYYKSDY FFNCDHIFIG
WPNNKLDFYF KSYYLIQMSC WLQQIVVLNI EERRKDYVQM FSHHIITCLL IIGSYYYYFL
QIGHVILVMM DIVDVFLSLA KMLKYCGYST LCDVMFFIFL VSWIAIRHVC YNYVFWHTCT
KSRDLMNADC SRYAIYGGPL DVTPVRCYTD STIRYFIFLL GGLQIITLIW MYLILKVFIG
VITGKGAEDV RSDDEESS
```

LCB1 amino acid sequence (SEQ ID NO: 5)

```
MSQREETKDA AKKQIAFSGI GACGPPNFYG TQDAHARLEE DLARFLGAER AILYSQDFCT
VPSVIACFLK RGDIVVYDSG IALATQKGIE LSRCTAYHFN HNDMDNLEKV LADLKPMLDE
GPLTRRFIIT EGLFQNFGDS PDLRRICELK KKFKYRLFLD ETLSIGVLGA TGRGLPELYG
IPRTDVEVTT GALSYALGSS GGFCVGENAM VHHQLISSSA YVFSAAIPPY FARVASVSLR
LLQEDDSVSR LQSSINFLYS KFKECQKLKK LVIITSSDVS PILHLRLHRD LRSRLDLPVS
YGGPGSAMEK IVQRGDEHGY FDENYNRESQ ILQQIVDRVL NNHNILITRC KRILHHEKLP
LLPELMIHIN VAFSESELSE AFEAVSSEIY NVLQQL
```

Figure 1 (cont'd)

LCB2 amino acid sequence (SEQ ID NO: 6)

MSKTIPDALI DNDSPQEKAE KEFGSLTSKE WLFVSKHNPG EPLPVPIEDE PPYFILIATY
LNYLILIIIG HIRDFFGKLF HPELFRDVMV KDGIAPWYAN FESFYTRRLK TRLDDCFARP
ICGVPGRYIK CYDRTSDDYN NTYNYSGTVT ERLNLSSYNY LGFAQSSGLC TSESIKTVEK
YGTNSAGPRV SVGTTDLHLE CEDVVAKFTG KDNALVFSMG YGTNANLFTS LVDSKCCVIS
DSLNHGSIRT GVRLSGASVK TFAHNDMAAL ERTLRSVISQ GQPKTHRPWK KIFVAVEGLY
SMEGTLCNLP KLVELRKRYK FYLFVDEAHS IGAMGPNGKG VCDYFGISSS NIDIMMGTFT
KSFGATGGYI AADKAIIDRL KLDLTTNTYG ESMSPAVLTQ IITSLKIIDG QLNGNEGKER
LQRIAFNSRY LRLGLKRLGF IVYGADDSPV IPLLLYLPPK MPAFSRMMYD RKVAVVVGY
PATDITSSRI RFCVSSSLKK EDIDYLLKCC DEIGDTLFLK FSTGIAGGEK HPGDYKKGIA
PRWTLEEVLE  KTPEDCKKAM Y

TSC13 amino acid sequence (SEQ ID NO: 7)

MVKLIVNPRS ETLRQINVDT TPNTRVRDIV VAYGKANNSL SSSRIRFTKL EEDAVSKKPK
HVTLDYEKSL AQNGIVFTDD SDSKEVYAKD LGPQISWKLV FLIEYVGPLI IHPLLYYGWF
KPDYNTLTQK VSFILVMLHF LKREYETTFV HLFSSDTMPL FNVFKNSAHY WILSGLSLAV
TIYAPDSYRN KFAPTWKQFF FHVSDHEDST VLALIGLWVF AELSNFITHQ KLASLRADGS
REHKIPYGYG FNLVSFPNYF FESVAWLAFA LLNNNWSSWV FLTIASIQMY IWAAKKHKRY
LKEFGDQYPK NRKAMIPFLL

LIP1$_{SC}$ amino acid sequence (SEQ ID NO: 8)

MSQPTPIITTKSAAKPKPKIFNLFRVCFISLLLIAAVEYFKYGTRINYEWFHCTPIKEPQSGSVIKLW
ARGGPSCDKRGEYKTIVKRITRDYEPNDEHLSFCIIENDNVPPVHYPIHEDKGEPGYVAYVGYDTDSE
LVQELCADSTIYHM

TSC3$_{SC}$ amino acid sequence (SEQ ID NO: 9)

MTQHKSSMVYIPTTKEAKRRNGKSEGILNTIEEVVEKLYWTYYIHLPFYLMASFDSFFLHVFFLTIFS
LSFFGILKYCFL

PAH1 amino acid sequence (SEQ ID NO: 10)

MQYVGRAIGS VSKTWSSINP ATLSGAIDII VVEQENGDLA CSPFHVRFGK FQLLRPSQKK
VDFIVNGEKT DLPMKLGDGG EAFFVFETDA AIPSELQTSP VISPVSSPEP ASPLSTPSRP
NSEPDYLELG DGESTTSELE NFKLNRYPYL STEVSHSDPG VGSVSSSPEN TKIIQKISRK
LNTKNIPSKV DNNGNLVLDI QGYKSDDLDD NSKSLKQLLL AELGEDVDLD KVIEKDHEGN
IMINGAISLL SGEDDLESFP QTDDQAESLK LDLESDKSDI ESDTNHELSR YFKTLRLTSD
QLKCLTLKKG INELKFSVNK GKSVVTANLY FWDYYDPIVI SDIDGTITKS DALGHVFTMI
GRDWTHKGVA KLFSDIKSNG YNIMYLTARS VGQADSTRYY LNNIEQEGLR LPQGPVILSP
DRTMAALRRE VILKKPEVFK MACLNDIKKL YLTNTKDLNP NTDSADFTDI NTNTLRSSSL
TEDVQTPFYA GFGNRITDAL SYRSVGIPSS RIFTINPDGD VHMELLELAG YRSSYVHISE
LVDHFFPPVN TELFKSMPSD TYRNTAKFSD VNYWKEPLYN FEELSDEDSS EDELRRRKEE
ERLQSAPRSP ILAAGASFFK GSSSLLGSPE RMTLSDPKPT EVAPSTIKPP KSVGSVSSDE
EKLKDHDDFI DVDHEDETLD DDDDPFDYDY EYEDEEEEND DVDEVDDGEE YSDDYYDEED
DYDEELDHTL EPDQKKELDQ TAEANQLPPS GPDEMESKSF KKASDLISKM RIDDS

Figure 1 (cont'd)

PRY1 amino acid sequence (SEQ ID NO: 11)

```
MKLSTNLILA IAAASAVVSA APVAPAEEAA NHLHKRAYYT DTTKTHTFTE VVTVYRTLKP
GESIPTDSPS HGGKSTKKGK GSTTHSGAPG ATSGAPTDDT TSTSGSVGLP TSATSVTSST
SSASTTSSGT SATSTGTGTS TSTSTGTGTG TTGTGTTSSS TSSSATSTPT GSIDAISQTL
LDTHNDKRAL HGVPDLTWST ELADYAQGYA DSYTCGSSLE HTGGPYGENL ASGYSPAGSV
EAWYNEISDY DFSNPGYSAG TGHFTQVVWK STTQLGCYK  ECSTDRYYII CEYAPRGNIV
SAGYFEDNVL PPV
```

ERG11 amino acid sequence (SEQ ID NO: 12)

```
MSLVQELIQK ISSLELTLVE KLSILFVAPF LLNALWQFIY SFRKDRVPLV FHWVPWVGSA
VTYGMQPYEF FADCQRKYGD VFAFVLLGKV MTVYLGPKGH EFILNAKLND VCAEDAYKHL
TTPVFGEGVI YDCPNWKLMD QKKFVKGSLT KESFRSYVPK IRDEVLDYIN NDPNFMGGDS
KKKTGKTNVL NSQSELTILT ASRSLLGDDM RKLLTKKWAK LFSDLDKGFT PLNFIFSHLP
LPSYWTRDHA QKTISETYLS LINKRRATND IGDRDLIDSL MKSSTYKDGS KMTDEEISHL
LIGVLMGGQH TSASTSSWFL LHLGEKPELQ EELFEEQERV LQGRELTYDD LANMPLHNQV
IKETLRMHMP LHSIFRKVTR PLPVPNSKYV VPKGHYVLVS PGFAMTNDAY FPNASDFQPH
RWDETVEPVS ADAKETVDYG FGKVSKGVSS PYLPFGGGRH RCIGEHFAYC QLGTILNTFV
RTFKWKAVVP QPDYTSMVTL PEPNLSTITW ERRDN
```

HMG1 amino acid sequence (SEQ ID NO: 13)

```
MLTGLSKICA HRPIHTIVVT ALLVSLAYLT IVEEYTSRSS LSNPFISFYH PPGNSDYQNW
IPVDDSVKLK SKSAQHLSVC ALKFKRVNGH QIPDLAGSFQ SADPTEIFVV QDFDKSFDYF
DSISTIEGKD GIQWKVRHPN RLGRYSEYFR SVFSKTLRLV QGAEPFDIVL IAFAYVAMWY
TFLQLYYEMK TKANSNFWLT FGSLLSSGCA FVFALAVTVK VYGIKVPLTS LTEGVPFLVA
TIGFKHKVAF TVPILQASRS KKAKEIPDTI ISVIEQTTGW PLIKDHLIMI SAFLACSFYA
PRMEGLKNFC ILSANILTFD LIMIFTFFTA VLSLKAQINK VHETTALQQV LEEDGIAEDV
AERIAASNRN MFSRSTSVVS FKVIMIAGFL GFHLFVLGTS WLYDSDVSSS SIFGKSNVSA
LSKAAAKHIP IGSEGTIVTI MPTRVYMPVD LLLKLEDDFL NIFSKISASI TDPLISKLLF
IITGISATIN VYLLNAARFH SSREIAVSTI AKPQTPDVVP TVEPLPNEND TSIRPLEEMV
SLLKEGKTRE LNNDEVSSLV VQGKLPLYAL EKQLVDKTRA VIVRRKAIAS LADAPVLRTE
KLPYKDYDYD RVFGACCENV IGFMPLPVGV AGPLIIDGKP YHIPMATTEG CLVASTMRGC
KAINSGGGVE TVLTADGMTR GPCVSFPSLS RAGAAKMWLD SEEGQKTIKG AFNSTSRFAR
LQHVKTTLAG TLLFIRFKTT TGDAMGMNMI SKGVEYSLKF MSEECDWPDM EVISVSGNYC
TDKKVAAINW IEGRGKSVVA EARIPADVVR SVLKSDVEAL VELNVSKNLI GSAMAGSIGG
FNAQAANLVT AVYLATGQDP AQNVESSNCI TLMNKLPNGD LQISVSMPSI EVGTIGGGTV
LEPQGSMLEL LGVKGPHPTN PGANSRQLAK IVASAVLAAE LSLCSALAAG HLVQSHMTHN
RKQAPVKEVN GTAARLAEQS KICIKS
``` t2HMG1 amino acid sequence (SEQ ID NO: 14)

```
MTPDVVPTVEPLPNENDTSIRPLEEMVSLLKEGKTRELNNDEVSSLVVQGKLPLYALEKQLVDKTRAV
IVRRKAIASLADAPVLRTEKLPYKDYDYDRVFGACCENVIGFMPLPVGVAGPLIIDGKPYHIPMATTE
GCLVASTMRGCKAINSGGGVETVLTADGMTRGPCVSFPSLSRAGAAKMWLDSEEGQKTIKGAFNSTSR
FARLQHVKTTLAGTLLFIRFKTTTGDAMGMNMISKGVEYSLKFMSEECDWPDMEVISVSGNYCTDKKV
AAINWIEGRGKSVVAEARIPADVVRSVLKSDVEALVELNVSKNLIGSAMAGSIGGFNAQAANLVTAVY
LATGQDPAQNVESSNCITLMNKLPNGDLQISVSMPSIEVGTIGGGTVLEPQGSMLELLGVKGPHPTNP
 GANSRQLAKIVASAVLAAELSLCSALAAGHLVQSHMTHNRKQAPVKEVNGTAARLAEQSKICIKS
```

Figure 1 (cont'd)

t1HMG1 amino acid sequence (SEQ ID NO: 15)

MGISATINVYLLNAARFHSSREIAVSTIAKPQTPDVVPTVEPLPNENDTSIRPLEEMVSLLKEGKTRE
LNNDEVSSLVVQGKLPLYALEKQLVDKTRAVIVRRKAIASLADAPVLRTEKLPYKDYDYDRVFGACCE
NVIGFMPLPVGVAGPLIIDGKPYHIPMATTEGCLVASTMRGCKAINSGGGVETVLTADGMTRGPCVSF
PSLSRAGAAKMWLDSEEGQKTIKGAFNSTSRFARLQHVKTTLAGTLLFIRFKTTTGDAMGMNMISKGV
EYSLKFMSEECDWPDMEVISVSGNYCTDKKVAAINWIEGRGKSVVAEARIPADVVRSVLKSDVEALVE
LNVSKNLIGSAMAGSIGGFNAQAANLVTAVYLATGQDPAQNVESSNCITLMNKLPNGDLQISVSMPSI
EVGTIGGGTVLEPQGSMLELLGVKGPHPTNPGANSRQLAKIVASAVLAAELSLCSALAAGHLVQSHMT
HNRKQAPVKEVNGTAARLAEQSKICIKS

DGA1 amino acid sequence (SEQ ID NO: 16)

MPEKKNSRSA DEALSFLAKT NVERPMHYSK TGNITPDTVS SREDHYQDYD DSQDDIINNK
LLQRRQGGPH NKIEKQRRFA LLRSSLNRRL ETLVILWHTI TIPFLASLFF VLCTIPMLWP
LIIVYLVYFY IDANTPSNGK SADRRVEWFR SLHIWKHFVN YYPISVYKTV DLEPTFKTKK
IEIILPKYHQ VTTYLPSSVR KYIPTHRVLI EKEIKTGPRY IFGYHPHGVV SLGITGAFGT
NGCNIGELLP GIRIYLLTLI TQFKLPLLRD YLMALGISSV SKRNVTALIK RNQSVCIVIG
GASESLLSKP HTIDIVLKKR KGFVKVALEL GDTELVPVFG FGENTAYNVF DPSVSGKSCS
VLNYVRKQMC GFQLWLKQHF GFTFPFFHAR GVFNHDFGLL PYRKPINLVI GRPIPVPYIH
SPTQEQIDHY HSLYVEELKR VFEQNKERFN AGSLELRIVE

LRO1 amino acid sequence (SEQ ID NO: 17)

MQLRKRGNER SRLESHIGDS DTVIDLDDSS VNDTLPDEDN IAKPRKASTH RRPSLRKIHS
AETVRRFYES KNVIFIFGAF IGIAVALYFG ATSSEYPIPD IDQLVNFDSL STYFDDWKDV
LPKSLQSIVE STQFNQNSKI LSSESFAVGK QLKSKSMIEA NHSIVLVPGV ISTGLESWGL
EGTPDCPSEG HFRKRLWGSF YMLRTMFLDK ACWLKHIMLD TTTGLDPPGI SLRAAQGFEA
ADFFIAGYWI WNKILQNLAV IGYNPNNMVS AAYDWRLAFL DLELRDAYFS KLKGFVELQK
HQSGKKSVLV GHSMGSQVIY YFMKWVEADG YGNGGPNWVN DHVDSFVDIS GCMLGTPKAI
PALLSGEMKD TVQLNALAVE GLEKFLSRRE RADMIRSFGG IASMIPKGGD LIWGNLESSP
DDATSIGDLG NDTYGNFIRF KEPVGKYSQK NLTVTDSIQF LMEQTPAWFQ DRMLRAYSYG
FTNSAKQLKK NNKDHTKWSN PLEASLPNAP DLKVFCFYGF GNPTERAYYY REEVDPAKTK
LNVTIEKNYD SVLMADGDGT VSLMTHSMCH IWKQANSVYN PGNSKVKIVE IDHEPDRFDI
RGGAKTAEHV DILGSAELNE LVLLVAAGKG DQIKEKIVSN LKEIVDNLEL DL

KAR2 amino acid sequence (SEQ ID NO: 18)

MLSLKPSWLT LAALMYAMLL VVVPFAKPVR ADDVESYGTV IGIDLGTTYS CVGVMKSGRV
EILANDQGNR ITPSYVSFTE DERLVGDAAK NLAASNPKNT IFDIKRLIGM KYDAPEVQRD
LKRLPYTVKS KNGQPVVSVE YKGEEKSFTP EEISAMVLGK MKLIAEDYLG KKVTHAVVTV
PAYFNDAQRQ ATKDAGLIAG LTVLRIVNEP TAAALAYGLD KTGEERQIIV YDLGGGTFDV
SLLSIEGGAF EVLATAGDTH LGGEDFDYRV VRHFVKIFKK KHNIDISNND KALGKLKREV
EKAKRTLSSQ MTTRIEIDSF VDGIDFSEQL SRAKFEEINI ELFKKTLKPV EQVLKDAGVK
KSEIDDIVLV GGSTRIPKVQ QLLEDYFDGK KASKGINPDE AVAYGAAVQA GVLSGEEGVD
DIVLLDVNPL TLGIETTGGV MTTLINRNTA IPTKKSQIFS TAADNQPTVL IQVYEGERAL
AKDNNLLGKF ELTGIPPAPR GTPQVEVTFV LDANGILKVS ATDKGTGKSE SITINNDRGR
LSKEEVDRMV EEAEKYAAED AALREKIEAR NALENYAHSL RNQVTDDSET GLGSKLDEDD
KETLTDAIKD TLEFLEDNFD TATKEELDEQ REKLSKIAYP ITSKLYGAPE GGTPPGGQGF
DDDDGDFDYD YDYDHDEL

Figure 1 (cont'd)

ELO3 nucleic acid sequence (SEQ ID NO: 19)

```
atgagtgaca ttaatactct gtcgcagaag attccgtcgt atgttcaata cggtattccc
agtattgatc atccttttgg aatccgttta tggccaattt tcagtcattt ctttgaagcg
gttgttggat acccggctga agatttccgc tttattcagg gtctgactac catggccaat
ctaaaagacg ccctcggtgt tattgctgtt tattactttg tgattttttgg tggacaatgg
ttgatgagga ccctgaacgc tcgtcctttc aagttgaatt tcttgtttca attgcacaat
ttggttttga ccggggcgtc gtttaccttg ttgatattga tcgtggaaca gttaatccca
ggtatttatc gccatggaat attttgggct atttgccaca aggattcttt caccaacgaa
cttgtcacgc tatattacct gaactacttg atcaagtacg tggagttgat cgataccgtg
tttttggtcc tgaaacgcaa aaagttactt ttcttgcaca cttaccacca tggtgccact
gcattactat gctacaccca gctactcgga cacactgccg tcgaatgggt cccaattgcc
ctgaatctgg ctgttcacgt cgtcttgtac tggtactact tcctctctgc acgtggaatt
cgtgtatggt ggaagcaatg ggtgaccaga ttccaaatta ttcagttctt gatcgaccta
gggtttgtct actttgctac ctataccttc tacgctgaca aatacttccc cgagctaccc
aacatgggaa catgttatgg gactgaggaa gctgctgctt tcggatactt gatcctcaca
tcgtatttgg tcctattcat tctcttttac attcgtgtct acaagtccgg gcccacaaca
agcaagggga aatcaaaggc agctgctact accggtcaaa aaactgagac tgcctcccct
tctggcaaaa gcactagtgt ccgtcgtgcc taa
```

ELO2 nucleic acid sequence (SEQ ID NO: 20)

```
ATGTCCATTCTCTCATTTGATAAGCCCTTTGGCATCGAACTATGGCCCATTTTCGATACTTTTGCCTC
TAAAGCCACCCACGGTGCTTTTGTTCCTTCCGAGTTTGAGTTTGTTGCTGGAAAACTGCCTTTATCCA
CTCTGGAACCAGTATTGTACAGCATTGCCGCGTACTACTTTATCGTCTTCGGTGGCTATTATTTTATT
AAGAAGCTGGAGCTAAAGCCACTAGTTTTAAATGCGTTGTTTTCTGCTCACAACTTGTTTTAACTAC
TGCTTCTTTGGTGCTGTTAACTTTGATGGTTGAACAGCTCGTTCCTATTATTTACCACCATGGACTTT
TCTATGCTATTTGCAACACTAGGGCTTGGACTCAAGAGCTTGTCACTTTGTACTACCTGAATTACCTG
ATCAAGTTCGTAGAGTTTATTGACACATTCTTTTTGGTTGTCAAACAGAAAAAGCTGACATTTTTACA
CACTTACCACCACGGTGCTACTGCTTTGCTATGTTACACTCAGTTGGTTGGTGTCACTTCCATCTCTT
GGGTCCCAATCTCCCTGAATCTGGGTGTCCACGTTGTCATGTACTGGTATTACTTTCTGGCTTCGAGA
GGTATCCGTGTATGGTGGAAGGAATGGGTCACTAGATTTCAAATTATGCAATTTATTTTGGATCTTGG
ATTTGTTTATTTTGCCAGTTACCAAAAGTTTGCCTACACTTATTTCAAGGACGTTCTGCCATACTGTG
GTGACTGTGCTGGAACCATGGTAGCCGCTGTGTCTGGTTGTGCCATTCTGTCGTCCTACTTGGTCCTT
TTCATTGCCTTCTACATTGAAGTCTACAGAAAACAAGGTAAAAGTCCAGATACGTTAAAAAGGTCAG
AGGTGGTGTTGCTGCCAAGGTCAACGAGTATGTTCTTTTGGAAGACAAACAGTTGGCATCCGGTGCTT
CCTCTCGTTCCAGCTCCCCTGTGACCAGAAATTTGCGCTCTCGCAAGGCCTGA
```

Figure 1 (cont'd)

LAG1 nucleic acid sequence (SEQ ID NO: 21)

```
atgtctaaag aggaaaagac aagacgtcga agagcgtcat ccattggaaa cataaaccta
ggtgacaatg cagttccttc tttgactacc cgaaagtcga atgctcagca gagaaagtct
agctccgccc gtattaattt aatcaacaag aagggaagtt ccgattgggg tttagttaaa
aaaattggac tttccttggt cgaactgagc tcgcgtcaca catggttgcc atttttggtt
tctttggttg ccatacatgg ctcgtatctg ttatctaata accacactcc atccaatcca
ttgcacaagt tcgttgatct ttcatataaa atcgaaggaa ctaaccctcc catgtatggc
aaaggatgga aagacttctg ctttgtgttt tacttcatga ttttcttcag tttctaccgt
gaatttttga tgcaagcgtt actgaaacct tggccagta agttgggtat cacaagagag
tctaaagtca gaagattcat ggaacagtct tattcaatgt gctactatgg attttctggg
cccttgggtc tatatatcat ggcaggtatg cccttgtggt acttcaacac gacagaattc
tatattactt accctcacaa aagtcatgaa tatctgttca agtactatta tttgggtcaa
gccgctttct ggtctcaaca agctgttgtc ttgatgctac aattggaaaa gccgagaaaa
gatttcaagg agctggttat tcaccacatt atcaccattg cactgattta ctgtagttac
agatttcatt tcacttggat ggggcttgca gtctacatta ccatggacat ctctgacttc
ttcctggctc tttccaagac cctgaactat gttgattcag cttacactgg tcccgcgttc
atgttctttg tgggtgtctg gttctacttg cgccattggc tcaatgtcaa gatcctttgg
tctgtattga ctgaattccg taccgtaggt ccatttgaat tgaactggat cacacagcaa
tacaaatgtt ggatttcaca accaattgta ttttcattga tttttgcctt gcagctggtg
aatctgtact ggtttgtgtt aattctccgg attttgtacc gtcacatctt tttagatgtt
accaaagacg aaagatccga cgatgaaagc gaagaagaag cccaagtaga accctccaag
aaggaagaat ag
```

LAC1 nucleic acid sequence (SEQ ID NO: 22)

```
atgggtgttg aaacatcttc ctctggaact caacatttca gtgatgacgg ttgtgtatct
tcaaggaagc caaatgctac tgtaagcttt gagaagcctg agcgtgctaa cgagctgaag
aatcacaaaa tctataaaaa gtccaaggct tcatggttac agagaaatca aattttacta
gcatcttcat tgttgaacgc gttgttcatc ttaaagcaaa ttccctcatt tcaatcactc
gttaataaat tctttcattt acagtacaag aacttagatg gtacttatga tattggtaaa
gacgactatt ttttcgttat ttactggata atcaacttga ctattattcg cagtgtcttg
atggattggg tcctagaacc cttggcaatt aagatagttg ggattaacaa tagaaaagct
cttaccagat taaagaaca gggttggtct ttattctact acaccacgtc atggactgtg
ggcttctatt tatactacaa gtccgactat ttttcaatt gtgatcatat tttcatcggc
tggcccaaca ataagctgga tttctacttc aaatcttact acttgattca aatgtcatgt
tggctccagc agatcgttgt tttgaacata gaggagagaa gaaaagatta tgttcaaatg
ttctcgcatc atataataac ctgtttgctg attattggct cttactacta ttactttta
cagattggac acgtcatttt ggttatgatg acattgttg acgttttct cagtcttgcc
aaaatgttaa atactgtgg ttacagcact ctctgcgacg tgatgttttt catattcttg
gtttcatgga tagctataag acacgtgtgt tacaactacg tgttctggca cacatgcacc
aagtctaggg atctaatgaa cgcagattgt tccaggtacg caatctacgg aggtcccttg
gacgttactc cagtacgatg ctatacagat agtaccatta gatacttcat tttccttctt
ggaggtctcc aaattatcac actaatctgg atgtacctca ttctaaaagt tttcataggg
gtaataacgg gcaaaggtgc tgaagacgtt agaagtgatg atgaggagag ttcttga
```

Figure 1 (cont'd)

LCB1 nucleic acid sequence (SEQ ID NO: 23)

```
atgagccaac gtgaagaaac aaaagatgct gcaaagaaac agatcgcctt ttcgggaatt
ggagcctgcg gtcctccaaa cttctatggt acacaggatg ctcacgctag attggaagaa
gatctagccc gatttcttgg tgctgaacgt gccatattgt attcccagga tttctgtact
gtgccgtcag ttatagcatg ttttttgaaa agaggtgata ttgttgtgta tgactctggt
attgctttgg caacccaaaa gggaatcgaa ttatccagat gtaccgccta ccatttcaac
cataatgaca tggataacct ggagaaagtg ttagctgatc tgaagcccat gttagatgaa
ggacctttaa ctaggagatt tattatcaca gaaggtcttt ttcaaaactt tggagactct
ccagacttgc gtcgtatatg tgagctgaag aaaaagttca agtacagact gttcttagat
gaaactcttt caattggtgt tctaggtgct actggtagag gattgccaga attatacgga
atccctcgca cagacgttga ggtgaccacc ggcgctttat cctacgccct gggttcttct
ggaggattct gcgtcggtga aaacgccatg gtacatcacc agctaatttc ctctagtgcc
tatgtgtttt ctgcagctat tccaccttat tttgccagag ttgcatcggt atctcttcga
ttactccaag aagatgactc cgtgtcaaga ttacaatcca gtattaattt cctttactca
aagtttaaag aatgccagaa actcaaaaag ctggtaataa tcacttcatc tgacgtatct
ccaatcctac atctacgatt gcatcgtgac ttgagaagca gactcgatct tccggtgagt
tatggtggtc ccggatctgc tatggagaaa atagtacaga ggggagatga acacggttac
ttcgacgaaa attacaacag ggagtctcag atcttacaac aaattgtaga cagagtttta
aacaaccata atatcctaat aacgagatgt aagaggatac ttcaccatga aaagctacca
ttactgcctg agcttatgat ccatattaat gttgcatttt cggaatctga gctttcagaa
gcatttgagg ccgtctcctc tgagatttac aatgttttgc aacagctttg a
```

LCB2 nucleic acid sequence (SEQ ID NO: 24)

```
atgtcaaaaa ctatcccaga tgctctcata gacaatgatt caccacaaga gaaggccgag
aaagaatttg ggtccttgac cagtaaagaa tggctctttg tctctaagca taaccctggc
gagccgcttc cagttcccat cgaggacgaa cctccatatt tcatcctgat tgcaacatac
cttaattacc ttatttgat cataataggc catattagag acttctttgg gaagttgttt
caccctgaac tattcagaga tgtgatggtg aaagatggta ttgctccatg gtatgccaat
tttgaaagtt tctacacgcg tcgtttgaaa acaagattag atgactgttt tgcaaggccc
atatgtggag ttcccggtag gtacatcaaa tgttacgaca gaaccagtga cgattacaac
aatacctata attattccgg caccgtcaca gagcgcttga atttgagttc atacaactat
ttagggttcg cacaatcctc tggtctgtgc acctcagaaa gtatcaagac ggtggagaag
tatggtacca acagtgctgg tcctcgagtt agtgtgggaa ctactgatct ccatcttgaa
tgtgaggacg tcgttgccaa atttactggc aaggacaatg ctttggtatt ttccatgggt
tatgggacca atgcaaatct cttcacctct ttggtggact ctaagtgttg tgttatctca
gattctttaa accacggatc tatcaggaca ggtgttcgtt tgtctggcgc ctcagtcaaa
acttttgctc acaacgacat ggcagcgctg gaaagaactt tgagaagtgt catttcccaa
ggtcagccaa agactcatag accctggaag aagatttttg ttgctgtaga gggactttat
tccatggaag gaacccttg taatttgcca aaactggtag aattgcgtaa gcgttacaag
tttatttat tgttgacga ggcacattct attggtgcta tgggacccaa tggtaagggt
gtttgtgact attttggcat ttcttcttcc aatattgata ttatgatggg tacttttacc
aaatcatttg gagccacagg cggttacatc gctgccgaca aagccatcat agacagattg
aagttagatc tcacaacaaa tacttatgga gaatcaatgt cacctgctgt gctcacacaa
atcattactt ctttgaaaat tatagatgga caactcaatg gtaatgaagg taaagagagg
ctacaaagga ttgccttcaa ttctaggtat ctgcgattag gactaaagcg attaggattt
attgtttatg gtgctgatga ttctcctgtt atccccttt tactgtatct tcccccaag
atgcctgcat ttagccgaat gatgtacgat agaaaggttg ctgtcgttgt tgtgggatat
cctgcaacgg atataacgtc ttctcgtatt cgattctgcg tttcctcttc tttgaagaag
gaggatatag attatttgct caaatgttgt gatgagatag agatactttt gttttttgaag
ttcagcacag ggattgctgg tggtgagaag cacccgggag actataagaa gggcattgct
cctaggtgga cattggagga ggttctggag aagacaccgg aggattgcaa gaaagccatg
tactaa
```

Figure 1 (cont'd)

TSC13 nucleic acid sequence (SEQ ID NO: 25)

ATGGTTAAACTCATTGTTAATCCAAGGTCTGAGACCCTGAGACAAATCAACGTAGACACTACCCCCAA
TACAAGAGTCAGAGACATTGTGGTAGCTTACGGAAAGGCAAATAACAGTTTATCCAGCTCCAGAATCA
GATTCACTAAACTGGAAGAAGACGCAGTTTCCAAGAAACCAAAGCATGTCACTCTGGACTACGAGAAA
TCCTTAGCTCAAAATGGGATAGTCTTCACAGATGATTCAGATTCCAAAGAAGTCTATGCGAAAGATTT
GGGACCCCAGATCAGTTGGAAATTAGTGTTCCTGATCGAATACGTGGGCCCGCTGATTATTCATCCAT
TGCTCTATTACGGCTGGTTCAAACCTGACTATAACACTCTTACACAGAAAGTTTCTTTCATTTTGGTG
ATGCTGCACTTCCTGAAACGTGAATACGAAACAACTTTTGTGCACCTGTTTTCATCTGATACAATGCC
TCTTTTCAACGTTTTCAAGAACTCAGCTCATTATTGGATTCTTAGTGGATTGAGCCTTGCTGTCACTA
TTTATGCTCCGGATTCATACCGAAATAAGTTTGCACCCACTTGGAAACAGTTTTTTTCCATGTATCTG
ACCATGAAGACTCCACAGTTCTAGCACTGATTGGACTGTGGGTATTTGCTGAATTGTCCAACTTCATC
ACTCACCAGAAATTGGCCAGTCTCAGAGCCGATGGCTCCAGAGAACATAAAATTCCCTATGGATATGG
CTTCAACCTGGTCTCTTTCCCCAACTATTTCTTTGAATCTGTAGCTTGGTTGGCATTTGCCCTTCTCA
ACAATAACTGGTCATCTTGGGTGTTCCTTACCATTGCCTCCATTCAGATGTATATTTGGGCCGCTAAG
AAACACAAAAGATATCTCAAGGAGTTTGGGGACCAATATCCCAAGAACAGGAAAGCAATGATTCCATT
CCTTTTGTAG

LIP1sc nucleic acid sequence (SEQ ID NO: 26)

ATGTCTCAACCCACTCCCATCATAACTACAAAATCAGCTGCTAAGCCAAAACCAAAAATTTTTAATTT
ATTCCGCGTTTGCTTCATTTCATTATTGCTGATCGCTGCGGTTGAATACTTCAAGTATGGTACAAGAA
TTAACTATGAATGGTTCCATTGTACCCCAATCAAAGAACCCCAGTCTGGCTCAGTAATCAAGCTTTGG
GCACGTGGTGGGCCAAGTTGTGACAAAAGAGGCGAATATAAAACTATAGTAAAGAGAATCACTAGAGA
TTATGAACCAAATGATGAACATCTCTCGTTCTGTATCATCGAGAATGATAATGTTCCACCCGTCCACT
ACCCAATTCACGAAGATAAAGGTGAACCTGGCTACGTAGCTTATGTCGGGTACGACACAGACTCTGAG
CTGGTTCAAGAACTATGTGCTGATTCCACAATTTATCACATGTGA

TSC3sc nucleic acid sequence (SEQ ID NO: 27)

ATGACACAACATAAAAGCTCGATGGTGTACATACCCACCACTAAGGAAGCTAAAAGACGTAATGGGAA
ATCAGAAGGCATACTAAATACTATTGAAGAAGTGGTGGAAAAGCTTTATTGGACCTACTACATACATT
TACCCTTTTATTTAATGGCCTCTTTTGATTCATTCTTCCTCCATGTTTTTTTTCTCACAATTTTCAGT
TTGAGTTTCTTCGGTATACTAAAGTATTGCTTCCTTTGA

Figure 1 (cont'd)

PAH1 nucleic acid sequence (SEQ ID NO: 28)

```
atgcagtacg taggtagagc cattggatca gtatccaaaa cctggtcgtc cattaacccg
gccacactga gtggtgctat tgatatcatc gtggtggaac aagaaaatgg tgatctggct
tgctctccct tccatgttcg gtttggaaag tttcaattat tgaggccttc ccaaaagaaa
gtggatttca tcgtcaatgg agaaaagaca gacttaccaa tgaaactggg cgatgggggc
gaagctttct ttgtgtttga aaccgatgct gccatcccga gtgagcttca aacttccccc
gtcatctcac ctgtatccag cccagaacca gcctctccac tgagtactcc ttccagacca
aactctgaac cagattattt agaattaggg gatggagaat ctacaaccag tgaattagag
aacttcaagt taaatcgata tccctattta tcaactgagg tatcgcattc agatcctggt
gttgggtctg tgagctcaag tcctgagaat acgaagatta ttcaaaagat ctctcggaaa
ctcaatacga aaaatattcc ttccaaggtt gataatacg gaaatcttgt attggatata
caaggttaca aaagtgatga tctagacgac aattccaaat ctttgaaaca gttgttattg
gctgaactcg gagaagatgt agatttggac aaggttattg aaaaagatca cgaaggaaac
attatgatca atggtgccat atctttgttg agcggagaag atgatctgga atcatttcct
cagaccgacg accaagctga gagtctcaaa ttggatctgg agtcagataa atctgacatt
gaatcagaca caaatcatga attgtctcgc tacttcaaaa cgctaagact tacatcagat
caattgaaat gtcttacact gaagaaggga attaacgagc tgaaattcag tgtcaacaag
ggcaaatctg tggtgacggc aaatctatac ttctgggact attatgaccc catagtcata
tcggatatag atggaaccat tactaaatct gatgccttag ccatgtatt taccatgatt
ggccgtgatt ggactcacaa aggtgtagcc aaattatttt cagatatcaa atccaatgga
tacaatatca tgtatttgac tgcaaggtct gttggtcaag ccgattcgac ccgctactat
ttaaacaaca ttgaacaaga aggcttgagg cttcctcaag ggccggtgat cctttctccg
gatcgcacaa tggccgcttt acgaagagag gtaattttga agaaacctga ggtgttcaag
atggcatgtt taaacgacat aaagaaactg tatctcacca ataccaaaga cctaaatccg
aacacagatt ctgcagattt cacggatatc aatacgaaca ctttgagatc ttcaagtctt
acagaggatg tacaaacgcc attttacgcc ggttttggta atagaattac cgatgctttg
tcctataggt cagtagggat accatcatca agaattttta ccataaaccc agacggtgat
gttcacatgg agctactcga attggctggg tatagaagtt cttatgtaca tattagtgag
ctggtagatc atttcttcc accagtgaac actgaactat ttaagtcgat gccttctgat
acctatcgga acacggcaaa gttctctgat gtcaattatt ggaaagagcc tttgtacaat
tttgaggagc tcagtgatga agattctagt gaagatgagc taagaagaag aaaggaggag
gaacgtttac agtctgctcc tcgtagtcca atattggcag caggagcatc gttttcaaa
ggaagtagta gccttttagg ttcaccagaa cggatgactt tgagtgaccc aaagccaact
gaagttgccc ctagcacaat caaaccccca aaatcagttg ttctgtatc atccgatgaa
gaaaagctga aagatcatga tgatttcatt gacgttgatc acgaagatga aaccttggat
gatgatgacg atcccttga ctacgattac gagtatgaag atgaagaaga ggaaaatgac
gacgtagatg aagttgatga tggggaagag tattcagatg attattatga cgaagaagac
gactacgatg aagaattaga tcatacttta gaaccagacc aaaagaaaga actggaccaa
acagctgaag ccaaccagtt acccccttca ggacccgatg aaatggaatc aaaatctttc
aagaaagcca gtgatttaat aagcaaaatg agaatcgatg acagctga
```

Figure 1 (cont'd)

PRY1 nucleic acid sequence (SEQ ID NO: 29)

```
atgaagctct ccaccaattt gattctagct attgcagcag cttccgccgt tgtctcagct
gctccagttg ctccagccga agaggcagca aaccacttgc acaagcgtgc ttactacacc
gacacaacca agactcacac tttcactgag gttgttactg tctaccgaac tttgaaaccg
ggcgaaagta tcccaactga ctctccaagc cacggtggta aaagtactaa aaagggtaag
ggtagtacca ctcactctgg tgctccagga gctacctctg tgctccaac tgacgacacc
acttcgacta gtggctcagt agggttacca actagcgcaa cttcagttac ctcttctacc
tcctctgcaa gtacaacaag cagtggaact tcagccacta gcactggtac cggtactagc
actagcacta gcactggtac tggtactggt actacaggca caggaaccac tagttccagc
actagctctt ctgctacttc gactccaacc ggttctatcg acgctatcag ccagacactt
ctggatactc acaatgataa gcgtgctttg cacggcgtcc cagaccttac ttggtctacc
gaactcgctg actacgccca aggttacgcc gattcataca cttgtggctc ttcattagaa
cacacaggtg gaccatacgg tgaaaatttg gcctctggat actctcctgc tggcagtgta
gaagcatggt acaacgagat cagcgactac gatttctcta acccaggtta ttctgctggt
accggtcact tcacccaagt tgtctggaaa tcaactacac agctgggctg tggatacaag
gagtgcagta ccgacagata ctacatcatc tgcgaatacg cacctcgtgg aaatattgtt
tctgccggct acttcgaaga caacgtcctg cctcctgttt ga
```

ERG11 nucleic acid sequence (SEQ ID NO: 30)

```
atgagtctgg tccaggagtt gattcaaaag ataagctctt tggagctcac cttggtggaa
aagcttttcca tcctgttcgt agctcccttc ttgttgaacg cgctatggca gtttatctac
agtttcagaa aggacagagt tcctttggta ttccactggg ttccatgggt aggctcagca
gtcacatatg gaatgcaacc atatgaattt tttgcagact gtcaaagaaa atacggagac
gtgtttgcct ttgttttgtt gggtaaagtt atgacagtgt acctcggacc aaaaggccat
gagtttattt taaatgctaa actaaacgac gtttgtgctg aagatgccta caagcacctg
accactcctg tatttggtga aggtgttatt tacgattgtc ccaactggaa gttgatggac
cagaagaagt ttgttaaagg atctttaacc aaggagtcct tcagatctta tgtccctaag
attagagatg aagtcctgga ttacatcaat aatgaccccta acttcatggg aggtgattct
aaaaagaaaa ctggaaagac caatgtcctg aactctcagt ccgagcttac gatcttgacc
gcttccagat ctctactggg agatgatatg agaaaactac tgactaagaa atgggctaaa
ctgtttagtg acctagacaa aggatttact cctttaaact tcattttctc tcatcttcct
ctaccaagtt actggactcg tgatcatgct caaaagacca tttctgagac ttatttatct
ttgattaaca agagaagagc tacaaacgac attggtgaca gagatttgat cgattcatta
atgaaatctt ctacatacaa agatggtagc aagatgaccg acgaggagat tcccacttg
ttaatcggag ttcttatggg tggccagcac acttctgcct ccacttcatc gtggttttg
ttgcatctcg gagagaaacc agagctgcag gaggaattat tgaagaaca ggaaagggta
cttcaaggc gtgagttgac ttatgacgat cttgctaata tgcctttaca caatcaagtc
atcaaggaaa ctttgcgcat gcacatgcct ctacactcaa tctttagaaa ggtcactcgt
cctcttcccg ttcctaactc aaagtatgtg gttcctaagg gtcattatgt attggtttca
cctggatttg ccatgaccaa cgatgcgtac ttcccaaacg ctagtgactt ccagccacac
agatgggatg aaactgttga accagtctca gctgacgcaa aggaaactgt tgactacgga
tttggtaaag tctccaaagg tgtttcttct ccttacttac catttggagg aggaagacat
agatgtattg gcgaacattt tgcgtactgt cagttaggaa ccatcttgaa cacattcgtt
agaaccttca agtggaaggc cgtagtccct cagccggact atacctcaat ggttactctt
cctgaaccta atttgtctac tattacatgg gaaagacgcg ataattag
```

Figure 1 (cont'd)

HMG1 nucleic acid sequence (SEQ ID NO: 31)

```
atgcttactg ggttgtccaa gatatgtgcg catagaccaa tccataccat agtggtgacc
gctctcttag tttccttagc atacctaacc attgtggagg agtacacatc gagatcttca
ttatccaatc cttttatatc gttttaccac ccaccaggaa acagtgatta ccaaaattgg
attccagtgg atgactctgt gaagctcaaa agcaagtcag cccagcatct ctctgtatgc
gctttgaagt ttaaaagggt taatggacat cagattcccg atctggcagg aagttttcag
agcgcagacc caactgaaat atttgtcgtt caggattttg acaaatcatt tgactatttt
gattcaattt caaccattga gggtaaggat ggcatccaat ggaaagtcag acacccaat
aggttgggac gttattctga gtacttcaga tctgtttttt caaaaacttt gagactggtt
cagggtgctg aaccattcga cattgtgctt attgcttttg cttacgttgc tatgtggtac
acattttgc agctctatta tgaaatgaaa acaaaggcca actctaactt ttggctgact
ttcggctctc tgctgtcttc aggttgtgca tttgtgtttg cattggccgt cactgtaaaa
gtatacggta tcaaggttcc actcacatct ttaactgaag gtgtcccatt tttggtagct
accattggtt tcaaacacaa agttgcattc actgttccta ttctccaagc ttcccgttca
aaaaaagcca aagaaattcc tgacaccatt atttcagtga ttgaacaaac cacagggtgg
cctctgatta aggatcatct cattatgatt tccgccttct tagcatgttc tttttatgcc
ccccgtatgg aaggactcaa aaacttttgc attctctccg ctaatatctt aacgtttgac
cttataatga ttttcacatt ttttaccgct gtattatctt taaaagctca gattaataag
gttcacgaaa caactgcttt gcagcaagtt ctggaggaag atggaattgc tgaagatgtt
gctgaacgca ttgctgcttc aaaccgaaat atgttttccc gtagtaccag cgtcgtcagc
ttcaaagtga taatgatcgc tgggttcctt ggattccatt tatttgtgtt gggaacttca
tggctctatg actctgacgt ttcaagctct tctatatttg gtaagagcaa tgtatctgcc
ttatccaaag ctgctgccaa acatattcct attggatccg aaggaactat tgtgaccatt
atgcctacga gggtttacat gcctgttgat ttacttctaa agttggaaga tgattttctg
aacatttttt ccaagatatc ggctagcata actgatcctt tgattagcaa acttcttttc
ataattaccg gataagtgc cacaatcaac gtttacttgt gaatgctgc tcgattccac
tcgtctagag aaattgctgt ctctacaatt gcaaagcctc aaacgccaga cgttgttccc
acagtagaac cgcttccaaa tgaaaatgac acaagcattc gaccattgga ggagatggtt
tcattgctga aggaaggtaa aacacgagag ctgaacaatg atgaggtatc atctctcgtt
gttcaaggaa aacttccctt gtacgcccta gaaaaacaac ttgttgataa gacccgcgca
gttattgtaa gaaggaaggc aattgcttcc ttagcagatg ctccggtctt gagaaccgaa
aagctgcctt acaaagatta tgattatgac cgtgtatttg gcgcttgttg tgagaatgtt
atcggattca tgcccttacc agtcggcgtt gctggtccct tgatcattga cggtaaacct
tatcacattc ccatggctac tactgaaggc tgcttagtag cctcaaccat gagaggttgt
aaagctatca attctggagg cggtgtagaa actgttctga cagccgacgg aatgacaaga
ggaccatgcg tttctttccc atctctttct cgtgcaggtg cagctaagat gtggctagat
agtgaagaag ggcaaaagac cattaagggt gcgtttaact ccacctctag atttgcccgt
ttgcagcatg ttaagacaac ccttgctggt acattattgt tcatccgatt caagactact
actggtgatg cgatgggtat gaacatgatt tctaagggtg tggagtattc actaaagttt
atgtcggaag aatgtgactg gcctgacatg gaagttattt ctgtttcagg taattactgt
acagacaaaa aagttgctgc aatcaactgg atcgaaggtc gtggtaagtc tgtcgttgct
gaagctcgta ttccagccga tgttgtcaga agcgttctga agtccgatgt tgaggcattg
gtagaattga atgttagcaa gaacttgatt ggatccgcaa tggcaggatc aattggtggt
ttcaacgcac aagctgccaa tctagttaca gcagtatact tagctacagg acaggatcca
gcccagaatg tcgaaagttc caactgtatt accttgatga caagctcccc aaatggagat
ttacaaattt cagtctctat gccatctatc gaagttggaa ccattggtgg aggaaccgtt
ttggaacctc aaggatcaat gttggaacta ttaggagtta aaggtcctca cccaactaat
ccaggtgcaa actcaaggca gttggctaag atcgttgctt ctgctgtctt ggctgcagag
ctgtccttgt gctctgccct tgcagctggt cacttagtcc aaagtcatat gacccataac
agaaagcaag ctccagtcaa ggaggtaaac ggcactgccg ctaggctagc ggaacaatct
aagatttgca ttaaatcttg a
```

Figure 1 (cont'd)

t2HMG1 nucleic acid sequence (SEQ ID NO: 32)

ATGACGCCAGACGTTGTTCCCACAGTAGAACCGCTTCCAAATGAAAATGACACAAGCATTCGACCATT
GGAGGAGATGGTTTCATTGCTGAAGGAAGGTAAAACACGAGAGCTGAACAATGATGAGGTATCATCTC
TCGTTGTTCAAGGAAAACTTCCCTTGTACGCCCTAGAAAAACAACTTGTTGATAAGACCCGCGCAGTT
ATTGTAAGAAGGAAGGCAATTGCTTCCTTAGCAGATGCTCCGGTCTTGAGAACCGAAAAGCTGCCTTA
CAAAGATTATGATTATGACCGTGTATTTGGCGCTTGTTGTGAGAATGTTATCGGATTCATGCCCTTAC
CAGTCGGCGTTGCTGGTCCCTTGATCATTGACGGTAAACCTTATCACATTCCCATGGCTACTACTGAA
GGCTGCTTAGTAGCCTCAACCATGAGAGGTTGTAAAGCTATCAATTCTGGAGGCGGTGTAGAAACTGT
TCTGACAGCCGACGGAATGACAAGAGGACCATGCGTTTCTTTCCCATCTCTTTCTCGTGCAGGTGCAG
CTAAGATGTGGCTAGATAGTGAAGAAGGGCAAAAGACCATTAAGGGTGCGTTTAACTCCACCTCTAGA
TTTGCCCGTTTGCAGCATGTTAAGACAACCCTTGCTGGTACATTATTGTTCATCCGATTCAAGACTAC
TACTGGTGATGCGATGGGTATGAACATGATTTCTAAGGGTGTGGAGTATTCACTAAAGTTTATGTCGG
AAGAATGTGACTGGCCTGACATGGAAGTTATTTCTGTTTCAGGTAATTACTGTACAGACAAAAAAGTT
GCTGCAATCAACTGGATCGAAGGTCGTGGTAAGTCTGTCGTTGCTGAAGCTCGTATTCCAGCCGATGT
TGTCAGAAGCGTTCTGAAGTCCGATGTTGAGGCATTGGTAGAATTGAATGTTAGCAAGAACTTGATTG
GATCCGCAATGGCAGGATCAATTGGTGGTTTCAACGCACAAGCTGCCAATCTAGTTACAGCAGTATAC
TTAGCTACAGGACAGGATCCAGCCCAGAATGTCGAAAGTTCCAACTGTATTACCTTGATGAACAAGCT
CCCAAATGGAGATTTACAAATTTCAGTCTCTATGCCATCTATCGAAGTTGGAACCATTGGTGGAGGAA
CCGTTTTGGAACCTCAAGGATCAATGTTGGAACTATTAGGAGTTAAAGGTCCTCACCCAACTAATCCA
GGTGCAAACTCAAGGCAGTTGGCTAAGATCGTTGCTTCTGCTGTCTTGGCTGCAGAGCTGTCCTTGTG
CTCTGCCCTTGCAGCTGGTCACTTAGTCCAAAGTCATATGACCCATAACAGAAAGCAAGCTCCAGTCA
AGGAGGTAAACGGCACTGCCGCTAGGCTAGCGGAACAATCTAAGATTTGCATTAAATCTTGA t1HMG1 nucleic acid sequence (SEQ ID NO: 33)

ATGGGAATAAGTGCCACAATCAACGTTTACTTGTTGAATGCTGCTCGATTCCACTCGTCTAGAGAAAT
TGCTGTCTCTACAATTGCAAAGCCTCAAACGCCAGACGTTGTTCCCACAGTAGAACCGCTTCCAAATG
AAAATGACACAAGCATTCGACCATTGGAGGAGATGGTTTCATTGCTGAAGGAAGGTAAAACACGAGAG
CTGAACAATGATGAGGTATCATCTCTCGTTGTTCAAGGAAAACTTCCCTTGTACGCCCTAGAAAAACA
ACTTGTTGATAAGACCCGCGCAGTTATTGTAAGAAGGAAGGCAATTGCTTCCTTAGCAGATGCTCCGG
TCTTGAGAACCGAAAAGCTGCCTTACAAAGATTATGATTATGACCGTGTATTTGGCGCTTGTTGTGAG
AATGTTATCGGATTCATGCCCTTACCAGTCGGCGTTGCTGGTCCCTTGATCATTGACGGTAAACCTTA
TCACATTCCCATGGCTACTACTGAAGGCTGCTTAGTAGCCTCAACCATGAGAGGTTGTAAAGCTATCA
ATTCTGGAGGCGGTGTAGAAACTGTTCTGACAGCCGACGGAATGACAAGAGGACCATGCGTTTCTTTC
CCATCTCTTTCTCGTGCAGGTGCAGCTAAGATGTGGCTAGATAGTGAAGAAGGGCAAAAGACCATTAA
GGGTGCGTTTAACTCCACCTCTAGATTTGCCCGTTTGCAGCATGTTAAGACAACCCTTGCTGGTACAT
TATTGTTCATCCGATTCAAGACTACTACTGGTGATGCGATGGGTATGAACATGATTTCTAAGGGTGTG
GAGTATTCACTAAAGTTTATGTCGGAAGAATGTGACTGGCCTGACATGGAAGTTATTTCTGTTTCAGG
TAATTACTGTACAGACAAAAAAGTTGCTGCAATCAACTGGATCGAAGGTCGTGGTAAGTCTGTCGTTG
CTGAAGCTCGTATTCCAGCCGATGTTGTCAGAAGCGTTCTGAAGTCCGATGTTGAGGCATTGGTAGAA
TTGAATGTTAGCAAGAACTTGATTGGATCCGCAATGGCAGGATCAATTGGTGGTTTCAACGCACAAGC
TGCCAATCTAGTTACAGCAGTATACTTAGCTACAGGACAGGATCCAGCCCAGAATGTCGAAAGTTCCA
ACTGTATTACCTTGATGAACAAGCTCCCAAATGGAGATTTACAAATTTCAGTCTCTATGCCATCTATC
GAAGTTGGAACCATTGGTGGAGGAACCGTTTTGGAACCTCAAGGATCAATGTTGGAACTATTAGGAGT
TAAAGGTCCTCACCCAACTAATCCAGGTGCAAACTCAAGGCAGTTGGCTAAGATCGTTGCTTCTGCTG
TCTTGGCTGCAGAGCTGTCCTTGTGCTCTGCCCTTGCAGCTGGTCACTTAGTCCAAAGTCATATGACC
CATAACAGAAAGCAAGCTCCAGTCAAGGAGGTAAACGGCACTGCCGCTAGGCTAGCGGAACAATCTAA
GATTTGCATTAAATCTTGA

Figure 1 (cont'd)

DGA1 nucleic acid sequence (SEQ ID NO: 34)

```
atgcctgaaa agaagaacag tcgttccgct gacgaagctc ttagctttct tgctaaaacg
aacgtagagc gcccgatgca ttactctaag acagggaaca taacgcccga cacggtatct
tcaagagaag atcactacca agattacgac gactcacaag atgacattat aaataacaaa
ctattacaaa gaagacaggg tgggccacac aacaagatag agaagcaaag gaggtttgct
ttgttgagga gttccctaaa caggagattg gaaactctag taatattgtg gcatactatc
acgattccat ttttagcatc actattttc gttctgtgta caattcccat gttgtggcct
cttataatag tttacttggt ttattttac atcgatgcca atactccaag caatggaaag
tctgctgacc gaagagtgga atggttcaga agtttgcata tttggaaaca ttttgtcaat
tattaccta tatctgtgta caaaactgtt gacctggaac cgacgttcaa gactaagaag
attgaaatta ttcttccgaa gtatcaccaa gtaaccactt atttgccaag ttctgttaga
aagtacatac cgacacacag agttctcata gaaaggaga tcaaaacagg gccaagatac
atatttggtt atcaccctca tggggtagtt tccctgggga tcactggagc ttttggcacc
aatggttgta acattggcga gttactacca ggaatcagaa tatatttatt aaccctcatc
actcaattca aacttcctct attgagagat tacttaatgg cattgggtat ttcttctgtt
tcgaaacgta atgtgactgc actgataaaa cgaaatcagt ctgtctgtat tgtcattgga
ggtgcttcgg agtccctatt atccaaacca catactattg atattgtcct gaaaaaaggg
aaaggctttg tgaaagtcgc actagagctg ggtgacactg agttagttcc agtatttggt
tttggagaaa acactgccta taatgttttt gacccaagtg tatctggcaa gtcttgctct
gtcctaaatt acgtgcggaa gcaaatgtgt gggtttcaat tatggttaaa acaacacttt
ggctttacct ttccattttt tcatgctagg ggtgttttca atcacgactt tggccttcta
ccatatcgga aacctatcaa cttggtcatc ggtagaccca tcccggttcc ttacattcat
tcaccaaccc aagaacagat tgaccattac cattccctat atgtcgaaga actgaaacga
gtttttgagc agaataagga gaggtttaat gctggatcct ggagctacg aattgtcgag
tga
```

Figure 1 (cont'd)

LRO1 nucleic acid sequence (SEQ ID NO: 35)

```
atgcaactac ggaaaagagg aaacgagaga tccagacttg aatcgcacat cggcgattcg
gacacggtta ttgacttgga tgactcttca gtaaacgaca cgcttccgga tgaagacaac
atcgctaaac caagaaaagc gtcaacgcac agaagaccat cacttcgaaa aatccacagc
gctgagactg tccgtcgttt ctatgagtca aagaatgtaa tttttatttt tggagccttc
ataggaatcg ctgttgcttt gtactttgga gctaccagtt ctgagtaccc tattccagac
atagatcaac tggtcaactt tgactctctt tccacctatt ttgacgattg aaggatgtc
ttaccaaagt cccttcaaag tattgttgag agtactcagt caatcagaa ttctaagata
ttgagctctg aatcatttgc agtaggtaag caattgaaga gtaagtcaat gattgaagct
aatcattcca ttgttcttgt tcctggtgtg atcagcaccg ggctggaaag ttgggcttg
gaaggaactc ctgactgccc ctccgaaggt catttagaa aacgtctatg gggatcattt
tacatgttgc ggacaatgtt tttggataag gcgtgttggc tgaaacatat tatgctagat
acaacaacgg gattagaccc tccaggaata agcctcagag cagctcaggg gtttgaagct
gctgatttct ttatagcagg ttactggatt tggaataaaa tccttcagaa cttggcagtt
attggatata atccaaacaa catggtgagc gctgcttatg attggagact tgcttttctg
gatttagaat tacgggatgc atactttca aaattaaaag gtttcgttga acttcaaaag
catcagagtg ggaaaaatc ggttttggta ggtcattcaa tggggtcaca agtgatttac
tattttatga agtgggttga agctgacgga tacggaaacg gaggccctaa ctgggtgaat
gatcatgtag attcttttgt ggacatatcc ggctgtatgc tgggtactcc taaggctata
cctgctcttt tatccggaga aatgaaggat acagttcaat taaacgccct cgccgtggag
ggcttagaaa agtttctgtc tagaagagaa cgtgctgata tgatccgttc ttttggtgga
atagccagca tgattcccaa aggcggagat ctaatctggg gaaatctcga gagttctcct
gatgacgcca cgtcaattgg agatttggga aacgacactt atggtaattt cattaggttc
aaggagccgg tggggaagta ctcccaaaag aacttaacgg tgactgatag tattcagttt
ttgatggagc agactcccgc ctggttccaa gacaggatgt tgagggctta ctcttatggg
ttcaccaatt ctgctaagca gctgaaaaaa aataataaag atcatacaaa atggtccaat
ccccttgagg catcacttcc aaatgcacct gatctgaaag tgttttgctt ttatgggttt
ggaaatccta cagaaagagc ttactactac cgagaagaag ttgatccggc taagaccaaa
ttgaacgtca ctattgaaaa gaactatgat tcggttctta tggcagatgg tgacggtacg
gtcagtctaa tgactcactc aatgtgccac atatggaagc aagctaatag tgtttacaac
ccaggaaata gcaaggtcaa gattgttgag attgatcatg aacctgatcg gtttgacatt
cgaggaggtg ccaaaactgc tgaacatgta gacattctgg gatctgcaga gttaaacgag
ctagtgttac tggtggccgc tggaaaggga gaccaaatta aggaaaagat tgttagtaat
ctgaaggaaa tagttgataa tcttgaacta gatctttaa
```

KAR2 nucleic acid sequence (SEQ ID NO: 36)

```
atgctgtcgt taaaaccatc ttggctgact ttggcggcat taatgtatgc catgctattg
gtcgtagtgc catttgctaa acctgttaga gctgacgatg tcgaatctta tggaacagtg
attggtatcg atttgggtac cacgtactct tgtgtcggtg tgatgaagtc gggtcgtgta
gaaattcttg ctaatgacca aggtaacaga atcactcctt cctacgttag tttcactgaa
gacgagagac tggttggtga tgctgctaag aacttagctg cttctaaccc aaaaaacacc
atctttgata ttaagagatt gatcggtatg aagtatgatg ccccagaggt ccaaagagac
ttgaagcgtc ttccttacac tgtcaagagc aagaacggcc aacctgtcgt ttctgtcgag
tacaaggtg aggagaagtc tttcactcct gaggagattt ccgccatggt cttgggtaag
atgaagttga tcgctgagga ctacttagga aagaaagtca ctcatgctgt cgttaccgtt
ccagcctact tcaacgacgc tcaacgtcaa gccactaagg atgccggtct catcgccggt
ttgactgttc tgagaattgt gaacgagcct accgccgctg cccttgctta cggtttggac
aagactggtg aggaaagaca gatcatcgtc tacgacttgg gtggaggaac cttcgatgtt
tctctgcttt ctattgaggg tggtgctttc gaggttcttg ctaccgccgg tgacacccac
ttgggtggtg aggactttga ctacagagtt gttcgccact tcgttaagat tttcaagaag
aagcataaca ttgacatcag caacaatgat aaggctttag gtaagctgaa gagagaggtc
gaaaaggcca agcgtacttt gtcttcccag atgactacca gaattgagat tgactctttc
```

Figure 1 (cont'd)

```
gtcgacggta tcgacttctc tgagcaactg tctagagcta agtttgagga gatcaacatt
gaattattca agaagacact gaaaccagtt gaacaagtcc tcaaagacgc tggtgtcaag
aaatctgaaa ttgatgacat tgtcttggtt ggtggttcta ccagaattcc aaaggttcaa
caattattgg aggattactt tgacggaaag aaggcttcta agggaattaa cccagatgaa
gctgtcgcat acggtgctgc tgttcaggct ggtgttttgt ctggtgagga aggtgtcgat
gacatcgtct tgcttgatgt gaaccccta actctgggta tcgagactac tggtggcgtt
atgactacct taatcaacag aaacactgct atcccaacta agaaatctca aattttctcc
actgctgctg acaaccagcc aactgtgttg attcaagttt atgagggtga gagagccttg
gctaaggaca acaacttgct tggtaaattc gagctgactg gtattccacc agctccaaga
ggtactcctc aagttgaggt tacttttgtt ttagacgcta acggaatttt gaaggtctct
gccaccgata agggaactgg aaaatccgag tccatcacca tcaacaatga tcgtggtaga
ttgtccaagg aggaggttga ccgtatggtt gaagaggccg agaagtacgc cgctgaggat
gctgcactaa gagaaaagat tgaggctaga aacgctctgg agaactacgc tcattccctt
aggaaccaag ttactgatga ctctgaaacc gggcttggtt ctaaattgga cgaggacgac
aaagagacat tgacagatgc catcaaagat accctagagt tcttggaaga caacttcgac
accgcaacca aggaagaatt agacgaacaa agagaaaagc tttccaagat tgcttaccca
atcacttcta agctatacgg tgctccagag ggtggtactc cacctggtgg tcaaggtttt
gacgatgatg atggagactt tgactacgac tatgactatg atcatgatga gttgtag
```

Figure 2

SDZ-Fab HC amino acid sequence (SEQ ID NO: 37)

*MRFPSIFTAVLFAASSALAAPVNTTTEDETAQIPAEAVIGYSDLEGDFDVAVLPFSNSTNNGLLFINTTIASIAA*
*KEEGVSLEKR*EVQLVQSGGGLVQPGGSLRLSCAASGFTFSHYWMSWVRQAPGKGLEWVANIEQDGSEKYYVDSVK
GRFTISRDNAKNSLYLQMNSLRAEDTAVYFCARDLEGLHGDGYFDLWGRGTLVTVSSASTKGPSVFPLAPCSRST
SESTAALGCLVKDYFPEPVTVSWNSGALTSGVHTFPAVLQSSGLYSLSSVVTVPSSSLGTKTYTCNVDHKPSNTK
VDKRVESKYGPP

SDZ-Fab LC amino acid sequence (SEQ ID NO: 38)

*MRFPSIFTAVLFAASSALAAPVNTTTEDETAQIPAEAVIGYSDLEGDFDVAVLPFSNSTNNGLLFINTTIASIAA*
*KEEGVSLEKR*AIQLTQSPSSLSASVGDRVILTCRASQGVSSALAWYQQKPGKAPKLLIYDASSLESGVPSRFSGS
GSGPDFTLTISSLQPEDFATYFCQQFNSYPLTFGGGTKLEIKRTVAAPSVFIFPPSDEQLKSGTASVVCLLNNFY
PREAKVQWKVDNALQSGNSQESVTEQDSKDSTYSLSSTLTLSKADYEKHKVYACEVTHQGLSSPVTKSFNRGEC

SDZ-Fab HC polynucleotide sequence(SEQ ID NO: 41)

*ATGAGATTCCCATCTATTTTCACCGCTGTCTTGTTCGCTGCCTCCTCTGCATTGGCTGCCCCTGTTAACACTACC*
*ACTGAAGACGAGACTGCTCAAATTCCAGCTGAAGCAGTTATCGGTTACTCTGACCTTGAGGGTGATTTCGACGTC*
*GCTGTTTTGCCTTTCTCTAACTCCACTAACAACGGTTTGTTGTTCATTAACACCACTATCGCTTCCATTGCTGCT*
*AAGGAAGAGGGTGTCTCTCTCGAGAAGAGA*GAGGTCCAATTGGTCCAATCTGGTGGAGGATTGGTTCAACCAGGT
GGATCTCTGAGATTGTCTTGTGCTGCTTCTGGTTTCACCTTCTCTCACTACTGGATGTCATGGGTTAGACAAGCT
CCTGGTAAGGGTTTGGAATGGGTTGCTAACATCGAGCAAGATGGATCAGAGAAGTACTACGTTGACTCTGTTAAG
GGAAGATTCACTATTTCCCGTGATAACGCCAAGAACTCCTTGTACCTGCAAATGAACTCCCTTAGAGCTGAGGAT
ACTGCTGTCTACTTCTGTGCTAGAGACTTGGAAGGTTTGCATGGTGATGGTTACTTCGACTTATGGGGTAGAGGT
ACTCTTGTCACCGTTTCATCTGCCTCTACCAAAGGACCTTCTGTGTTCCCATTAGCTCCATGTTCCAGATCCACC
TCCGAATCTACTGCAGCTTTGGGTTGTTTGGTGAAGGACTACTTTCCTGAACCAGTGACTGTCTCTTGGAACTCT
GGTGCTTTGACTTCTGGTGTTCACACCTTTCCTGCAGTTTTGCAGTCATCTGGTCTGTACTCTCTGTCCTCAGTT
GTCACTGTTCCTTCCTCATCTCTTGGTACCAAGACCTACACTTGCAACGTTGACCATAAGCCATCCAATACCAAG
GTTGACAAGAGAGTTGAGTCCAAGTATGGTCCACCTtaa

SDZ-Fab LC polynucleotide sequence (SEQ ID NO: 42)

*ATGAGATTCCCATCTATTTTCACCGCTGTCTTGTTCGCTGCCTCCTCTGCATTGGCTGCCCCTGTTAACACTACC*
*ACTGAAGACGAGACTGCTCAAATTCCAGCTGAAGCAGTTATCGGTTACTCTGACCTTGAGGGTGATTTCGACGTC*
*GCTGTTTTGCCTTTCTCTAACTCCACTAACAACGGTTTGTTGTTCATTAACACCACTATCGCTTCCATTGCTGCT*
*AAGGAAGAGGGTGTCTCTCTCGAGAAGAGA*GCTATCCAGTTGACTCAATCACCATCCTCTTTGTCTGCTTCTGTT
GGTGATAGAGTCATCCTGACTTGTCGTGCATCTCAAGGTGTTTCCTCAGCTTTAGCTTGGTACCAACAAAAGCCA
GGTAAAGCTCCAAAGTTGCTGATCTACGACGCTTCATCCCTTGAATCTGGTGTTCCTTCACGTTTCTCTGGATCT
GGATCAGGTCCTGATTTCACTCTGACTATCTCATCCCTTCAACCAGAAGACTTTGCTACCTACTTCTGTCAACAG
TTCAACTCTTACCCTTTGACCTTTGGAGGTGGAACTAAGTTGGAGATCAAGAGAACTGTTGCTGCACCATCAGTG
TTCATCTTTCCTCCATCTGATGAGCAACTGAAGTCTGGTACTGCATCTGTTGTCTGCTTACTGAACAACTTCTAC
CCAAGAGAAGCTAAGGTCCAATGGAAGGTTGACAATGCCTTGCAATCTGGTAACTCTCAAGAGTCTGTTACTGAG
CAAGACTCTAAGGACTCTACTTACTCCCTTTCTTCCACCTTGACTTTGTCTAAGGCTGATTACGAGAAGCACAAG
GTTTACGCTTGTGAGGTTACTCACCAAGGTTTGTCTTCTCCTGTTACCAAGTCTTTCAACAGAGGTGAATGCTAA

Figure 2 (cont'd)

HyHEL-Fab HC amino acid sequence (SEQ ID NO: 39)

*MRFPSIFTAVLFAASSALAAPVNTTTEDETAQIPAEAVIGYSDLEGDFDVAVLPFSNSTNNGLLFINTTIASIAA*
*KEEGVSLEKR*DVQLQESGPSLVKPSQTLSLTCSVTGDSITSDYWSWIRKFPGNRLEYMGYVSYSGSTYYNPSLKS
RISITRDTSKNQYYLDLNSVTTEDTATYYCANWDGDYWGQGTLVTVSSASTKGPSVFPLAPSSKSTSGGTAALGC
LVKDYFPEPVTVSWNSGALTSGVHTFPAVLQSSGLYSLSSVVTVPSSSLGTQTYICNVNHKPSNTKVDKRVEPKS
CDK

HyHEL-Fab LC amino acid sequence (SEQ ID NO: 40)

*MRFPSIFTAVLFAASSALAAPVNTTTEDETAQIPAEAVIGYSDLEGDFDVAVLPFSNSTNNGLLFINTTIASIAA*
*KEEGVSLEKR*DIVLTQSPATLSVTPGNSVSLSCRASQSIGNNLHWYQQKSHESPRLLIKYASQSISGIPSRFSGS
GSGTDFTLSINSVETEDFGMYFCQQSNSWPYTFGGGTKLEIKRTVAAPSVFIFPPSDEQLKSGTASVVCLLNNFY
PREAKVQWKVDNALQSGNSQESVTEQDSKDSTYSLSSTLTLSKADYEKHKVYACEVTHQGLSSPVTKSFNRGEC

HyHEL-Fab HC polynucleotide sequence (SEQ ID NO: 43)

*ATGAGATTCCCATCTATTTTCACCGCTGTCTTGTTCGCTGCCTCCTCTGCATTGGCTGCCCCTGTTAACACTACC*
*ACTGAAGACGAGACTGCTCAAATTCCAGCTGAAGCAGTTATCGGTTACTCTGACCTTGAGGGTGATTTCGACGTC*
*GCTGTTTTGCCTTTCTCTAACTCCACTAACAACGGTTTGTTGTTCATTAACACCACTATCGCTTCCATTGCTGCT*
*AAGGAAGAGGGTGTCTCTCTCGAGAAGAGA*GACGTTCAATTGCAAGAATCTGGTCCATCCTTGGTTAAGCCATCC
CAGACTTTGTCCTTGACTTGTTCCGTTACTGGTGACTCCATCACTTCTGACTACTGGTCCTGGATCAGAAAGTTC
CCAGGTAACAGATTGGAGTACATGGGTTACGTTTCTTACTCCGGTTCCACTTACTACAACCCATCCTTGAAGTCC
AGAATCTCCATCACTAGAGACACTTCCAAGAACCAGTACTACTTGGACTTGAACTCCGTTACTACTGAGGACACT
GCTACTTACTACTGTGCTAACTGGGACGGTGACTATTGGGGTCAAGGTACTTTGGTTACTGTTTCCTCCGCTTCC
ACTAAGGGTCCATCTGTTTTTCCATTGGCTCCATCCTCCAAGTCTACTTCAGGTGGTACTGCTGCTTTGGGTTGT
TTGGTTAAGGACTACTTCCCAGAGCCAGTTACTGTTTCTTGGAACTCCGGTGCTTTGACTTCCGGTGTTCACACT
TTCCCAGCTGTCTTGCAATCCTCCGGTCTGTACTCCTTGTCCTCCGTTGTTACTGTTCCTTCTTCCTCCTTGGGT
ACTCAAACTTACATCTGTAACGTTAACCACAAGCCATCCAACACTAAGGTTGACAAGAGAGTTGAGCCAAAGTCC
TGTGACAAGTAATAG

HyHEL-Fab LC polynucleotide sequence (SEQ ID NO: 44)

*ATGAGATTCCCATCTATTTTCACCGCTGTCTTGTTCGCTGCCTCCTCTGCATTGGCTGCCCCTGTTAACACTACC*
*ACTGAAGACGAGACTGCTCAAATTCCAGCTGAAGCAGTTATCGGTTACTCTGACCTTGAGGGTGATTTCGACGTC*
*GCTGTTTTGCCTTTCTCTAACTCCACTAACAACGGTTTGTTGTTCATTAACACCACTATCGCTTCCATTGCTGCT*
*AAGGAAGAGGGTGTCTCTCTCGAGAAGAGA*GACATCGTTTTGACTCAATCCCCAGCTACTTTGTCCGTTACTCCA
GGTAACTCCGTTTCCTTGTCCTGTAGAGCTTCCCAGTCCATCGGTAACAACTTGCACTGGTATCAGCAGAAGTCT
CACGAGTCCCCAAGACTGTTGATCAAGTACGCTTCCCAATCCATCTCCGGTATCCCATCTAGATTCTCTGGTTCT
GGTTCCGGTACTGACTTCACTTTGTCCATCAACTCCGTTGAGACTGAGGACTTCGGTATGTACTTCTGTCAGCAA
TCCAACTCCTGGCCATACACTTTTGGTGGTGGTACTAAGTTGGAGATCAAGAGAACTGTTGCTGCTCCATCCGTT
TTCATCTTCCCACCATCTGACGAGCAGTTGAAGTCTGGTACTGCTTCCGTTGTTTGTTTGTTGAACAACTTCTAC
CCAAGAGAAGCTAAGGTTCAGTGGAAGGTTGACAACGCCTTGCAATCCGGTAACTCCCAAGAGTCCGTTACTGAA
CAAGACTCCAAGGACTCTACTTACTCCTTGTCCTCCACTTTGACTTTGTCCAAGGCTGACTACGAGAAGCACAAG
GTTTACGCTTGTGAGGTTACTCACCAGGGTTTGTCCTCCCCAGTTACTAAGTCCTTCAACAGAGGTGAGTGTTAA
TAG (Underlined and italics: S. cerevisiae-alfa mating factor prepro leader)

Figure 2 (cont'd)

*S. cerevisiae* alpha mating factor signal leader sequence (SEQ ID NO: 45)

MRFPSIFTAVLFAASSALAAPVNTTTEDETAQIPAEAVIGYSDLEGDFDVAVLPFSNSTNNGLLFINTTIASIAA
KEEGVSLEKR

*S. cerevisiae* alpha mating factor signal leader sequence (SEQ ID NO: 46)

ATGAGATTCCCATCTATTTTCACCGCTGTCTTGTTCGCTGCCTCCTCTGCATTGGCTGCCCCTGTTAACACTACC
ACTGAAGACGAGACTGCTCAAATTCCAGCTGAAGCAGTTATCGGTTACTCTGACCTTGAGGGTGATTTCGACGTC
GCTGTTTTGCCTTTCTCTAACTCCACTAACAACGGTTTGTTGTTCATTAACACCACTATCGCTTCCATTGCTGCT
AAGGAAGAGGGTGTCTCTCTCGAGAAGAGA

RECOMBINANT HOST CELL WITH ALTERED MEMBRANE LIPID COMPOSITION

FIELD OF INVENTION

The present invention is in the field of recombinant biotechnology, in particular in the field of protein expression. The invention generally relates to a method of expressing a protein of interest (POI) from a host cell by over- or underexpressing a polynucleotide encoding a protein involved in lipid metabolism. The invention relates particularly to improving a host cell's capacity to express and/or secrete a protein of interest and use of the host cell for protein expression. The invention also relates to cell culture technology, and more specifically to culturing cells to produce desired molecules for medical purposes or food products or feed products.

BACKGROUND OF THE INVENTION

Successful production of proteins of interest (POI) has been accomplished both with prokaryotic and eukaryotic hosts. The most prominent examples are bacteria like *Escherichia coli*, yeasts like *Saccharomyces cerevisiae*, *Pichia pastoris* or *Hansenula polymorpha*, filamentous fungi like *Aspergillus awamori* or *Trichoderma reesei*, or mammalian cells like CHO cells. While the yield of some proteins is readily achieved at high rates, many other proteins are only produced at comparatively low levels.

Generally, heterologous protein synthesis may be limited at different levels. Potential limits are transcription and translation, protein folding and, if applicable, secretion, disulfide bridge formation and glycosylation, as well as aggregation and degradation of the target proteins. Transcription can be enhanced by utilizing strong promoters or increasing the copy number of the heterologous gene. However, these measures clearly reach a plateau, indication that other bottlenecks downstream of transcription limit expression.

High level of protein yield in host cells may also be limited at one or more different steps, like folding, disulfide bond formation, glycosylation, transport within the cell, or release from the cell. Many of the mechanisms involved are still not fully understood and cannot be predicted on the basis of the current knowledge of the state-of-the-art, even when the DNA sequence of the entire genome of a host organism is available. Moreover, the phenotype of cells producing recombinant proteins in high yields can be decreased growth rate, decreased biomass formation and overall decreased cell fitness.

Various attempts were made in the art for improving production of a protein of interest, such as overexpressing chaperones which should facilitate protein folding, external supplementation of amino acids, and the like.

However, there is still a need for methods to improve a host cell's capacity to produce and/or secrete proteins of interest. The technical problem underlying the present invention is to comply with this need.

The solution of the technical problem is the provision of means, such as engineered host cells, methods and uses applying said means for increasing the yield of a non-membrane protein of interest in a eukaryotic host cell by over- or underexpressing in said host cell at least one polynucleotide encoding a protein which is involved in lipid metabolism. These means, methods and uses are described in detail herein, set out in the claims, exemplified in the Examples and illustrated in the Figures.

Accordingly, the present invention provides new methods and uses to increase the yield of recombinant proteins in host cells which are simple and efficient and suitable for use in industrial methods. The present invention also provides host cells to achieve this purpose.

It must be noted that as used herein, the singular forms "a", "an" and "the" include plural references and vice versa unless the context clearly indicates otherwise. Thus, for example, a reference to "a host cell" or "a method" includes one or more of such host cells or methods, respectively, and a reference to "the method" includes equivalent steps and methods that could be modified or substituted known to those of ordinary skill in the art. Similarly, for example, a reference to "methods" or "host cells" includes "a host cell" or "a method", respectively.

Unless otherwise indicated, the term "at least" preceding a series of elements is to be understood to refer to every element in the series. Those skilled in the art will recognize, or be able to ascertain using no more than routine experimentation, many equivalents to the specific embodiments of the invention described herein. Such equivalents are intended to be encompassed by the present invention.

The term "and/or" wherever used herein includes the meaning of "and", "or" and "all or any other combination of the elements connected by said term". For example, A, B and/or C means A, B, C, A+B, A+C, B+C and A+B+C.

The term "about" or "approximately" as used herein means within 20%, preferably within 10%, and more preferably within 5% of a given value or range. It includes also the concrete number, e.g., about 20 includes 20.

The term "less than", "more than" or "larger than" includes the concrete number. For example, less than 20 means ≤20 and more than 20 means ≥20.

Throughout this specification and the claims or items, unless the context requires otherwise, the word "comprise" and variations such as "comprises" and "comprising" will be understood to imply the inclusion of a stated integer (or step) or group of integers (or steps). It does not exclude any other integer (or step) or group of integers (or steps). When used herein, the term "comprising" can be substituted with "containing", "composed of", "including", "having" or "carrying" and vice versa, by way of example the term "having" can be substituted with the term "comprising". When used herein, "consisting of" excludes any integer or step not specified in the claim/item. When used herein, "consisting essentially of" does not exclude integers or steps that do not materially affect the basic and novel characteristics of the claim/item. In each instance herein any of the terms "comprising", "consisting essentially of" and "consisting of" may be replaced with either of the other two terms.

Further, in describing representative embodiments of the present invention, the specification may have presented the method and/or process of the present invention as a particular sequence of steps. However, to the extent that the method or process does not rely on the particular order of steps set forth herein, the method or process should not be limited to the particular sequence of steps described. As one of ordinary skill in the art would appreciate, other sequences of steps may be possible. Therefore, the particular order of the steps set forth in the specification should not be construed as limitations on the claims. In addition, the claims directed to the method and/or process of the present invention should not be limited to the performance of their steps in the order written, and one skilled in the art can readily appreciate that the sequences may be varied and still remain within the spirit and scope of the present invention.

It should be understood that this invention is not limited to the particular methodology, protocols, material, reagents, and substances, etc., described herein. The terminologies used herein are for the purpose of describing particular embodiments only and are not intended to limit the scope of the present invention, which is defined solely by the claims/items.

All publications and patents cited throughout the text of this specification (including all patents, patent applications, scientific publications, manufacturer's specifications, instructions, etc.), whether supra or infra, are hereby incorporated by reference in their entirety. Nothing herein is to be construed as an admission that the invention is not entitled to antedate such disclosure by virtue of prior invention. To the extent the material incorporated by reference contradicts or is inconsistent with this specification, the specification will supersede any such material.

SUMMARY

The present invention is based on the surprising findings of polynucleotide sequences ("polynucleotides of the present invention") encoding a protein which is involved in lipid metabolism ("helper protein" of the present invention) whose expression, preferably overexpression led to an increase in the yield of protein of interest (POI). This disclosure provides methods and materials useful for improving the yield of POI by engineering host cells such that they are capable of overexpressing at least one, i.e., one or more proteins which are involved in lipid metabolism. Preferred polynucleotides encode a helper protein (involved in lipid metabolism) comprising an amino acid sequence as shown in any one of SEQ ID NOs: 1-15, such as SEQ ID NO:1, 2, 3, 4, 5, 6, 7, 8, 9, 10, 11, 12, 13, 14, or 15 or a functional homologue thereof, wherein the functional homologue has at least 30% sequence identity to an amino acid sequence as shown in any one of SEQ ID NOs: 1-15, respectively.

The present invention is also based on the surprising findings of polynucleotide sequences ("polynucleotides of the present invention") encoding a protein which is involved in lipid metabolism ("helper protein of the present invention") whose underexpression led to an increase in the yield of protein of interest (POI). Such helper proteins are sometimes also referred to herein as "KO protein" or "KO helper protein". Accordingly, the term "helper protein" or "helper gene" or "helper factor" etc. also includes "KO helper protein" or "KO helper gene" or "KO helper factor", if this technically makes sense (i.e. if underexpression results in an increase in the yield of POI), even if in the text of the present application the term used is only "helper protein" or "helper gene" or "helper factor" etc. This disclosure also provides methods and materials useful for improving the yield of POI by engineering host cells such that they are capable of underexpressing at least one, i.e., one or more proteins which are involved in lipid metabolism. Preferred polynucleotides encode a KO protein (involved in lipid metabolism) comprising an amino acid sequence as shown in SEQ ID NO: 16 or 17, or a functional homologue thereof, wherein the functional homologue has at least 30% sequence identity to an amino acid sequence as shown in any one of SEQ ID NOs: 16 or 17, respectively.

The findings of the present inventors are rather surprising, since lipid metabolism was to the best of one's knowledge up to the present invention not brought in connection with increasing the yield of a protein of interest in a eukaryotic host cell, particularly in a fungal host cell. Without being bound by theory, modification of lipid metabolism modifies biomembrane lipid composition in a eukaryotic host cell, particularly in a fungal host cell, thereby positively affecting recombinant protein production.

It is assumed that overexpression of at least one protein involved in lipid metabolism, preferably of at least one of the helper proteins described herein changes the lipid composition of a membrane, in particular the cellular membrane or the endoplasmatic reticulum membrane, of a host cell as described herein which results in increasing the yield of a protein of interest.

Specifically, it is assumed that overexpression of at least one protein involved in lipid metabolism, preferably of at least one of the helper proteins described herein, alters the molecular species pattern of sphingolipids, preferably by increasing the amount of C26 fatty acyl moieties of ceramides and/or inositol-containing phosphorylceramides (such as inositolphosphorylceramide (IPC), mannosyl-inositolphosphorylceramide (MIPC), mannosyl-diinositol-phosphorylceramide (M(IP)2C)) and/or decreasing the amount of C24 fatty acyl moieties of ceramides and/or inositol-containing phosphorylceramides (such as inositolphosphorylceramide (IPC), mannosyl-inositolphosphorylceramide (MIPC), mannosyl-diinositol-phosphorylceramide M(IP)2C) results in increasing the yield of a protein of interest.

Preferably, the relative amount of fatty acyls of a chain length of 26 carbons (C26) incorporated in ceramides, e.g. IPC, MIPC and M(IP)2C is increased by at least 100%, whereas the relative amount of fatty acyls of a chain length of 24 carbons (C24) are decreased by at least 70%.

Preferably, overexpression of at least one protein involved in lipid metabolism, preferably of at least one of the helper proteins described herein, leads to an altered molecular species pattern of most sphingolipids, othat is fatty acyl moieties of ceramides and IPC-classes inositol-containing phosphorylceramides (IPC, MIPC, M(IP)2C) preferentially contain C26 instead of C24. The amount of C26 is depending on the kind of sphingolipid (ceramides, IPC, MIPC and M(IP)2C) enhanced at least by 100% compared to the empty vector.

It is also assumed that overexpression of at least one protein involved in lipid metabolism, preferably of at least one of the helper proteins described herein, reduces the amount of IPC and MIPC (of approximately 230%) and/or increases the formation of the mature form of inositol-containing phosphorylceramides, M(IP)2C by at least 6-fold (600%) which results in increasing the yield of a protein of interest It is further assumed that underexpression of at least one protein involved in lipid metabolism, preferably of at least one of the helper proteins—here a KO helper protein—described herein depletes the non-polar storage lipid triacylglycerol (TG) which results in increasing the yield of a protein of interest.

The term "yield" refers to the amount of POI or model protein(s) as described herein, in particular SDZ-Fab (SEQ ID NO: 37 for heavy chain and SEQ ID NO: 38 for light chain) and HyHEL-Fab (SEQ ID NO: 39 for heavy chain and SEQ ID NO: 40 for light chain), respectively, which is, for example, harvested from the engineered host cell, and increased yields can be due to increased amounts of production or secretion of the POI by the host cell. Yield may be presented by mg POI/g biomass (measured as dry cell weight or wet cell weight) of a host cell. The term "titer" when used herein refers similarly to the amount of produced POI or model protein, presented as mg POI/L culture supernatant. An increase in yield can be determined when the yield obtained from an engineered host cell is compared to the yield obtained from a host cell prior to engineering, i.e., from a non-engineered host cell. Preferably, "yield" when used herein in the context of a model protein as described herein, is determined as described in Example 4c. Accordingly, the "yield" when used herein in the context of a model protein as described herein is also referred to as "Fab yield" or "Fab titer". A Fab titer is given as mg/L and a Fab yield as mg/g biomass (measured as dry cell weight or wet cell weight). SDZ-Fab and HyHEL-Fab are encoded by the nucleotide sequences shown in SEQ ID NOs: 41 and 42 and SEQ ID NOs: 43 and 44, respectively.

Briefly, *P. pastoris* strains CBS7435mut$^S$ pPM2d_pAOX HyHEL and/or CBS7435mut$^S$ pPM2d_pAOX SDZ (see Example 1 for their generation) which express the model protein HyHEL-Fab and SDZ-Fab, respectively, are engineered with a polynucleotide encoding a helper protein or functional homologue thereof as described herein. For co-overexpression, the gene encoding a helper protein is cloned under control of the *P. pastoris* GAP promoter and transformed into the Fab producing strains as described in Example 3b and Example 4. A gene may also be under control of the *P. pastoris* AOX promoter. For underexpression the gene encoding a KO protein or its functional homologue is knocked out from the genome of the Fab producing strain (see Example 5). Engineered cells are grown in YP-medium containing 10 g/L glycerol and 50 μg/mL Zeocin overnight at 25° C. (see Example 4a). Aliquots of such a culture (corresponding to a final $OD_{600}$ of 2.0) are transferred to synthetic medium M2 containing 20 g/L glucose and a glucose feed tablet (described in Example 4a) and incubated for 25 h at 25° C. Cultures are washed and resuspended in synthetic medium M2 and aliquots (corresponding to a final $OD_{600}$ of 4.0) are transferred into synthetic medium M2 supplemented with 5 g/L methanol. Methanol (5 g/L) is added every 12 hours. After 48 h, cells are harvested by centrifugation. Biomass is determined by measuring the weight of the cell pellet derived from 1 mL cell suspension. The supernatant is used for quantification of SDZ-Fab or HyHEL-Fab, respectively, by ELISA (described in Example 4c). Specifically, an anti-human IgG antibody (e.g. ab7497, Abcam) is used as coating antibody and a e.g. goat anti-human anti-human IgG (Fab specific) antibody (e.g. Sigma A8542, alkaline phosphatase conjugated) is used as detection antibody. Commercial Human Fab/Kappa, IgG fragment is used as standard with a starting concentration of 100 ng/mL, supernatant samples are diluted accordingly. An increase in the yield may be determined based on a comparison of POI yield before and after the cell is engineered to overexpress the polypeptide. A standard test involving model proteins SDZ-Fab and/or HyHEL-Fab as shown in the example may be used to determine the yield difference.

Accordingly, the present invention relates to one or more newly discovered polypeptides involved in lipid metabolism (herein also referred to as "helper proteins") and its or their use to increase POI yield. The present invention is based on, but not limited to, the helper proteins shown in any one of SEQ ID NOs: 1 to 17 or functional homologues thereof. The meaning of functional homologue is defined in the latter part of the application. The nucleotide sequences of the helper proteins of the present invention are listed respectively in SEQ ID NOs: 19 to 35, respectively. As used herein, such proteins are referred to in the present invention interchangeably in plural or singular forms, which however should be understood as in singular form unless expressly stated otherwise. A helper protein involved in lipid metabolism comprising an amino acid sequence as shown in any one of SEQ ID NOs: 1-15 is preferably overexpressed in a eukaryotic host cell, while a helper protein involved in lipid metabolism comprising an amino acid sequence as shown in SEQ ID NO: 16 or 17 is preferably underexpressed in a eukaryotic host cell.

The invention additionally relates to the polynucleotides encoding the helper proteins (hereinafter referred to as "polynucleotides of the present invention" or "a polynucleotide of the present invention") and their individual or combined use to increase POI yield. The polynucleotide(s) can be introduced into a host cell or, if already existing in the cell, manipulated in a way such that they are overexpressed. The polynucleotide of the present invention used for overexpression of a helper protein encodes any one of SEQ ID NOs: 1 to 15, such as SEQ ID NO:1, 2, 3, 4, 5, 6, 7, 8, 9, 10, 11, 12, 13, 14, or 15 or functional homologues thereof. Examples of the polynucleotide sequences are as set forth in SEQ ID NOs: 19 to 33, such as SEQ ID NO: 19, 20, 21, 22, 23, 24, 25, 26, 27, 28, 29, 30, 31, 32, or 33. A polynucleotide encoding a helper protein involved in lipid metabolism comprising a nucleotide sequence as shown in any one of SEQ ID NOs: 19-33 is preferably overexpressed in a eukaryotic host cell, while a polynucleotide encoding a helper protein involved in lipid metabolism comprising a nucleotide sequence as shown in SEQ ID NO: 34 or 35 is preferably underexpressed in a eukaryotic host cell.

Accordingly, the present invention provides a method of increasing the yield of a protein of interest in a eukaryotic host cell, comprising overexpressing in said host cell at least one polynucleotide encoding a helper protein which is involved in lipid metabolism, thereby increasing the yield of said protein of interest in comparison to a host cell which does not overexpress a polynucleotide encoding a protein which is involved in lipid metabolism. Preferably, said helper protein which is involved in lipid metabolism is not a transcription factor. Preferably, said helper protein which is involved in lipid metabolism comprises an amino acid sequence as shown in any one of SEQ ID NOs: 1-15 such as SEQ ID NO:1, 2, 3, 4, 5, 6, 7, 8, 9, 10, 11, 12, 13, 14, or 15 or a functional homologue thereof, wherein the functional homologue has at least 30% sequence identity to an amino acid sequence as shown in any one of SEQ ID NOs: 1-15, respectively.

Preferably, in the context of overexpression of helper proteins, lipid metabolism is sphingolipid biosynthesis, phospholipid biosynthesis, lipid transport, or ergosterol biosynthesis. Modifying lipid metabolism by overexpression of a helper protein of the present invention can modify biomembrane lipid composition in a eukaryotic host cell, particularly in a fungal host cell, thereby positively affecting recombinant protein production. Hence, when used herein, the term "lipid metabolism" in the context of overexpression can be replaced by the term "modification of biomembrane lipid composition", preferably modification of biomembrane lipid composition in a eukaryotic host cells, particularly in a fungal host cell. Modification of biomembrane lipid composition may be affected by sphingolipid biosynthesis, phospholipid biosynthesis, lipid transport, or ergosterol biosynthesis.

The present invention furthermore provides a method for increasing the yield of a protein of interest in a eukaryotic host cell comprising
  engineering the host cell to overexpress a polynucleotide encoding a protein which is involved in lipid metabolism and which comprises an amino acid sequence as shown in any one of SEQ ID NOs: 1-15, such as SEQ ID NO:1, 2, 3, 4, 5, 6, 7, 8, 9, 10, 11, 12, 13, 14, or 15, preferably as shown in any one of SEQ ID NOs: 1-9, SEQ ID NO: 10, SEQ ID NO: 11, or SEQ ID NOs: 12-15, or a functional homologue thereof, wherein the functional homologue has at least 30% sequence identity to an amino acid sequence as shown in any one of SEQ ID NOs: 1-15;

engineering said host cell to comprise a heterologous polynucleotide encoding said protein of interest, culturing said host cell under suitable conditions to express said protein of interest, and optionally isolating said protein of interest from the cell culture.

The present invention moreover provides a method for increasing the yield of a protein of interest in a eukaryotic host cell comprising providing the host cell engineered to overexpress a polynucleotide encoding a protein which is involved in lipid metabolism and which comprises an amino acid sequence as shown in any one of SEQ ID NOs: 1-15, such as SEQ ID NO:1, 2, 3, 4, 5, 6, 7, 8, 9, 10, 11, 12, 13, 14, or 15, preferably as shown in any one of SEQ ID NOs: 1-9, SEQ ID NO: 10, SEQ ID NO: 11, or SEQ ID NOs: 12-15, or a functional homologue thereof, wherein the functional homologue has at least 30% sequence identity to an amino acid sequence as shown in any one of SEQ ID NOs: 1-15, wherein said host cell comprises a heterologous polynucleotide encoding said protein of interest;

culturing the host cell under suitable conditions to overexpress the protein involved in lipid metabolism or functional homologue thereof and express said protein of interest, and optionally isolating said protein of interest from the cell culture.

In the context of methods for increasing the yield of a protein the order of the "engineering to overexpress/underexpress a polynucleotide encoding a helper protein step" and "engineering to comprise a heterologous polynucleotide encoding the protein of interest step" can alternatively be reversed such that the "engineering to comprise a heterologous polynucleotide encoding the protein of interest step" precedes the "engineering to overexpress/underexpress a polynucleotide encoding a helper protein step". Notably, as described herein, the yield of a protein of interest is increased when a helper protein is overexpressed and/or a KO protein is underexpressed.

The present invention also provides a recombinant eukaryotic host cell for manufacturing a protein of interest, wherein the host cell is engineered to overexpress a polynucleotide encoding a protein which is involved in lipid metabolism.

Preferably, the present invention provides a recombinant host cell for manufacturing a protein of interest, wherein the host cell is engineered to overexpress a polynucleotide encoding a helper protein comprising any one of SEQ ID NOs: 1-15, such as SEQ ID NO:1, 2, 3, 4, 5, 6, 7, 8, 9, 10, 11, 12, 13, 14, or 15, preferably any one of SEQ ID NOs: 1-9, SEQ ID NO: 10, SEQ ID NO: 11, or SEQ ID NOs: 12-15, or a functional homologue thereof, wherein the functional homologue has at least 30% sequence identity to an amino acid sequence as shown in any one of SEQ ID NOs: 1-15, respectively.

In a preferred embodiment, the helper protein, preferably when overexpressed, may increase the yield of the model protein SDZ-Fab (SEQ ID NO: 37 for heavy chain and SEQ ID NO: 38 for light chain; FIG. 2) or HyHEL-Fab (SEQ ID NO: 39 for heavy chain and SEQ ID NO: 40 for light chain; FIG. 2) in the host cell by at least 10, 11, 12, 13, 14, 15, 16, 17, 18, 19, 20, 21, 22, 23, 24, 25, 26, 27, 28, 29, 30, 40, 50, 60, 70, 80, 90, 100, 110, 120, 130, 140, 150, 160, 170, 180, 190 or at least 200%, and preferably by at least 10% compared to the host cell prior to being engineered to overexpress said helper protein. A host cell prior to engineering does not overexpress the helper protein of the present invention and after engineering is able to overexpress the helper protein under suitable culturing conditions. It has been surprisingly found that exemplary recombinant cells described in the Examples were all able to increase the yield of the model protein SDZ-Fab or HyHEL-Fab by at least 20% (1.2 fold change).

The present invention also relates to a method of increasing the yield of a protein of interest in a eukaryotic host cell, comprising underexpressing in said host cell at least one polynucleotide encoding a helper protein which is involved in lipid metabolism, thereby increasing the yield of said protein of interest in comparison to said host cell which does not underexpress a polynucleotide encoding a protein which is involved in lipid metabolism. Preferably, said helper protein which is involved in lipid metabolism comprises an amino acid sequence as shown in SEQ ID NO: 16 or 17 or a functional homologue thereof, wherein the functional homologue has at least 30% sequence identity to an amino acid sequence as shown in SEQ ID NO: 16 or 17.

Accordingly, the present invention provides for a method of increasing the yield of a protein of interest in a eukaryotic host cell, comprising engineering the host cell to underexpress a polynucleotide encoding a protein which is involved in lipid metabolism and which comprises an amino acid sequence as shown in SEQ ID NO: 16 or 17, or a functional homologue thereof, wherein the functional homologue has at least 30% sequence identity to an amino acid sequence as shown in SEQ ID NO: 16 or 17, engineering said host cell to comprise a heterologous polynucleotide encoding said protein of interest, culturing said host cell under suitable conditions to express said protein of interest, and optionally isolating said protein of interest from the cell culture.

Also, the present invention provides a method of increasing the yield of a protein of interest in a eukaryotic host cell, comprising providing the host cell engineered to underexpress a polynucleotide encoding a protein which is involved in lipid metabolism and which comprises an amino acid sequence as shown in SEQ ID NO: 16 or 17, or a functional homologue thereof, wherein the functional homologue has at least 30% sequence identity to an amino acid sequence as shown in SEQ ID NOs: 16 or 17, wherein said host cell comprises a heterologous polynucleotide encoding said protein of interest;

culturing the host cell under suitable conditions to underexpress the protein which is involved in lipid metabolism or functional homologue thereof and express said protein of interest, and optionally isolating said protein of interest from the cell culture.

In the context of methods for increasing the yield of a protein the order of the "engineering to overexpress/underexpress a polynucleotide encoding a helper protein step" and "engineering to comprise a heterologous polynucleotide encoding the protein of interest step" can alternatively be reversed such that the "engineering to comprise a heterologous polynucleotide encoding the protein of interest step" precedes the "engineering to overexpress/underexpress a polynucleotide encoding a helper protein step". Notably, as described herein, the yield of a protein of interest is increased when a helper protein is overexpressed and/or a KO protein is underexpressed.

Also provided herein is a recombinant eukaryotic host cell for manufacturing a protein of interest, wherein the host cell is engineered to underexpress a polynucleotide encoding a protein which is involved in lipid metabolism. Preferably, said protein involved in lipid metabolism comprises an amino acid sequence as shown in SEQ ID NO: 16 or 17, or a functional homologue thereof, wherein the functional homologue has at least 30% sequence identity to an amino acid sequence as shown in SEQ ID NO: 16 or 17.

Preferably, in the context of underexpression of a helper protein, the lipid metabolism in which the helper protein is involved is lipid storage. Preferably, in the context of underexpression of a helper protein, the helper protein is not a transcription factor. Modifying lipid metabolism by underexpression of a helper protein of the present invention can modify biomembrane lipid composition in a eukaryotic host cell, particularly in a fungal host cell, thereby positively affecting recombinant protein production. Hence, when used herein, the term "lipid metabolism" in the context of underexpression can be replaced by the term "modification of biomembrane lipid composition", preferably modification of biomembrane lipid composition in a eukaryotic host cells, particularly in a fungal host cell. Modification of biomembrane lipid composition may be affected by non-polar storage lipid biosynthesis or phospholipid metabolism.

In a preferred embodiment, the helper protein, preferably when underexpressed, may increase the yield of the model protein SDZ-Fab (SEQ ID NO: 37 for heavy chain and SEQ ID NO: 38 for light chain) or HyHEL-Fab (SEQ ID NO: 39 for heavy chain and SEQ ID NO: 40 for light chain) in the host cell by at least 10, 11, 12, 13, 14, 15, 16, 17, 18, 19, 20, 21, 22, 23, 24, 25, 26, 27, 28, 29, 30, 40, 50, 60, 70, 80, 90, 100, 110, 120, 130, 140, 150, 160, 170, 180, 190 or at least 200%, and preferably by at least 10% compared to the host cell prior to being engineered to underexpress said helper protein. A host cell prior to engineering does not underexpress the helper protein of the present invention and after engineering is able to underexpress the helper protein under suitable culturing conditions. It has been surprisingly found that exemplary recombinant cells described in the Examples were all able to increase the yield of the model protein SDZ-Fab or HyHEL-Fab by at least 20% (1.2 fold change). In some instances, the yield increased by 80%, as shown in Example 6b.

The present invention also provides for uses of the host cell as described herein for manufacturing a protein of interest (POI). The host cells can be advantageously used for introducing polynucleotides encoding one or more POI(s), and thereafter can be cultured under suitable condition to express the POI, whereby a helper protein of the present invention is overexpressed or underexpressed.

An isolated polynucleotide encoding a helper protein involved in lipid metabolism and comprising an amino acid sequence as shown in any one of SEQ ID NOs: 1-17, such as SEQ ID NO:1, 2, 3, 4, 5, 6, 7, 8, 9, 10, 11, 12, 13, 14, 15, 16, or 17, or a functional homologue thereof, wherein the functional homologue has at least 30% sequence identity to an amino acid sequence as shown in any one of SEQ ID NOs: 1-17, respectively, is also provided by the present invention. Preferably, an isolated polynucleotide encoding a helper protein involved in lipid metabolism and comprising an amino acid sequence as shown in any one of SEQ ID NOs: 1-15, such as SEQ ID NO:1, 2, 3, 4, 5, 6, 7, 8, 9, 10, 11, 12, 13, 14, or 15, or a functional homologue thereof, wherein the functional homologue has at least 30% sequence identity to an amino acid sequence as shown in any one of SEQ ID NOs: 1-15, respectively, is also provided by the present invention.

Likewise, an isolated polynucleotide encoding a helper protein and comprising the nucleotide sequence as shown in any one of SEQ ID NOs: 19-36 is also provided by the present invention. A polynucleotide that is used for integration in a host cell or for manufacturing a protein of interest comprises preferably a nucleotide sequence as shown in any one of SEQ ID NOs: 19-33 or 36. Similarly, an isolated helper protein as described herein is used for manufacturing a protein of interest. Such a polynucleotide encodes a helper protein comprising an amino acid sequence as shown in any one of SEQ ID NOs: 1-15.

The present invention also relates to a composition comprising at least 0.25%, 0.5%, 1%, 2%, 3%, 4%, 5%, or 10%, of a protein of interest and a polynucleotide encoding a helper protein of the present invention, wherein said polynucleotide is operably linked with a heterologous promoter.

BRIEF DESCRIPTION OF THE DRAWINGS

FIG. 1 shows the amino acid and polynucleotide sequences of the helper proteins of the present invention.

FIG. 2 shows the amino acid and polynucleotide sequences of the heavy chain and light chain of the model proteins SDZ-Fab and HyHEL-Fab, respectively and the *S. cerevisiae* alpha mating factor signal leader sequence. The underlined sequences parts represent leader sequences of SEQ ID NO. 45 or 46 fused to the model protein sequence.

ITEMS OF THE INVENTION

1. A method of increasing the yield of a protein of interest in a eukaryotic host cell, comprising overexpressing in said host cell at least one polynucleotide encoding at least one protein which is involved in lipid metabolism, thereby increasing the yield of said protein of interest in comparison to a host cell which does not overexpress a polynucleotide encoding a protein which is involved in lipid metabolism.
2. The method of item 1, wherein said protein which is involved in lipid metabolism is involved in sphingolipid biosynthesis, phospholipid biosynthesis, lipid transport, lipid storage, ergosterol biosynthesis, fatty acid biosynthesis, phosphatidic acid biosynthesis and/or phospholipid metabolic process.
3. The method of item 1 or 2, wherein said protein which is involved in lipid metabolism is not a transcription factor.
4. The method of any one of items 1-3, wherein said at least one protein which is involved in lipid metabolism comprises an amino acid sequence as shown in any one of SEQ ID NOs: 1-15 or a functional homologue thereof, wherein the functional homologue has at least 30% sequence identity to an amino acid sequence as shown in any one of SEQ ID NOs: 1-15.
5. The method of any one of items 1-4, wherein said at least one protein which is involved in sphingolipid biosynthesis comprises an amino acid sequence as shown in any one of SEQ ID NOs: 1-9 or a functional homologue thereof, wherein the functional homologue has at least 30% sequence identity to an amino acid sequence as shown in any one of SEQ ID NOs: 1-9.
6. The method of any one of items 1-4, wherein said at least one protein which is involved in phospholipid biosynthesis comprises an amino acid sequence as shown in SEQ ID NO: 10 or a functional homologue thereof, wherein the functional homologue has at least 30% sequence identity to an amino acid sequence as shown in SEQ ID NO: 10.

7. The method of any one of items 1-4, wherein said at least one protein which is involved in lipid transport comprises an amino acid sequence as shown in SEQ ID NO: 11 or a functional homologue thereof, wherein the functional homologue has at least 30% sequence identity to an amino acid sequence as shown in SEQ ID NO: 11.

8. The method of any one of items 1-4, wherein said at least one protein which is involved in ergosterol biosynthesis comprises an amino acid sequence as shown in any one of SEQ ID NOs: 12-15 or a functional homologue thereof, wherein the functional homologue has at least 30% sequence identity to an amino acid sequence as shown in any one of SEQ ID NOs: 12-15.

9. The method of any one of items 1-4, wherein said protein which is involved in lipid storage comprises an amino acid sequence as set forth between PP7435_Chr4-0493 and PP7435_Chr4-0494 (ARV1) or a functional homologue thereof, wherein the functional homologue has at least 30% sequence identity to an amino acid sequence as as set forth between PP7435_Chr4-0493 and PP7435_Chr4-0494.

10. The method of any one of items 1-9 comprising:
engineering the host cell to overexpress a polynucleotide encoding a protein which is involved in lipid metabolism and which comprises an amino acid sequence as shown in any one of SEQ ID NOs: 1-15, preferably as shown in any one of SEQ ID NOs: 1-9, SEQ ID NO: 10, SEQ ID NO: 11 or SEQ ID NOs: 12-15, or a functional homologue thereof, wherein the functional homologue has at least 30% sequence identity to an amino acid sequence as shown in any one of SEQ ID NOs: 1-1529;
engineering said host cell to comprise a heterologous polynucleotide encoding a protein of interest,
culturing said host cell under suitable conditions to express said protein of interest, and optionally
isolating said protein of interest from the cell culture.

11. A method of manufacturing a protein of interest according to any one of items 1-9 comprising:
providing the host cell engineered to overexpress at least one polynucleotide encoding at least one protein which is involved in lipid metabolism and which comprises an amino acid sequence as shown in any one of SEQ ID NOs: 1-15, preferably as shown in any one of SEQ ID NOs: 1-9, SEQ ID NO: 10, SEQ ID NO: 11 or SEQ ID NOs: 12-15, or a functional homologue thereof, wherein the functional homologue has at least 30% sequence identity to an amino acid sequence as shown in any one of SEQ ID NOs: 1-15, wherein said host cell comprises a heterologous polynucleotide encoding a protein of interest;
culturing the host cell under suitable conditions to overexpress the protein involved in lipid metabolism or functional homologue thereof and express said protein of interest, and optionally
isolating said protein of interest from the cell culture.

12. The method of any one of items 1-11, wherein overexpression is achieved by having 1, 2, 3, 4 or more copies of said polynucleotide encoding a protein which is involved in lipid metabolism or functional homologue thereof in said host cell.

13. The method of any one of items 1-12, wherein said polynucleotide encoding a protein which is involved in lipid metabolism or functional homologue thereof is integrated into at least one chromosome of said host cell.

14. The method of item 13, wherein the integration is ectopically and/or in the natural locus.

15. The method of item 14, wherein the polynucleotide encoding a protein which is involved in lipid metabolism or functional homologue thereof is integrated in AOX1, GAP, ENO1, TEF, HIS4, TYR1, HIS3, LEU2, URA3, LYS2, ADE2, TRP1, GAL1, or ADH1 locus of the host cell genome.

16. The method of any one of items 1-12, wherein the polynucleotide encoding a protein which is involved in lipid metabolism or functional homologue thereof is contained in a vector or plasmid.

17. The method of item 15, wherein the vector is YIp type vector, YEp type vector, YRp type vector, YCp type vector, pGPD-2, pAO815, pGAPZ, pGAPZα, pHIL-D2, pHIL-S1, pPIC3.5K, pPIC9K, pPICZ, pPICZα, pPIC3K, pHWO10, pPUZZLE, or 2 µm plasmid.

18. The method of any one of items 1-17, wherein the overexpression of the polynucleotide encoding a protein which is involved in lipid metabolism or functional homologue thereof is achieved by using a recombinant promoter which drives expression of said polynucleotide.

19. The method of any one of items 1-17, wherein overexpression of the polynucleotide encoding a protein which is involved in lipid metabolism or functional homologue thereof is achieved by modifying a regulatory sequence operably linked to the endogenous polynucleotide encoding a protein which is involved in lipid metabolism or functional homolog thereof.

20. The method of item 18, wherein the promoter is PAOX1, PTPI, PPGK, PGAPDH, PLAC, PGAL, PPGI, PGAP, PTEF, PENO1, PTPI, PRPS2, PRPS7, PRPS31, PRPL1, PFLD, PICL, PTHI, PSSA1, PHSP90, PKAR2, PGND1, PGPM1, PTKL1, PPIS1, PFET3, PFTR1, PPHO8, PNMT1, PMCM1, PUBI4, PRAD2, PPET9, PFMD, PGAL1, PADH1, PADH2/GAP, PCUP1, or PMAL.

21. The method of any one of items 1-17, wherein the overexpression of the polynucleotide encoding a protein which is involved in lipid metabolism or functional homologue thereof is achieved by using an enhancer to enhance the promoter activity.

22. The method of item 21, wherein the enhancer is the yeast upstream activating sequence UAS/GAL.

23. The method of any one of items 1-22, wherein the eukaryotic host cell is a non-mammalian eukaryotic host cell.

24. The method of item 23, wherein the non-mammalian eukaryotic host cell is a fungal host cell.

25. The method of item 24, wherein the fungal host cell is *Pichia pastoris, Hansenula polymorpha, Trichoderma reesei, Saccharomyces cerevisiae, Kluyveromyces lactis, Yarrowia lipolytica, Pichia methanolica, Candida boidinii, Komagataella* sp., *Aspergillus* sp. or *Schizosaccharomyces pombe*.

26. The method of any one of items 1-25, wherein 1, 2, 3, 4, 5, 6, 7, 8 or more proteins involved in lipid metabolism selected from any one of SEQ ID NOs: 1-15, PP7435_Chr3-0788 (SUR2), PP7435_Chr3-1005 (AUR1), PP7435_Chr4-0626 (IFA38), PP7435_Chr3-0669 (SCS7), PP7435_Chr3-0636 (CRD1), PP7435_Chr3-0950 (SLC4), PP7435_Chr2-0585 (PIS1), PP7435_chr1-0934 (PRY2), PP7435_Chr4-0963 (FAD12) and PP7435_Chr1-0794 (PSD1) or a functional homologues thereof are overexpressed.

27. The method of item 26, wherein the following at least one protein involved in sphingolipid biosynthesis is overexpressed
   (a) protein comprising the amino acid sequence as shown in SEQ ID NO: 1 or a functional homologue thereof, wherein the functional homologue has at least 30% sequence identity to an amino acid sequence as shown in SEQ ID NO: 1;
   (b) protein comprising the amino acid sequence as shown in SEQ ID NO: 2 or a functional homologue thereof, wherein the functional homologue has at least 30% sequence identity to an amino acid sequence as shown in SEQ ID NO: 2;
   (c) protein comprising the amino acid sequence as shown in SEQ ID NO: 3 or a functional homologue thereof, wherein the functional homologue has at least 30% sequence identity to an amino acid sequence as shown in SEQ ID NO: 3;
   (d) proteins comprising the amino acid sequences as shown in SEQ ID NOs: 1 and 2 or a functional homologue thereof, wherein the functional homologue has at least 30% sequence identity to an amino acid sequence as shown in SEQ ID NOs: 1 and 2, respectively;
   (e) proteins comprising the amino acid sequences as shown in SEQ ID NOs: 1 and 3 or a functional homologue thereof, wherein the functional homologue has at least 30% sequence identity to an amino acid sequence as shown in SEQ ID NOs: 1 and 3, respectively;
   (f) proteins comprising the amino acid sequences as shown in SEQ ID NOs: 1, 3 and 4 or a functional homologue thereof, wherein the functional homologue has at least 30% sequence identity to an amino acid sequence as shown in SEQ ID NOs: 1, 3 and 4, respectively;
   (g) proteins comprising the amino acid sequences as shown in SEQ ID NOs: 1, 3, 4 and 8 or a functional homologue thereof, wherein the functional homologue has at least 30% sequence identity to an amino acid sequence as shown in SEQ ID NOs: 1, 3, 4 and 8, respectively;
   (h) proteins comprising the amino acid sequences as shown in SEQ ID NOs: 5 and 6 or a functional homologue thereof, wherein the functional homologue has at least 30% sequence identity to an amino acid sequence as shown in SEQ ID NOs: 5 and 6, respectively;
   (i) proteins comprising the amino acid sequences as shown in SEQ ID NOs: 1 and 7 or a functional homologue thereof, wherein the functional homologue has at least 30% sequence identity to an amino acid sequence as shown in SEQ ID NOs: 1 and 7, respectively;
   (j) proteins comprising the amino acid sequences as shown in SEQ ID NOs: 5, 6 and 9 or a functional homologue thereof, wherein the functional homologue has at least 30% sequence identity to an amino acid sequence as shown in SEQ ID NOs: 5, 6 and 9, respectively;
   (k) proteins comprising the amino acid sequences as shown in SEQ ID NOs: 1, 5, 6 and 9 or a functional homologue thereof, wherein the functional homologue has at least 30% sequence identity to an amino acid sequence as shown in SEQ ID NOs: 1, 5, 6 and 9, respectively;
   (l) protein comprising the amino acid sequence as shown in SEQ ID NO: 4 or a functional homologue thereof, wherein the functional homologue has at least 30% sequence identity to an amino acid sequence as shown in SEQ ID NO: 4;
   (m) protein comprising the amino acid sequence as shown in SEQ ID NO: 5 or a functional homologue thereof, wherein the functional homologue has at least 30% sequence identity to an amino acid sequence as shown in SEQ ID NO: 5;
   (n) protein comprising the amino acid sequence as shown in SEQ ID NO: 6 or a functional homologue thereof, wherein the functional homologue has at least 30% sequence identity to an amino acid sequence as shown in SEQ ID NO: 6;
   (o) protein comprising the amino acid sequence as shown in SEQ ID NO: 7 or a functional homologue thereof, wherein the functional homologue has at least 30% sequence identity to an amino acid sequence as shown in SEQ ID NO: 7
   (p) protein comprising the amino acid sequence as shown in SEQ ID NO: 8 or a functional homologue thereof, wherein the functional homologue has at least 30% sequence identity to an amino acid sequence as shown in SEQ ID NO: 8;
   (q) protein comprising the amino acid sequence as shown in SEQ ID NO: 9 or a functional homologue thereof, wherein the functional homologue has at least 30% sequence identity to an amino acid sequence as shown in SEQ ID NO: 9;
   (r) protein comprising the amino acid sequence as shown in PP7435_Chr3-0788 (SUR2) or a functional homologue thereof, wherein the functional homologue has at least 30% sequence identity to an amino acid sequence as shown in PP7435_Chr3-0788;
   (s) protein comprising the amino acid sequence as shown in PP7435_Chr3-1005 (PHS1) or a functional homologue thereof, wherein the functional homologue has at least 30% sequence identity to an amino acid sequence as shown in PP7435_Chr3-1005;
   (t) protein comprising the amino acid sequence as shown in PP7435_Chr2-0350 (AUR1) or a functional homologue thereof, wherein the functional homologue has at least 30% sequence identity to an amino acid sequence as shown in PP7435_Chr2-0350;
   (u) protein comprising the amino acid sequence as shown in PP7435_Chr4-0626 (IFA38) or a functional homologue thereof, wherein the functional homologue has at least 30% sequence identity to an amino acid sequence as shown in PP7435_Chr4-0626;
   (v) protein comprising the amino acid sequence as shown in PP7435_Chr3-0669 (SCS7) or a functional homologue thereof, wherein the functional homologue has at least 30% sequence identity to an amino acid sequence as shown in PP7435_Chr3-0669;
   (w) proteins comprising the amino acid sequences as shown in SEQ ID NOs: 3 and 4 or a functional homologue thereof, wherein the functional homologue has at least 30% sequence identity to an amino acid sequence as shown in SEQ ID NOs: 3 and 4, respectively;
   (x) proteins comprising the amino acid sequences as shown in SEQ ID NOs: 3, 4 and 8 or a functional homologue thereof, wherein the functional homologue has at least 30% sequence identity to an amino acid sequence as shown in SEQ ID NOs: 3, 4 and 8, respectively;

(y) proteins comprising the amino acid sequences as shown in SEQ ID NOs: 1 and 5 or a functional homologue thereof, wherein the functional homologue has at least 30% sequence identity to an amino acid sequence as shown in SEQ ID NOs: 1 and 5, respectively;

(z) proteins comprising the amino acid sequences as shown in SEQ ID NOs: 1, 5 and 6 or a functional homologue thereof, wherein the functional homologue has at least 30% sequence identity to an amino acid sequence as shown in SEQ ID NOs: 1, 5 and 6, respectively;

(aa) proteins comprising the amino acid sequences as shown in SEQ ID NO: 1 and PP7435_Chr3-0788 (SUR1) or a functional homologue thereof, wherein the functional homologue has at least 30% sequence identity to an amino acid sequence as shown in SEQ ID NO: 1 and PP7435_Chr3-0788, respectively;

(bb) proteins comprising the amino acid sequences as shown in SEQ ID NO: 1 and PP7435_Chr3-1005 (PHS1) or a functional homologue thereof, wherein the functional homologue has at least 30% sequence identity to an amino acid sequence as shown in SEQ ID NO: 1 and PP7435_Chr3-1005, respectively;

(cc) proteins comprising the amino acid sequences as shown in SEQ ID NO: 1 and 8 or a functional homologue thereof, wherein the functional homologue has at least 30% sequence identity to an amino acid sequence as shown in SEQ ID NO: 1 and 8, respectively;

(dd) proteins comprising the amino acid sequences as shown in SEQ ID NO: 1 and PP7435_Chr2-0350 (AUR1) or a functional homologue thereof, wherein the functional homologue has at least 30% sequence identity to an amino acid sequence as shown in SEQ ID NO: 1 and PP7435_Chr2-0350, respectively;

(ee) proteins comprising the amino acid sequences as shown in SEQ ID NO: 1 and PP7435_Chr4-0626 (IFA38) or a functional homologue thereof, wherein the functional homologue has at least 30% sequence identity to an amino acid sequence as shown in SEQ ID NO: 1 and PP7435_Chr4-0626, respectively; or (ff) proteins comprising the amino acid sequences as shown in SEQ ID NO: 1 and PP7435_Chr3-0669 (SCS7) or a functional homologue thereof, wherein the functional homologue has at least 30% sequence identity to an amino acid sequence as shown in SEQ ID NO: 1 and PP7435_Chr3-0669, respectively.

28. The method of item 26, wherein the following proteins involved in phospholipid biosynthesis are overexpressed
(a) protein comprising the amino acid sequence as shown in SEQ ID NO: 10 or a functional homologue thereof, wherein the functional homologue has at least 30% sequence identity to an amino acid sequence as shown in SEQ ID NO: 10;
(b) protein comprising the amino acid sequence as shown in PP7435_Chr3-0636 (CRD1) or a functional homologue thereof, wherein the functional homologue has at least 30% sequence identity to an amino acid sequence as shown in PP7435_Chr3-0636;
(c) protein comprising the amino acid sequence as shown in PP7435_Chr3-0950 (SLC4) or a functional homologue thereof, wherein the functional homologue has at least 30% sequence identity to an amino acid sequence as shown in PP7435_Chr3-0950;
(d) protein comprising the amino acid sequence as shown in PP7435_Chr2-0585 (PIS1) or a functional homologue thereof, wherein the functional homologue has at least 30% sequence identity to an amino acid sequence as shown in PP7435_Chr2-0585.

29. The method of item 26, wherein the following proteins involved in lipid transport are overexpressed
(a) protein comprising the amino acid sequence as shown in SEQ ID NO: 11 or a functional homologue thereof, wherein the functional homologue has at least 30% sequence identity to an amino acid sequence as shown in SEQ ID NO: 11;
(b) protein comprising the amino acid sequence as shown in PP7435_Chr1-0934 (PRY1) or a functional homologue thereof, wherein the functional homologue has at least 30% sequence identity to an amino acid sequence as shown in PP7435_Chr1-0934;
(c) proteins comprising the amino acid sequence as shown in SEQ ID NO: 11 and PP7435_Chr1-0934 (PRY1) or a functional homologue thereof, wherein the functional homologue has at least 30% sequence identity to an amino acid sequence as shown in SEQ ID NO: 11 and PP7435_Chr1-0934, respectively.

30. The method of item 26, wherein the following proteins involved in fatty acid biosynthesis are overexpressed
(a) protein comprising the amino acid sequence as shown in PP7435_Chr4-0963 (FAD12) or a functional homologue thereof, wherein the functional homologue has at least 30% sequence identity to an amino acid sequence as shown in PP7435_Chr4-0963.

31. The method of item 26, wherein at least one protein involved in sphingolipid biosynthesis and at least one protein involved in lipid transport is overexpressed.

32. The method of item 31, wherein the protein involved in sphingolipid biosynthesis comprises an amino acid sequence as shown in SEQ ID NO: 1 or a functional homologue thereof and the protein involved in lipid transport comprises an amino acid sequence as shown in SEQ ID NO: 11 or a functional homologue thereof, wherein the functional homologue has at least 30% sequence identity to an amino acid sequence as shown in SEQ ID NOs: 1 and 11, respectively.

33. The method of item 26, wherein at least one protein involved in phospholipid biosynthesis and at least one protein involved in lipid transport is overexpressed.

34. The method of item 33, wherein the protein involved in phospholipid biosynthesis comprises an amino acid sequence as shown in SEQ ID NO: 10 or PP7435_Chr1-0794 (PSD1) and the protein involved in lipid transport comprises an amino acid sequence as shown in SEQ ID NO: 11.

35. The method of item 34, wherein the following proteins involved in phospholipid biosynthesis or in in lipid transport are overexpressed
a) proteins comprising the amino acid sequence as shown in SEQ ID NO: 10 and 11 or a functional homologue thereof, wherein the functional homologue has at least 30% sequence identity to an amino acid sequence as shown in SEQ ID NO: 10 and 11, respectively;
b) proteins comprising the amino acid sequence as shown in PP7435_Chr1-0794 (PSD1) and SEQ ID NO: 11 or a functional homologue thereof, wherein the functional homologue has at least 30% sequence identity to an amino acid sequence as shown in PP7435_Chr1-0794 and SEQ ID NO: 11, respectively.

36. The method of item 26, wherein at least one protein involved in sphingolipid biosynthesis and at least one protein involved in phospholipid biosynthesis is overexpressed.

37. The method of item 36, wherein the protein involved in sphingolipid biosynthesis comprises an amino acid sequence as shown in SEQ ID NO: 1 and the protein involved in phospholipid biosynthesis comprises an amino acid sequence as shown in PP7435_Chr2-0585 (PIS1), PP7435_Chr3-0636 (CRD1) or SEQ ID NO: 10.
38. The method of item 37, wherein the following proteins involved in sphingolipid biosynthesis or in in phospholipid biosynthesis are overexpressed
    a) proteins comprising the amino acid sequence as shown in SEQ ID NO: 1 and PP7435_Chr2-0585 (PIS1) or a functional homologue thereof, wherein the functional homologue has at least 30% sequence identity to an amino acid sequence as shown in SEQ ID NO: 1 and PP7435_Chr2-0585, respectively;
    b) proteins comprising the amino acid sequence as shown in SEQ ID NO: 1 and 10 or a functional homologue thereof, wherein the functional homologue has at least 30% sequence identity to an amino acid sequence as shown in SEQ ID NO: 1 and 10, respectively;
    c) proteins comprising the amino acid sequence as shown in SEQ ID NO: 1 and PP7435_Chr3-0636 (CRD1) or a functional homologue thereof, wherein the functional homologue has at least 30% sequence identity to an amino acid sequence as shown in SEQ ID NO: 1 and PP7435_Chr3-0636, respectively.
39. The method of item 26, wherein at least one protein involved in sphingolipid biosynthesis and at least one protein involved in phospholipid biosynthesis is overexpressed.
40. The method of item 26, wherein at least one protein involved in sphingolipid biosynthesis and at least one protein involved in ergosterol biosynthesis is overexpressed.
41. The method of item 40, wherein the protein involved in sphingolipid biosynthesis comprises an amino acid sequence as shown in SEQ ID NO: 1 and the protein involved in ergosterol biosynthesis comprises an amino acid sequence as shown in SEQ ID NO: 12.
42. The method of item 26, wherein at least one protein involved in ergosterol biosynthesis and at least one protein involved in lipid transport is overexpressed.
43. The method of item 42, wherein the protein involved in ergosterol biosynthesis comprises an amino acid sequence as shown in SEQ ID NO: 12 or 13 and the protein involved in lipid transport comprises an amino acid sequence as shown in SEQ ID NO: 11.
44. The method of item 37, wherein the following proteins involved in ergosterol biosynthesis or in in lipid transport are overexpressed
    a) proteins comprising the amino acid sequence as shown in SEQ ID NO: 12 and 11 or a functional homologue thereof, wherein the functional homologue has at least 30% sequence identity to an amino acid sequence as shown in SEQ ID NO: 12 and 11, respectively;
    b) proteins comprising the amino acid sequence as shown in SEQ ID NO: 13 and 11 or a functional homologue thereof, wherein the functional homologue has at least 30% sequence identity to an amino acid sequence as shown in SEQ ID NO: 13 and 11, respectively.
45. The method of item 26, wherein at least one protein involved in sphingolipid biosynthesis and at least one protein involved in lipid storage is overexpressed.
46. The method of item 45, wherein the protein involved in sphingolipid biosynthesis comprises an amino acid sequence as shown in SEQ ID NO: 1 and the protein involved in lipid storage is ARV1, which comprises an amino acid sequence located between PP7435_Chr4-0493 and PP7435_Chr4-0493.
47. The method of any one of items 1-46, further comprising overexpressing a chaperone.
48. The method of item 47, wherein the chaperone comprises an amino acid sequence as shown in SEQ ID NO: 18 or a functional homologue thereof, wherein the functional homologue has at least 30% sequence identity to an amino acid sequence as shown in SEQ ID NO: 18.
49. The method of item 47 or 48, wherein at least one protein involved in sphingolipid biosynthesis and at least one chaperone is overexpressed.
50. The method of item 49, wherein the protein involved in sphingolipid biosynthesis comprises an amino acid sequence as shown in SEQ ID NO: 1 or a functional homologue thereof and the chaperone comprises an amino acid sequence as shown in SEQ ID NO: 18 or a functional homologue thereof, wherein the functional homologue has at least 30% sequence identity to an amino acid sequence as shown in SEQ ID NOs: 1 and 18, respectively.
51. The method of item 47 or 48, wherein at least one protein involved in ergosterol biosynthesis and at least one chaperone is overexpressed.
52. The method of item 51, wherein the protein involved in ergosterol biosynthesis comprises an amino acid sequence as shown in SEQ ID NO: 13, SEQ ID NO: 14 or SEQ ID NO: 15 or a functional homologue thereof and the chaperone comprises an amino acid sequence as shown in SEQ ID NO: 18 or a functional homologue thereof, wherein the functional homologue has at least 30% sequence identity to an amino acid sequence as shown in SEQ ID NOs: 13 and 18, respectively.
53. The method of any one of items 1-52, wherein overexpression of the at least one polynucleotide encoding a protein which is involved in lipid metabolism changes the lipid composition of a membrane of the host cell, wherein the membrane of the host cell is preferably the cellular membrane or the endoplasmatic reticulum membrane.
54. The method of any one of items 1-53, wherein said protein of interest is a non-membrane protein of interest.
55. The method of item 54, wherein said non-membrane protein of interest is an enzyme, a therapeutic protein, a food additive or feed additive.
56. The method of item 55, wherein the therapeutic protein comprises an antibody or an antibody fragment still having the activity of binding its antigen.
57. The method of any one of items 1-56, wherein said protein involved in lipid metabolism or functional homologue thereof increases the yield of the model protein HyHEL (SEQ ID NO: 39 for heavy chain and SEQ ID NO: 40 for light chain) compared to the host cell prior to engineering by at least 10%, at least 15%, at least 20%, at least 25%, at least 30%.
58. A recombinant eukaryotic host cell for manufacturing a protein of interest, wherein the host cell is engineered to overexpress at least one polynucleotide encoding at least one protein which is involved in lipid metabolism.
59. The host cell of item 58, wherein said protein which is involved in lipid metabolism is involved in sphingolipid biosynthesis, phospholipid biosynthesis, lipid transport, ergosterol biosynthesis, fatty acid biosynthesis, phosphatidic acid biosynthesis and/or phospholipid metabolic process.

60. The host cell of item 58 or 59, wherein said protein which is involved in lipid metabolism is not a transcription factor.
61. The host cell of any one of items 58-59, wherein said protein involved in lipid metabolism comprises an amino acid sequence as shown in any one of SEQ ID NOs: 1-15, preferably as shown in any one of SEQ ID NOs: 1-9, SEQ ID NO: 10, SEQ ID NO: 11 or SEQ ID NOs: 12-15, or a functional homologue thereof, wherein the functional homologue has at least 30% sequence identity to an amino acid sequence as shown in any one of SEQ ID NOs: 1-15.
62. The host cell of any one of items 58-61, wherein said protein involved in lipid metabolism or said functional homologue thereof increases the yield of the model protein HyHEL (SEQ ID NO: 39 for heavy chain and SEQ ID NO: 40 for light chain) compared to the host cell prior to engineering by at least 10%.
63. The host cell of any one of items 58-62, wherein the overexpression is achieved by having 1, 2, 3, 4 or more copies of said polynucleotide encoding a protein involved in lipid metabolism or functional homologue thereof in said host cell.
64. The host cell of any one items 58-63, wherein said polynucleotide encoding a protein which is involved in lipid metabolism or functional homologue thereof is integrated in the genome of said host cell.
65. The host cell of item 64, wherein the integration is ectopically and/or in the natural locus.
66. The host cell of item 65, wherein at least one of the polynucleotide encoding a protein which is involved in lipid metabolism or functional homologue thereof is integrated in AOX1, GAP, ENO1, TEF, HIS4, TYR1, HIS3, LEU2, URA3, LYS2, ADE2, TRP1, GAL1, or ADH1 locus of the host cell genome.
67. The host cell of any one of items 58-66, wherein the polynucleotide encoding a protein which is involved in lipid metabolism or functional homologue thereof is contained in a vector or plasmid.
68. The host cell of item 67, wherein the vector is YIp type vector, YEp type vector, YRp type vector, YCp type vector, pGPD-2, pAO815, pGAPZ, pGAPZα, pHIL-D2, pHIL-S1, pPIC3.5K, pPIC9K, pPICZ, pPICZα, pPIC3K, pHWO10, pPUZZLE, or 2 μm plasmid.
69. The host cell of any one of items 58-68, wherein the overexpression of the polynucleotide encoding a protein which is involved in lipid metabolism or functional homologue thereof is achieved by using a recombinant promoter which drives expression of said polynucleotide.
70. The host cell of item 69, wherein the promoter is PAOX1, PTPI, PPGK, PGAPDH, PLAC, PGAL, PPGI, PGAP, PTEF, PENO1, PTPI, PRPS2, PRPS7, PRPS31, PRPL1, PFLD, PICL, PTHI, PSSA1, PHSP90, PKAR2, PGND1, PGPM1, PTKL1, PPIS1, PFET3, PFTR1, PPHO8, PNMT1, PMCM1, PUBI4, PRAD2, PPET9, PFMD, PGAL1, PADH1, PADH2/GAP, PCUP1, or PMAL.
71. The host cell of item 69, wherein the overexpression of the polynucleotide of the polynucleotide encoding a protein which is involved in lipid metabolism or functional homologue thereof is achieved by using an enhancer to enhance the promoter activity.
72. The host cell of item 71, wherein the enhancer is the yeast upstream activating sequence UAS/GAL.
73. The host cell of any one of items 58-72, wherein the eukaryotic host cell is a non-mammalian eukaryotic host cell.
74. The host cell of any one of item 73, wherein the non-mammalian eukaryotic host cell is a fungal host cell.
75. The host cell of item 74, wherein the host cell is *Pichia pastoris, Hansenula polymorpha, Trichoderma reesei, Saccharomyces cerevisiae, Kluyveromyces lactis, Yarrowia lipolytica, Pichia methanolica, Candida boidinii, Komagataella* sp., *Aspergillus* sp. and *Schizosaccharomyces pombe*.
76. The host cell of any one items 58-75, wherein 1, 2, 3, 4, 5, 6, 7, 8 or more of the proteins which are involved in lipid metabolism are selected from any one of SEQ ID NOs: 1 to 15, PP7435_Chr3-0788 (SUR2), PP7435_Chr3-1005 (AUR1), PP7435_Chr4-0626 (IFA38), PP7435_Chr3-0669 (SCS7), PP7435_Chr3-0636 (CRD1), PP7435_Chr3-0950 (SLC4), PP7435_Chr2-0585 (PIS1), PP7435_chr1-0934 (PRY2), PP7435_Chr4-0963 (FAD12) and PP7435_Chr1-0794 (PSD1) or functional homologues thereof are overexpressed.
77. The host cell of item 76, wherein the proteins as defined in items 27-46 are overexpressed.
78. The host cell of any one of items 58-77, which is further engineered to overexpress a polynucleotide encoding a chaperone.
79. The host cell of item 78, wherein the chaperone comprises an amino acid sequence as shown in SEQ ID NO: 18 or a functional homologue thereof, wherein the functional homologue has at least 30% sequence identity to an amino acid sequence as shown in SEQ ID NO: 18.
80. The host cell of item 78 or 79, wherein the proteins as defined in items 48-52 are overexpressed.
81. The host cell of any one of items 58-80, comprising a heterologous polynucleotide sequence encoding said protein of interest.
82. The host cell of item 81, wherein said protein of interest is a non-membrane protein of interest.
83. The host cell of item 82, wherein said non-membrane protein of interest is an enzyme, a therapeutic protein, a food additive or feed additive.
84. The host cell of item 83, wherein the therapeutic protein comprises an antibody or an antibody fragment still having the activity of binding its antigen.
85. The host cell of any one of items 58-84, wherein overexpression is achieved by modifying a regulatory sequence operably linked to the endogenous polynucleotide encoding the protein involved in lipid metabolism or functional homolog thereof.
86. The host cell of any one of items 58-85, wherein overexpression of the at least one polynucleotide encoding a protein which is involved in lipid metabolism changes the lipid composition of a biomembrane of the host cell.
87. Use of the host cell of any one of items 58-86 for manufacturing a protein of interest.
88. Use of the host cell according to item 87, wherein the protein of interest is a non-membrane protein of interest.
89. An isolated polynucleotide encoding a protein involved in lipid metabolism and comprising an amino acid sequence as shown in any one of SEQ ID NOs: 1-15 or a functional homologue thereof or an isolated polynucleotide encoding a chaperone and comprising an amino acid sequence as shown in SEQ ID NO: 18 or a functional homologue thereof, wherein the functional homologue has at least 30% sequence identity to an amino acid sequence as shown in any one of SEQ ID NOs: 1-15 and 18, respectively.

90. An isolated polynucleotide comprising the nucleotide sequence as shown in any one of SEQ ID NOs: 19-33 and 36.
91. Use of the isolated polynucleotide according to item 89 or 90 for integration in a host cell.
92. Use of a polynucleotide according to item 89 or 90 for manufacturing a protein of interest, preferably a non-membrane protein of interest.
93. Use of a polynucleotide according to item 89 or 90 for manufacturing a host cell.
94. An isolated polypeptide comprising an amino acid sequence having at least 30% identity to an amino acid sequence shown in any one of SEQ ID NOs: 1-15 and 18.
95. Use of the isolated polypeptide according to item 94 for manufacturing a protein of interest, preferably a non-membrane protein of interest.
96. A composition comprising at least 0.25%, 0.5%, 1%, 2%, 3%, 4%, 5%, or 10%, of a protein of interest and a polynucleotide according to item 86 or 87, wherein said polynucleotide is operably linked with a heterologous promoter and wherein the protein of interest is preferably a non-membrane protein of interest.
97. A method of increasing the yield of a protein of interest in a eukaryotic host cell, comprising underexpressing in said host cell at least one polynucleotide encoding a protein which is involved in lipid metabolism, thereby increasing the yield of said protein of interest in comparison to said host cell which does not underexpress a polynucleotide encoding a protein which is involved in lipid metabolism.
98. The method of item 97, wherein said protein which is involved in lipid metabolism is involved in lipid storage.
99. The method of item 97 or 98, wherein said protein which is involved in lipid metabolism is not a transcription factor.
100. The method of item 98 or 99, wherein said protein which is involved in lipid storage comprises an amino acid sequence as shown in any one of SEQ ID NOs: 16 or 17 or a functional homologue thereof, wherein the functional homologue has at least 30% sequence identity to an amino acid sequence as shown in SEQ ID NO: 16 or 17.
101. The method of item 100, wherein the following proteins involved in lipid storage are underexpressed
    a) proteins comprising amino acid sequences as shown in SEQ ID NOs: 16 and 17 or a functional homologue thereof, wherein the functional homologue has at least 30% sequence identity to an amino acid sequence as shown in SEQ ID NO: 16 and 17, respectively;
    b) protein comprising an amino acid sequence as shown in SEQ ID NO: 16 or a functional homologue thereof, wherein the functional homologue has at least 30% sequence identity to an amino acid sequence as shown in SEQ ID NO: 16;
    c) protein comprising an amino acid sequence as shown in SEQ ID NO: 17 or a functional homologue thereof, wherein the functional homologue has at least 30% sequence identity to an amino acid sequence as shown in SEQ ID NO: 17.
102. The method of any one of items 97-101, wherein the protein of interest is a non-membrane protein of interest.
103. The method of any one of items 97-102, wherein the eukaryotic host cell is a non-mammalian eukaryotic host cell.
104. The method of item 103, wherein the non-mammalian eukaryotic host cell is a fungal host cell, wherein the fungal host cell is preferably *Pichia pastoris, Hansenula polymorpha, Trichoderma reesei, Saccharomyces cerevisiae, Kluyveromyces lactis, Yarrowia lipolytica, Pichia methanolica, Candida boidinii, Komagataella* sp., *Aspergillus* sp. and *Schizosaccharomyces pombe*, wherein the fungal host cell is even more preferred *Pichia pastoris*.
105. The method of any one of items 97-104 comprising:
    engineering the host cell to underexpress a polynucleotide encoding a protein which is involved in lipid metabolism and which comprises an amino acid sequence as shown in SEQ ID NO: 16 or 17, or a functional homologue thereof, wherein the functional homologue has at least 30% sequence identity to an amino acid sequence as shown in SEQ ID NO: 16 or 17,
    engineering said host cell to comprise a heterologous polynucleotide encoding said protein of interest,
    culturing said host cell under suitable conditions to express said protein of interest, and optionally
    isolating said protein of interest from the cell culture.
106. A method of manufacturing a protein of interest according to any one of items 97-104 comprising:
    providing the host cell engineered to underexpress a polynucleotide encoding a protein which is involved in lipid and which comprises an amino acid sequence as shown in SEQ ID NO: 16 or 17, or a functional homologue thereof, wherein the functional homologue has at least 30% sequence identity to an amino acid sequence as shown in SEQ ID NO: 16 or 17, wherein said host cell comprises a heterologous polynucleotide encoding said protein of interest;
    culturing the host cell under suitable conditions to underexpress the protein which is involved in lipid metabolism or functional homologue thereof and express said protein of interest, and optionally
    isolating said protein of interest from the cell culture.
107. The method of any one of items 97-106, wherein the following proteins involved in lipid metabolism are underexpressed
    a) proteins comprising the amino acid sequence as shown in SEQ ID NOs: 16 and 17 or a functional homologue thereof, wherein the functional homologue has at least 30% sequence identity to an amino acid sequence as shown in SEQ ID NOs: 16 and 17, respectively.
108. The method of any one of items 97-106, comprising overexpressing in said host cell at least one polynucleotide encoding a protein which is involved in lipid metabolism.
109. The method of item 108, wherein said protein which is overexpressed and involved in lipid metabolism is involved in lipid storage, sphingolipid biosynthesis, phospholipid biosynthesis, phospholipid metabolic process, or phosphatidic acid biosynthesis.
110. The method of item 109, wherein at least one protein involved in sphingolipid biosynthesis is overexpressed and at least two proteins involved in lipid storage are underexpressed.
111. The method of item 110, wherein the following protein involved in sphingolipid biosynthesis is overexpressed and the following proteins involved in lipid storage are underexpressed
    a) protein comprising the amino acid sequence as shown in SEQ ID NO: 1 or a functional homologue thereof is overexpressed and proteins comprising the amino acid sequences as shown in SEQ ID NO: 16 and 17 or functional homologues thereof are underexpressed, wherein the functional homologue has at least 30% sequence identity to an amino acid sequence as shown in SEQ ID NO: 1, 16 and 17, respectively.

112. The method of item 109, wherein at least one protein involved in phospholipid biosynthesis is overexpressed and at least two proteins involved in lipid storage are underexpressed.

113. The method of item 112, wherein the protein involved in phospholipid biosynthesis comprises an amino acid sequence as shown in PP7435_Chr3-0950 (SLC4), PP7435_Chr1-0160 (SLC1), PP7435_CHR1-0078 (GPT2) or SEQ ID NO: 10 and the proteins involved in lipid storage comprise amino acid sequences as shown in SEQ ID NO: 16 and 17.

114. The method of item 113, wherein the following protein involved in phospholipid biosynthesis is overexpressed and the following proteins involved in lipid storage are underexpressed
    a) protein comprising the amino acid sequence as shown in PP7435_Chr3-0950 (SLC4) or a functional homologue thereof is overexpressed and proteins comprising the amino acid sequences as shown in SEQ ID NO: 16 and 17 or functional homologues thereof are underexpressed, wherein the functional homologue has at least 30% sequence identity to an amino acid sequence as shown in PP7435_Chr3-0950, SEQ ID NO: 16 and 17, respectively;
    b) protein comprising the amino acid sequence as shown in PP7435_Chr1-0160 (SLC1) or a functional homologue thereof is overexpressed and proteins comprising the amino acid sequences as shown in SEQ ID NO: 16 and 17 or functional homologues thereof are underexpressed, wherein the functional homologue has at least 30% sequence identity to an amino acid sequence as shown in PP7435_Chr1-0160, SEQ ID NO: 16 and 17, respectively;
    c) protein comprising the amino acid sequence as shown in PP7435_CHR1-0078 (GPT2) or a functional homologue thereof is overexpressed and proteins comprising the amino acid sequences as shown in SEQ ID NO: 16 and 17 or functional homologues thereof are underexpressed, wherein the functional homologue has at least 30% sequence identity to an amino acid sequence as shown in PP7435_CHR1-0078, SEQ ID NO: 16 and 17, respectively;
    d) protein comprising the amino acid sequence as shown in SEQ ID NO: 10 or a functional homologue thereof is overexpressed and proteins comprising the amino acid sequences as shown in SEQ ID NO: 16 and 17 or functional homologues thereof are underexpressed, wherein the functional homologue has at least 30% sequence identity to an amino acid sequence as shown in SEQ ID NO: 10, 16 and 17, respectively.

115. The method of item 109, wherein at least one protein involved in phospholipid metabolic process is overexpressed and at least two proteins involved in lipid storage are underexpressed.

116. The method of item 115, wherein the protein involved in phospholipid metabolic process is overexpressed and comprises an amino acid sequence as shown in PP7435_Chr2-0045 (CDS1) or a functional homologue thereof and the proteins involved in lipid storage are underexpressed and comprise amino acid sequences as shown in SEQ ID NO: 16 or 17 or a functional homologue thereof, wherein the functional homologue has at least 30% sequence identity to an amino acid sequence as shown in PP7435_Chr2-0045, SEQ ID NOs: 16 and 17, respectively.

117. The method of item 116, wherein at least one protein involved in phosphatidic acid biosynthesis is overexpressed and at least two proteins involved in lipid storage are underexpressed.

118. The method of item 117, wherein the protein involved in phosphatidic acid biosynthesis is overexpressed and comprises an amino acid sequence as shown in PP7435_Chr3-1169 (DGK1) or a functional homologue thereof and the proteins involved in lipid storage are underexpressed and comprise amino acid sequences as shown in SEQ ID NO: 16 or 17 or a functional homologue thereof, wherein the functional homologue has at least 30% sequence identity to an amino acid sequence as shown in PP7435_Chr3-1169, SEQ ID NOs: 16 and 17, respectively.

119. The method of item 109, wherein at least one protein involved in lipid storage is overexpressed and at least two proteins involved in lipid storage are underexpressed.

120. The method of item 119, wherein the protein involved in lipid storage which is overexpressed comprises an amino acid sequence as shown in PP7435_Chr3-0741 (ARE2) or a functional homologue thereof and the proteins involved in lipid storage which underexpressed comprise amino acid sequences as shown in SEQ ID NO: 16 or 17 or a functional homologue thereof, wherein the functional homologue has at least 30% sequence identity to an amino acid sequence as shown in PP7435_Chr3-0741, SEQ ID NOs: 16 and 17, respectively.

121. A recombinant eukaryotic host cell for manufacturing a protein of interest, wherein the host cell is engineered to underexpress at least one polynucleotide encoding a protein which is involved in lipid metabolism, wherein the protein of interest is preferably a non-membrane protein.

122. The host cell of item 121, wherein said protein involved in lipid metabolism is involved in lipid storage and comprises an amino acid sequence as shown in any one of SEQ ID NOs: 16 or 17, or a functional homologue thereof, wherein the functional homologue has at least 30% sequence identity to an amino acid sequence as shown in any one of SEQ ID NOs: 16 or 17.

123. The host cell of item 121 or 122, wherein the following proteins involved in lipid metabolism are underexpressed
    a) proteins comprising the amino acid sequence as shown in SEQ ID NOs: 16 and 17 or a functional homologue thereof, wherein the functional homologue has at least 30% sequence identity to an amino acid sequence as shown in SEQ ID NOs: 16 and 17, respectively;
    b) protein comprising the amino acid sequence as shown in SEQ ID NO: 16 or a functional homologue thereof, wherein the functional homologue has at least 30% sequence identity to an amino acid sequence as shown in SEQ ID NO: 16;
    c) protein comprising the amino acid sequence as shown in SEQ ID NO: 17 or a functional homologue thereof, wherein the functional homologue has at least 30% sequence identity to an amino acid sequence as shown in SEQ ID NO: 17.

124. The host cell of any one of items 121 to 123, wherein at least one polynucleotide encoding a protein which is involved in lipid metabolism is overexpressed as defined in items 109-120.

125. The host cell of any one of items 121 to 124, wherein said protein involved in lipid metabolism or said functional homologue thereof increases the yield of the model protein HyHEL (SEQ ID NO: 39 for heavy chain and SEQ ID NO: 40 for light chain) compared to the host cell prior to engineering by at least 10%.

126. A method of increasing the yield of a protein of interest in a eukaryotic host cell by changing the lipid composition of a membrane of the host cell, wherein the membrane of the host cell is preferably the cellular membrane or the endoplasmatic reticulum membrane.

127. The method of item 126, wherein the lipid composition of a membrane of said host cell is changed by overexpression of at least one protein involved in lipid metabolism, preferably by one of the helper proteins described herein.

128. A method of increasing the yield of a protein of interest in a eukaryotic host cell by altering the molecular species pattern of sphingolipids, preferably by increasing the amount of C26 fatty acyl moieties of ceramides and/or inositol-containing phosphorylcerarmides (inositolphosphorylceramide, mannosyl-inositolphosphorylceramide, mannosyl-diinositol-phosphorylceramide) and/or decreasing the amount of C24 fatty acyl moieties of ceramides and/or inositol-containing phosphorylceramides (inositolphosphorylceramide, mannosyl-inositolphosphorylceramide, mannosyl-diinositol-phosphorylceramide).

129. The method of item 128, wherein the molecular species pattern of sphingolipids is altered by overexpression of at least one protein involved in lipid metabolism, preferably by one of the helper proteins described herein.

130. The method of item 128 or 129, wherein the relative amount of fatty acyls of a chain length of 26 carbons (C26) incorporated in ceramides, IPC, MIPC and M(IP)$_2$C is increased by at least 100%, whereas the relative amount of fatty acyls of a chain length of 24 carbons (C24) are decreased by at least 70%.

131. A method of increasing the yield of a protein of interest in a eukaryotic host cell by reducing the amount of IPC and MIPC (of approximately 30%) and/or by increasing the formation of the mature form of inositol-containing phosphorylceramides, M(IP)$_2$C by at least 6-fold (600%).

132. The method of item 131, wherein said reduction and/or increment is achieved by overexpression of at least one protein involved in lipid metabolism, preferably by one of the helper proteins described herein 133. The method of item 131 or 132, wherein the relative distribution of sphingolipids is affected as follows: 6-fold (600%) increase in M(IP)$_2$C and approximately 30% decrease in the relative distribution of IPC and MIPC.

134. A method of increasing the yield of a protein of interest in a eukaryotic host cell by depleting the cell of the non-polar storage lipid triacylglycerol (TG).

135. The method of item 134, wherein said depletion is achieved by underexpression of at least one protein involved in lipid metabolism, preferably by one of the helper proteins described herein.

DETAILED DESCRIPTION OF THE INVENTION

The present invention is partly based on the surprising finding of the expression of the helper proteins involved in lipid metabolism as described herein, which were found to increase the yield of a protein of interest, if overexpressed (helper protein comprising an amino acid sequence shown in SEQ ID Nos: 1-15) or underexpressed (KO helper protein comprising an amino acid sequence shown in SEQ ID Nos: 16 and 17). The amino acid sequence and nucleotide sequences of each helper protein and its corresponding gene identifier which is sometimes used herein, particularly in the Examples are listed in Table 1 designated as "OE" (overexpressed helper proteins) and as "KO" (underexpressed helper proteins), below. Combinations of overexpressed and underexpressed helper proteins are described herein and in detail in Example 6.

TABLE 1

Gene identities of *Pichia pastoris* sequences are retrieved from Sturmberger et al. . [J. Biotechnol. (2016). 235(4): 121-131)] and gene identities of *Saccharomyces cerevisiae* sequences are retrieved from Cherry J. M. et al. [Nucleic Acids Res. (2012) 40 (Database issue D700-5)]. Gene ontology terms are defined as follows: "Sphingolipid" means sphingolipid biosynthesis including fatty acid elongation; "Transport" means lipid transport; "Phospholipid" means.phospholipid biosynthesis; "Sterol" meansergosterol biosynthesis and "Storage" means lipid storage. Gene accession numbers were retrieved from the European Nucleotide Archive (ENA) and Protein accession numbers were retrieved from UniProtKB.

| OE or KO | Gene | Gene Identifier (ORF name *Pichia pastoris* CBS7435) | SEQ IN NO (AA) | SEQ ID NO (DNA) | Gene Ontology Term | Gene accession number | Protein accession number |
|---|---|---|---|---|---|---|---|
| OE | ELO3 | PP7435_chr3-0987 | 1 | 19 | Sphingolipid | CCA39933.1 | F2QX05 |
| OE | ELO2 | PP7435_Chr3-0603 | 2 | 20 | Sphingolipid | CCA39561.1 | F2QVY3 |
| OE | LAG1 | PP7435_Chr1-0676 | 3 | 21 | Sphingolipid | CCA36821.1 | F2QP79 |
| OE | LAC1 | PP7435_Chr2-0202 | 4 | 22 | Sphingolipid | CCA37899.1 | F2QR71 |
| OE | LCB1 | PP7435_Chr1-1525 | 5 | 23 | Sphingolipid | CCA37636.1 | F2QQF8 |
| OE | LCB2 | PP7435_Chr3-0462 | 6 | 24 | Sphingolipid | CCA39423.1 | F2QVJ5 |
| OE | TSC13 | PP7435_Chr4-0176 | 7 | 25 | Sphingolipid | CCA40351.1 | F2QY73 |

| OE or KO | Gene | Gene Identifier (ORF name *Saccharomyces cerevisiae* S288C) | SEQ IN NO (AA) | SEQ IN NO (DNA) | Gene Ontology Term | | |
|---|---|---|---|---|---|---|---|
| OE | LIP1$_{Sc}$ | YMR298W | 8 | 26 | Sphingolipid | CAA56807.1 | Q03579 |
| OE | TSC3$_{Sc}$ | YBR058C-A | 9 | 27 | Sphingolipid | DAA07178.2 | Q3E790 |

| OE or KO | Gene | Gene Identifier (ORF name *Pichia pastoris* CBS7435) | SEQ IN NO (AA) | SEQ IN NO (DNA) | Gene Ontology Term | | |
|---|---|---|---|---|---|---|---|
| OE | PAH1 | PP7435_chr3-0694 | 10 | 28 | Phospholipid | CCA39650.1 | F2QW72 |
| OE | PRY1 | PP7435_chr3-1160 | 11 | 29 | Transport | CCA40103.1 | F2QXH5 |

TABLE 1-continued

Gene identities of *Pichia pastoris* sequences are retrieved from Sturmberger et al. . [J. Biotechnol. (2016). 235(4): 121-131)] and gene identities of *Saccharomyces cerevisiae* sequences are retrieved from Cherry J. M. et al. [Nucleic Acids Res. (2012) 40 (Database issue D700-5)]._Gene ontology terms are defined as follows: "Sphingolipid" means sphingolipid biosynthesis including fatty acid elongation; "Transport" means lipid transport; "Phospholipid" means.phospholipid biosynthesis; "Sterol" meansergosterol biosynthesis and "Storage" means lipid storage. Gene accession numbers were retrieved from the European Nucleotide Archive (ENA) and Protein accession numbers were retrieved from UniProtKB.

| OE | ERG11 | PP7435_chr3-0214 | 12 | 30 | Sterol | CCA39186.1 | F2QUV8 |
|---|---|---|---|---|---|---|---|
| OE | HMG1 | PP7435_chr2-0242 | 13 | 31 | Sterol | CCA37938.1 | F2QRB0 |
| OE | t2HMG1§ | PP7435_chr2-0242_truncated | 14 | 32 | Sterol | CCA37938.1 | F2QRB0 |
| OE | t1HMG1§ | PP7435_chr2-0242_truncated | 15 | 33 | Sterol | CCA37938.1 | F2QRB0 |
| KO | DGA1 | PP7435_chr3-1009 | 16 | 34 | Storage | CCA39955.1 | F2QX27 |
| KO | LRO1 | PP7435_chr2-0587 | 17 | 35 | Storage | CCA38274.1 | F2QS96 |
| OE | KAR2 | PP7435_Chr2-1167 | 18 | 36 | Chaperone | CAY68747.1* | C4QZS3* |

*KAR2 sequences (nucleotide as well as amino acid) are only annotated for *P. pastoris* strain GS115 which is almost identical to CBS7435. Therefore, Gene/Protein accession numbers for KAR2 are listed for the sequeneces annotated in the background of *P. pastoris* strain GS115. Notably, for avoidance of doubt, the amino acid or nucleotide sequences referred to in the SEQ ID NOs. supersede any other source of such sequences.
§DNA-Sequences of HMG1 in the table above were next to the full-length sequence used as two truncated variants (t1, t2) which were depleted of their membrane anchoring domains that is depletion of 1449 nucleotides at the 5'-end for variant t1HMG1 or 1543 nucleotides in case of t2HMG1 (except their starting ATG-codon).

A "helper protein" or "helper protein of the present invention" as used in the present invention means a protein which is involved in lipid metabolism and which increases the yield of a model protein as described herein or of a protein of interest (POI), preferably when being either overexpressed in case of the helper proteins shown in SEQ ID NOs: 1-15, such as SEQ ID NO: 1, 2, 3, 4, 5, 6, 7, 8, 9, 10, 11, 12, 13, 14, or 15, or when being underexpressed in case of the helper proteins shown in SEQ ID NOs: 16 or 17, in a host cell which also expresses the protein of interest. Additional helper proteins of the present invention that are involved in lipid metabolism and which enhance the yield of a model protein when being overexpressed are shown in PP7435_Chr3-0788 (SUR2), PP7435_Chr3-1005 (PHS1), PP7435_Chr2-0350 (AUR1), PP7435_Chr4-0626 (IFA38), PP7435_Chr3-0669 (SCS7), PP7435_Chr3-0636 (CRD1), PP7435_Chr3-0950 (SLC4), PP7435_Chr2-0585 (PIS1), PP7435_chr1-0934 (PRY2), ARV1 (ORF not annotated; located between PP7435_Chr4-0493/0494), PP7435_Chr3-0741 (ARE2), PP7435_Chr4-0963 (FAD12), PP7435_Chr1-0794 (PSD1), PP7435_Chr1-0160 (SLC1), PP7435_CHR1-0078 (GPT2) PP7435_Chr3-1169 (DGK1) and PP7435_Chr2-0045 (CDS1) or functional homologues thereof. This term should be understood broadly and should not be limited to, e.g. chaperones or chaperone-like proteins. As will appear evident from the present disclosure, helper proteins of the present invention are varied in their functions, however are all involved in certain classes of lipid metabolism. A preferred helper protein of the present invention comprises the amino acid sequences of any one of SEQ ID NOs: 1 to 17 or a functional homologue thereof. A preferred helper protein of the present invention can be encoded by the nucleotide sequences of any one of SEQ ID NOs: 19 to 36 or variants thereof encoding a functional homologue of SEQ ID NO: 1, 2, 3, 4, 5, 6, 7, 8, 9, 10, 11, 12, 13, 14, or 15, respectively. For the purpose of the present invention, the term "helper protein" is also meant to encompass functional homologues of a helper protein as shown in any one of SEQ ID NOs: 1 to 17, respectively. The invention provides an isolated polynucleotide sequence encoding a helper protein comprising an amino acid sequence as shown in SEQ ID NO: 1, 2, 3, 4, 5, 6, 7, 8, 9, 10, 11, 12, 13, 14, or 15, or a functional homologue thereof, wherein the functional homologue has at least 30% sequence identity to an amino acid sequence as shown in SEQ ID NO: 1, 2, 3, 4, 5, 6, 7, 8, 9, 10, 11, 12, 13, 14, or 15. The invention provides an isolated polynucleotide sequence encoding a helper protein comprising an amino acid sequence as shown in PP7435_Chr3-0788 (SUR2), PP7435_Chr3-1005 (PHS1), PP7435_Chr2-0350 (AUR1), PP7435_Chr4-0626 (IFA38), PP7435_Chr3-0669 (SCS7), PP7435_Chr3-0636 (CRD1), PP7435_Chr3-0950 (SLC4), PP7435_Chr2-0585 (PIS1), PP7435_chr1-0934 (PRY2), ARV1 (ORF not annotated; located between PP7435_Chr4-0493/0494), PP7435_Chr3-0741 (ARE2), PP7435_Chr4-0963 (FAD12), PP7435_Chr1-0794 (PSD1), PP7435_Chr1-0160 (SLC1), PP7435_CHR1-0078 (GPT2) PP7435_Chr3-1169 (DGK1) and PP7435_Chr2-0045 (CDS1) or a functional homologue thereof, wherein the functional homologue has at least 30% sequence identity to an amino acid sequence as shown in PP7435_Chr3-0788 (SUR2), PP7435_Chr3-1005 (PHS1), PP7435_Chr2-0350 (AUR1), PP7435_Chr4-0626 (IFA38), PP7435_Chr3-0669 (SCS7), PP7435_Chr3-0636 (CRD1), PP7435_Chr3-0950 (SLC4), PP7435_Chr2-0585 (PIS1), PP7435_chr1-0934 (PRY2), ARV1 (ORF not annotated; located between PP7435_Chr4-0493/0494), PP7435_Chr3-0741 (ARE2), PP7435_Chr4-0963 (FAD12), PP7435_Chr1-0794 (PSD1), PP7435_Chr1-0160 (SLC1), PP7435_CHR1-0078 (GPT2) PP7435_Chr3-1169 (DGK1) and PP7435_Chr2-0045 (CDS1).

The term "involved in lipid metabolism" means that a helper protein has function/activity in lipid metabolism of a eukaryotic cell. Lipid metabolism includes, among others, functions such as lipid synthesis, lipid degradation, lipid transport (mediated via proteins, vesicles or direct membrane contact with the purpose of bringing lipids from their site of synthesis to their site of destination e.g. incorporation into biomembranes; or the transport of excess or malfunctioning lipids to the cell exterior), lipid storage (storage of lipids in biologically inert forms as steryl esters or triacylglycerols to avoid lipotoxicity caused by excess amounts of free sterols or fatty acids; lipid storage occurs in specialized organelles the so-called lipid droplets), lipid modification, lipid stability, lipid-lipid interaction, fatty acid biosynthesis and modification, sphingolipid biosynthesis, phospholipid biosynthesis, ergosterol biosynthesis, altering the molecular species pattern of highly abundant sphingolipids, that is fatty acyl moieties of ceramides (ceramides and hexosyl-ceramides) and inositol-containing phosphorylceramides (IPC . . . inositolphosphorylceramide, MIPC . . . Mannosyl-inositolphosphorylceramide, M(IP)$_2$C . . . Mannosyl-diinositol-phosphorylceramide) preferentially contain C26 (26 carbons in the fatty acyl chain) instead of C24 (24 carbons in the fatty acyl chain); altering the sphingolipid distribution pattern towards higher occurrence of the mature form of complex sphingolipids that is more $M(IP)_2C$ which comes at the expense of IPC; depleting cells of triacylglycerols that is the major storage lipid of *P. pastoris*. Preferably, said helper protein which is involved in lipid metabolism is not a transcription factor. Accordingly, a helper protein that is involved in lipid metabolism, either when it is over- or underexpressed as described herein, can modify biomembrane lipid composition in a eukaryotic host cell, particularly in a fungal host cell, thereby positively affecting recombinant protein production. The term "biomembrane" as used herein includes but is not limited to cell membranes and endoplasmatic reticulum membrane, vesicle membrane, golgi membrane, etc. Hence, when used herein, the term "lipid metabolism" in the context of over- and underexpression of a helper protein, respectively, can be replaced by the term "modification of biomembrane lipid composition", preferably modification of biomembrane lipid composition in a eukaryotic host cells, particularly in a fungal host cell. As mentioned herein, in the context of overexpression of helper proteins, such helper proteins are involved in sphingolipid biosynthesis (helper proteins comprising SEQ ID NOs: 1-9), phospholipid biosynthesis (helper protein comprising SEQ ID NO: 10), lipid transport (helper protein comprising SEQ ID NO: 11), ergosterol biosynthesis (helper proteins comprising SEQ ID NOs: 12-15), fatty acid biosynthesis, phosphatidic acid biosynthesis and/or phospholipid metabolic process. The term "sphingolipid biosynthesis" as used herein includes fatty acid elongation. Consequently, helper proteins involved in sphingolipid biosynthesis can be involved in sphingolipid biosynthesis and/or in fatty acid elongation. Biosynthesis of complex sphingolipids such as IPC, MIPC or $M(IP)_2C$ is inseparably linked to the elongation of fatty acids. Long chain fatty acids undergo a consecutive 4-step cycle in the process of fatty acid elongation leading to the formation of very long chain fatty acids (e.g. C24 or C26). Very long chain fatty acids produced by the elongation of fatty acids are then readily incorporated as direct substrates in the process of sphingolipid biosynthesis yielding complex sphingolipids (IPC, MIPC, $M(IP)_2C$). The initial steps in the biosynthesis of sphingolipids occur in the endoplasmic reticulum but the further modification and maturation process on ceramides to yield complex inositol-containing phosphorylceramides takes place in the Golgi. Therefore, substantial amounts of ceramides and hexosyl-ceramides can be found in the biomembranes of the endoplasmic reticulum but as well to a lower extent in further organelles of the secretory route (vesicles and Golgi) and the cellular plasma membrane. Complex sphingolipids (IPC, MIPC, $M(IP)_2C$) are highest enriched in the cellular plasma membrane co-localizing with sterols in so-called lipid rafts but can as well be found at lower amounts in the biomembranes of the endoplasmic reticulum and other organelles along the secretory route (vesicles, Golgi). As also mentioned herein, in the context of underexpression of helper proteins, such helper proteins are for example involved in lipid storage (e.g. KO helper proteins comprising SEQ ID NO: 16 or 17). Accordingly, modification of biomembrane lipid composition may be preferably affected by sphingolipid biosynthesis, phospholipid biosynthesis, lipid transport, or ergosterol biosynthesis in case of overexpression of a helper protein as described herein or may be preferably affected by lipid storage in case of underexpression of a helper protein as described herein. Helper proteins of the present invention being involved in lipid metabolism are preferably not transcription factors. The different groups of helper proteins (i.e. involved in sphingolipid biosynthesis, phospholipid biosynthesis, lipid transport, ergosterol biosynthesis and lipid storage) described herein are based on *Pichia pastoris* genes.

The term "protein of interest" as used herein generally relates to any protein but preferably relates to a "heterologous protein" or "recombinant protein" and even more preferred to a "non-membrane protein of interest". A "non-membrane protein of interest" means that the protein of interest is preferably not an integral membrane protein which is in its natural environment (i.e. in situ) permanently part of or attached to biological membranes of an eukaryotic cell, such as fungal cells. Such proteins are classified as spanning across a biological membrane at least once. Accordingly, a non-membrane protein of interest as used herein does preferably not have a transmembrane domain. The term "non-membrane protein" as used herein however includes GPI-anchored proteins.

As used herein, a "homologue" or "functional homologue" of a helper protein of the present invention shall mean that a protein has the same or conserved residues at a corresponding position in their primary, secondary or tertiary structure. The term also extends to two or more nucleotide sequences encoding homologous polypeptides. In particular, polypeptides homologous to the present helper proteins have at least about 30% amino acid sequence identity with regard to a sequence disclosed herein (SEQ ID-Nos 1-18). Preferably, a homologous polypeptide will have at least about 35% amino acid sequence identity, more preferably at least about 40% amino acid sequence identity, more preferably at least about 45% amino acid sequence identity, more preferably at least about 50% amino acid sequence identity, more preferably at least about 55% amino acid sequence identity, more preferably at least about 60% amino acid sequence identity, more preferably at least about 65% amino acid sequence identity, more preferably at least about 70% amino acid sequence identity, more preferably at least about 75% amino acid sequence identity, more preferably at least about 80% amino acid sequence identity, more preferably at least about 85% amino acid sequence identity, more preferably at least about 90%, such as 91, 92, 93, 94, 95, 96, 97, 98 or 99% amino acid sequence identity, more preferably at least about 95% amino acid sequence identity to a native sequence, or any other specifically defined fragment of a full-length compound. When the function as a helper protein is proven with such a homologue, the homologue is called "functional homologue". A functional homologue performs the same or substantially the same function as the helper protein from which it is derived from, i.e. it has the same enzymatic activity or catalyses the same metabolic reaction in the lipid metabolism of the cell. In the case of nucleotide sequences a "functional homologue" preferably means a nucleotide sequence having a sequence different form the original nucleotide sequence, but which still codes for the same amino acid sequence, due to the use of the degenerated genetic code. A functional homologue may also be a biologically active fragment of a helper protein. Generally, a biologically active fragment of a helper protein shall mean a fragment of said helper protein that exerts a biological effect similar or comparable to that of the full length helper protein, which means said biologically active fragment results in at least 50%, at least 60%, at least 70%, at least 80%, or at least 90% of the increase of the POI yield observed with the corresponding full length helper protein (SEQ ID-NOs 1-18). Such active fragment can be obtained e.g. by amino- and/or carboxy-terminal deletions and/or by deletion of at least 1 amino acid which is not the amino- and/or carboxy terminal amino acid of the amino acid sequence of said full length helper protein.

Generally, homologues can be prepared using any mutagenesis procedure known in the art, such as site-directed mutagenesis, synthetic gene construction, semisynthetic gene construction, random mutagenesis, shuffling, etc. Site-directed mutagenesis is a technique in which one or more (e.g., several) mutations are introduced at one or more defined sites in a polynucleotide encoding the parent. Site-directed mutagenesis can be accomplished in vitro by PCR involving the use of oligonucleotide primers containing the desired mutation. Site-directed mutagenesis can also be performed in vitro by cassette mutagenesis involving the cleavage by a restriction enzyme at a site in the plasmid comprising a polynucleotide encoding the parent and subsequent ligation of an oligonucleotide containing the mutation in the polynucleotide. Usually the restriction enzyme that digests the plasmid and the oligonucleotide is the same, permitting sticky ends of the plasmid and the insert to ligate to one another. See, e.g., Scherer and Davis, 1979, Proc. Natl. Acad. Sci. USA 76: 4949-4955; and Barton et ai, 1990, Nucleic Acids Res. 18: 7349-4966. Site-directed mutagenesis can also be accomplished in vivo by methods known in the art. See, e.g., U.S. Patent Application Publication No. 2004/0171 154; Storici et ai, 2001, Nature Biotechnol. 19: 773-776; Kren et ai, 1998, Nat. Med. 4: 285-290; and Calissano and Macino, 1996, Fungal Genet. Newslett. 43: 15-16. Synthetic gene construction entails in vitro synthesis of a designed polynucleotide molecule to encode a polypeptide of interest. Gene synthesis can be performed utilizing a number of techniques, such as the multiplex microchip-based technology described by Tian et al. (2004, Nature 432: 1050-1054) and similar technologies wherein oligonucleotides are synthesized and assembled upon photo-programmable microfluidic chips. Single or multiple amino acid substitutions, deletions, and/or insertions can be made and tested using known methods of mutagenesis, recombination, and/or shuffling, followed by a relevant screening procedure, such as those disclosed by Reidhaar-Olson and Sauer, 1988, Science 241:53-57; Bowie and Sauer, 1989, Proc. Natl. Acad. Sci. USA 86: 2152-2156; WO 95/17413; or WO 95/22625. Other methods that can be used include error-prone PCR, phage display (e.g., Lowman et al, 1991, Biochemistry 30: 10832-10837; U.S. Pat. No. 5,223,409; WO 92/06204) and region-directed mutagenesis (Derbyshire et al., 1986, Gene 46: 145; Ner et al., 1988, DNA 7:127). Mutagenesis/shuffling methods can be combined with high-throughput, automated screening methods to detect activity of cloned, mutagenized polypeptides expressed by host cells (Ness et al., 1999, Nature Biotechnology 17: 893-896). Mutagenized DNA molecules that encode active polypeptides can be recovered from the host cells and rapidly sequenced using standard methods known in the art. These methods allow the rapid determination of the importance of individual amino acid residues in a polypeptide. Semi-synthetic gene construction is accomplished by combining aspects of synthetic gene construction, and/or site-directed mutagenesis, and/or random mutagenesis, and/or shuffling. Semisynthetic construction is typified by a process utilizing polynucleotide fragments that are synthesized, in combination with PCR techniques. Defined regions of genes may thus be synthesized de novo, while other regions may be amplified using site-specific mutagenic primers, while yet other regions may be subjected to error-prone PCR or non-error prone PCR amplification. Polynucleotide subsequences may then be shuffled. Alternatively, homologues can be obtained from a natural source such as by screening cDNA libraries of other organisms, preferably closely related or related organisms.

The function of a homologue of any one of SEQ ID NOs: 1 to 17 or the additional helper proteins disclosed herein can be tested by providing expression cassettes into which the homologue sequences have been inserted, transforming host cells that carry the sequence encoding a test protein such as one of the model proteins used in the Example section or another POI, and determining the difference in the yield of the model protein or POI under identical conditions.

The present invention provides an isolated polynucleotide sequence encoding SEQ ID NO: 1, 2, 3, 4, 5, 6, 7, 8, 9, 10, 11, 12, 13, 14, 15, 16, or 17, or functional homologues of SEQ ID NO: 1, 2, 3, 4, 5, 6, 7, 8, 9, 10, 11, 12, 13, 14, 15, 16, or 17. The isolated polynucleotide sequence may comprise any one of SEQ ID NOs: 19-35. Preferably, the isolated polynucleotide sequence consists of the nucleotide sequence of any one of SEQ ID NOs: 30-58. The present invention also provides an isolated polynucleotide sequence encoding PP7435_Chr3-0788 (SUR2), PP7435_Chr3-1005 (PHS1), PP7435_Chr2-0350 (AUR1), PP7435_Chr4-0626 (IFA38), PP7435_Chr3-0669 (SCS7), PP7435_Chr3-0636 (CRD1), PP7435_Chr3-0950 (SLC4), PP7435_Chr2-0585 (PIS1), PP7435_chr1-0934 (PRY2), ARV1 (ORF not annotated; located between PP7435_Chr4-0493/0494), PP7435_Chr3-0741 (ARE2), PP7435_Chr4-0963 (FAD12), PP7435_Chr1-0794 (PSD1), PP7435_Chr1-0160 (SLC1), PP7435_CHR1-0078 (GPT2) PP7435_Chr3-1169 (DGK1) and PP7435_Chr2-0045 (CDS1) or functional homologues thereof.

Furthermore, the present invention provides an isolated polypeptide comprising a polypeptide sequence having at least 30%, such as at least 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99 or 100% sequence identity to an amino acid sequence selected from the group consisting of SEQ ID NO: 1, 2, 3, 4, 5, 6, 7, 8, 9, 10, 11, 12, 13, 14, 15, 16, 17, or 18. Furthermore, the present invention provides an isolated polypeptide comprising a polypeptide sequence having at least 30%, such as at least 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99 or 100% sequence identity to an amino acid sequence selected from the group consisting of PP7435_Chr3-0788 (SUR2), PP7435_Chr3-1005 (PHS1), PP7435_Chr2-0350 (AUR1), PP7435_Chr4-0626 (IFA38), PP7435_Chr3-0669 (SCS7), PP7435_Chr3-0636 (CRD1), PP7435_Chr3-0950 (SLC4), PP7435_Chr2-0585 (PIS1), PP7435_chr1-0934 (PRY2), ARV1 (ORF not annotated; located between PP7435_Chr4-0493/0494), PP7435_Chr3-0741 (ARE2), PP7435_Chr4-0963 (FAD12), PP7435_Chr1-0794 (PSD1), PP7435_Chr1-0160 (SLC1), PP7435_CHR1-0078 (GPT2) PP7435_Chr3-1169 (DGK1) and PP7435_Chr2-0045 (CDS1).

The term "isolated" means a substance in a form or environment that does not occur in nature. Non-limiting examples of isolated substances include (1) any non-naturally occurring substance, (2) any substance including, but not limited to, any enzyme, variant, nucleic acid, protein, peptide or cofactor, that is at least partially removed from one or more or all of the naturally occurring constituents with which it is associated in nature; (3) any substance modified by the hand of man relative to that substance found in nature, e.g. cDNA made from mRNA; or (4) any substance modified by increasing the amount of the substance relative to other components with which it is naturally associated (e.g., recombinant production in a host cell; multiple copies of a gene encoding the substance; and use of a stronger promoter than the promoter naturally associated with the gene encoding the substance).

The present invention provides use of any one of the above mentioned isolated polynucleotides for integration in a host cell. Alternatively, if the polynucleotide(s) already exist in the host cell, the host cell can be manipulated in a way such that they are overexpressed, as will be described later. In another aspect, the invention relates to the use of said polynucleotide for increasing a POI yield from a host cell, wherein the nucleotide sequence encoding the POI is co-expressed with said polynucleotides.

"Sequence identity" or "% identity" refers to the percentage of residue matches between at least two polypeptide or polynucleotide sequences aligned using a standardized algorithm. Such an algorithm may insert, in a standardized and reproducible way, gaps in the sequences being compared in order to optimize alignment between two sequences, and therefore achieve a more meaningful comparison of the two sequences. For purposes of the present invention, the sequence identity between two amino acid sequences or nucleotide sequences is determined using the NCBI BLAST program version 2.2.29 (Jan. 6, 2014) (Altschul et al., Nucleic Acids Res. (1997) 25:3389-3402). Sequence identity of two amino acid sequences can be determined with blastp set at the following parameters: Matrix: BLOSUM62, Word Size: 3; Expect value: 10; Gap cost: Existence=11, Extension=1; Filter=low complexity activated; Filter String: L; Compositional adjustments: Conditional compositional score matrix adjustment. For purposes of the present invention, the sequence identity between two nucleotide sequences is determined using the NCBI BLAST program version 2.2.29 (Jan. 6, 2014) with blastn set at the following exemplary parameters: Word Size: 11; Expect value: 10; Gap costs: Existence=5, Extension=2; Filter=low complexity activated; Match/Mismatch Scores: 2,-3; Filter String: L; m.

Moreover, the present invention provides for a host cell engineered to overexpress a polynucleotide encoding a helper protein of the present invention. The helper proteins include any one of SEQ ID NOs: 1-15, respectively, or functional homologues thereof. The helper proteins also include PP7435_Chr3-0788 (SUR2), PP7435_Chr3-1005 (PHS1), PP7435_Chr2-0350 (AUR1), PP7435_Chr4-0626 (IFA38), PP7435_Chr3-0669 (SCS7), PP7435_Chr3-0636 (CRD1), PP7435_Chr3-0950 (SLC4), PP7435_Chr2-0585 (PIS1), PP7435_chr1-0934 (PRY2), ARV1 (ORF not annotated; located between PP7435_Chr4-0493/0494), PP7435_Chr3-0741 (ARE2), PP7435_Chr4-0963 (FAD12), PP7435_Chr1-0794 (PSD1), PP7435_Chr1-0160 (SLC1), PP7435_CHR1-0078 (GPT2) PP7435_Chr3-1169 (DGK1) and PP7435_Chr2-0045 (CDS1) or functional homologues thereof. Similarly, the present invention provides for a host cell engineered to underexpress a polynucleotide encoding a helper protein of the present invention (KO helper protein). KO helper proteins include any one of SEQ ID NOs: 16 or 17, respectively, or functional homologues thereof. A host cell engineered to underexpress a polynucleotide encoding a KO helper protein or a helper protein of the present invention may further overexpress one or more helper proteins as set forth in the items disclosed herein.

Preferably, the invention provides a recombinant host cell for manufacturing a protein of interest, wherein the host cell is engineered to overexpress a polynucleotide encoding a helper protein comprising an amino acid having at least 30% sequence identity to an amino acid sequence as shown in any one of SEQ ID NOs: 1-15.

Preferably, the invention provides a recombinant host cell for manufacturing a protein of interest, wherein the host cell is engineered to underexpress a polynucleotide encoding a KO helper protein comprising an amino acid having at least 30% sequence identity to an amino acid sequence as shown in any one of SEQ ID NOs: 16 or 17.

The term "expressing a polynucleotide" means when a polynucleotide is transcribed to mRNA and the mRNA is translated to a polypeptide. The term "overexpress" generally refers to any amount greater than or equal to an expression level exhibited by a reference standard. The terms "overexpress," "overexpressing," "overexpressed" and "overexpression" in the present invention refer an expression of a gene product or a polypeptide at a level greater than the expression of the same gene product or polypeptide prior to a genetic alteration of the host cell or in a comparable host which has not been genetically altered at defined conditions. In the present invention, a helper protein comprising an amino acid sequence as shown in any one of SEQ ID NOs: 1-15 is overexpressed. If a host cell does not comprise a given gene product, it is possible to introduce the gene product into the host cell for expression; in this case, any detectable expression is encompassed by the term "overexpression."

The term "underexpress" generally refers to any amount less than an expression level exhibited by a reference standard, which is the host cell prior to the engineering to underexpress the KO helper protein as described herein. The terms "underexpress," "underexpressing," "underexpressed" and "underexpression" in the present invention refer an expression of a gene product or a polypeptide at a level less than the expression of the same gene product or polypeptide prior to a genetic alteration of the host cell or in a comparable host which has not been genetically altered. For example the KO protein maybe underexpressed compared to the reference standard by at least 10%, 20%, 30%, 40%, 50%, 60%, 70%, 80%, 90%, 95%, 99% or may be even not expressed at all (reduced by 100%). No expression of the gene product or a polypeptide, for example obtained by deletion/knock-out of the KO helper gene, is also encompassed by the term "underexpression".

As used herein, "engineered" host cells are host cells which have been manipulated using genetic engineering, i.e. by human intervention. When a host cell is "engineered to overexpress" a given protein, the host cell is manipulated such that the host cell has the capability to express, preferably overexpress a helper protein or functional homologue thereof, thereby expression of a given protein, e.g. POI or model protein is increased compared to the host cell under the same condition prior to manipulation.

When a host cell "underexpresses" or is "engineered to underexpress" a given protein, the host cell is manipulated such that the host cell has the capability to underexpress a KO helper protein or functional homologue thereof, thereby expression of a given protein, e.g. POI or model protein is increased compared to the host cell under the same condition prior to manipulation. Underexpression can be carried out by any method that prevents the functional expression of a KO helper protein comprising the amino acid sequence as shown in any one of SEQ ID NOs: 16 or 17 or functional homologues thereof. This results in the incapability to exert its function. Means of underexpression may include gene silencing (e.g. RNAi genes antisense), knocking-out, altering expression level, altering expression pattern, by mutagenizing the gene sequence, disrupting the sequence, insertions, additions, mutations, modifying expression control sequences, and the like. Preferred means of underexpression are knocking-out the functional expression of the KO helper protein, e.g. by deleting the coding sequence of the KO helper protein or fragments thereof or by deleting a regulatory sequence required for expression of the KO helper protein (e.g. the promoter).

"Prior to engineering" when used in the context of host cells of the present invention means that such host cells are not engineered using a polynucleotide encoding a helper protein or functional homologue thereof. Said term thus also means that host cells do not over- or underexpress a polynucleotide encoding a helper protein or functional homologue thereof or are not engineered to over- or underexpress a polynucleotide encoding a helper protein or functional homologue thereof.

The term "engineering said host cell to comprise a heterologous polynucleotide encoding said protein of interest" as used herein means that a host cell of the present invention is equipped with a heterologous polynucleotide encoding a protein of interest, i.e., a host cell of the present invention is engineered to contain a heterologous polynucleotide encoding a protein of interest. This can be achieved, e.g., by transformation or transfection or any other suitable technique known in the art for the introduction of a polynucleotide into a host cell.

Overexpression

Overexpression can be achieved in any ways known to a skilled person in the art as will be described later in detail. In general, it can be achieved by increasing transcription/translation of the gene, e.g. by increasing the copy number of the gene or altering or modifying regulatory sequences or sites associated with expression of a gene, e.g. an endogenous polynucleotide encoding a protein which is involved in lipid metabolism or functional homolog thereof. For example, overexpression can be achieved by introducing one or more copies of the polynucleotide encoding a helper protein or a functional homologue operably linked to regulatory sequences (e.g. a promoter). For example, the gene can be operably linked to a strong constitutive promoter and/or strong ubiquitous promoter in order to reach high expression levels. Such promoters can be endogenous promoters or recombinant promoters. Alternatively, it is possible to remove regulatory sequences such that expression becomes constitutive. One can substitute the native promoter of a given gene with a heterologous promoter which increases expression of the gene or leads to constitutive expression of the gene. For example, the helper protein maybe overexpressed by more than 10%, 20%, 30%, 40%, 50%, 60%, 70%, 80%, 90%, 100%, 200%, or more than 300% by the host cell compared to the host cell prior to engineering and cultured under the same conditions. Using inducible promoters additionally makes it possible to increase the expression in the course of host cell cultivation. Furthermore, overexpression can also be achieved by, for example, modifying the chromosomal location of a particular gene, altering nucleic acid sequences adjacent to a particular gene such as a ribosome binding site or transcription terminator, modifying proteins (e.g., regulatory proteins, suppressors, enhancers, transcriptional activators and the like) involved in transcription of the gene and/or translation of the gene product, or any other conventional means of deregulating expression of a particular gene routine in the art including but not limited to use of antisense nucleic acid molecules, for example, to block expression of repressor proteins or deleting or mutating the gene for a transcriptional factor which normally represses expression of the gene desired to be overexpressed. Prolonging the life of the mRNA may also improve the level of expression. For example, certain terminator regions may be used to extend the half-lives of mRNA (Yamanishi et al., Biosci. Biotechnol. Biochem. (2011) 75:2234 and US 2013/0244243). If multiple copies of genes are included, the genes can either be located in plasmids of variable copy number or integrated and amplified in the chromosome. If the host cell does not comprise the gene encoding the helper protein, it is possible to introduce the gene into the host cell for expression. In this case, "overexpression" means expressing the gene product using any methods known to a skilled person in the art.

Those skilled in the art will find relevant instructions in Martin et al. (Bio/Technology 5, 137-146 (1987)), Guerrero et al. (Gene 138, 35-41 (1994)), Tsuchiya and Morinaga (Bio/Technology 6, 428-430 (1988)), Eikmanns et al. (Gene 102, 93-98 (1991)), EP 0 472 869, U.S. Pat. No. 4,601,893, Schwarzer and Pühler (Bio/Technology 9, 84-87 (1991)), Reinscheid et al. (Applied and Environmental Microbiology 60, 126-132 (1994)), LaBarre et al. (Journal of Bacteriology 175, 1001-1007 (1993)), WO 96/15246, Malumbres et al. (Gene 134, 15-24 (1993)), JP-A-10-229891, Jensen and Hammer (Biotechnology and Bioengineering 58, 191-195 (1998)) and Makrides (Microbiological Reviews 60, 512-538 (1996)), inter alia, and in well-known textbooks on genetics and molecular biology.

Helper Proteins

The helper proteins of the present invention were originally isolated from *Pichia pastoris* CBS7435 strain or in case of SEQ ID NO: 8 and 9 from *Saccharomyces cerevisiae*. The methylotrophic yeast *Pichia pastoris* (*Komagataella phaffii*) CBS7435 is the parental strain of commonly used *P. pastoris* recombinant protein production hosts. Its complete genomic sequence is described in Sturmberger et al. [J. Biotechnol. (2016). 235(4):121-131)]. The genes encoding the helper proteins identified herein have so far not been associated with a beneficial effect on protein yield. The complete genomic sequence of very closely related *Pichia pastoris* strain, GS115, is almost identical to the genomic sequence of CBS7435 (Nat. Biotechnol. 27 (6), 561-566) and the sequences of GS115 corresponding to the sequences of CBS7435 might also be used in the invention.

It is envisioned that the helper proteins can be overexpressed over a wide range of host cells. Thus, instead of using the sequences native to the species or the genus, the helper protein sequences may also be taken or derived from other prokaryotic or eukaryotic organisms. The foreign DNA sequences encoding the helper proteins may be obtained from a variety of sources, such as from a plant, insect, fungal or mammalian species, preferably from the class of Saccharomycetes, preferably from the order of Saccharomycetales, preferably from the family of Saccharomycetaceae, and preferably from the genus of *Komagataella*.

In particular, the invention refers to a genetically modified host cell which is capable of overexpressing the helper proteins comprising an amino acid sequence as shown in any one of SEQ ID NOs: 1-15 or functional homologues thereof alone or combinations thereof. Host cells being engineered to reflect a combination of helper proteins are envisaged in a preferred embodiment. These host cells are preferably applied in the methods and uses described herein. A combination includes that 2 or more, such as 2, 3, 4, 5, 6, 7, 8 or more, helper proteins or a functional homologue thereof are chosen from any one of SEQ ID NOs: 1-15.

Likewise, a combination includes a combination of one or more helper protein(s) chosen from any one of SEQ ID NOs: 1-15 and PP7435_Chr3-0788 (SUR2), PP7435_Chr3-1005 (PHS1), PP7435_Chr2-0350 (AUR1), PP7435_Chr4-0626 (IFA38), PP7435_Chr3-0669 (SCS7), PP7435_Chr3-0636 (CRD1), PP7435_Chr3-0950 (SLC4), PP7435_Chr2-0585 (PIS1), PP7435_chr1-0934 (PRY2), ARV1 (ORF not annotated; located between PP7435_Chr4-0493/0494), PP7435_Chr3-0741 (ARE2), PP7435_Chr4-0963 (FAD12), PP7435_Chr1-0794 (PSD1), PP7435_Chr1-0160 (SLC1), PP7435_CHR1-0078 (GPT2) PP7435_Chr3-1169 (DGK1) and PP7435_Chr2-0045 (CDS1) or a functional homologue thereof, which are overexpressed, and a helper protein chosen from any one of SEQ ID NOs: 16 or 17 or a functional homologue thereof, which are underexpressed. Host cells being engineered to reflect such a combination are envisaged in a preferred embodiment. These host cells may be applied in the methods and uses described herein.

The following helper proteins and combinations of helper proteins of the present invention involved in sphingolipid biosynthesis are preferably applied in host cell, methods and uses described herein:
(a) protein comprising the amino acid sequence as shown in SEQ ID NO: 1 or a functional homologue thereof, wherein the functional homologue has at least 30% sequence identity to an amino acid sequence as shown in SEQ ID NO: 1;
(b) protein comprising the amino acid sequence as shown in SEQ ID NO: 2 or a functional homologue thereof, wherein the functional homologue has at least 30% sequence identity to an amino acid sequence as shown in SEQ ID NO: 2;
(c) protein comprising the amino acid sequence as shown in SEQ ID NO: 3 or a functional homologue thereof, wherein the functional homologue has at least 30% sequence identity to an amino acid sequence as shown in SEQ ID NO: 3;
(d) proteins comprising the amino acid sequence as shown in SEQ ID NOs: 1 and 2 or a functional homologue thereof, wherein the functional homologue has at least 30% sequence identity to an amino acid sequence as shown in SEQ ID NOs: 1 and 2, respectively;
(e) proteins comprising the amino acid sequence as shown in SEQ ID NOs: 1 and 3 or a functional homologue thereof, wherein the functional homologue has at least 30% sequence identity to an amino acid sequence as shown in SEQ ID NOs: 1 and 3, respectively;
(f) proteins comprising the amino acid sequence as shown in SEQ ID NOs: 1, 3 and 4 or a functional homologue thereof, wherein the functional homologue has at least 30% sequence identity to an amino acid sequence as shown in SEQ ID NOs: 1, 3 and 4, respectively;
(g) proteins comprising the amino acid sequence as shown in SEQ ID NOs: 1, 3, 4 and 8 or a functional homologue thereof, wherein the functional homologue has at least 30% sequence identity to an amino acid sequence as shown in SEQ ID NOs: 1, 3, 4 and 8, respectively;
(h) proteins comprising the amino acid sequence as shown in SEQ ID NOs: 5 and 6 or a functional homologue thereof, wherein the functional homologue has at least 30% sequence identity to an amino acid sequence as shown in SEQ ID NOs: 5 and 6, respectively;
(i) proteins comprising the amino acid sequence as shown in SEQ ID NOs: 1 and 7 or a functional homologue thereof, wherein the functional homologue has at least 30% sequence identity to an amino acid sequence as shown in SEQ ID NOs: 1 and 7, respectively;
(j) proteins comprising the amino acid sequence as shown in SEQ ID NOs: 5, 6 and 9 or a functional homologue thereof, wherein the functional homologue has at least 30% sequence identity to an amino acid sequence as shown in SEQ ID NOs: 5, 6 and 9, respectively;
(k) proteins comprising the amino acid sequence as shown in SEQ ID NOs: 1, 5, 6 and 9 or a functional homologue thereof, wherein the functional homologue has at least 30% sequence identity to an amino acid sequence as shown in SEQ ID NOs: 1, 5, 6 and 9, respectively.

A combination of helper proteins of the present invention includes overexpressing at least one protein involved in sphingolipid biosynthesis and at least one protein involved in lipid transport. In a preferred combination applied in host cell, methods and uses described herein, the protein involved in sphingolipid biosynthesis comprises an amino acid sequence as shown in SEQ ID NO: 1 or a functional homologue thereof and the protein involved in lipid transport comprises an amino acid sequence as shown in SEQ ID NO: 11 or a functional homologue thereof, wherein the functional homologue has at least 30% sequence identity to an amino acid sequence as shown in SEQ ID NOs: 1 and 11, respectively.

A combination of helper proteins of the present invention includes overexpressing at least one protein involved in phospholipid biosynthesis and at least one protein involved in lipid transport. In a preferred combination applied in host cell, methods and uses described herein, the protein involved in phospholipid biosynthesis comprises an amino acid sequence as shown in SEQ ID NO: 10 or a functional homologue thereof and the protein involved in lipid transport comprises an amino acid sequence as shown in SEQ ID NO: 11 or a functional homologue thereof, wherein the functional homologue has at least 30% sequence identity to an amino acid sequence as shown in SEQ ID NOs: 10 and 11, respectively.

The present invention further pertains to overexpressing a chaperone in addition to the helper proteins of the present invention. The term "chaperone as used herein relates to polypeptides that assist the folding, unfolding, assembly or disassembly of other polypeptides. Preferably, the chaperone comprises an amino acid sequence as shown in SEQ ID NO: 18 or a functional homologue thereof, wherein the functional homologue has at least 30% sequence identity to an amino acid sequence as shown in SEQ ID NO: 18.

Accordingly, a combination of helper proteins of the present invention includes overexpressing at least one protein involved in sphingolipid biosynthesis and at least one chaperone. Preferably, the protein involved in sphingolipid biosynthesis comprises an amino acid sequence as shown in SEQ ID NO: 1 or a functional homologue thereof and the chaperone comprises an amino acid sequence as shown in SEQ ID NO: 18 or a functional homologue thereof, wherein the functional homologue has at least 30% sequence identity to an amino acid sequence as shown in SEQ ID NOs: 1 and 18, respectively.

A further combination of helper proteins of the present invention includes overexpressing at least one protein involved in ergosterol biosynthesis and at least one chaperone. Preferably, the protein involved in ergosterol biosynthesis comprises an amino acid sequence as shown in SEQ ID NO: 13, SEQ ID NO: 14 or SEQ ID NO: 15 or a functional homologue thereof and the chaperone comprises an amino acid sequence as shown in SEQ ID NO: 18 or a functional homologue thereof, wherein the functional homologue has at least 30% sequence identity to an amino acid sequence as shown in SEQ ID NOs: 13 and 18, respectively.

Protein of Interest

The term "protein of interest" (POI) as used herein refers to a protein that is produced by means of recombinant technology in a host cell. More specifically, the protein may either be a polypeptide not naturally occurring in the host cell, i.e. a heterologous protein, or else may be native to the host cell, i.e. a homologous protein to the host cell, but is produced, for example, by transformation with a self-replicating vector containing the nucleic acid sequence encoding the POI, or upon integration by recombinant techniques of one or more copies of the nucleic acid sequence encoding the POI into the genome of the host cell, or by recombinant modification of one or more regulatory sequences controlling the expression of the gene encoding the POI, e.g. of the promoter sequence. In general, the proteins of interest referred to herein may be produced by methods of recombinant expression well known to a person skilled in the art. A protein of interest is preferably not a membrane protein, i.e. a POI preferably is a non-membrane protein of interest.

Host Cell

As used herein, a "host cell" refers to a cell which is capable of protein expression and optionally protein secretion. Such host cell is applied in the methods of the present invention. For that purpose, for the host cell to over- or underexpress a polypeptide which is involved in lipid metabolism, a nucleotide sequence encoding said polypeptide is present or introduced in the cell. Host cells provided by the present invention can be eukaryotic host cells. More preferred are non-mammalian eukaryotic host cells. Even more preferred are fungal host cells. As will be appreciated by one of skill in the art, a prokaryotic cell lacks a membrane-bound nucleus, while a eukaryotic cell has a membrane-bound nucleus. Examples of eukaryotic cells include, but are not limited to, vertebrate cells, mammalian cells, human cells, animal cells, invertebrate cells, plant cells, nematodal cells, insect cells, stem cells, fungal cells or yeast cells.

Examples of yeast cells include but are not limited to the *Saccharomyces* genus (e.g. *Saccharomyces cerevisiae, Saccharomyces kluyveri, Saccharomyces uvarum*), the *Komagataella* genus (*Komagataella pastoris, Komagataella pseudopastoris* or *Komagataella phaffii*), *Kluyveromyces* genus (e.g. *Kluyveromyces lactis, Kluyveromyces marxianus*), the *Candida* genus (e.g. *Candida utilis, Candida cacaoi*), the *Geotrichum* genus (e.g. *Geotrichum fermentans*), as well as *Hansenula polymorpha* and *Yarrowia lipolytica,*

The genus *Pichia* is of particular interest. *Pichia* comprises a number of species, including the species *Pichia pastoris, Pichia methanolica, Pichia kluyveri*, and *Pichia angusta*. Most preferred is the species *Pichia pastoris*.

The former species *Pichia pastoris* has been divided and renamed to *Komagataella pastoris* and *Komagataella phaffii*. Therefore *Pichia pastoris* is synonymous for both *Komagataella pastoris* and *Komagataella phaffii*.

Examples for *Pichia pastoris* strains useful in the present invention are X33 and its subtypes GS115, KM71, KM71H; CBS7435 (mut+) and its subtypes CBS7435 mut$^s$, CBS7435 mut$^s$ΔArg, CBS7435 mut$^s$ΔHis, CBS7435 mut$^s$ΔArg, ΔHis, CBS7435 mut$^s$ PDI+, CBS 704 (=NRRL Y-1603=DSMZ 70382), CBS 2612 (=NRRL Y-7556), CBS 9173-9189 and DSMZ 70877 as well as mutants thereof. These yeast strains are available from cell repositories such as the American Tissue Culture Collection (ATCC), the "Deutsche Sammlung von Mikroorganismen und Zellkulturen" (DSMZ) in Braunschweig, Germany, or from the Dutch "Centraalbureau voor Schimmelcultures" (CBS) in Uetrecht, The Netherlands.

According a further preferred embodiment, the host cell is a *Pichia pastoris, Hansenula polymorpha, Trichoderma reesei, Saccharomyces cerevisiae, Kluyveromyces lactis, Yarrowia lipolytica, Pichia methanolica, Candida boidinii*, and *Komagataella*, and *Schizosaccharomyces pombe*. It may also be a host cell from *Ustilago maydis*. These yeast strains are available from cell repositories such as the American Tissue Culture Collection (ATCC), the "Deutsche Sammlung von Mikroorganismen und Zellkulturen" (DSMZ) in Braunschweig, Germany, or from the Dutch "Centraalbureau voor Schimmelcultures" (CBS) in Uetrecht, The Netherlands.

Examples of *E. coli* include those derived from *Escherichia coli* K12 strain, specifically, HMS 174, HMS174 (DE3), NM533, XL1-Blue, C600, DH1, HB101, JM109, as well as those derived from B-strains, specifically BL-21, BL21 (DE3) and the like. *E. coli* cells may be used, for example, for cloning purposes, but may also be used as host cells of the present invention. These bacterial strains are available from cell repositories such as the American Tissue Culture Collection (ATCC), the "Deutsche Sammlung von Mikroorganismen und Zellkulturen" (DSMZ) in Braunschweig, Germany, or from the Dutch "Centraalbureau voor Schimmelcultures" (CBS) in Uetrecht, The Netherlands.

Preferably, the helper proteins expressed by the host cell is from the same cell or recombined from a cell of the same species, genus or family. As used herein, "recombinant" refers to the alteration of genetic material by human intervention. Typically, recombinant refers to the manipulation of DNA or RNA in a virus, cell, plasmid or vector by molecular biology (recombinant DNA technology) methods, including cloning and recombination. A recombinant cell, polypeptide, or nucleic acid can be typically described with reference to how it differs from a naturally occurring counterpart (the "wild-type"). A "recombinant cell" or "recombinant host cell" refers to a cell or host cell that has been genetically altered to comprise a nucleic acid sequence which was not native to said cell.

The term "manufacture" or "manufacturing" as used presently refers to the process in which the protein of interest is expressed. A "host cell for manufacturing a protein of interest" refers to a host cell in which nucleic acid sequences encoding a protein of interest may be introduced. The recombinant host cell within the present invention does not necessarily contain the nucleic acid sequences encoding a protein of interest. It is appreciated by a skilled person in the art that the host cells can be provided for inserting desired nucleotide sequences into the host cell, for example, in a kit. "Manufacturing" or "manufacture" also refers to a process of producing a POI using a host cell of the present invention, cultivating the host cell of the present invention under suitable conditions to overexpress the protein involved in lipid metabolism or functional homologue thereof and express said protein of interest, and optionally isolating said protein of interest from the cell culture.

The term "nucleotide sequence" or "nucleic acid sequence" used herein refers to either DNA or RNA. "Nucleic acid sequence" or "polynucleotide sequence" or simply "polynucleotide" refers to a single or double-stranded polymer of deoxyribonucleotide or ribonucleotide bases read from the 5' to the 3' end. It includes both self-replicating plasmids, infectious polymers of DNA or RNA, and non-functional DNA or RNA.

The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, γ-carboxyglutamate, and O-phosphoserine. Amino acid analogs refers to compounds that have the same basic chemical structure as a naturally occurring amino acid, i.e., a carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. Amino acid mimetics refers to chemical compounds that have a structure that is different from the general chemical structure of an amino acid, but that function in a manner similar to a naturally occurring amino acid.

The terms "polypeptide" and "protein" are interchangeably used. The term "polypeptide" refers to a protein or peptide that contains two or more amino acids, typically at least 3, preferably at least 20, more preferred at least 30, such as at least 50 amino acids. Accordingly, a polypeptide comprises an amino acid sequence, and, thus, sometimes a polypeptide comprising an amino acid sequence is referred to herein as a "polypeptide comprising a polypeptide sequence". Thus, herein the term "polypeptide sequence" is interchangeably used with the term "amino acid sequence". As mentioned, overexpression can be achieved by insertion of one or more than one extra copy of the selected helper protein. According to a preferred embodiment, the polynucleotide encoding the helper protein can be presented in a single copy or in multiple copies per cell. The copies may be adjacent to or distant from each other. According to another preferred embodiment, the method of the invention employs recombinant nucleotide sequences encoding the helper proteins provided on one or more plasmids suitable for integration into the genome of the host cell, in a single copy or in multiple copies per cell. The copies may be adjacent to or distant from each other. Overexpression can be in one embodiment achieved by expressing one or multiple copies of the polynucleotide, such as 2, 3, 4, 5, 6 or more copies of said polynucleotide per host cell. The polynucleotides are preferably operably linked to transcriptional and translational regulatory sequences that provide for expression of the polypeptide in the host cells. The term "transcriptional regulatory sequences" as used herein refers to nucleotide sequences that are associated with a gene nucleic acid sequence and which regulate the transcription of the gene. The term "translational regulatory sequences" as used herein refers to nucleotide sequences that are associated with a gene nucleic acid sequence and which regulate the translation of the gene. Transcriptional and/or translational regulatory sequences can either be located in plasmids or vectors or integrated in the chromosome of the host cell. Transcriptional and/or translational regulatory sequences are located in the same nucleic acid molecule of the gene which it regulates. Preferably, the overexpression can be achieved by having 1, 2, 3, 4 or more copies of a polynucleotide encoding a helper protein comprising an amino acid sequence shown in any one of SEQ ID NOs: 1-15 or functional homologues thereof per host cell or by having 1, 2, 3, 4, 5, 6, 7, 8, 9, 10, 11, 12, 13, 14, 15, 16, 17, 18, 19 or 20 copies of a polynucleotide encoding a helper protein comprising an amino acid sequence shown in any one of SEQ ID NOs: 1-15 or functional homologues thereof per host cell.

The polynucleotide encoding the helper protein and/or the polynucleotide encoding the POI is/are preferably integrated into the genome of the host cell. The term "genome" generally refers to the whole hereditary information of an organism that is encoded in the DNA (or RNA for certain viral species). It may be present in the chromosome, on a plasmid or vector, or both. Preferably, the polynucleotide encoding the helper protein is integrated into the chromosome of said cell.

The polynucleotide encoding the helper protein or functional homologue thereof may be integrated in its natural locus. "Natural locus" means the location on a specific chromosome, where the polynucleotide encoding the helper protein is located, for example at the natural locus of the gene encoding a helper protein of the present invention. Any such gene can be identified in accordance with the gene identifier as shown in Table 1, above. However, in another embodiment, the polynucleotide encoding the helper protein is present in the genome of the host cell not at their natural locus, but integrated ectopically. The term "ectopic integration" means the insertion of a nucleic acid into the genome of a microorganism at a site other than its usual chromosomal locus, i.e., predetermined or random integration. In the alternative, the polynucleotide encoding the helper protein or functional homologue thereof may be integrated in its natural locus and ectopically.

For yeast cells, the polynucleotide encoding the helper protein and/or the polynucleotide encoding the POI may be inserted into a desired locus, such as but not limited to AOX1, GAP, ENO1, TEF, HIS4 (Zamir et al., Proc. NatL Acad. Sci. USA (1981) 78(6):3496-3500), HO (Voth et al. Nucleic Acids Res. 2001 Jun. 15; 29(12): e59), TYR1 (Mirisola et al., Yeast 2007; 24: 761-766), His3, Leu2, Ura3 (Taxis et al., BioTechniques (2006) 40:73-78), Lys2, ADE2, TRP1, GAL1, ADH1 or on the integration of 5S ribosomal RNA gene.

In other embodiments, the polynucleotide encoding the helper protein and/or the polynucleotide encoding the POI can be integrated in a plasmid or vector. The terms "plasmid" and "vector" include autonomously replicating nucleotide sequences as well as genome integrating nucleotide sequences. A skilled person is able to employ suitable plasmids or vectors depending on the host cell used.

Preferably, the plasmid is a eukaryotic expression vector, preferably a yeast expression vector.

Plasmids can be used for the transcription of cloned recombinant nucleotide sequences, i.e. of recombinant genes and the translation of their mRNA in a suitable host organism. Plasmids can also be used to integrate a target polynucleotide into the host cell genome by methods known in the art, such as described by J. Sambrook et al., Molecular Cloning: A Laboratory Manual (3rd edition), Cold Spring Harbor Laboratory, Cold Spring Harbor Laboratory Press, New York (2001). A "plasmid" usually comprise an origin for autonomous replication in the host cells, selectable markers, a number of restriction enzyme cleavage sites, a suitable promoter sequence and a transcription terminator, which components are operably linked together. The polypeptide coding sequence of interest is operably linked to transcriptional and translational regulatory sequences that provide for expression of the polypeptide in the host cells.

A nucleic acid is "operably linked" when it is placed into a functional relationship with another nucleic acid sequence on the same nucleic acid molecule. For example, a promoter is operably linked with a coding sequence of a recombinant gene when it is capable of effecting the expression of that coding sequence.

Most plasmids exist in only one copy per bacterial cell. Some plasmids, however, exist in higher copy numbers. For example, the plasmid ColE1 typically exists in 10 to 20 plasmid copies per chromosome in E. coli. If the nucleotide sequences of the present invention are contained in a plasmid, the plasmid may have a copy number of 1-10, 10-20, 20-30, 30-100 or more per host cell. With a high copy number of plasmids, it is possible to overexpress helper proteins by the cell.

Large numbers of suitable plasmids or vectors are known to those of skill in the art and many are commercially available. Examples of suitable vectors are provided in Sambrook et al, eds., Molecular Cloning: A Laboratory Manual (2nd Ed.), Vols. 1-3, Cold Spring Harbor Laboratory (1989), and Ausubel et al, eds., Current Protocols in Molecular Biology, John Wiley & Sons, Inc., New York (1997).

A vector or plasmid of the present invention encompass yeast artificial chromosome, which refers to a DNA construct that can be genetically modified to contain a heterologous DNA sequence (e.g., a DNA sequence as large as 3000 kb), that contains telomeric, centromeric, and origin of replication (replication origin) sequences.

A vector or plasmid of the present invention also encompasses bacterial artificial chromosome (BAC), which refers to a DNA construct that can be genetically modified to contain a heterologous DNA sequence (e.g., a DNA sequence as large as 300 kb), that contains an origin of replication sequence (Ori), and may contain one or more helicases (e.g., parA, parB, and parC).

Examples of plasmids using yeast as a host include YIp type vector, YEp type vector, YRp type vector, YCp type vector (Yxp vectors are e.g. described in Romanos et al. 1992, Yeast. 8(6):423-488), pGPD-2 (described in Bitter et al., 1984, Gene, 32:263-274), pYES, pAO815, pGAPZ, pGAPZα, pHIL-D2, pHIL-S1, pPIC3.5K, pPIC9K, pPICZ, pPICZα, pPIC3K, pPINK-HC, pPINK-LC (all available from Thermo Fisher Scientific/Invitrogen), pHWO10 (described in Waterham et al., 1997, Gene, 186:37-44), pPZeoR, pPKanR, pPUZZLE and pPUZZLE-derivatives (described in Stadlmayr et al., 2010, J Biotechnol. 150(4): 519-29; Marx et al. 2009, FEMS Yeast Res. 9(8):1260-70.); pJ-vectors (e.g. pJAN, pJAG, pJAZ and their derivatives; all available from BioGrammatics, Inc), pJexpress-vectors, pD902, pD905, pD915, pD912 and their derivatives, pD12xx, pJ12xx (all available from ATUM/DNA2.0), pRG plasmids (described in Gnijgge et al., 2016, Yeast 33:83-98) 2 μm plasmids (described e.g. in Ludwig et al., 1993, Gene 132(1):33-40). Such vectors are known and are for example described in Cregg et al., 2000, Mol Biotechnol. 16(1):23-52 or Ahmad et al. 2014., Appl Microbiol Biotechnol. 98(12): 5301-17. Additionally suitable vectors can be readily generated by advanced modular cloning techniques as for example described by Lee et al. 2015, ACS Synth Biol. 4(9):975-986; Agmon et al. 2015, ACS Synth. Biol., 4(7): 853-859; or Wagner and Alper, 2016, Fungal Genet Biol. 89:126-136. Additionally, these and other suitable vectors may be also available from Addgene.

Examples of plasmids using Escherichia coli as their host include pBR322 (available e.g. from New England Biolabs and ThermoFisher Scientific), pBAD-vectors, pET-vector series (both available from e.g. ThermoFisher Scientific, pET vectors also from Novagen), pUC18, pUC19, pUC118/119 (all available from e.g Takara), pVC119 (described in Del Sol et al., 2006, J Bacteriol. 188(4):1540-1550), pSP64, pSP65 (both from Promega), pTZ-18R/-18U (from Amersham), pTZ-19R/-19U (available from Sigma-Aldrich), pGEM-3, pGEM-4, pGEM-3Z, pGEM-4Z, pGEM-5Zf(−) (pGEM vectors are available from Promega), and pBluescript KS (available from Agilent). Examples of plasmids suitable for expression in Escherichia coli include, pKK223 (described in Brosius and Holy, 1984, Proc. Natl. Acad. Sci. U.S.A. 81:6929-6933), pMC1403, pMC931 (both described in Casadaban et al. 1980, J Bacteriol. 143(2):971-980), and pKC30 (described in Rao, 1984, Gene 31(1-3):247-250). Additionally, these and other suitable vectors may be also available from Addgene.

Promoter

Overexpression of the endogenous polypeptide in the recombinant cell can be achieved by modifying transcriptional and translational regulatory sequences, including, for example, promoters, enhancers, polyadenylation signals, transcription terminators, internal ribosome entry sites (IRES), and the like, that provide for the expression of the polynucleotide sequence in a host cell. Such sequences interact specifically with cellular proteins involved in transcription (Maniatis et al., Science, 236: 1237-1245 (1987)). Exemplary sequences are described in, for example, Goeddel, Gene Expression Technology: Methods in Enzymology, Vol. 185, Academic Press, San Diego, Calif. (1990).

For example, overexpression of the endogenous helper protein in the recombinant cell can be achieved by modifying the promoters, for example, by replacing the endogenous promoter which is operably linked to the helper protein with another stronger promoter in order to reach high expression levels. Such promoter may be inducible or constitutive. Modification of endogenous promoter may be performed by mutation or homologous recombination using methods known in the art.

The overexpression of the polynucleotide encoding the helper proteins, can be achieved by other methods known in the art, for example by genetically modifying their endogenous regulatory regions, as described by Marx et al., 2008 (Marx, H., Mattanovich, D. and Sauer, M. Microb Cell Fact 7 (2008): 23), and Pan et al., 2011 (Pan et al., FEMS Yeast Res. (2011) May; (3):292-8.), such methods include, for example, integration of a recombinant promoter that increases expression of the helper proteins. Transformation is described in Cregg et al. (1985) Mol. Cell. Biol. 5:3376-3385. A "recombinant" promoter is referred to with respect to the sequence whose expression it drives. As used herein, a recombinant promoter means when the promoter is not a native promoter to the given sequence, i.e., when the promoter is different from a naturally occurring promoter (the "native promoter"). Such a promoter is sometimes also referred to herein as heterologous promoter.

The term "promoter" as used herein refers to a region that facilitates the transcription of a particular gene. A promoter typically increases the amount of recombinant product expressed from a nucleotide sequence as compared to the amount of the expressed recombinant product when no promoter exists. A promoter from one organism can be utilized to enhance recombinant product expression from a sequence that originates from another organism. The promoter can be integrated into a host cell chromosome by homologous recombination using methods known in the art (e.g. Datsenko et al, Proc. Natl. Acad. Sci. U.S.A., 97(12): 6640-6645 (2000)). In addition, one promoter element can increase the amount of products expressed for multiple sequences attached in tandem. Hence, one promoter element can enhance the expression of one or more recombinant products.

Promoter activity may be assessed by its transcriptional efficiency. This may be determined directly by measurement of the amount of mRNA transcription from the promoter, e.g. by Northern Blotting, quantitative PCR or indirectly by measurement of the amount of gene product expressed from the promoter.

The promoter could be an "inducible promoter" or "constitutive promoter." "Inducible promoter" refers to a promoter which can be induced by the presence or absence of certain factors, and "constitutive promoter" refers to an unregulated promoter that allows for continuous transcription of its associated gene or genes.

In a preferred embodiment, both the transcription of the nucleotide sequences encoding the helper protein and the POI are each driven by an inducible promoter. In another preferred embodiment, both the transcription of the nucleotide sequences encoding the helper protein and the POI are each driven by a constitutive promoter. In yet another preferred embodiment, the transcription of the nucleotide sequence encoding the helper protein is driven by a constitutive promoter and the transcription of the nucleotide sequence encoding the POI is driven by an inducible promoter. In yet another preferred embodiment, the transcription of the nucleotide sequences encoding the helper protein is driven by an inducible promoter and the transcription of the nucleotide sequence encoding the POI is driven by a constitutive promoter. As an example, the transcription of the helper protein gene may be driven by a constitutive GAP promoter and the transcription of the nucleotide sequence encoding the POI may be driven by an inducible AOX1 promoter. In one embodiment, the transcription of the nucleotide sequences encoding the helper protein and the POI is driven by the same promoter or similar promoters in terms of promoter activity and/or expression behaviour.

Many inducible promoters are known in the art. Many are described in a review by Gatz, Curr. Op. Biotech., 7: 168 (1996) (see also Gatz, Ann. Rev. Plant. Physiol. Plant Mol. Biol., 48:89 (1997)). Examples include tetracycline repressor system, Lac repressor system, copper-inducible systems, salicylate-inducible systems (such as the PR1 a system), glucocorticoid-inducible (Aoyama et al., 1997), alcohol-inducible systems, e.g., AOX promoters, and ecdysone-inducible systems. Also included are the benzene sulphonamide-inducible (U.S. Pat. No. 5,364,780) and alcohol-inducible (WO 97/06269 and WO 97/06268) inducible systems and glutathione S-transferase promoters.

Suitable promoter sequences for use with yeast host cells are described in Mattanovich et al., Methods Mol. Biol. (2012) 824:329-58 and include glycolytic enzymes like triosephosphate isomerase (TPI), phosphoglycerate kinase (PGK), glyceraldehyde-3-phosphate dehydrogenase (GAPDH or GAP) and variants thereof, lactase (LAC) and galactosidase (GAL), P. pastoris glucose-6-phosphate isomerase promoter (PPGI), the 3-phosphoglycerate kinase promoter (PPGK), the glycerol aldehyde phosphate dehydrogenase promoter (PGAP), translation elongation factor promoter (PTEF), and the promoters of P. pastoris enolase 1 (PENO1), triose phosphate isomerase (PTPI), ribosomal subunit proteins (PRPS2, PRPS7, PRPS31, PRPL1), alcohol oxidase promoter (PAOX) or variants thereof with modified characteristics, the formaldehyde dehydrogenase promoter (PFLD), isocitrate lyase promoter (PICL), alpha-ketoisocaproate decarboxylase promoter (PTHI), the promoters of heat shock protein family members (PSSA1, PHSP90, PKAR2), 6-Phosphogluconate dehydrogenase (PGND1), phosphoglycerate mutase (PGPM1), transketolase (PTKL1), phosphatidylinositol synthase (PPIS1), ferro-O2-oxidoreductase (PFET3), high affinity iron permease (PFTR1), repressible alkaline phosphatase (PPHO8), N-myristoyl transferase (PNMT1), pheromone response transcription factor (PMCM1), ubiquitin (PUBI4), single-stranded DNA endonuclease (PRAD2), the promoter of the major ADP/ATP carrier of the mitochondrial inner membrane (PPET9) (WO2008/128701) and the formate dehydrogenase (FMD) promoter. The GAP promoter, AOX promoter or a promoter derived from GAP or AOX promoter is particularly preferred. AOX promoters can be induced by methanol and are repressed by e.g. glucose.

Further examples of suitable promoters include Saccharomyces cerevisiae enolase (ENO-1), Saccharomyces cerevisiae galactokinase (GAL1), Saccharomyces cerevisiae alcohol dehydrogenase/glyceraldehyde-3-phosphate dehydrogenase (ADH1, ADH2/GAP), Saccharomyces cerevisiae triose phosphate isomerase (TPI), Saccharomyces cerevisiae metallothionein (CUP1), and Saccharomyces cerevisiae 3-phosphoglycerate kinase (PGK), and the maltase gene promoter (MAL).

Other useful promoters for yeast host cells are described by Romanos et al, 1992, Yeast 8:423-488.

Suitable promoter sequences for use with E. coli include T7 promoter, T5 promoter, tryptophan (trp) promoter, lactose (lac) promoter, tryptophan/lactose (tac) promoter, lipoprotein (lpp) promoter, and λ phage PL promoter in plasmids.

The promoter which drives the expression of the polynucleotide encoding the helper protein is preferably not the endogenous to the promoter of the helper gene. Preferably, a recombinant promoter is used instead of the endogenous promoter of the helper protein gene.

Enhancer

In a preferred embodiment, the overexpression is achieved by using an enhancer to enhance the promoter activity which drives the expression of the helper protein. Transcriptional enhancers are relatively orientation and position independent, having been found 5' and 3' to the transcription unit, within an intron, as well as within the coding sequence itself. The enhancer may be spliced into the expression vector at a position 5' or 3' to the coding sequence, but is preferably located at a site 5' from the promoter. Most yeast genes contain only one UAS, which generally lies within a few hundred base pairs of the cap site and most yeast enhancers (UASs) cannot function when located 3' of the promoter, but enhancers in higher eukaryotes can function both 5' and 3' of the promoter.

Many enhancer sequences are now known from mammalian genes (globin, RSV, SV40, EMC, elastase, albumin, a-fetoprotein and insulin). One may also use an enhancer from a eukaryotic cell virus, such as the SV40 late enhancer, the cytomegalovirus early promoter enhancer, the polyoma enhancer on the late side of the replication origin, and adenovirus enhancers. Yeast enhancers, also called upstream activating sequences (UASs), such as the UAS/GAL system from Saccharomyces cerevisiae, can be advantageously used with yeast promoters (described in European Patent No. 0317254 and Rudoni et al., The International Journal of Biochemistry and Cell Biology, (2000), 32(2):215-224).

In a preferred embodiment, 2, 3, 4, 5, 6, 7, 8, 9 or more types of helper proteins disclosed by present invention are overexpressed. For example, the host cell can be engineered to overexpress 2, 3, 4, 5, 6, 7, 8, 9 or more of helper proteins selected from any one of SEQ ID NOs: 1-15 or functional homologues thereof, where a functional homologue thereof comprises an amino acid having at least 30% sequence identity to any one of SEQ ID NOs: 1-15, respectively. In a further embodiment the host cell can be engineered to overexpress 2, 3, 4, 5, 6, 7, 8, 9 or more of helper proteins selected from any one of SEQ ID NOs: 1-15, PP7435_Chr3-

0788 (SUR2), PP7435_Chr3-1005 (PHS1), PP7435_Chr2-0350 (AUR1), PP7435_Chr4-0626 (IFA38), PP7435_Chr3-0669 (SCS7), PP7435_Chr3-0636 (CRD1), PP7435_Chr3-0950 (SLC4), PP7435_Chr2-0585 (PIS1), PP7435_chr1-0934 (PRY2), ARV1 (ORF not annotated; located between PP7435_Chr4-0493/0494), PP7435_Chr3-0741 (ARE2), PP7435_Chr4-0963 (FAD12), PP7435_Chr1-0794 (PSD1), PP7435_Chr1-0160 (SLC1), PP7435_CHR1-0078 (GPT2) PP7435_Chr3-1169 (DGK1) and PP7435_Chr2-0045 (CDS1) or functional homologues thereof, where a functional homologue thereof comprises an amino acid having at least 30% sequence identity to any one of SEQ ID NOs: 1-15, PP7435_Chr3-0788 (SUR2), PP7435_Chr3-1005 (PHS1), PP7435_Chr2-0350 (AUR1), PP7435_Chr4-0626 (IFA38), PP7435_Chr3-0669 (SCS7), PP7435_Chr3-0636 (CRD1), PP7435_Chr3-0950 (SLC4), PP7435_Chr2-0585 (PIS1), PP7435_chr1-0934 (PRY2), ARV1 (ORF not annotated; located between PP7435_Chr4-0493/0494), PP7435_Chr3-0741 (ARE2), PP7435_Chr4-0963 (FAD12), PP7435_Chr1-0794 (PSD1), PP7435_Chr1-0160 (SLC1), PP7435_CHR1-0078 (GPT2) PP7435_Chr3-1169 (DGK1) and PP7435_Chr2-0045 (CDS1), respectively.

Protein of Interest

It is envisioned that when the host cell may be cultured under a suitable condition for the overexpression of the helper protein and the protein of interest, the host cell would express the protein of interest and overexpresses the polynucleotide encoding a helper protein comprising an amino acid sequence as shown in any one of SEQ ID NOs: 1-15 or a functional homologue thereof, wherein the functional homologue has at least 30% sequence identity to an amino acid sequence as shown in any one of SEQ ID NOs: 1-15, respectively. It is further envisioned that when the host cell may be cultured under a suitable condition for the coexpression of the helper protein and the protein of interest, the host cell would express the protein of interest and overexpresses the polynucleotide encoding a helper protein comprising an amino acid sequence as shown in any one of SEQ ID NOs: 1-15, PP7435_Chr3-0788 (SUR2), PP7435_Chr3-1005 (PHS1), PP7435_Chr2-0350 (AUR1), PP7435_Chr4-0626 (IFA38), PP7435_Chr3-0669 (SCS7), PP7435_Chr3-0636 (CRD1), PP7435_Chr3-0950 (SLC4), PP7435_Chr2-0585 (PIS1), PP7435_chr1-0934 (PRY2), ARV1 (ORF not annotated; located between PP7435_Chr4-0493/0494), PP7435_Chr3-0741 (ARE2), PP7435_Chr4-0963 (FAD12), PP7435_Chr1-0794 (PSD1), PP7435_Chr1-0160 (SLC1), PP7435_CHR1-0078 (GPT2) PP7435_Chr3-1169 (DGK1) and PP7435_Chr2-0045 (CDS1) or a functional homologue thereof, wherein the functional homologue has at least 30% sequence identity to an amino acid sequence as shown in any one of SEQ ID NOs: 1-15, PP7435_Chr3-0788 (SUR2), PP7435_Chr3-1005 (PHS1), PP7435_Chr2-0350 (AUR1), PP7435_Chr4-0626 (IFA38), PP7435_Chr3-0669 (SCS7), PP7435_Chr3-0636 (CRD1), PP7435_Chr3-0950 (SLC4), PP7435_Chr2-0585 (PIS1), PP7435_chr1-0934 (PRY2), ARV1 (ORF not annotated; located between PP7435_Chr4-0493/0494), PP7435_Chr3-0741 (ARE2), PP7435_Chr4-0963 (FAD12), PP7435_Chr1-0794 (PSD1), PP7435_Chr1-0160 (SLC1), PP7435_CHR1-0078 (GPT2) PP7435_Chr3-1169 (DGK1) and PP7435_Chr2-0045 (CDS1), respectively.

The term "protein of interest" (POI) as used herein refers to a protein that is produced by means of recombinant technology in a host cell. More specifically, the protein may either be a polypeptide not naturally occurring in the host cell, i.e. a heterologous protein, or else may be native to the host cell, i.e. a homologous protein to the host cell, but is produced, for example, by transformation with a self-replicating vector containing the nucleic acid sequence encoding the POI, or upon integration by recombinant techniques of one or more copies of the nucleic acid sequence encoding the POI into the genome of the host cell, or by recombinant modification of one or more regulatory sequences controlling the expression of the gene encoding the POI, e.g. of the promoter sequence. In general, the proteins of interest referred to herein may be produced by methods of recombinant expression well known to a person skilled in the art.

There is no limitation with respect to the protein of interest (POI). The POI is usually a eukaryotic or prokaryotic polypeptide, variant or derivative thereof. The POI can be any eukaryotic or prokaryotic protein. Examples of POIs are described in Schmidt, Appl. Microbiol. Biotechnol. (2004), 65: 363-372 or in Kirk et al., Curr. Opin. Biotechnol. (2002), 13: 345-351. Any of the proteins mentioned in Tables 1 and 2 of Schmidt and in Table 1 of Kirk et al. is encompassed by the term "POI" as used herein. The protein can be a naturally secreted protein or an intracellular protein, i.e. a protein which is not naturally secreted. The present invention also includes biologically active fragments of proteins. In another embodiment, a POI may be an amino acid chain or present in a complex, such as a dimer, trimer, hetero-dimer, multimer or oligomer.

The protein of interest may be a protein used as nutritional, dietary, digestive, supplements, such as in food products, feed products, or cosmetic products. The food products may be, for example, bouillon, desserts, cereal bars, confectionery, sports drinks, dietary products or other nutrition products. Preferably, the protein of interest is a food additive.

In another embodiment, the protein of interest may be used in animal feeds. The POI may be a detoxifying enzyme such as a mycotoxin degrading enzyme. Mycotoxin degrading enzymes include aflatoxin detoxizyme, zearalenone esterases, zearalenone lactonases, zearalenone hydrolase, fumonisin carboxylesterases, fumonisin aminotransferases, aminopolyol amine oxidases, deoxynivalenol epoxide hydrolases. The POI may also be an enzyme which degrades ochratoxin derivatives or ergot alkaloid. These compounds are toxic to living organisms including humans and farm animals. Examples of such enzymes include ochratoxin amidase, ergotamine hydrolase, ergotamine amylase. Mycotoxin degrading enzymes in animal feed is useful in controlling mycotoxin contamination of feed.

Further examples of POI include anti-microbial proteins, such as lactoferrin, lysozyme, lactoferricin, lactohedrin, kappa-casein, haptocorrin, lactoperoxidase, a milk protein, acute-phase proteins, e.g., proteins that are produced normally in production animals in response to infection. Examples of enzymes which can be used as feed additive include phytase, xylanase and β-glucanase. A "food" means any natural or artificial diet meal or the like or components of such meals intended or suitable for being eaten, taken in, digested, by a human being.

Examples of enzymes which can be used as food additive include protease, lipase, lactase, pectin methyl esterase, pectinase, transglutaminase, amylase, β-glucanase, acetolactate decarboxylase and laccase.

Enzyme

A POI may be an enzyme. Preferred enzymes are those which can be used for industrial application, such as in the manufacturing of a detergent, starch, fuel, textile, pulp and paper, oil, personal care products, or such as for baking, organic synthesis, and the like. (see Kirk et al., Current Opinion in Biotechnology (2002) 13:345-351)

Therapeutic Protein

A POI may be a therapeutic protein. A POI may be but is not limited to a protein suitable as a biopharmaceutical substance like an antibody or antibody fragment, or antibody derived scaffold, single domain antibodies and derivatives thereof other not antibody derived affinity scaffolds, growth factor, hormone, enzyme, vaccine, etc. as described in more detail herein.

Preferably, the protein of interest is a mammalian polypeptide or even more preferably a human polypeptide. Especially preferred therapeutic proteins, which refer to any polypeptide, protein, protein variant, fusion protein and/or fragment thereof which may be administered to a mammal. It is envisioned but not required that therapeutic protein according to the present invention is heterologous to the cell. Examples of proteins that can be produced by the cell of the present invention are, without limitation, enzymes, regulatory proteins, receptors, peptide hormones, growth factors, cytokines, scaffold binding proteins (e.g. anticalins), structural proteins, lymphokines, adhesion molecules, receptors, and any other polypeptides that can serve as agonists or antagonists and/or have therapeutic or diagnostic use. Moreover, the proteins of interest may be antigens as used for vaccination, vaccines, antigen-binding proteins, immune stimulatory proteins.

Such therapeutic proteins include, but are not limited to, insulin, insulin-like growth factor, hGH, tPA, cytokines, e.g. interleukines such as IL-1, IL-2, IL-3, IL-4, IL-5, IL-6, IL-7, IL-8, IL-9, IL-10, IL-11, IL-12, IL-13, IL-14, IL-15, IL-16, IL-17, IL-18, interferon (IFN) alpha, IFN beta, IFN gamma, IFN omega or IFN tau, tumor necrosisfactor (TNF) TNF alpha and TNF beta, TRAIL; G-CSF, GM-CSF, M-CSF, MCP-1 and VEGF.

In a preferred embodiment, the protein is an antibody. The term "antibody" is intended to include any polypeptide chain-containing molecular structure with a specific shape that fits to and recognizes an epitope, where one or more non-covalent binding interactions stabilize the complex between the molecular structure and the epitope. The archetypal antibody molecule is the immunoglobulin, and all types of immunoglobulins, IgG, IgM, IgA, IgE, IgD, IgY, etc., from all sources, e.g. human, rodent, rabbit, cow, sheep, pig, dog, other mammals, chicken, other avians, etc., are considered to be "antibodies." For example, an antibody fragment may include but not limited to Fv (a molecule comprising the VL and VH), single-chain Fv (scFV) (a molecule comprising the VL and VH connected with by peptide linker), Fab, Fab', F(ab)$_2$, single domain antibody (sdAb) (molecules comprising a single variable domain and 3 CDR), and multivalent presentations thereof. The antibody or fragments thereof may be murine, human, humanized or chimeric antibody or fragments thereof. Examples of therapeutic proteins include an antibody, polyclonal antibody, monoclonal antibody, recombinant antibody, antibody fragments, such as Fab', F(ab')2, Fv, scFv, di-scFvs, bi-scFvs, tandem scFvs, bispecific tandem scFvs, sdAb, nanobodies, $V_H$, and $V_L$, or human antibody, humanized antibody, chimeric antibody, IgA antibody, IgD antibody, IgE antibody, IgG antibody, IgM antibody, intrabody, diabody, tetrabody, minibody or monobody.

Further examples of therapeutic proteins include blood coagulation factors (VII, VIII, IX), alkaline protease from *Fusarium*, calcitonin, CD4 receptor darbepoetin, DNase (cystic fibrosis), erythropoetin, eutropin (human growth hormone derivative), follicle stimulating hormone (follitropin), gelatin, glucagon, glucocerebrosidase (Gaucher disease), glucosamylase from *A. niger*, glucose oxidase from *A. niger*, gonadotropin, growth factors (GCSF, GMCSF), growth hormones (somatotropines), hepatitis B vaccine, hirudin, human antibody fragment, human apolipoprotein AI, human calcitonin precursor, human collagenase IV, human epidermal growth factor, human insulin-like growth factor, human interleukin 6, human laminin, human proapolipoprotein AI, human serum albumin, insulin, insulin and muteins, insulin, interferon alpha and muteins, interferon beta, interferon gamma (mutein), interleukin 2, luteinization hormone, monoclonal antibody 5T4, mouse collagen, OP-1 (osteogenic, neuroprotective factor), oprelvekin (interleukin 11-agonist), organophosphohydrolase, PDGF-agonist, phytase, platelet derived growth factor (PDGF), recombinant plasminogen-activator G, staphylokinase, stem cell factor, tetanus toxin fragment C, tissue plasminogen-activator, and tumor necrosis factor (see Schmidt, Appl Microbiol Biotechnol (2004) 65:363-372).

Leader Sequence

The protein of interest may be linked with a leader sequence which causes secretion of the POI from the host cell. The presence of such a secretion leader sequence in the expression vector is required when the POI intended for recombinant expression and secretion is a protein which is not naturally secreted and therefore lacks a natural secretion leader sequence, or its nucleotide sequence has been cloned without its natural secretion leader sequence. In general, any secretion leader sequence effective to cause secretion of the POI from the host cell may be used in the present invention. The secretion leader sequence may originate from yeast source, e.g. from yeast α-factor such as MFa of *Saccharomyces cerevisiae*, or yeast phosphatase, from mammalian or plant source, or others. The selection of the appropriate secretion leader sequence is apparent to a skilled person. Alternatively, the secretion leader sequence can be fused to the nucleotide sequence encoding a POI intended for recombinant expression by conventional cloning techniques known to a skilled person prior to cloning of the nucleotide sequence in the expression vector or the nucleotide sequence encoding a POI comprising a natural secretion leader sequence is cloned in the expression vector. In these cases the presence of a secretion leader sequence in the expression vector is not required.

The recombinant nucleotide sequence(s) encoding the POI(s), as well as those encoding the helper proteins, may also be provided on one or more autonomously replicating plasmids in a single copy or in multiple copies per cell.

Alternatively, the recombinant nucleotide sequence encoding the POI and the recombinant nucleotide sequence encoding a helper protein are present on the same plasmid in single copy or multiple copies per cell.

Underexpression of Helper Proteins

The inventors have also identified several helper proteins (KO helper proteins) involved in lipid storage whose expression was observed to have a negative impact on the yield of POI from a host cell. Such helper proteins a negative impact on the yield of POI from a host cell are preferably not transcription factors. Preferred are helper protein comprising an amino acid sequence shown in any one of SEQ ID NOs: 16 or 17, or functional homologues thereof, A functional homologue of a helper protein comprising an amino acid sequence shown in any one of SEQ ID NOs: 16 or 17 has at least 30%, such as at least 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99 or 100%, sequence identity to an amino acid sequence shown in any one of SEQ ID NOs: 16 or 17. Furthermore, it has been discovered that a modification of the genes encoding the KO helper proteins of SEQ ID NOs: 16 or 17 such as mutation or deletion is able to increase the yield of POI. This disclosure provides methods and materials useful for further improving the yield of POI by engineering host cells such that they underexpress the KO helper genes identified by the inventors. If such a helper protein is present in the host cell, it can be modified, e.g. mutated or knocked-out to improve the POI yield. The presence of such a KO helper protein can be identified with any method known to the art in view of the gene identifiers or nucleotide sequences provided herein. The KO helper proteins that are advantageously absent from a host cell in order to improve the yield of a non-membrane protein of interest are listed in Table 1 above.

Preferably, the host cell may be engineered to underexpress a polynucleotide encoding a KO protein comprising an amino acid sequence as shown in SEQ ID NO: 16 or 17 or a functional homologue thereof, wherein the functional homologue has at least 30% sequence identity to an amino acid sequence as shown in SEQ ID NO: 16 or 17. For example, the host cell may be engineered to underexpress a polynucleotide encoding a protein comprising an amino acid having at least 30% sequence identity to an amino acid sequence as shown in SEQ ID NO: 16. For example, the host cell may be engineered to underexpress a polynucleotide encoding a protein comprising an amino acid having at least 30% sequence identity to an amino acid sequence as shown in SEQ ID NO: 17.

Preferably, when KO1 (helper protein comprising an amino acid sequence shown in SEQ ID NO: 16) and/or KO2 (helper protein comprising an amino acid sequence shown in SEQ ID NO: 17) is/are underexpressed, the yield of the model protein SDZ-Fab or HyHEL-Fab in the host cell may be increased by at least 10, 11, 12, 13, 14, 15, 16, 17, 18, 19, 20, 21, 22, 23, 24, 25, 26, 27, 28, 29, 30, 40, 50, 60, 70, 80, 90, 100, 110, 120, 130, 140, 150, 160, 170, 180, 190, 200, 210, 220, 230, 240, 250, 260, 270, 280, 290 or at least 300% and preferably by at least 10%, compared to the host cell prior to the engineering to underexpress the KO protein.

The term "underexpress" generally refers to any amount less than an expression level exhibited by a reference standard, wherein the reference standard is the host cell prior to the engineering to underexpress the KO protein. The terms "underexpress," "underexpressing," "underexpressed" and "underexpression" in the present invention refer an expression of a gene product or a polypeptide at a level less than the expression of the same gene product or polypeptide prior to a genetic alteration of the host cell or in a comparable host which has not been genetically altered. For example the KO protein maybe underexpressed compared to the reference standard by at least 10%, 20%, 30%, 40%, 50%, 60%, 70%, 80%, 90%, 95%, 99% or may be even not expressed at all (reduced by 100%). No expression of the gene product or a polypeptide is also encompassed by the term "underexpression."

Underexpression can be carried out by any method that prevents the functional expression of one or more of KO1 and KO2 or functional homologues thereof. This results in the incapability to exert its function or full function. Means of underexpression may include gene silencing (e.g. RNAi genes antisense), knocking-out, altering expression level, altering expression pattern, by mutagenizing the gene sequence, disrupting the sequence, insertions, additions, mutations, modifying expression control sequences, and the like.

Preferably, underexpression is achieved by knocking-out the polynucleotide encoding the KO protein in the host cell. A gene can be knocked out by deleting the entire or partial coding sequence. Methods of making gene knockouts are known in the art, e.g., see Kuhn and Wurst (Eds.) Gene Knockout Protocols (Methods in Molecular Biology) Humana Press (Mar. 27, 2009). A gene can also be knocked out by removing part or all of the gene sequence. Alternatively, a gene can be knocked-out or inactivated by the insertion of a nucleotide sequence, such as a resistance gene. Alternatively, a gene can be knocked-out or inactivated by inactivating its promoter. Accordingly, with respect to underexpression of KO1 and KO2 a preferred host cell expresses SEQ ID NO: 16 or 17 or a functional homologue thereof, wherein the functional homologue has at least 30% sequence identity to an amino acid sequence as shown in SEQ ID NO: 16 or 17, a fungal host cell such as *Pichia pastoris, Hansenula polymorpha, Trichoderma reesei, Saccharomyces cerevisiae, Kluyveromyces lactis, Yarrowia lipolytica, Pichia methanolica, Candida boidinii,* and *Komagataella,* and *Schizosaccharomyces pombe* being preferred. Even more preferred is a fungal host cell from the genus *Pichia pastoris,* expressing SEQ ID NO: 16 or 17.

In an embodiment, underexpression is achieved by disrupting the polynucleotide representing the gene coding for said KO protein in the host cell.

A "disruption" is a change in a nucleotide or amino acid sequence, which resulted in the addition, deleting, or substitution of one or more nucleotides or amino acid residues, as compared to the original sequence prior to the disruption.

An "insertion" or "addition" is a change in a nucleic acid or amino acid sequence in which one or more nucleotides or amino acid residues have been added as compared to the original sequence prior to the disruption.

A "deletion" is defined as a change in either nucleotide or amino acid sequence in which one or more nucleotides or amino acid residues, respectively, have been removed (i.e., are absent). A deletion encompasses deletion of the entire sequence, deletion of part of the coding sequence, or deletion of single nucleotides or amino acid residue.

A "substitution" generally refers to replacement of nucleotides or amino acid residues with other nucleotides or amino acid residues. "Substitution" for example can be performed by site-directed mutation, generation of random mutations, and gapped-duplex approaches (See e.g., U.S. Pat. No. 4,760,025; Moring et al., Biotech. (1984) 2:646; and Kramer et al., Nucleic Acids Res., (1984) 12:9441).

Preferably, disruption results in a frame shift mutation, early stop codon, point mutations of critical residues, translation of a nonsense or otherwise non-functional protein product.

In another embodiment, underexpression is achieved by disrupting the promoter which is operably linked with said polypeptide to be knocked out. A promoter directs the transcription of a downstream gene. The promoter is necessary, together with other expression control sequences such as enhancers, ribosomal binding sites, transcriptional start and stop sequences, translational start and stop sequences, and enhancer or activator sequences, to express a given gene. Therefore, it is also possible to disrupt any of the expression control sequence to hinder the expression of the polypeptide.

In another embodiment, underexpression is achieved by post-transcriptional gene silencing (PTGS). A technique commonly used in the art, PTGS reduces the expression level of a gene via expression of a heterologous RNA sequence, frequently antisense to the gene requiring disruption (Lechtreck et al., J. Cell Sci (2002). 115:1511-1522; Smith et al., Nature (2000). 407:319-320; Furhmann et al., J. Cell Sci (2001). 114:3857-3863; Rohr et al., Plant J (2004). 40(4):611-21.

"Underexpression" can be achieved with any known techniques in the art which lowers gene expression. For example, the promoter which is operably linked with the polypeptide can be replaced with another promoter which has lower promoter activity. Promoter activity may be assessed by its transcriptional efficiency. This may be determined directly by measurement of the amount of mRNA transcription from the promoter, e.g. by Northern Blotting, quantitative PCR or indirectly by measurement of the amount of gene product expressed from the promoter. Underexpression may in another embodiment achieved by intervening in the folding of the expressed KO protein so that the KO protein is not properly folded to become functional. For example, mutation can be introduced to remove a disulfide bond formation of the KO protein or to disruption the formation of an alpha helices and beta sheets.

In a further embodiment a host cell that underexpresses helper protein KO1 and/or KO2 can overexpress one or more helper proteins of the invention. Specific combinations of underexpressed and overexpressed helper proteins are disclosed in the items herein.

Use

The present invention further provides the use of the engineered host cells for manufacturing a protein of interest. The host cells can be advantageously used for introducing polypeptides encoding one or more POI(s), and thereafter can be cultured under suitable conditions to express the POI. Details of such use are described herein in the section concerning methods of the present invention.

Polynucleotides encoding the helper proteins and the POI may be recombined in to the host cell by ligating the relevant genes each into one vector. It is possible to construct single vectors carrying the genes, or two separate vectors, one to carry the helper protein genes and the other one the POI genes. These genes can be integrated into the host cell genome by transforming the host cell using such vector or vectors. In some embodiments, the genes encoding the POI is integrated in the genome and the gene encoding the helper protein is integrated in a plasmid or vector. In some embodiments, the genes encoding the helper protein is integrated in the genome and the gene encoding the POI is integrated in a plasmid or vector. In some embodiments, the genes encoding the POI and the helper protein are integrated in the genome. In some embodiments, the gene encoding the POI and the helper protein is integrated in a plasmid or vector. If multiple genes encoding the POI are used, some genes encoding the POI are integrated in the genome while others are integrated in the same or different plasmids or vectors. If multiple genes encoding the helper proteins are used, some of the genes encoding the helper protein are integrated in the genome while others are integrated in the same or different plasmids or vectors. More teaching ca be found in the following sections of the application.

Generally, proteins of interest can be produced using the recombinant host cell by culturing the host cell in an appropriate medium, isolating the expressed POI from the culture, and purifying it by a method appropriate for the expressed product, in particular to separate the POI from the cell.

The present invention further provides the use of an isolated polypeptide comprising an amino acid sequence having at least 30% identity to an amino acid sequence shown in any one of SEQ ID NOs: 1-15 and 18 for manufacturing a protein of interest.

Method

The present invention further relates to a method of increasing the yield of a protein of interest in a host cell, comprising overexpressing a polynucleotide of the present invention. The polynucleotide encodes a helper protein comprising an amino acid having at least 30% sequence identity to an amino acid sequence as shown in any one of SEQ ID NOs: 1-15.

The present invention further relates to a method of increasing the yield of a protein of interest in a host cell, comprising underexpressing a helper protein comprising an amino acid having at least 30% sequence identity to an amino acid sequence as shown in SEQ ID NO: 16 and/or 17.

As used herein, the term "increasing the yield of a protein of interest in a host cell" means that the yield of the protein of interest is increased when compared to the same cell expressing the same POI under the same culturing conditions, however, without the polynucleotide encoding the helper protein being overexpressed.

As will be appreciated by a skilled person in the art, the overexpression of the helper proteins of the present invention have been shown to increase product yield of POI. Therefore, for a given host cell which expressed a POI with a level that should be increased, it is possible to apply the present invention by expressing any one or several of the helper proteins in the host cell, if helper protein is not present in the host cell, or further increasing the level of expression the helper proteins in the cell, if genes encoding the helper protein is already present in the host cell.

The present invention further provides a method of increasing the yield of a protein of interest in a host cell. The method comprises (i) engineering the host cell to express or overexpress a helper protein, (ii) engineering said host cell to comprise a heterologous polynucleotide encoding said protein of interest, and (iii) culturing said host cell under suitable conditions to overexpress the helper protein and to express the protein of interest and optionally (iv) isolating the protein of interest from the cell culture. It should be noted that the steps recited in (i) and (ii) does not have to be performed in the recited sequence. It is possible to first perform the step recited in (ii) and then (i). In step (i), the host cell can be engineered to overexpress a polynucleotide encoding a helper protein comprising an amino acid having at least 30% sequence identity to an amino acid sequence as shown in any one of SEQ ID NOs: 1-15.

The present invention further provides a method of increasing the yield of a protein of interest in a host cell. The method comprises (i) engineering the host cell to underexpress a helper protein, (ii) engineering said host cell to comprise a heterologous polynucleotide encoding said protein of interest, and (iii) culturing said host cell under suitable conditions to express the protein of interest and optionally (iv) isolating the protein of interest from the cell culture. It should be noted that the steps recited in (i) and (ii) do not have to be performed in the recited sequence. It is possible to first perform the step recited in (ii) and then (i). In step (i), the host cell can be engineered to underexpress a polynucleotide encoding a helper protein comprising an amino acid having at least 30% sequence identity to an amino acid sequence as shown in SEQ ID NO: 16 and 17.

Procedures used to manipulate polynucleotide sequences, e.g. coding for the helper proteins and/or the POI, the promoters, enhancers, leaders, etc., are well known to persons skilled in the art, e.g. described by J. Sambrook et al., Molecular Cloning: A Laboratory Manual (3rd edition), Cold Spring Harbor Laboratory, Cold Spring Harbor Laboratory Press, New York (2001).

A foreign or target polynucleotide such as the polynucleotides encoding the overexpressed helper protein or POI can be inserted into the chromosome by various means, e.g., by homologous recombination or by using a hybrid recombinase that specifically targets sequences at the integration sites. The foreign or target polynucleotide described above is typically present in a vector ("inserting vector"). These vectors are typically circular and linearized before used for homologous recombination. As an alternative, the foreign or target polynucleotides may be DNA fragments joined by fusion PCR or synthetically constructed DNA fragments which are then recombined into the host cell. In addition to the homology arms, the vectors may also contain markers suitable for selection or screening, an origin of replication, and other elements. It is also possible to use heterologous recombination which results in random or non-targeted integration. Heterologous recombination refers to recombination between DNA molecules with significantly different sequences. Methods of recombinations are known in the art and for example described in Boer et al., Appl Microbiol Biotechnol (2007) 77:513-523. One may also refer to Principles of Gene Manipulation and Genomics by Primrose and Twyman (7$^{th}$ edition, Blackwell Publishing 2006) for genetic manipulation of yeast cells.

Polynucleotides encoding the overexpressed helper protein and/or POI may also be present on an expression vector. Such vectors are known in the art and already described above. In expression vectors, a promoter is placed upstream of the gene encoding the heterologous protein and regulates the expression of the gene. Multi-cloning vectors are especially useful due to their multi-cloning site. For expression, a promoter is generally placed upstream of the multi-cloning site. A vector for integration of the polynucleotide encoding a helper protein and/or the POI may be constructed either by first preparing a DNA construct containing the entire DNA sequence coding for the helper protein and/or the POI and subsequently inserting this construct into a suitable expression vector, or by sequentially inserting DNA fragments containing genetic information for the individual elements, such as the leader sequence, the target DNA sequence, followed by ligation. As an alternative to restriction and ligation of fragments, recombination methods based on attachment sites (att) and recombination enzymes may be used to insert DNA sequences into a vector. Such methods are described, for example, by Landy (1989) Ann. Rev. Biochem. 58:913-949; and are known to those of skill in the art.

Host cells according to the present invention can be obtained by introducing a vector or plasmid comprising the target polynucleotide sequences into the cells. Techniques for transfecting or transforming eukaryotic cells or transforming prokaryotic cells are well known in the art. These can include lipid vesicle mediated uptake, heat shock mediated uptake, calcium phosphate mediated transfection (calcium phosphate/DNA co-precipitation), viral infection, particularly using modified viruses such as, for example, modified adenoviruses, microinjection and electroporation. For prokaryotic transformation, techniques can include heat shock mediated uptake, bacterial protoplast fusion with intact cells, microinjection and electroporation. Techniques for plant transformation include *Agrobacterium* mediated transfer, such as by *A. tumefaciens*, rapidly propelled tungsten or gold microprojectiles, electroporation, microinjection and polyethylyne glycol mediated uptake. The DNA can be single or double stranded, linear or circular, relaxed or supercoiled DNA. For various techniques for transfecting mammalian cells, see, for example, Keown et al. (1990) Processes in Enzymology 185:527-537.

The present invention further provides a method of manufacturing a protein of interest in a host cell comprising (i) providing the host cell engineered to overexpress a polynucleotide encoding a helper protein comprising an amino acid sequence as shown in any one of SEQ ID NOs: 1-15 or a functional homologue thereof, wherein the functional homologue has at least 30% sequence identity to an amino acid sequence as shown in any one of SEQ ID NOs: 1-15, wherein said host cell comprises a heterologous polynucleotide encoding a protein of interest; and (ii) culturing the host cell under suitable conditions to overexpress the helper protein or functional homologue thereof and to express the protein of interest and optionally isolating the protein of interest from the cell culture.

The present invention further provides a method of manufacturing a protein of interest in a host cell comprising (i) providing the host cell engineered to underexpress a polynucleotide encoding a helper protein comprising an amino acid as shown in any one of SEQ ID NOs: 16 or 17 or a functional homologue thereof, wherein the functional homologue has at least 30% sequence identity to an amino acid sequence as shown in SEQ ID NO: 16 or 17 wherein said host cell comprises a heterologous polynucleotide encoding a protein of interest; and (ii) culturing the host cell under suitable conditions to express protein of interest and optionally isolating the protein of interest. Preferably, the host cell is engineered to underexpress both polynucleotides encoding a helper protein comprising an amino acid as shown in any one of SEQ ID NOs: 16 or 17 or a functional homologue thereof.

It is understood that the methods disclosed herein may further include cultivating said recombinant host cells under conditions permitting the expression of the POI and helper protein. A recombinantly produced POI can then be isolated from the cell or the cell culture medium, depending on the nature of the expression system and the expressed protein, e.g. whether the protein is fused to a signal peptide and whether the protein is soluble or non-soluble. As will be understood by the skilled artisan, cultivation conditions will vary according to factors that include the type of host cell, in particular the expression vector employed. Signal peptides generally contain a positively charged N-terminus followed by a hydrophobic core, followed by a recognition site for an enzyme known as signal peptidase. This enzyme cleaves the signal peptide from the protein during translocation. The protein is transported from the endoplasmic reticulum to the Golgi apparatus, and then follows one of a number of routes in the secretory pathway, depending on the nature of the protein. The protein may be secreted into the culture medium or may be retained in the cell, for example. The leader sequences of certain secreted proteins comprise peptides that are located C-terminal to the signal peptide and are processed from the mature protein of interest subsequent to cleavage of the signal peptide. Such leaders often are referred to as prepro peptides, wherein the pre region is the signal sequence and the pro region designates the remainder of the leader.

One example is the yeast α-factor leader, which contains a signal peptide (including a C-terminal signal peptidase recognition site (Ala-Leu-Ala) followed by a pro region containing a basic amino acid pair (Lys-Arg) that constitutes a KEX2 protease processing site, immediately followed by the peptide Glu-Ala-Glu-Ala at the C-terminus of the pro region. Processing of this leader involves removal of the signal peptide by signal peptidase, followed by cleavage between the Lys and Arg residues by KEX2 protease. The GluAlaGluAla residues are subsequently removed by a peptidase that is the product of the STE13 gene (Julius et al., Cell (1983) 32:839). The yeast α-factor leader is described in U.S. Pat. No. 4,546,082. Signal peptides derived from proteins naturally secreted by yeast cells have been employed in recombinant expression systems for production of heterologous proteins in yeast. The use of mammalian signal peptides in yeast expression systems also has been reported, although certain of the mammalian signal peptides were not effective in promoting secretion of heterologous proteins in yeast.

The phrase "culturing under suitable condition such that a desired polypeptide is expressed" refers to maintaining and/or growing microorganisms under conditions (e.g., temperature, pressure, pH, induction, growth rate, medium, duration, etc.) appropriate or sufficient to obtain production of the desired compound or to obtain desired polypeptide.

A host cell according to the invention obtained by transformation with the helper protein gene(s), and/or the POI genes or by underexpressing the helper protein gene(s) and/or by transformation the POI genes may preferably first be cultivated at conditions to grow efficiently to a large cell number without the burden of expressing a heterologous protein. When the cells are prepared for POI expression, suitable cultivation conditions are selected and optimized to produce the POI.

By way of example, using different promoters and/or copies and/or integration sites for the helper gene(s) and the POI(s), the expression of the helper genes can be controlled with respect to time point and strength of induction in relation to the expression of the POI(s). For example, prior to induction of POI expression, the helper protein(s) may be first expressed. This has the advantage that the helper proteins is/are already present at the beginning of POI translation. Alternatively, the helper protein(s) and POI(s) can be induced at the same time. In another example, prior to induction of POI expression, the helper protein(s) may be first underexpressed. This has the advantage that the helper proteins is/are already absent at the beginning of POI translation.

An inducible promoter may be used that becomes activated as soon as an inductive stimulus is applied, to direct transcription of the gene under its control. Under growth conditions with an inductive stimulus, the cells usually grow more slowly than under normal conditions, but since the culture has already grown to a high cell number in the previous stage, the culture system as a whole produces a large amount of the heterologous protein. An inductive stimulus is preferably the addition of an appropriate agents (e.g. methanol for the AOX-promoter) or the depletion of an appropriate nutrient (e.g., methionine for the MET3-promoter). Also, the addition of ethanol, methylamine, cadmium or copper as well as heat or an osmotic pressure increasing agent can induce the expression depending on the promotors operably linked to the helper gene(s) and the POI(s).

It is preferred to cultivate the hosts according to the invention in a bioreactor under optimized growth conditions to obtain a cell density of at least 1 g/L, preferably at least 10 g/L cell dry weight, more preferably at least 50 g/L cell dry weight. It is advantageous to achieve such yields of biomolecule production not only on a laboratory scale, but also on a pilot or industrial scale.

According to the present invention, due to overexpression of the helper proteins, and/or underexpression of KO proteins, the POI is obtainable in high yields, even when the biomass is kept low. Thus, a high specific yield, which is measured in mg POI/g dry biomass, may be in the range of 1 to 200, such as 50 to 200, such as 100-200, in the laboratory, pilot and industrial scale is feasible. The specific yield of a production host according to the invention preferably provides for an increase of at least 1.1 fold, more preferably at least 1.2 fold, at least 1.3 or at least 1.4 fold, in some cases an increase of more than 2 fold can be shown, when compared to the expression of the product without the overexpression of helper proteins and/or underexpression of KO proteins.

The host cell according to the invention may be tested for its expression/secretion capacity or yield by standard tests, e.g. ELISA, activity assays, HPLC, Surface Plasmon Resonance (Biacore), Western Blot, capillary electrophoresis (Caliper) or SDS-Page.

Preferably, the cells are cultivated in a minimal medium with a suitable carbon source, thereby further simplifying the isolation process significantly. By way of example, the minimal medium contains an utilizable carbon source (e.g. glucose, glycerol, ethanol or methanol), salts containing the macro elements (potassium, magnesium, calcium, ammonium, chloride, sulphate, phosphate) and trace elements (copper, iodide, manganese, molybdate, cobalt, zinc, and iron salts, and boric acid).

In the case of yeast cells, the cells may be transformed with one or more of the above-described expression vector(s), mated to form diploid strains, and cultured in conventional nutrient media modified as appropriate for inducing promoters, selecting transformants or amplifying the genes encoding the desired sequences. A number of minimal media suitable for the growth of yeast are known in the art. Any of these media may be supplemented as necessary with salts (such as sodium chloride, calcium, magnesium, and phosphate), buffers (such as HEPES, citric acid and phosphate buffer), nucleosides (such as adenosine and thymidine), antibiotics, trace elements, vitamins, and glucose or an equivalent energy source. Any other necessary supplements may also be included at appropriate concentrations that would be known to those skilled in the art. The culture conditions, such as temperature, pH and the like, are those previously used with the host cell selected for expression and are known to the ordinarily skilled artisan. Cell culture conditions for other type of host cells are also known and can be readily determined by the artisan. Descriptions of culture media for various microorganisms are for example contained in the handbook "Manual of Methods for General Bacteriology" of the American Society for Bacteriology (Washington D.C., USA, 1981).

Cells can be cultured (e.g., maintained and/or grown) in liquid media and preferably are cultured, either continuously or intermittently, by conventional culturing methods such as standing culture, test tube culture, shaking culture (e.g., rotary shaking culture, shake flask culture, etc.), aeration spinner culture, or fermentation. In some embodiments, cells are cultured in shake flasks or deep well plates. In yet other embodiments, cells are cultured in a bioreactor (e.g., in a bioreactor cultivation process). Cultivation processes include, but are not limited to, batch, fed-batch and continuous methods of cultivation. The terms "batch process" and "batch cultivation" refer to a closed system in which the composition of media, nutrients, supplemental additives and the like is set at the beginning of the cultivation and not subject to alteration during the cultivation; however, attempts may be made to control such factors as pH and oxygen concentration to prevent excess media acidification and/or cell death. The terms "fed-batch process" and "fed-batch cultivation" refer to a batch cultivation with the exception that one or more substrates or supplements are added (e.g., added in increments or continuously) as the cultivation progresses. The terms "continuous process" and "continuous cultivation" refer to a system in which a defined cultivation media is added continuously to a bioreactor and an equal amount of used or "conditioned" media is simultaneously removed, for example, for recovery of the desired product. A variety of such processes has been developed and is well-known in the art.

In some embodiments, cells are cultured for about 12 to 24 hours, in other embodiments, cells are cultured for about 24 to 36 hours, about 36 to 48 hours, about 48 to 72 hours, about 72 to 96 hours, about 96 to 120 hours, about 120 to 144 hours, or for a duration greater than 144 hours. In yet other embodiments, culturing is continued for a time sufficient to reach desirable production yields of POI.

The above mentioned methods may further comprise a step of isolating the expressed POI. If the POI is secreted from the cells, it can be isolated and purified from the culture medium using state of the art techniques. Secretion of the POI from the cells is generally preferred, since the products are recovered from the culture supernatant rather than from the complex mixture of proteins that results when cells are disrupted to release intracellular proteins. A protease inhibitor, such as phenyl methyl sulfonyl fluoride (PMSF) may be useful to inhibit proteolytic degradation during purification, and antibiotics may be included to prevent the growth of adventitious contaminants. The composition may be concentrated, filtered, dialyzed, etc., using methods known in the art. Alternatively, cultured host cells may also be ruptured sonically or mechanically, enzymatically or chemically to obtain a cell extract containing the desired POI, from which the POI may be isolated and purified.

As isolation and purification methods for obtaining the POI may be based on methods utilizing difference in solubility, such as salting out and solvent precipitation, methods utilizing difference in molecular weight, such as ultrafiltration and gel electrophoresis, methods utilizing difference in electric charge, such as ion-exchange chromatography, methods utilizing specific affinity, such as affinity chromatography, methods utilizing difference in hydrophobicity, such as reverse phase high performance liquid chromatography, and methods utilizing difference in isoelectric point, such as isoelectric focusing may be used. Specific purification steps are preferably employed to remove any helper protein that is also expressed and would contaminate the POI preparation.

The isolated and purified POI can be identified by conventional methods such as Western Blotting or specific assays for POI activity. The structure of the purified POI can be determined by amino acid analysis, amino-terminal peptide sequencing, primary structure analysis for example by mass spectrometry, and the like. It is preferred that the POI is obtainable in large amounts and in a high purity level, thus meeting the necessary requirements for being used as an active ingredient in pharmaceutical compositions or as feed or food additive.

EXAMPLES

The following examples are put forth so as to provide those of ordinary skill in the art with a complete disclosure and description of how to make and use the subject invention, and are not intended to limit the scope of what is regarded as the invention and defined in the claims. Efforts have been made to ensure accuracy with respect to the numbers used (e.g. amounts, temperature, concentrations, etc.) but some experimental errors and deviations should be allowed for. Unless otherwise indicated, parts are parts by weight, molecular weight is average molecular weight, temperature is in degrees centigrade; and pressure is at or near atmospheric.

The examples below will demonstrate that the newly identified proteins involved in lipid biosynthesis (i.e. helper protein(s) increase(s) upon their over-respectively underexpression the titer (product per volume in mg/L) and the yield (product per biomass in mg/g biomass measured as dry cell weight or wet cell weight), respectively, of a POI upon its expression. As an example, the yield of recombinant antibody Fab fragments and recombinant enzymes in the yeast *Pichia pastoris* are increased. The positive effect was shown in shaking cultures (conducted in shake flasks or deep well plates) and in lab scale fed-batch cultivations.

Example 1: Generation of *P. pastoris* Production Strains a) Construction of *P. pastoris* Strains Secreting Antibody Fab Fragment HyHEL

*P. pastoris* CBS7435 (CBS, genome sequenced by Küberl et al. 2011) mut$^S$ (obtained from CBS-KNAW Fungal Biodiversity Center, Uetrecht, The Netherlands) variant was used as host strain. The pPM2d_pGAP and pPM2d_pAOX expression vectors are derivatives of the pPuzzle_ZeoR vector backbone described in WO2008/128701A2, consisting of the pUC19 bacterial origin of replication and the Zeocin antibiotic resistance cassette. Expression of the heterologous gene is mediated by the *P. pastoris* glyceraldehyde-3-phosphate dehydrogenase (GAP) promoter or alcohol oxidase (AOX) promoter, respectively, and the *S. cerevisiae* CYC1 transcription terminator. The light chain (LC) (SEQ ID NO: 44) and the heavy chain (HC) (SEQ ID NO: 43) of the antibody Fab fragment HyHEL (FIG. 2) were amplified from vector DNA template (carrying the gene of interests with N-terminal *S. cerevisiae* alpha mating factor signal leader sequence) using the primers for HyHEL-HC and HyHEL-LC in Table 3, and each ligated into both vectors pPM2d_pGAP and pPM2d_pAOX digested with SbfI and SfiI. The LC fragments were ligated into variants of pPM2d_pGAP and pPM2d_pAOX, where one restriction enzyme site in the promoter region was exchanged for another to allow subsequent linearization (NdeI instead of AvrII in pPM2d_pGAP, Bsu36I instead of Bpu1102I in pPM2d_pAOX), the HC fragments were ligated into the unmodified versions of the vectors. After sequence verification of LC and HC, the expression cassettes for both chains were combined onto one vector by using the compatible restriction enzymes MreI and AgeI.

Plasmids were linearized using NdeI restriction enzyme (for pPM2d_pGAP) or Bsu36I restriction enzyme (for pPM2d_pAOX), respectively, prior to electroporation (using a standard transformation protocol described in Gasser et al. 2013. Future Microbiol. 8(2):191-208) into *P. pastoris*. Selection of positive transformants was performed on YPD plates (per liter: 10 g yeast extract, 20 g peptone, 20 g glucose, 20 g agar-agar) containing 50 µg/mL of Zeocin. Colony PCR was used to ensure the presence of the transformed plasmid. Therefore, genomic DNA was obtained by cooking and freezing of *P. pastoris* colonies for 5 minutes each and directly applied for PCR with the appropriate primers. The resulting strains were named CBS7435 mutS pAOX HyHEL-Fab or CBS7435 mutS pGAP HyHEL-Fab, respectively.

b) Construction of a *P. pastoris* Strain Secreting Antibody Fab Fragment SDZ

The light chain (LC) and the heavy chain (HC) of the antibody Fab fragment SDZ (FIG. 2) were amplified from vector DNA template (carrying the gene of interests with N-terminal alpha mating factor signal leader sequence) using the primers for SDZ-HC and SDZ-LC in Table 2, and each ligated into pPM2d_pAOX or the variant of pPM2d_pAOX with the Bsu36I restriction site, respectively, each digested with SbfI and SfiI. After sequence verification of LC and HC, the expression cassettes for both chains were combined onto one vector by using the compatible restriction enzymes MreI and AgeI.

Plasmids were linearized using Bsu36I restriction enzyme prior to electroporation (using a standard transformation protocol described in Gasser et al. 2013. Future Microbiol. 8(2):191-208) into *P. pastoris*. Selection of positive transformants was performed on YPD plates (per liter: 10 g yeast extract, 20 g peptone, 20 g glucose, 20 g agar-agar) containing 50 µg/mL of Zeocin. Colony PCR was used to ensure the presence of the transformed plasmid. Therefore, genomic DNA was obtained by cooking and freezing of *P. pastoris* colonies for 5 minutes each and directly applied for PCR with the appropriate primers. The resulting strains were named CBS7435 mutS pAOX SDZ-Fab or CBS7435 mutS pGAP SDZ-Fab, respectively.

Table 2 shows oligonucleotide primers for PCR amplification of HyHEL LC and HC as well as SDZ LC and HC (Alpha-mating factor_forward is the forward primer for amplification of all Fab chains).

aiming to improve *P. pastoris* hosted recombinant protein production/secretion were not considering *P. pastoris*' cell biology in a broader context.

Despite its frequent utilization in biotechnological relevant applications, the amount of cell biological information such as for example membrane characteristics and features available on *P. pastoris* is poor. Therefore investigated was the effect of over- or underexpression as defined herein of proteins involved in lipid metabolism such as sphingolipid biosynthesis including fatty acid elongation, phospholipid biosynthesis, lipid transport, ergosterol biosynthesis, or lipid storage alone or in combination on recombinant or heterologous protein production/secretion. As model protein for such a protein of interest, two different Fab proteins were used. Additionally, also the overexpression of a chaperone in combination with a protein involved in lipid metabolism was investigated.

Example 3: Generation of Strains Overexpressing Target Genes

For the investigation of positive effects on Fab secretion, diverse proteins involved in lipid metabolism (see Table 1 herein) were overexpressed alone or in combination, or in combination with a chaperone in two different Fab producing strains: CBS7435 pPM2d_pAOX HyHEL and CBS7435 pPM2d_pAOX SDZ (generation see Example 1).

a) Amplification and Cloning of the Lipid Metabolism or Chaperone Genes into pPM2aK21 Expression Vectors The genes overexpressed alone (Table 3; see results of Experiment 4 a-c) and in combination (Table 3 results of Experiment 6a) were amplified by PCR (Phusion Polymerase, ThermoFisher Scientific) from start (including initial 3 or 4 nucleotides of the authentic Kozak sequence) to stop codon using the primers shown in Table 3 and 5. Genomic DNA from *P. pastoris* strain CBS7435 mut$^S$ served as a template (Table 3) except no corresponding coding sequence could be retrieved for wanted genes from sequence searches. In this case, more precisely concerning LIP1 or TSC3, *S. cerevisiae* encoded sequences were amplified from genomic DNA from *S. cerevisiae* BY4741 using the primers shown in Table 3. The sequences were cloned into the MCS of the pPM2aK21 expression vector with the two restriction enzymes SbfI and SfiI. pPMKaK21 is a derivative of pPM2d (described in Example 1a), consisting of an AOX terminator

TABLE 2

| Primer | Restriction site attached | sequence |
|---|---|---|
| Alpha-mating factor_forward* | SbfI | ACTACCTGCAGGCGAAACGATGAGATTCCCATC<br>SEQ ID NO: 99 |
| HyHEL-HC backward | SfiI | TCATGGCCGAGGCGGCCCTATTACTTGTCACAGG<br>ACTTTGGCTC<br>SEQ ID NO: 100 |
| HyHEL-LC backward | SfiI | CTATGGCCGAGGCGGCCCTATTAACACTCACCTCT<br>GTTG<br>SEQ ID NO: 101 |
| SDZ-HC back | SfiI | TATCGGCCGAGGCGGCCCTATTACTTACCTGGGG<br>ACAAG<br>SEQ ID NO: 102 |
| SDZ-LC back | SfiI | CTATGGCCGAGGCGGCCCTATTAACACTCACCTCT<br>GTTG<br>SEQ ID NO: 103 |

Example 2: Evaluation of Engineered *P. pastoris* Strains

The methylotrophic yeast *P. pastoris* is a well accepted host for the overexpression and production of heterologous or recombinant proteins including proteins of interest (POI) already employing manifold applications which provide a surplus in the production/secretion capacity. Such host strain engineering strategies include for example overexpression of helper proteins such as chaperones or other components of the protein folding machinery (Zhang et al., Biotechnol Prog. (2006). 22(4):1090-1095). Most of the applications sequence (for integration into the native AOX terminator locus), an origin of replication for E. coli (pUC19), an antibiotic resistance cassette (kanMX conferring resistance to Kanamycin and G418) for selection in E. coli and yeast, an expression cassette for the gene of interest (GOI), coding for the protein involved in lipid metabolism or the chaperone, comprising a GAP promoter, a multiple cloning site (MCS) and the S. cerevisiae CYC1 transcription terminator. Gene sequences were verified by Sanger sequencing.

Table 3 Gene identities of Pichia pastoris sequences are retrieved from Sturmberger et al. [J. Biotechnol. (2016). 235(4):121-131)] and gene identities of Saccharomyces cerevisiae sequences are retrieved from Cherry J. M. et al. [Nucleic Acids Res. (2012) 40 (Database issue)].

TABLE 3

| Gene | Gene identifier (ORF name Pichia pastoris CBS7435) | Forward primer (SbfI attached) | Backward primer (SfiI attached) |
|---|---|---|---|
| ELO3 | PP7435_Chr3-0987 | CTCGCCTGCAGGACCATGAGTGACATTAATACTCTGTCGC SEQ ID NO: 47 | ACGGCCGAGGCGGCCAGTTAGGCACGACGGACACTAG SEQ ID NO: 48 |
| ELO2 | PP7435_Chr3-0603 | TCTACCTGCAGGAACGATGTCCATTCTCTCATTTG SEQ ID NO: 49 | TATGGCCGAGGCGGCCTCAGGCCTTGCGAGAGCGCAAATTTC SEQ ID NO: 50 |
| LAG1 | PP7435_Chr1-0676 | ATACCTGCAGGACAATGTCTAAAGAGGAAAAGACAAG SEQ ID NO: 51 | ATTGGCCGAGGCGGCCCTATTCTTCCTTCTTGGAGG SEQ ID NO: 52 |
| LAC1 | PP7435_Chr2-0202 | ATACCTGCAGGACAATGGGTGTTGAAACATCTTC SEQ ID NO: 53 | ATTGGCCGAGGCGGCCTCAAGAACTCTCCTCATCATC SEQ ID NO: 54 |
| LCB1 | PP7435_Chr1-1525 | ATACCTGCAGGACAATGAGCCAACGTGAAG SEQ ID NO: 55 | ATTGGCCGAGGCGGCCTCAAAGCTGTTGCAAAAC SEQ ID NO: 56 |
| LCB2 | PP7435_Chr3-0462 | ATACCTGCAGGACAATGTCAAAAACTATCCCAGATG SEQ ID NO: 57 | ATTGGCCGAGGCGGCCTTAGTACATGGCTTTCTTGC SEQ ID NO: 58 |
| TSC13 | PP7435_Chr4-0176 | ATACCCTGCAGGCACCAATGGTTAAACTCATTG SEQ ID NO: 59 | ATAGGCCGAGGCGGCCCTACAAAAGGAATGG SEQ ID NO: 60 |

| Gene | Gene identifier (ORF name Saccharomyces cerevisiae S288C) | Forward primer (SbfI attached) | Backward primer (SfiI attached) |
|---|---|---|---|
| LIP1 | YMR298W | TTCCCTGCAGGACCATGTCTCAACCCACTC SEQ ID NO: 61 | ACGGCCGAGGCGGCCTCACATGTGATAAATTGTG SEQ ID NO: 62 |
| TSC3 | YBR058C-A | TTCCCTGCAGGGAAATGACACAACATAAAAGCTCGATGG SEQ ID NO: 63 | ACGGCCGAGGCGGCCTCAAAGGAAGCAATACTTTAG SEQ ID NO: 64 |

| Gene | Gene identifier (ORF name Pichia pastoris CBS7435) | Forward primer (SbfI attached) | Backward primer (SfiI attached) |
|---|---|---|---|
| PAH1 | PP7435_Chr3-0694 | TTCCCTGCAGGACCATGCAGTACGTAGGTAG SEQ ID NO: 65 | TATGGCCGAGGCGGCCTCAGCTGTCATCGATTC SEQ ID NO: 66 |

TABLE 3-continued

| | | | |
|---|---|---|---|
| PRY1 | PP7435_Chr3-1160 | ATACCTGCAGGACAAT GAAGCTCTCCACCAATT TG SEQ ID NO: 67 | ATAGGCCGAGGCGGC CGTCAAACAGGAGGC AGGAC SEQ ID NO: 68 |
| ERG11 | PP7435_Chr3-0214 | TCTCCTGCAGGCAAACATG AGTCTGGTCCAG SEQ ID NO: 69 | TATGGCCGAGGCGGCCA ACTAATTATCGCGTCTTT C SEQ ID NO: 70 |
| HMG1 | PP7435_Chr2-0242 | TTCCCTGCAGGACGAT GCTTACTGGGTTGTC SEQ ID NO: 71 | AGGCCGAGGCGGCC TCAAGATTTAATGCAA ATCTTAG SEQ ID NO: 72 |
| t1HMG1§ | PP7435_Chr2-0242 | TACCCTGCAGGACGAT GGGAATAAGTGCCACA ATC SEQ ID NO: 73 | AGGCCGAGGCGGCC TCAAGATTTAATGCAA ATCTTAG SEQ ID NO: 74 |
| t2HMG1§ | PP7435_Chr2-0242 | TTCCCTGCAGGACGAT GACGCCAGACGTTGTT CC SEQ ID NO: 75 | AGGCCGAGGCGGCC TCAAGATTTAATGCAA ATCTTAG SEQ ID NO: 76 |
| KAR2 | PP7435_Chr2-1167 | ATACCTGCAGGACAAT GCTGTCGTTAAAACCAT C SEQ ID NO: 77 | ATAGGCCGAGGCGGC CCTACAACTCATCATG ATCATAGTC SEQ ID NO: 78 |

§DNA-Sequences of HMG1 were next to the full-length sequence used as two truncated variants (t1, t2) which were depleted of their membrane anchoring domains that is depletion of initial 1449 nucleotides for variant t1HMG1 or 1543 nucleotides in case of t2HMG1 (except their starting ATG-codon).

b) Overexpression of at Least Two Genes Encoding Proteins Involved in Lipid Metabolism or a Chaperone in Fab Producing Strains The P. pastoris Fab overproducing strains CBS7435 mut$^S$ pAOX HyHEL-Fab and CBS7435 mut$^S$ pAOX SDZ-Fab were used as host strains for overexpression of two, three, or four genes encoding proteins involved in lipid metabolism or a chaperone (see Example 3a). Before transformation (using a standard transformation protocol described in Gasser et al. 2013. Future Microbiol. 8(2):191-208) into the Fab producing strains, the pPM2aK21 vectors containing the genes selected from Table 3 are linearized in the AOX terminator sequence with the restriction enzyme AscI. Positive transformants were selected on YPD agar plates containing G418 and Zeocin.

Example 4: Screening for Fab Expression

In small-scale screenings, 8 to 12 transformants of each overexpressing one gene (see Table 1 and 3) encoding a protein involved in lipid metabolism were tested in P. pastoris Fab production strain CBS7435 mut$^S$ pAOX HyHEL-Fab. Transformants were evaluated by comparison to the parental host CBS7435 mut$^S$ pAOX HyHEL-Fab which was co-transformed with the linearized empty vector (pPM2aK21) and ranked, based on their impact on cell growth, Fab titer and Fab yield.

A selection of genes encoding a protein involved in lipid metabolism were re-evaluated in the background of an additional host strain, CBS7435 mutS pAOX SDZ-Fab. Again, 8-12 transformants were tested in comparison to the parental host CBS7435 mut$^S$ pAOX SDZ-Fab which was co-transformed with the linearized empty vector (pPM2aK21).

a) Small Scale Cultivation of Pichia pastoris Fab Production Strains 2 mL YP-medium (10 g/L yeast extract, 20 g/L peptone) containing 10 g/L glycerol and 50 µg/mL Zeocin were inoculated with a single colony of P. pastoris strains and grown overnight at 25° C. Aliquots of these cultures (corresponding to a final $OD_{600}$ of 2.0) were transferred to 2 mL of Synthetic screening medium M2 (media composition is given below) supplemented with 20 g/L glucose and a glucose feed tablet (Kuhner, Switzerland; CAT #SMFB63319) and incubated for 25 h at 25° C. at 280 rpm in 24 deep well plates. The cultures were washed once by centrifugation, then the pellets were resuspended in Synthetic screening medium M2 and aliquots (corresponding to a final $OD_{600}$ of 4.0) were transferred into 2 mL of Synthetic screening medium M2 in fresh 24 deep well plates. Methanol (5 g/L) was added repeatedly every 12 h for 48 hours, before cells were harvested by centrifugation at 2,500×g for 10 min at room temperature and prepared for analysis. Biomass was determined by measuring the cell weight of 1 mL cell suspension, while determination of the recombinant secreted protein in the supernatant is described in the following Examples 4b-4c.

Synthetic screening medium M2 contained per litre: 22.0 g Citric acid monohydrate 3.15 g $(NH_4)_2PO_4$, 0.49 g $MgSO_4*7H_2O$, 0.80 g KCl, 0.0268 g $CaCl_2*2H_2O$, 1.47 mL PTM1 trace metals, 4 mg Biotin; pH was set to 5 with KOH (solid).

b) SDS-PAGE & Western Blot Analysis

For protein gel analysis the Bio-Rad Mini-Protean Tetra Cell system was used, using 12.5% separation gels (Tris-based discontinuous buffer system) and Tris-Glycin running buffer. After electrophoresis, the proteins were either visualized by colloidal Coomassie staining or transferred to a nitrocellulose membrane for Western blot analysis. Therefore, the proteins were electroblotted onto a nitrocellulose membrane using the Mini Trans-Blot® Cell for wet (tank) transfer (Bio-Rad) according to the manufacturer's instructions. After blocking, the Western Blots were probed with the following antibodies: For Fab light chain: anti-human kappa light chains (bound and free)—peroxidase (HRP) conjugated antibody, Sigma A7164 (1:5,000); For Fab heavy chain: Mouse Anti-Human IgG antibody (Ab7497, Abcam) diluted 1:1,000 and Anti-Mouse IgG (whole molecule)—Peroxidase conjugated antibody produced in goat (A4416, Sigma) as secondary antibody diluted 1:5,000.

Detection was performed with the chemoluminescent Super Signal West Chemiluminescent Substrate (Thermo Scientific) for HRP-conjugates.

c) Quantification of Fab by ELISA

Quantification of intact Fab by ELISA was done using anti-human IgG antibody (ab7497, Abcam) as coating antibody and a goat anti-human IgG (Fab specific)—peroxidase conjugated antibody (Sigma A0293) as detection antibody. Human Fab/Kappa, IgG fragment (Bethyl P80-115) was used as standard with a starting concentration of 100 ng/mL, supernatant samples were diluted accordingly. TMB (biomol E102) was used as substrate for detection. Coating-, Dilution- and Washing buffer were based on PBS (2 mM $KH_2PO_4$, 10 mM $Na_2HPO_4.2\ H_2O$, 2.7 mM g KCl, 8 mM NaCl, pH 7.4) and completed with BSA (1% (w/v)) and/or Tween20 (0.1% (v/v)) accordingly.

Table 4 shows the Fold Change (FC) levels of titers and yields for the model POI HyHEL-Fab estimated by ELISA of engineered strains overexpressing a gene as indicated in Table 5. The values are given as relative numbers compared to the parental strain CBS7435 $mut^S$ pAOX HyHEL-Fab overexpressing the empty integration vector. The number of clones investigated is given in brackets (n, number of clones tested). Gene identities of *Pichia pastoris* sequences are retrieved from Sturmberger et al. [J. Biotechnol. (2016). 235(4):121-131)] and gene identities of *Saccharomyces cerevisiae* sequences are retrieved from Cherry J. M. et al. [Nucleic Acids Res. (2012) 40 (Database issue D700-D705)].

TABLE 4

| Gene | Gene Identifier (ORF name *Pichia pastoris* CBS7435) | CBS7435 mut$^s$ pAOX HyHEL-Fab | |
|---|---|---|---|
| | | FC of Titer average | FC of Yield average |
| ELO3 | PP7435_chr3-0987 | 1.80 (n = 8) | 1.90 (n = 8) |
| LAG1 | PP7435_Chr1-0676 | 1.01 (n = 12) | 1.18 (n = 12) |
| PAH1 | PP7435_chr3-0694 | 0.94 (n = 3) | 1.43 (n = 3) |
| PRY1 | PP7435_chr3-1160 | 1.48 (n = 9) | 1.39 (n = 9) |
| ERG11 | PP7435_chr3-0214 | 1.53 (n = 10) | 1.85 (n = 10) |
| HMG1 | PP7435_chr2-0242 | 1.00 (n = 8) | 1.30 (n = 8) |
| t1HMG1$^§$ | PP7435_chr2-0242_trunc | 1.21 (n = 8) | 1.30 (n = 8) |
| t2HMG1$^§$ | PP7435_chr2-0242_trunc | 1.53 (n = 8) | 1.30 (n = 8) |

$^§$DNA-Sequences of HMG1 were next to the full-length sequence used as two truncated variants (t1, t2) which were depleted of their membrane anchoring domains that is depletion of initial 1449 nucleotides for variant t1HMG1 or 1543 nucleotides in case of t2HMG1 (except their starting ATG-codon).

The yield of HyHEL-Fab produced/secreted by the engineered strains overexpressing a gene encoding a protein involved in involved in lipid metabolism according to Table 4 above is increased by at least by 20% as shown in Table 4. ELO3 (PP7435_chr3-0987) was also overexpressed in CBS7435 mutS pAOX SDZ-Fab with a FC in Titer of 1.3 (n=11) and a FC in Yield of 1.4 (n=11).

Example 5: Generation of Strains Underexpressinq Selected Genes

*P. pastoris* POI production strains were engineered to comprise a knock out of a gene involved lipid biosynthesis pathway genes such as a gene involved in lipid storage. Selected were two genes encoding triacylglycerol synthases: dga1 (PP7435_Chr3-1009 (Table 1) and lro1 (PP7435_Chr2-0587 Table 1)).

The *P. pastoris* Fab overproducing strain CBS7435 mut$^S$ pAOX HyHEL-Fab was used as host strains. A split marker cassette approach was used as described by Heiss et al. (2013) [Appl Microbiol Biotechnol. 97(3):1241-9.] to generate transformants with a disrupted gene locus. Verification of positive knock-out strains was done by PCR, using genomic DNA of transformants which had been able to grow on G418 and primers outside of the disruption cassettes.

Table 5 lists all primers that were used for the construction of the knock-out cassettes (2 overlapping split marker cassettes per knock-out target): The primer pairs A_forward/A_backward, B_forward/B_backward, C_forward/C_backward, D_forward/D_backward were used to amplify the fragments A, B, C and D by PCR (Phusion Polymerase, Thermo Scientific). Fragment A is amplified from genomic *P. pastoris* DNA, starting 1000 bp in 5 prime direction of the respective ATG (of the targeted gene) until approximately 200 bp in 5 prime direction of ATG. Fragment D is amplified from genomic *P. pastoris* DNA, starting 200 bp in 3 prime direction of the respective ATG (of the targeted gene) until 1000 bp in 3 prime direction of ATG. Fragment B consists of the first two thirds of the KanMX selection marker cassette and is amplified from pPM2aK21 vector DNA template. Fragment B consists of the last two thirds of the KanMX selection marker cassette and is amplified from pPM2aK21 vector DNA template. Fragments A and B are annealed together (AB) by overlap PCR using the primers A_forward and B_backward. Fragments C and D are annealed together (CD) by overlap PCR using the primers C_forward and D_backward. To generate knock-out strains, a Fab producing host strain was transformed with total 1 µg DNA of fragments AB and CD, which both overlap as well. Cells were selected on YPD agar plates containing 500 µg/mL G418. Positive knock-out clones were verified by PCR using the primer pair check_forward (binds within selection marker cassette) and check_backward (binds in 3 prime region behind primer sequence D_backward). Due to the replacement of a 400 bp region (around ATG) with a KanMX cassette, PCR product bands of proper size confirm integration of the selection marker cassette at the anticipated locus.

TABLE 5

| Gene identifier | Primer | Sequence |
|---|---|---|
| Δdga1: PP7435_Chr3-1009 | A_forward | AGATATAGTTCTGTTTTATTCCATTAGAGGAGGATCCG SEQ ID NO: 79 |
| | A_backward | GTTGTCGACCTGCAGCGTACTAGATACTGGCACATAACAC SEQ ID NO: 80 |
| | B_forward | GTGTTATGTGCCAGTATCTAGTACGCTGCAGGTCGACAAC SEQ ID NO: 81 |
| | B_backward | CGGTGAGAATGGCAAAAGCTTATG SEQ ID NO: 82 |
| | C_forward | AAGCCCGATGCGCCAGAGTTG SEQ ID NO: 83 |
| | C_backward | ACCTCCTTTGCTTCTCTATCAGTGGATCTGATATCACCTA SEQ ID NO: 84 |
| | D_forward | TAGGTGATATCAGATCCACTGATAGAGAAGCAAAGGAGGT SEQ ID NO: 85 |
| | D_backward | ACTAACTCAGTGTCACCCAGCTC SEQ ID NO: 86 |
| | check_forward | TCTTGCCATCCTATGGAACTG SEQ ID NO: 87 |
| | check_backward | ACAGAGCAAGACTTGCCAG SEQ ID NO: 88 |
| Δlro1: PP7435_Chr2-0587 | A_forward | ACTCTAGCTGTTGTCCGCCAGTTC SEQ ID NO: 89 |
| | A_backward | GTTGTCGACCTGCAGCGTACTATCAATTGTGAACATAATG SEQ ID NO: 90 |
| | B_forward | CATTATGTTCACAATTGATAGTACGCTGCAGGTCGACAAC SEQ ID NO: 91 |
| | B_backward | CGGTGAGAATGGCAAAAGCTTATG SEQ ID NO: 92 |
| | C_forward | AAGCCCGATGCGCCAGAGTTG SEQ ID NO: 93 |
| | C_backward | GACTCATAGAAACGACGGAAGTGGATCTGATATCACCTA SEQ ID NO: 94 |
| | D_forward | TAGGTGATATCAGATCCACTTCCGTCGTTTCTATGAGTC SEQ ID NO: 95 |
| | D_backward | ATTCACCCAGTTAGGGCCTCCG SEQ ID NO: 96 |
| | check_forward | TCTTGCCATCCTATGGAACTG SEQ ID NO: 97 |
| | check_backward | TAGGAGTACCCAGCATACAG SEQ ID NO: 98 |

Examples 6: Combination of Genes Encoding Proteins Involved in Lipid Metabolism (Over- and Underexpression)

For combinations of overexpressions of genes encoding proteins involved in lipid metabolism, CBS7435 mut$^S$ pAOX HyHEL-Fab strains overexpressing ELO3 (PP7435_Chr3-0987) or CBS7435 mut$^S$ pAOX HyHEL-Fab strains overexpressing PRY1 (PP7435_Chr3-1160) or CBS7435 mut$^S$ pAOX HyHEL-Fab strains overexpressing HMG1 (PP7435_Chr2-0242), all of them under control of the constitutive pGAP promoter (generated as described in Examples 3a and b) were used as originating strains. For combination of underexpressions of genes encoding proteins involved in lipid metabolism, CBS7435 mutS pAOX HyHEL-Fab strain with a disruption in the gene locus DGA1 (Δdga1, PP7435_Chr3-1009; as described in Example 5) was used as originating strains. In all those strains, the plasmid encoding for the model protein (POI) HyHEL-Fab was based on Zeocin as selection marker, whereas the plasmids for co-overexpression of any additional gene encoding a protein involved in lipid metabolism_or the cassettes used for disruption of the gene loci carried the KanMX resistance cassette flanked by co-directional loxP recognition sites.

Prior to transformation with an at least one further gene encoding a protein involved in lipid metabolism_or a chaperone or a cassette used for disruption of the gene loci encoding a further protein involved in lipid biosynthesis, the marker gene expression cassette (KanMX—flanked by loxP sites) was recycled by Cre recombinase. Therefore, the strains selected for marker rescue were transformed with the episomal pTAC_Cre_HphMX4 plasmid, which is expressing Cre recombinase under control of S. cerevisiae TPI promoter and is transiently kept in P. pastoris as long as selection pressure by hygromycin (Hyg) is present in the culture medium. Transformants were grown on YPD/Zeo/Hyg agar plates at 28° C. for 2 days, and replica-plated on selective agar plates for growth at 28° C. for further 2 days. Only clones that lost their ability to grow on G418 and on Hyg after 2-3 plating rounds were selected for 24 deep well plate (DWP) screening (described in Example 4a). Fab titer and yield were determined as described in Example 4c. The best strain in terms of Fab yield and/or titer was then transformed with another plasmid overexpressing a further gene encoding a protein involved in lipid biosynthesis (described in Examples 3a and b) or was then transformed with a new set of overlapping split marker knock-out cassettes (described in Example 5). 8 to 16 transformants (with two combined proteins involved in lipid biosynthesis or knock-outs of proteins involved in lipid biosynthesis were selected on selective agar plates (containing Zeo and G418) and screened for Fab secretion as described in Example 4. For further combinatorial steps, the procedure described above was repeated, thus yielding a strain with three combinations and so on. In all screening experiments, the parental (overproducing host strain with or without empty vector) strain was used as a reference.

a) Results on Overexpression of Combinations of Genes Encoding Proteins Involved in Lipid Metabolism Combination of overexpression of at least two genes encoding proteins involved in lipid metabolism in the background of overproducing strain CBS7435 mut$^S$ pAOX HyHEL-Fab revealed clear improvements in terms of Fab yield and/or titer when enzymatic components of the sphingolipid biosynthesis including fatty acid elongation pathway were overexpressed in combinations, when enzymatic components of the sphingolipid biosynthesis including fatty acid elongation pathway were overexpressed in combination with components of the lipid transport pathway or in combination with a chaperone, when enzymatic components of the lipid transport pathway were overexpressed in combination with components of the phospholipid biosynthesis pathway, or when enzymatic components of the ergosterol biosynthesis pathway were overexpressed in combination with a chaperone.

The results are shown in Table 6

Table 6 shows the results of overexpressing combination (+) of genes encoding proteins involved in lipid metabolism_in *P. pastoris*. Fold Change (FC) levels for HyHEL-Fab titers/yields estimated by ELISA are given as relative numbers compared to the parental strain CBS7435 mut$^S$ pAOX HyHEL-Fab overexpressing the empty integration vector. CBS7435 mut$^S$ pAOX HyHEL-Fab ELO3 was the originating strain for further combinations, therefore given FC values of Titer and/or FC values of Yield refer to this explicit clone (n=1).

TABLE 6

| | CBS7435 mut$^s$ pAOX HyHEL-Fab | |
| --- | --- | --- |
| Combination (+) overexpression of genes | FC of Titer average | FC of Yield average |
| ELO3 | 1.50 (n = 1) | 1.60 (n = 1) |
| ELO3 + ELO2 | 1.66 (n = 8) | 1.92 (n = 8) |
| ELO3 + LAG1 | 1.50 (n = 10) | 1.60 (n = 10) |
| ELO3 + LAG1 + LAC1 | 1.28 (n = 10) | 1.43 (n = 10) |
| ELO3 + LAG1 + LAC1 + LIP1sc* | 2.08 (n = 16) | 2.09 (n = 16) |
| LCB1 + LCB2 | 1.5 (n = 6) | 1.1 (n = 6) |
| ELO3 + TSC13 | 1.6 (n = 8) | 1.8 (n=) |
| LCB1 + LCB2 + TSC3sc* | 1.5 (n = 10) | 1.1 (n = 10) |
| ELO3 + LCB1 + LCB2 + TSC3sc* | 1.46 (n = 10) | 1.28 (n = 10) |
| ELO3 + KAR2 | 2.2 (n = 11) | 2.3 (n = 11) |
| ELO3 + PRY1 | 1.7 (n = 12) | 1.7 (n = 12) |
| PRY1 + PAH1 | 2.2 (n = 8) | 1.4 (n = 8) |
| HMG1 + KAR2 | 1.4 (n = 12) | 1.8 (n = 12) |

*sc: Saccharomyces cerevisiae

ELO3 (PP7435_chr3-0987) in combination with ELO2 (PP7435_Chr3-0603) and ELO3 (PP7435_chr3-0987) in combination with PRY1 (PP7435_chr3-1160), were also overexpressed in CBS7435 mutS pAOX SDZ-Fab giving raise to a FC in Titer of 1.2 (n=12) and a FC in Yield of 1.4 (n=12), and FC in Titer of 1.3 (n=10) and a FC in Yield of 1.3 (n=10) respectively.

It can be seen that each of the combinations listed lead to an increase of the Fab titer and/or Fab yield of the model protein HyHEL-Fab (POI) in comparison to the parental strain CBS7435 mut$^S$ pAOX HyHEL-Fab transformed with the empty vector control (see results Table 7). The increase of the Fab titer and/or yield in comparison to the originating strain indicates that combinations of genes involved in sphingolipid biosynthesis including fatty acid elongation pathway, phospholipid biosynthesis pathway, ergosterol biosynthesis pathway, or lipid transport pathway, and optionally in combination with a chaperone can even further improve the titer and/or yield of a POI exemplified by the model protein HyHEL-Fab.

b) Results on Underexpression of Combinations of Genes Encoding Proteins Involved in Lipid Metabolism For combination of two knock-outs of genes encoding proteins involved in lipid metabolism, the CBS7435 mutS pAOX HyHEL-Fab strain with a disruption in the gene loci DGA1 (PP7435_Chr3-1009) and LRO1 (PP7435_Chr2-0587) was used. The strain CBS7435 mutS pAOX HyHEL-Fab which had the gene loci DGA1 and LRO1 successfully disrupted and displayed the results in terms of Fab yield and titer as shown in Table 7:

Table 7 shows results of two knock-outs of genes encoding proteins involved in lipid biosynthesis (lipid storage pathway). Fold Change (FC) levels for HyHEL-Fab titers and yields estimated by ELISA are given as relative numbers compared to the parental strain CBS7435 mutS pAOX HyHEL.

TABLE 7

| | CBS7435 mut$^s$ pAOX HyHEL-Fab | |
| --- | --- | --- |
| Combination (+) of knock-outs | FC of Titer average | FC of Yield average |
| Δdga1 + Δlro1 | 1.9 (n = 4) | 1.44 (n = 4) |

Example 7: Fed Batch Cultivations

Engineered strains from Examples 3 and 6 which directly or indirectly influence lipid metabolism such as for example sphingolipid biosynthesis including fatty acid elongation and lipid transport were analyzed in fed batch bioreactor cultivations for verification of production host strain improvement.

a) Fed Batch Protocol

Respective strains were inoculated into wide-necked, baffled, covered 300 mL shake flasks filled with 50 mL of YPhyG and shaken at 110 rpm at 28° C. over-night (pre-culture 1). Pre-culture 2 (100 mL YPhyG in a 1000 mL wide-necked, baffled, covered shake flask) was inoculated from pre-culture 1 in a way that the OD$_{600}$ (optical density measured at 600 nm) reached approximately 20 (measured against YPhyG media) in late afternoon (doubling time: approximately 2 hours). Incubation of pre-culture 2 was performed at 110 rpm at 28° C., as well.

The fed batches were carried out in 1.0 L working volume bioreactor (Minifors, Infors, Switzerland). All bioreactors (filled with 400 mL BSM-media with a pH of approximately 5.5) were individually inoculated from pre-culture 2 to an OD600 of 2.0. Generally, *P. pastoris* was grown on glycerol to produce biomass and the culture was subsequently subjected to glycerol feeding followed by methanol feeding.

In the initial batch phase, the temperature was set to 28° C. Over the period of the last hour before initiating the production phase it was decreased to 25° C. and kept at this level throughout the remaining process, while the pH dropped to 5.0 and was kept at this level. Oxygen saturation was set to 30% throughout the whole process (cascade control: stirrer, flow, oxygen supplementation). Stirring was applied between 700 and 1200 rpm and a flow range (air) of 1.0-2.0 L/min was chosen. Control of pH at 5.0 was achieved using 25% ammonium. Foaming was controlled by addition of antifoam agent Glanapon 2000 on demand.

During the batch phase, biomass was generated (p 0.30/h) up to a wet cell weight (WCW) of approximately 110-120 g/L. The classical batch phase (biomass generation) would last about 14 hours. Glycerol was fed with a rate defined by the equation 2.6+0.3*t (g/h), so a total of 30 g glycerol (60%) was supplemented within 8 hours. The first sampling point was selected to be 20 hours.

In the following 18 hours (from process time 20 to 38 hours), a mixed feed of glycerol/methanol was applied: glycerol feed rate defined by the equation: 2.5+0.13*t (g/h), supplying 66 g glycerol (60%) and methanol feed rate defined by the equation: 0.72+0.05*t (g/h), adding 21 g of methanol.

During the next 72 hours (from process time 38 to 110 hours) a total of 215-216 g of methanol was supplied (with a feed rate defined by the equation 2.2+0.016*t (g/L)).

Samples were taken at various time points with the following procedure: the first 3 mL of sampled cultivation broth (with a syringe) were discarded. 1 mL of the freshly taken sample (3-5 mL) was transferred into a 1.5 mL centrifugation tube and spun for 5 minutes at 13,200 rpm (16,100 g). Supernatants were diligently transferred into a separate vial.

1 mL of cultivation broth was centrifuged in a tared Eppendorf vial at 13,200 rpm (16,100 g) for 5 minutes and the resulting supernatant was accurately removed. The vial was weighed (accuracy 0.1 mg), and the tare of the empty vial was subtracted to obtain wet cell weights.

The media were as follows:

YPhyG preculture medium (per litre) contained: 20 g Phytone-Peptone, 10 g Bacto-Yeast Extract, 20 g glycerol Batch medium: Modified Basal salt medium (BSM) (per litre) contained: 13.5 mL $H_3PO_4$ (85%), 0.5 g $CaCl_2.2H_2O$, 7.5 g $MgSO_4.7H_2O$, 9 g $K_2SO_4$, 2 g KOH, 40 g glycerol, 0.25 g NaCl, 4.35 mL PTM1, 0.1 mL Glanapon 2000 (antifoam)

PTM1 Trace Elements (per litre) contains: 0.2 g Biotin, 6.0 g $CuSO_4.5H_2O$, 0.09 g KI, 3.00 g $MnSO_4 \cdot H_2O$, 0.2 g $Na_2MoO_4.2H_2O$, 0.02 g $H_3BO_3$, 0.5 g $CoCl_2$, 42.2 g $ZnSO_4.7H_2O$, 65.0 g $FeSO_4.7H_2O$, and 5.0 mL $H_2SO_4$ (95%-98%).

Feed-solution glycerol (per kg) contained: 600 g glycerol, 12 mL PTM1

Feed-solution Methanol contained: pure methanol.

b) Results

Table 8 lists the genes or gene combinations whose overexpression was shown to increase Fab secretion/production in *P. pastoris* in fed batch production processes in comparison to the not engineered Fab producing strains containing the empty vector (control strain). The Fab product titer was quantified by ELISA (Example 4c). Biomass was determined as wet cell weight. Changes in product titers and yields are represented as fold change values relative to the respective control strain. Fold change values show the improvement in titers and product yields in fed batch production processes relative to the AOX HyHEL parental host (empty vector control) which was grown and sampled in parallel for direct comparison.

Table 8 shows the results of overexpressing genes encoding proteins involved in lipid metabolism_alone or in combination in *P. pastoris* in fed batch cultivations. Fold Change (FC) levels for HyHEL-Fab titers/yields estimated by ELISA are given as relative numbers compared to the parental strain CBS7435 $mut^S$ pAOX HyHEL-Fab overexpressing the empty integration vector.

TABLE 8

| Combination (+) overexpression of genes | CBS7435 $mut^s$ pAOX HyHEL-Fab | | |
|---|---|---|---|
| | FC of Titer average | FC of Yield average | Cultivation Time (h) |
| ELO3 | 1.16 | 1.22 | 110.5 |
| ELO3 + ELO2 | 1.29 | 1.29 | 112 |
| LAG1 | 1.22 | 1.19 | 110 |
| ELO3 + LAG1 | 1.89 | 1.63 | 110.5 |
| ELO3 + LCB1 + LCB2 + TSC3sc* | 1.68 | 1.80 | 108.5 |
| PRY1 | 1.98 | 2.09 | 110.5 |
| ELO3 + PRY1 | 1.69 | 1.84 | 110.5 |
| ELO3 + KAR2 | 1.34 | 2.33 | 110.5 |

*sc: Saccharomyces cerevisiae

As shown in Table 8, all the listed genes or gene combinations succeeded in increasing the yield (mg/biomass) of the model protein HyHEL-Fab by at least 20% (fold change >1.2) upon overexpression. Combinatorial overexpression which are directly or indirectly affecting sphingolipid biosynthesis including fatty acid elongation or metabolism or in combination with genes involved in lipid transport or a chaperone were outperforming the originating strain overexpressing ELO3 (PP7435_chr3-0987) alone in the bioreactor.

Example 8: Lipid Analysis of Small Scale Cultivation

Biomass of *P. pastoris* productions strains overexpressing selected genes (listed in Table 3) produced in small scale cultivation (following the description in Example 4a) was used to perform lipid analysis. After resuspension in 10 mM Tris/HCl [pH7.5] cells were disintegrated for 10 minutes with glass beads at 4° C. in a Genie Disruptor (Scientific Industries). The resulting homogenates as well as cell debris and glass beads were transferred to 10 ml glass Pyrex tubes and lipids were extracted as described by Folch et al. [Folch J. et al., A simple method for the isolation and purification of total lipids from animal tissues, J. Biol. Chem. 226 (1957) 497-509.]. In brief, lipids were extracted with 3 ml of $CHCl_3$:MeOH (2:1; v/v) vigorously shaking at room temperature for 1 h. Proteins and non-polar substances were removed by consecutive washing steps with 0.2 volumes 0.034% $MgCl_2$, 1 ml of 2 N KCl/MeOH (4:1; v/v), and 1 ml of an artificial upper phase ($CHCl_3$:MeoH:$H_2O$; 3:48:47; per volume). After centrifugation for 3 min at 2,000 g in a table-top centrifuge, the aqueous phase is removed by aspiration. Finally, lipids are dried under a stream of nitrogen and stored at −20° C.

For phospholipid analysis lipid extracts were loaded manually onto silica gel 60 plates (Merck, Darmstadt, Germany). Individual phospholipids were separated by two-dimensional thin-layer chromatography using ($CHCl_3$/

MeOH/25% NH$_3$; per volume) as the first, and CHCl$_3$/C$_3$H$_6$O/MeOH/CH$_3$COOH/H$_2$O; per volume) as the second solvent system. Phospholipids were detected by staining with iodine vapor. Stained spots were scraped off and phospholipids were quantified by the procedure of Broekhuyse [Broekhuyse R. M., Phospholipids in tissues of the eye I isolation, characterization and quantitative analysis by two-dimensional thin-layer chromatography of diacyl and vinyl-ether phospholipids, Biochim. Biophys. Acta 152 (1968) 307-315]. For total phospholipid analysis, aliquots of dried lipid extracts were directly subjected to phosphate determination using phosphate as standard.

For analysis of non-polar lipids (sterylester (SE) and triacylglycerols (TG)) lipid extracts were loaded on Silica Gel 60 plates (Merck, Darmstadt, Germany) and separated by thin layer chromatography. Chromatograms were developed in an ascending manner by a two-step developing system. First, light petroleum/diethyl ether/acetic acid (35/15/1; per volume) was used as mobile phase, and chromatograms were developed to half-distance of the plate. Then, plates were dried and chromatographs were further developed to the top of the plate using light petroleum/diethyl ether (49/1; v/v) as the second mobile phase. Bands were visualized by dipping the plate for 15 s into a solution consisting of 0.63 MnCL2.4H2O, 60 ml H2O, 60 ml methanol, and 4 ml concentrated sulfuric acid, and incubated in a heating chamber at 105° C. for 30 min. SE and TG bands were identified and quantified by comparison to appropriate standards (cholesteryl oleate and triolein) and densitometric scanning at 400 nm with a Scanner (CAMAG TLC Scanner 3).

Sterol analysis was performed as described by Quail and Kelly [Quail M. A., Kelly S I L., The extraction and analysis of sterols from yeast, Methods Mol. Biol. 53 (1996) 123-31]. After alkaline hydrolysis of lipid extracts using cholesterol as internal standard, gas liquid chromatography/mass spectrometry (GLC/MS) was carried out with a Hewlett-Packard 5890 Gas-Chromatograph equipped with a mass selective detector (HP 5972), using an HP 5-MS capillary column (20 m×0.25 mm i.d.×0.25 μm film thickness). Sample aliquots of 1 μl were injected in the splitless mode at 270° C. injection temperature with helium as carrier gas and with a flow rate set at 0.9 ml/min in constant flow mode. The temperature program was 100° C. for 1 min, 10° C./min to 250° C., and 3° C./min to 310° C. Sterols were identified by their mass fragmentation pattern.

Table 9. Lipid characterization of the parental strain CBS7435 mut$^S$ pAOX HyHEL-Fab and the double deletion mutant Δdga1Δlro1 in the respective parental background. Lipids are listed as mg lipid (phospholipid, ergosterol, triacylglycerol, steryl ester) per g cell wet weight (CWW). If available, standard deviations are given. N.d. (not detected).

TABLE 9

| Strain | mg phospholipid/g CWW | mg ergosterol/g CWW | mg triacyl-glycerol/g CWW | mg steryl ester/g CWW |
|---|---|---|---|---|
| parent | 7.55 ± 0.73 | 0.85 ± 0.33 | 4.6 | 0.30 |
| Δdga1Δlro1 | 5.10 ± 0.21 | 0.58 ± 0.21 | n.d. | 0.03 |

Table 10. Phospholipid pattern of total cell extracts of the parental strain CBS7435 mut$^S$ pAOX HyHEL-Fab and the double deletion mutant Δdga1Δlro1 in the respective parental background. PI, phosphatidylinositol; PS, phosphatidylserine; PC, phosphatidylcholine; PE, phosphatidylethanolamine; CL, cardiolipin; PA, phosphatidic acid.

TABLE 10

| | % of total phospholipids | | | | | |
|---|---|---|---|---|---|---|
| Strain | PI | PS | PC | PE | CL | PA |
| parent | 7.52 | 5.41 | 52.11 | 23.09 | 3.83 | 8.05 |
| Δdga1Δlro1 | 10.00 | 10.41 | 51.63 | 21.02 | 4.69 | 2.24 |

Deletion of DGA1 and LRO1 results in double deletion mutant Δdga1Δlro1. DGA1 and LRO1 encode acyltransferases, which are required for the synthesis of triacylglycerols. Both enzymes are capable to acylate diacylglycerols. DGA1 esterifies diacylglycerols in an acyl-CoA dependent manner, whereas LRO1 is independent of acyl-CoA as acyl-donor. Deletion of both triacylglycerol-acyltransferases leads to the total loss of triacylglycerols as can be seen from Table 9. Triacylglycerols and sterylesters are both non-polar lipids, which are involved in the storage of excess sterols and/or fatty acids. However, their presence is not essential for the viability of cells. Along the strong effect of triacylglycerol depletion, the double deletion mutant Δdga1Δlro1 shows as well a strong reduction in the second class of storage lipids, the steryl esters (Table 9). Steryl esters are reduced by 10-fold compared to the parental production strain. The depletion of triacylglycerols and the strong reduction of steryl esters is accompanied by a general reduction of phospholipids and sterols (Table 9). However, individual phospholipids of the double deletion mutant Δdga1Δlro1 is not largely affected (Table 10). Minor changes were observed for phosphatidylserine and phosphatidylinositol that both were increased at the expense of phosphatidic acid compared to the parental production strain.

Table 11. Sterol composition of total cell extracts of the parental strain CBS7435 mut$^S$ pAOX HyHEL-Fab overexpressing the empty integration vector (empty vector) or overexpressing genes encoding proteins involved in ergosterol biosynthesis of P. pastoris. HMG1 is overexpressed as its native full-length version but as well as two truncated versions (t1HMG1 and t2HMG1) both lacking their N-terminal transmembrane domains (for details see foot note of Table 1).

TABLE 11

| | Empty vector | HMG1 | t1HMG1 | t2HMG1 | ERG11 |
|---|---|---|---|---|---|
| zymosterol | 0.03 | 0.03 | 0.07 | 0.04 | 0.05 |
| ergosterol | 1.38 | 1.33 | 1.78 | 1.85 | 2.36 |
| ergosta-5,8,14,22-tetraenol | 0.05 | 0.04 | 0.07 | 0.05 | 0.12 |
| episterol | 0.01 | 0.01 | 0.03 | 0.01 | 0.02 |

The ergosterol biosynthetic pathway is very complex, highly regulated and involves up to 25 enzymes. Some enzymes positioned at key roles or rate-limiting steps were chosen for overexpression. The effect on sterol composition and total sterol amount is displayed in Table 11. Overexpression of HMG1 as its full length variant did not lead to any changes regarding sterol pattern and amount compared to the parental production strain overexpressing the empty integration vector. However, overexpression of HMG1 as truncated versions, which are depleted for their N-terminal transmembrane domain, lead to an increase in the production of ergosterol. Highest changes in the amount of total sterols were achieved when ERG11, a protein involved further down-stream in the ergosterol biosynthetic pathway, was overexpressed.

The double deletion mutant Δdga1Δlro1 is completely depleted of the storage lipid triacylglycerol.

The double deletion mutant Δdga1Δlro1 shows a strong reduction of steryl esters compared to the parental production strain. Upon deletion of Δdga1Δlro1, only 10% of steryl esters compared to the parental production strain remain left.

The total amount of phospholipids is reduced to ~65% in the double deletion mutant Δdga1Δlro1 compared to the parental production strain.

Similarly, the deletion of Δdga1Δlro1 leads to a reduction in the total amount of sterols to roughly 68%.

Overexpression of ERG11 leads to the highest increase in ergosterol and sterol precursors. The amount of ergosterol is compared to the parental production strain overexpressing the empty integration vector increased by 70%.

Example 9: Lipid Analysis of Fed Batch Cultivations

Cell pellets obtained at the final sampling point of bioreactor cultivations (results shown above) were used to analyse sphingolipids. Characterization of the sphingolipid distribution pattern regarding sphingolipid classes and molecular species of respective classes showed distinct changes when helper protein ELO3 was overexpressed. The effect caused by helper protein ELO3 overexpression could further be enhanced or altered when additional components of the sphingolipid biosynthetic process or lipid transport were overexpressed.

Cell pellets from fed batch cultivations were dissolved in TE-buffer (10 mM Tris; 1 mM EDTA; pH 7.4) and total cell extracts prepared by vigorous shaking with glass beads at 4° C. for 15 minutes. Identical amounts (300 µg protein) from total cell extracts were spiked with 30 µl of the internal standard mix (0.15 nmol N-(dodecanoyl)-sphing-4-enine, 0.15 nmol N-(dodecanoyl)-1-β-glucosyl-sphing-4-enine, 4.5 nmol C17 sphinganine, Avanti Polar Lipids, Inc., Alabaster, Ala., USA), suspended in 6 ml propan-2-ol/hexane/water (60:26:14; per vol) and incubated at 60° C. for 30 min slightly modifying a protocol described previously by J. E. Markham et al. [J. Biol. Chem. (2006). 281:22684-22694.]. During the incubation, samples were shortly vortexed and sonicated after 0, 10, 20 and 30 min. Then, the extracts were cleared from cell debris by centrifugation, dried under nitrogen, redissolved in 800 µl tetrahydrofuran/methanol/water (4:4:1; per vol.) [C. Buré et al., Rapid Commun. Mass Spectrom. (2011). 25:3131-3145.] and stored under argon at −20° C. For analysis, samples were resolubilized by gentle heating and sonication.

UPLC-nanoESI-MS/MS was initiated by Ultra Performance Liquid Chromatography (UPLC) performed on an ACQUITY UPLC® system (Waters Corp., Milford, Mass., USA) equipped with an ACQUITY UPLC® HSS T3 Column (100 mm×1 mm, 1 µm; Waters Corp., Milford, Mass., USA). Aliquots of 2 µl were injected in the partial loop with needle overfill mode. The flow rate was 0.12 ml/min, and the separation temperature was 35° C. Inositol containing sphingolipids were separated by linear gradient elution as follows: 65% solvent B held for 2 min, linear increase to 100% solvent B for 8 min, 100% solvent B held for 2 min and equilibration to 65% solvent B in 2 min. Ceramides (Cer) and hexosylceramides (HexCer) were separated as follows: 80% solvent B held for 2 min, linear increase to 100% solvent B for 8 min, 100% solvent B held for 2 min and equilibration to 80% solvent B in 2 min. Solvent B was tetrahydrofuran/methanol/20 mM ammonium acetate containing 0.1% (v/v) acetic acid, and solvent A was Methanol/20 mM ammonium acetate containing 0.1% (v/v) acetic acid. Chip-based nanoelectrospray ionization was achieved with a TriVersa Nanomate® (Advion, Ithaca, N.Y., USA) in the positive ion mode with 5 µm internal diameter nozzles, a flow rate of 209 nl/min and a voltage of 1.5 kV. Detection of sphingolipid molecular species was carried out with a 4000 QTRAP® tandem mass spectrometer (AB Sciex, Framingham, Mass., USA) by monitoring (i) the transition from $[M+H]^+$ molecular ions to dehydrated long chain base (LCB) fragments for Cer, HexCer and LCB; and (ii) the loss of phosphoinositol containing head groups for inositol containing sphingolipids [C. S. Ejsing et al., J. Mass Spectrom (2006). 41:372-389. J. E. Markham et al., Rapid Commun. Mass Spectrom. (2007). 21:1304-1314]. Dwell time was 30 ms and MS parameters were optimized to maximize detector response.

Overexpression of helper protein ELO3 leads to several significant changes in the total amount, the composition and in the molecular species distribution of sphingolipids. In detail, a pronounced shift in the molecular species distribution of ceramides and the IPC-class (IPC, MIPC, $M(IP)_2C$) of sphingolipids was observed when helper protein ELO3 was overexpressed (see Table 12 through 16). Species composition of hexosyl-ceramides were not affected by overexpression of helper protein ELO3. Sphingolipids of the parental host strain (empty vector control) were mostly containing molecular species variants containing very long chain fatty acid (VLCFA) C24:0 in their fatty acyl moiety, whereas engineered strains overexpressing helper protein ELO3 displayed a pronounced shift towards the VLCFA C26:0.

Overexpression of further components of sphingolipid biosynthetic processes or lipid transport did not greatly influence the molecular species distribution compared to the originating strain overexpressing helper protein ELO3 (data not shown), however clear changes regarding the relative and total abundance of certain sphingolipid classes were observed. Tables 17 and 18 displays the relative distribution of all sphingolipids. Overexpression of helper protein ELO3 leads to an altered distribution pattern where the mature inositol-containing phosphorylceramide $M(IP)_2C$ is enhanced at the expense of IPC. All combinations with ELO3 show a marked decrease in IPC which is either accompanied by a strong increase in $M(IP)_2C$ as in the case of combinations ELO3+LAG1, ELO3+KAR2, and ELO3+LCB1+LCB2+TSC3 or is accompanied with a high increase in hexosyl-ceramides as in the case of the combination ELO3+PRY1.

Evaluation of helper protein ELO3 overexpression in terms of absolute values shows as well marked changes (see Table 18). That is, overexpression of ELO3 alone, or in combination with additional factors involved in sphingolipid biosynthesis, lipid transport or chaperones leads to a marked decrease of IPC. Simultaneously, absolute levels of $M(IP)_2C$ are elevated markedly when ELO3 is overexpressed. Accumulation of $M(IP)_2C$ is even more efficiently enhanced when along to ELO3 further components are co-overexpressed. Highest accumulation of $M(IP)_2C$ is achieved when ELO3 overexpression is combined with KAR2 overexpression. Combination of ELO3 with PRY1 leads to a general reduction in the occurrence of complex inositol containing phosphorylceramides.

Overexpression of ELO3 leads to an altered molecular species pattern of most sphingolipids, that is fatty acyl moieties of ceramides and inositol-containing phosphorylceramides (IPC, MIPC, M(IP)$_2$C) preferentially contain C26 instead of C24 The amount of C26 is depending on the kind of sphingolipid (ceramides, IPC, MIPC and M(IP)$_2$C) enhanced at least by 100% compared to the empty vector. (Tables 12-16).

TABLE 12

Table 12. Composition of molecular species of ceramides from fed batch samples of production strain CBS7435 mutS pAOX HyHEL-Fab overexpressing the empty integration vector (empty vector) or ELO3. Results are shown as relative amounts of all ceramide species within the respective strains. Molecular species were excluded from the table when their relative amount was below 0.3% in both tested strains. Sphingolipids consist of a long-chain-base, which is linked via amide bond to a fatty acid. Therefore, molecular species are expressed as '(Long-chain-base/Fatty-acyl)'. Long-chain-bases and fatty acyls are further expressed in detail as XX:YY; Z (XX: number of carbons in the acyl-chain; YY: number of C—C bonds in the acyl-chain which describes the degree of saturation/unsaturation, Z: number of hydroxyl groups in the acyl-chain).

Relative amount of ceramide species [%]

|              | 18:0; 2/16:0; 0 | 18:0; 2/18:0; 0 | 18:0; 2/18:0; 1 | 18:1; 2/18:0; 0 | 18:1; 2/18:0; 0 | 18:1; 2/16:0; 1 | 18:1; 2/18:0; 1 | 18:2; 2/16:0; 0 |
|---|---|---|---|---|---|---|---|---|
| Empty vector | 0.88 ± 0.18 | 3.04 ± 0.30 | 0.62 ± 0.36 | 1.49 ± 0.36 | 10.24 ± 1.09 | 0.22 ± 0.11 | 1.88 ± 0.22 | 0.85 ± 0.27 |
| ELO3         | 0.40 ± 0.21 | 3.46 ± 1.21 | 0.99 ± 0.44 | 1.50 ± 0.62 | 6.17 ± 2.03 | 0.51 ± 0.53 | 2.52 ± 0.86 | 1.46 ± 0.52 |

|              | 18:2; 2/18:0; 0 | 18:2; 2/18:0; 1 | 19:2; 2/18:0; 1 | 18:0; 3/24:0; 0 | 18:0; 3/26:0; 0 | 18:0; 3/24:0; 1 | 18:0; 3/26:0; 1 |
|---|---|---|---|---|---|---|---|
| Empty vector | 4.50 ± 1.08 | 0.65 ± 0.28 | 0.81 ± 0.27 | 3.11 ± 0.30 | 2.55 ± 0.35 | 40.80 ± 0.58 | 27.99 ± 1.96 |
| ELO3         | 4.85 ± 1.98 | 2.57 ± 0.56 | 2.03 ± 0.56 | 0.36 ± 0.13 | 2.92 ± 0.53 | 6.19 ± 0.88 | 63.57 ± 7.34 |

TABLE 13

Table 13. Composition of molecular species of hexosyl-ceramides from fed batch samples of production strain CBS7435 mutS pAOX HyHEL-Fab overexpressing the empty integration vector (empty vector) or ELO3. Results are shown as relative amounts of all hexosyl-ceramide species within the respective strains. Molecular species were excluded from the table when their relative amount was below 0.3% in both tested strains. Sphingolipids consist of a long-chain-base, which is linked via amide bond to a fatty acid. Therefore, molecular species are expressed as '(Long-chain-base/Fatty-acyl)'. Long-chain-bases and fatty acyls are further expressed in detail as XX:YY; Z (XX: number of carbons in the acyl-chain; YY: number of C—C bonds in the acyl-chain which describes the degree of saturation/unsaturation, Z: number of hydroxyl groups in the acyl-chain).

Relative amount of hexosyl-cereamide species [%]

|              | 18:0; 2/18:0; 1 | 18:1; 2/18:0; 1 | 18:2; 2/16:0; 1 | 18:2; 2/18:0; 1 | 19:2; 2/16:0; 1 | 19:2; 2/18:0; 1 |
|---|---|---|---|---|---|---|
| Empty vector | 2.85 ± 0.20 | 3.14 ± 0.21 | 9.67 ± 0.62 | 15.91 ± 0.81 | 6.10 ± 0.34 | 62.04 ± 1.10 |
| ELO3         | 1.37 ± 0.17 | 2.97 ± 0.12 | 8.62 ± 0.72 | 24.14 ± 2.04 | 3.35 ± 0.35 | 59.44 ± 2.20 |

Overexpression of ELO3 does not affect the distribution pattern of hexosyl-ceramide species (Table 13).

TABLE 14

Table 14. Composition of molecular species of inositolphosphorylceramides (IPC) from fed batch samples of production strain CBS7435 mutS pAOX HyHEL-Fab overexpressing the empty integration vector (empty vector) or ELO3. Results are shown as relative amounts of all IPC species within the respective strains. Molecular species were excluded from the table when their relative amount was below 0.3% in both tested strains. Sphingolipids consist of a long-chain-base, which is linked via amide bond to a fatty acid. Therefore, molecular species are expressed as '(Long-chain-base/Fatty-acyl)'. Long-chain-bases and fatty acyls are further expressed in detail as XX:YY; Z (XX: number of carbons in the acyl-chain; YY: number of C—C bonds in the acyl-chain which describes the degree of saturation/unsaturation, Z: number of hydroxyl groups in the acyl-chain).

Relative amount of IPC species [%]

|              | 34:0; 3 | 36:0; 3 | 36:0; 4 | 42:0; 3 | 42:0; 4 | 42:0; 5 |
|---|---|---|---|---|---|---|
| Empty vector | 0.25 ± 0.07 | 0.50 ± 0.13 | 0.43 ± 0.11 | 0.84 ± 0.08 | 23.01 ± 0.69 | 39.48 ± 1.59 |
| ELO3         | 0.39 ± 0.10 | 0.89 ± 0.10 | 0.78 ± 0.08 | 0.10 ± 0.01 | 4.87 ± 0.38 | 9.05 ± 0.99 |

|              | 44:0; 3 | 44:0; 4 | 44:0; 5 | 46:0; 2 | 46:0; 4 | 46:0; 5 |
|---|---|---|---|---|---|---|
| Empty vector | 0.81 ± 0.04 | 16.08 ± 0.84 | 15.64 ± 1.48 | 1.28 ± 0.33 | 1.24 ± 0.14 | 0.17 ± 0.02 |
| ELO3         | 1.40 ± 0.18 | 38.26 ± 1.06 | 34.49 ± 0.99 | 1.03 ± 0.14 | 7.09 ± 0.47 | 1.34 ± 0.21 |

TABLE 15

Table 15. Composition of molecular species of mannosyl-inositolphosphorylceramides (MIPC) from fed batch samples of production strain CBS7435 mutS pAOX HyHEL-Fab overexpressing the empty integration vector (empty vector) or ELO3. Results are shown as relative amounts of all MIPC species within the respective strains. Molecular species were excluded from the table when their relative amount was below 0.3% in both tested strains. Sphingolipids consist of a long-chain-base, which is linked via amide bond to a fatty acid. Therefore, molecular species are expressed as '(Long-chain-base/Fatty-acyl)'. Long-chain-bases and fatty acyls are further expressed in detail as XX:YY; Z (XX: number of carbons in the acyl-chain; YY: number of C—C bonds in the acyl-chain which describes the degree of saturation/unsaturation, Z: number of hydroxyl groups in the acyl-chain).

Relative amount of MIPC species [%]

| | 36:0; 3 | 36:0; 4 | 42:0; 3 | 42:0; 4 | 42:0; 5 | 44:0; 3 | 44:0; 4 | 44:0; 5 | 46:0; 4 |
|---|---|---|---|---|---|---|---|---|---|
| Empty vector | 0.11 ± 0.03 | 0.44 ± 0.15 | 0.36 ± 0.11 | 39.31 ± 1.72 | 39.39 ± 4.20 | 0.10 ± 0.04 | 12.83 ± 1.74 | 6.28 ± 0.73 | 1.18 ± 0.22 |
| ELO3 | 0.41 ± 0.13 | 0.77 ± 0.11 | 0.00 ± 0.00 | 10.08 ± 0.59 | 7.62 ± 1.64 | 0.33 ± 0.04 | 59.59 ± 0.25 | 14.19 ± 0.50 | 7.02 ± 0.55 |

TABLE 16

Table 16. Composition of molecular species of mannosyl-diinositol-phosphorylceramides (M(IP)2C) from fed batch samples of production strain CBS7435 mutS pAOX HyHEL-Fab overexpressing the empty integration vector (empty vector) or ELO3. Results are shown as relative amounts of all M(IP)2C species within the respective stains. Molecular species were excluded from the table when their relative amount was below 0.3% in both tested strains. Sphingolipids consist of a long-chain-base, which is linked via amide bond to a fatty acid. Therefore, molecular species are expressed as '(Long-chain-base/Fatty-acyl)'. Long-chain-bases and fatty acyls are further expressed in detail as XX:YY; Z (XX: number of carbons in the acyl-chain; YY: number of C—C double bonds in the acyl-chain which describes the degree of saturation/unsaturation, Z: number of hydroxyl groups in the acyl-chain).

Relative amount of M(IP)$_2$C species [%]

| | 42:0; 4 | 42:0; 5 | 44:0; 4 | 44:0; 5 |
|---|---|---|---|---|
| Empty vector | 62.31 ± 4.71 | 16.48 ± 3.60 | 18.97 ± 0.77 | 2.24 ± 0.64 |
| ELO3 | 21.00 ± 5.74 | 4.43 ± 0.92 | 66.18 ± 7.27 | 8.39 ± 1.46 |

Combining the overexpression of helper protein ELO3 with additional helper proteins such as LAG1, LCB1+LCB2+TSC3$_{Sc}$, KAR2 or PRY1 leads to identical trends in molecular species patterns of ceramides and inositol-containing phosphorylceramides (IPC, MIPC, M(IP)$_2$C) as the single overpression of ELO3 does (less C24 containing species, more C26 containing species). The amount of C26 is depending on the kind of sphingolipid (ceramides, IPC, MIPC and M(IP)$_2$C) enhanced at least by 100% compared to the empty vector. (Data not shown).

Combining the overexpression of ELO3 with additional helper proteins such as KAR2 enhances the shift from C24 containing species towards C26 containing species in ceramides and inositol-containing phosphorylceramides (IPC, MIPC, M(IP)$_2$C) The amount of C26 is depending on the kind of sphingolipid (ceramides, IPC, MIPC and M(IP)$_2$C) enhanced at least by 200% compared to the empty vector. (Data not shown).

The overexpression of ELO3 leads to marked changes in the relative distribution of sphingolipids. (Table 17).

Overexpression of ELO3 leads to a reduction of IPC and MIPC of approximately 30% and strongly increases the formation of the mature form of inositol-containing phosphorylceramides, M(IP)$_2$C that is elevated by 6-fold compared to the empty vector overexpressing strain. (Table 17).

The effect of ELO3-overexpression on accumulating M(IP)$_2$C is synergistically enhanced by co-overexpression with either LAG1 or KAR2. M(IP)$_2$C is at least elevated by 10-fold compared to the empty vector overexpressing strain. (Table 17).

Overexpression of ELO3 does not increase the general formation of sphingolipids. (Table 18).

Overexpression of LAG1 does not alter the fatty acyl moieties of sphingolipids as overexpression of ELO3 does but behaves like the empty vector control. No shift from C24 towards C26 observed. (Data not shown).

However, overexpression of LAG1 leads to similar changes in the relative distribution pattern of sphingolipids, that is, increase in M(IP)$_2$C at the expense of IPC. (Table 17).

Overexpression of LAG1 increases the formation of M(IP)$_2$C by at least 10-fold compared to the empty vector overexpressing strain. (Table 18).

Overexpression of PRY1 does neither show changes in the species distribution nor in the sphingolipid distribution. (Table 17).

Overexpression of PRY1 shows in general reduced levels of inositol-containing phosphorylceramides (less IPC, MIPC and M(IP)$_2$C). (Table 18).

TABLE 17

Table 17. Sphingolipid analysis from fed batch samples of production strain CBS7435 mutS pAOX HyHEL-Fab overexpressing the empty integration vector (empty vector) of overexpressing ELO3, ELO3 LAG1, LAG1, ELO3 LCB1, LCB2 TSC3Sc, PRY1, ELO3 PRY1 or ELO3 KAR2. Results shown the relative distribution of all sphingolipid classes (Cer, ceramide; HexCer, hexosyl-ceramide; IPC, inositolphosphorylceramide; MIPC, mannosyl-inositolphosphoryl-ceramide; M(IP)2C, mannosyl-diinositol-phosphorylceramide) within the respective stains.

| | %-total sphingolipids | | | | | | | |
|---|---|---|---|---|---|---|---|---|
| | Empty vector | ELO3 | ELO3 LAG1 | LAG1 | ELO3 LCB1 LCB2 TSC3$_{Sc}$ | PRY1 | ELO3 PRY1 | ELO3 KAR2 |
| Cer | 0.74 | 3.55 | 3.62 | 2.98 | 3.55 | 1.68 | 4.09 | 4.67 |
| HexCer | 30.06 | 35.00 | 37.18 | 24.58 | 41.10 | 39.65 | 50.60 | 25.19 |
| IPC | 54.72 | 38.06 | 25.15 | 42.77 | 35.31 | 40.29 | 35.13 | 32.34 |
| MIPC | 12.15 | 8.51 | 9.15 | 7.20 | 5.11 | 13.52 | 7.28 | 6.02 |
| M(IP)$_2$C | 2.33 | 14.89 | 24.91 | 22.47 | 14.93 | 4.86 | 2.89 | 31.78 |

TABLE 18

Table 18. Comparison of absolute values of analyzed sphingolipids from fed batch samples of production strain CBS7435 mutS pAOX HyHEL-Fab overexpressing the empty integration vector (empty vector) or overexpressing ELO3, ELO3 LAG1, LAG1, ELO3 LCB1 LCB2 TSC3Sc, PRY1, ELO3 PRY1 or ELO3 KAR2. Identical amounts of sample were analyzed. Presentaton of peak intensities enables the direct comparison of the relative abundance all sphingolipid classes (Cer, ceramide; HexCer, hexosyl-ceramide; IPC, inositolphosphorylceramide; MIPC, mannosyl-inositolphosphorylceramide; M(IP)2C, mannosyl-diinositol-phosphorylceramide) amongst the analyzed strains.

| | Peak area (counts) | | | | | | | |
|---|---|---|---|---|---|---|---|---|
| | Empty vector | ELO3 | ELO3 LAG1 | LAG1 | ELO3 LCB1 LCB2 TSC3$_{Sc}$ | PRY1 | ELO3 PRY1 | ELO3 KAR2 |
| Cer | 38546 | 160685 | 156753 | 223371 | 124251 | 64033 | 118798 | 287553 |
| HexCer | 1555970 | 1585610 | 1612210 | 1844410 | 1437820 | 1506930 | 1469250 | 1551850 |
| IPC | 2832338 | 1724000 | 1090460 | 3208697 | 1235200 | 1531320 | 1020090 | 1991970 |
| MIPC | 528725 | 385407 | 396573 | 540399 | 178834 | 513662 | 211342 | 370634 |
| M(IP)$_2$C | 120482 | 674311 | 1080140 | 1685574 | 522132 | 184649 | 83904 | 1957911 |

The invention claimed is:

1. A method of increasing the yield of a protein of interest in a eukaryotic host cell, comprising overexpressing in said host cell at least one polynucleotide encoding at least one protein which is involved in lipid metabolism, thereby increasing the yield of said protein of interest in comparison to a host cell which does not overexpress a polynucleotide encoding a protein which is involved in lipid metabolism, wherein said protein which is involved in lipid metabolism is involved in sphingolipid biosynthesis and comprises an amino acid sequence as shown in SEQ ID NO: 1 or a homologue thereof having at least 70% sequence identity to an amino acid sequence as shown in SEQ ID NO: 1.

2. A method of manufacturing a protein of interest according to claim 1 comprising:

providing the host cell engineered to overexpress at least one polynucleotide encoding at least one protein, wherein said protein which is involved in lipid metabolism is involved in sphingolipid biosynthesis and comprises an amino acid sequence as shown in SEQ ID NO: 1 or a homologue thereof, wherein the homologue has at least 70% sequence identity to an amino acid sequence as shown in SEQ ID NO: 1, wherein said host cell comprises a heterologous polynucleotide encoding a protein of interest;

culturing the host cell under suitable conditions to overexpress the protein involved in lipid metabolism or homologue thereof and to express said protein of interest; and optionally isolating said protein of interest from the cell culture.

3. A recombinant eukaryotic host cell for manufacturing a protein of interest, wherein the host cell is engineered to overexpress at least one polynucleotide encoding at least one protein which is involved in lipid metabolism, wherein said protein which is involved in lipid metabolism is involved in sphingolipid biosynthesis and comprises an amino acid sequence as shown in SEQ ID NO: 1 or a homologue thereof, wherein the homologue has at least 70% sequence identity to an amino acid sequence as shown in SEQ ID NO: 1.

4. The method of claim 1, wherein the host cell is selected from the group consisting of *Pichia pastoris*, *Hansenula polymorpha*, *Trichoderma reesei*, *Saccharomyces cerevisiae*, *Kluyveromyces lactis*, *Yarrowia lipolytica*, *Pichia methanolica*, *Candida boidinii*, *Komagataella* sp., *Aspergillus* sp. and *Schizosaccharomyces pombe*.

5. The method of claim 2, wherein the host cell is selected from the group consisting of *Pichia pastoris*, *Hansenula polymorpha*, *Trichoderma reesei*, *Saccharomyces cerevisiae*, *Kluyveromyces lactis*, *Yarrowia lipolytica*, *Pichia methanolica*, *Candida boidinii*, *Komagataella* sp., *Aspergillus* sp. and *Schizosaccharomyces pombe*.

6. The recombinant eukaryotic host cell of claim 3, wherein the host cell is selected from the group consisting of *Pichia pastoris*, *Hansenula polymorpha*, *Trichoderma reesei*, *Saccharomyces cerevisiae*, *Kluyveromyces lactis*, *Yarrowia lipolytica*, *Pichia methanolica*, *Candida boidinii*, *Komagataella* sp., *Aspergillus* sp. and *Schizosaccharomyces pombe*.

* * * * *

SEQUENCE LISTING

<160> NUMBER OF SEQ ID NOS: 103

<210> SEQ ID NO 1
<211> LENGTH: 330
<212> TYPE: PRT
<213> ORGANISM: Pichia pastoris

<400> SEQUENCE: 1

Met Ser Asp Ile Asn Thr Leu Ser Gln Lys Ile Pro Ser Tyr Val Gln
1               5                   10                  15

Tyr Gly Ile Pro Ser Ile Asp His Pro Phe Gly Ile Arg Leu Trp Pro
            20                  25                  30

Ile Phe Ser His Phe Phe Glu Ala Val Val Gly Tyr Pro Ala Glu Asp
        35                  40                  45

Phe Arg Phe Ile Gln Gly Leu Thr Thr Met Ala Asn Leu Lys Asp Ala
    50                  55                  60

Leu Gly Val Ile Ala Val Tyr Tyr Phe Val Ile Phe Gly Gly Gln Trp
65                  70                  75                  80

```
Leu Met Arg Thr Leu Asn Ala Arg Pro Phe Lys Leu Asn Phe Leu Phe
                85                  90                  95

Gln Leu His Asn Leu Val Leu Thr Gly Ala Ser Phe Thr Leu Leu Ile
            100                 105                 110

Leu Ile Val Glu Gln Leu Ile Pro Gly Ile Tyr Arg His Gly Ile Phe
        115                 120                 125

Trp Ala Ile Cys His Lys Asp Ser Phe Thr Asn Glu Leu Val Thr Leu
130                 135                 140

Tyr Tyr Leu Asn Tyr Leu Ile Lys Tyr Val Glu Leu Ile Asp Thr Val
145                 150                 155                 160

Phe Leu Val Leu Lys Arg Lys Lys Leu Leu Phe Leu His Thr Tyr His
                165                 170                 175

His Gly Ala Thr Ala Leu Leu Cys Tyr Thr Gln Leu Leu Gly His Thr
            180                 185                 190

Ala Val Glu Trp Val Pro Ile Ala Leu Asn Leu Ala Val His Val Val
        195                 200                 205

Leu Tyr Trp Tyr Tyr Phe Leu Ser Ala Arg Gly Ile Arg Val Trp Trp
210                 215                 220

Lys Gln Trp Val Thr Arg Phe Gln Ile Ile Gln Phe Leu Ile Asp Leu
225                 230                 235                 240

Gly Phe Val Tyr Phe Ala Thr Tyr Thr Phe Tyr Ala Asp Lys Tyr Phe
                245                 250                 255

Pro Glu Leu Pro Asn Met Gly Thr Cys Tyr Gly Thr Glu Glu Ala Ala
            260                 265                 270

Ala Phe Gly Tyr Leu Ile Leu Thr Ser Tyr Leu Val Leu Phe Ile Leu
        275                 280                 285

Phe Tyr Ile Arg Val Tyr Lys Ser Gly Pro Thr Thr Ser Lys Gly Lys
290                 295                 300

Ser Lys Ala Ala Ala Thr Thr Gly Gln Lys Thr Glu Thr Ala Ser Pro
305                 310                 315                 320

Ser Gly Lys Ser Thr Ser Val Arg Arg Ala
                325                 330

<210> SEQ ID NO 2
<211> LENGTH: 334
<212> TYPE: PRT
<213> ORGANISM: Pichia pastoris

<400> SEQUENCE: 2

Met Ser Ile Leu Ser Phe Asp Lys Pro Phe Gly Ile Glu Leu Trp Pro
1               5                   10                  15

Ile Phe Asp Thr Phe Ala Ser Lys Ala Thr His Gly Ala Phe Val Pro
            20                  25                  30

Ser Glu Phe Glu Phe Val Ala Gly Lys Leu Pro Leu Ser Thr Leu Glu
        35                  40                  45

Pro Val Leu Tyr Ser Ile Ala Ala Tyr Tyr Phe Ile Val Phe Gly Gly
    50                  55                  60

Tyr Tyr Phe Ile Lys Lys Leu Glu Leu Lys Pro Leu Val Leu Asn Ala
65                  70                  75                  80

Leu Phe Ser Ala His Asn Leu Phe Leu Thr Thr Ala Ser Leu Val Leu
                85                  90                  95

Leu Thr Leu Met Val Glu Gln Leu Val Pro Ile Ile Tyr His His Gly
            100                 105                 110
```

Leu Phe Tyr Ala Ile Cys Asn Thr Arg Ala Trp Thr Gln Glu Leu Val
            115                 120                 125

Thr Leu Tyr Tyr Leu Asn Tyr Leu Ile Lys Phe Val Glu Phe Ile Asp
    130                 135                 140

Thr Phe Leu Val Val Lys Gln Lys Leu Thr Phe Leu His Thr
145                 150                 155                 160

Tyr His His Gly Ala Thr Ala Leu Leu Cys Tyr Thr Gln Leu Val Gly
                165                 170                 175

Val Thr Ser Ile Ser Trp Val Pro Ile Ser Leu Asn Leu Gly Val His
                180                 185                 190

Val Val Met Tyr Trp Tyr Phe Leu Ala Ser Arg Gly Ile Arg Val
                195                 200                 205

Trp Trp Lys Glu Trp Val Thr Arg Phe Gln Ile Met Gln Phe Ile Leu
            210                 215                 220

Asp Leu Gly Phe Val Tyr Phe Ala Ser Tyr Gln Lys Phe Ala Tyr Thr
225                 230                 235                 240

Tyr Phe Lys Asp Val Leu Pro Tyr Cys Gly Asp Cys Ala Gly Thr Met
                245                 250                 255

Val Ala Ala Val Ser Gly Cys Ala Ile Leu Ser Ser Tyr Leu Val Leu
                260                 265                 270

Phe Ile Ala Phe Tyr Ile Glu Val Tyr Arg Lys Gln Gly Lys Lys Ser
            275                 280                 285

Arg Tyr Val Lys Lys Val Arg Gly Gly Val Ala Ala Lys Val Asn Glu
            290                 295                 300

Tyr Val Leu Leu Glu Asp Lys Gln Leu Ala Ser Gly Ala Ser Ser Arg
305                 310                 315                 320

Ser Ser Ser Pro Val Thr Arg Asn Leu Arg Ser Arg Lys Ala
                325                 330

<210> SEQ ID NO 3
<211> LENGTH: 403
<212> TYPE: PRT
<213> ORGANISM: Pichia pastoris

<400> SEQUENCE: 3

Met Ser Lys Glu Glu Lys Thr Arg Arg Arg Ala Ser Ser Ile Gly
1               5                   10                  15

Asn Ile Asn Leu Gly Asp Asn Ala Val Pro Ser Leu Thr Thr Arg Lys
            20                  25                  30

Ser Asn Ala Gln Gln Arg Lys Ser Ser Ala Arg Ile Asn Leu Ile
        35                  40                  45

Asn Lys Lys Gly Ser Ser Asp Trp Gly Leu Val Lys Lys Ile Gly Leu
    50                  55                  60

Ser Leu Val Glu Leu Ser Ser Arg His Thr Trp Leu Pro Phe Leu Val
65                  70                  75                  80

Ser Leu Val Ala Ile His Gly Ser Tyr Leu Leu Ser Asn Asn His Thr
                85                  90                  95

Pro Ser Asn Pro Leu His Lys Phe Val Asp Leu Ser Tyr Lys Ile Glu
            100                 105                 110

Gly Thr Asn Pro Pro Met Tyr Gly Lys Gly Trp Lys Asp Phe Cys Phe
        115                 120                 125

Val Phe Tyr Phe Met Ile Phe Phe Ser Phe Tyr Arg Glu Phe Leu Met
    130                 135                 140

Gln Ala Leu Leu Lys Pro Leu Ala Ser Lys Leu Gly Ile Thr Arg Glu
145                 150                 155                 160

Ser Lys Val Arg Arg Phe Met Glu Gln Ser Tyr Ser Met Cys Tyr Tyr
            165                 170                 175

Gly Phe Ser Gly Pro Leu Gly Leu Tyr Ile Met Ala Gly Met Pro Leu
        180                 185                 190

Trp Tyr Phe Asn Thr Thr Glu Phe Tyr Ile Thr Tyr Pro His Lys Ser
    195                 200                 205

His Glu Tyr Leu Phe Lys Tyr Tyr Leu Gly Gln Ala Ala Phe Trp
210                 215                 220

Ser Gln Gln Ala Val Val Leu Met Leu Gln Leu Glu Lys Pro Arg Lys
225                 230                 235                 240

Asp Phe Lys Glu Leu Val Ile His His Ile Ile Thr Ile Ala Leu Ile
                245                 250                 255

Tyr Cys Ser Tyr Arg Phe His Phe Thr Trp Met Gly Leu Ala Val Tyr
                260                 265                 270

Ile Thr Met Asp Ile Ser Asp Phe Leu Ala Leu Ser Lys Thr Leu
                275                 280                 285

Asn Tyr Val Asp Ser Ala Tyr Thr Gly Pro Ala Phe Met Phe Val
290                 295                 300

Gly Val Trp Phe Tyr Leu Arg His Trp Leu Asn Val Lys Ile Leu Trp
305                 310                 315                 320

Ser Val Leu Thr Glu Phe Arg Thr Val Gly Pro Phe Glu Leu Asn Trp
                325                 330                 335

Ile Thr Gln Gln Tyr Lys Cys Trp Ile Ser Gln Pro Ile Val Phe Ser
                340                 345                 350

Leu Ile Phe Ala Leu Gln Leu Val Asn Leu Tyr Trp Phe Val Leu Ile
                355                 360                 365

Leu Arg Ile Leu Tyr Arg His Ile Phe Leu Asp Val Thr Lys Asp Glu
                370                 375                 380

Arg Ser Asp Asp Glu Ser Glu Glu Ala Gln Val Glu Pro Ser Lys
385                 390                 395                 400

Lys Glu Glu

<210> SEQ ID NO 4
<211> LENGTH: 378
<212> TYPE: PRT
<213> ORGANISM: Pichia pastoris

<400> SEQUENCE: 4

Met Gly Val Glu Thr Ser Ser Gly Thr Gln His Phe Ser Asp Asp
1               5                   10                  15

Gly Cys Val Ser Ser Arg Lys Pro Asn Ala Thr Val Ser Phe Glu Lys
            20                  25                  30

Pro Glu Arg Ala Asn Glu Leu Lys Asn His Lys Ile Tyr Lys Lys Ser
            35                  40                  45

Lys Ala Ser Trp Leu Gln Arg Asn Gln Ile Leu Leu Ala Ser Ser Leu
50                  55                  60

Leu Asn Ala Leu Phe Ile Leu Lys Gln Ile Pro Ser Phe Gln Ser Leu
65                  70                  75                  80

Val Asn Lys Phe Phe His Leu Gln Tyr Lys Asn Leu Asp Gly Thr Tyr
                85                  90                  95

Asp Ile Gly Lys Asp Asp Tyr Phe Phe Val Ile Tyr Trp Ile Ile Asn
                100                 105                 110

```
Leu Thr Ile Ile Arg Ser Val Leu Met Asp Trp Val Leu Glu Pro Leu
            115                 120                 125

Ala Ile Lys Ile Val Gly Ile Asn Asn Arg Lys Ala Leu Thr Arg Phe
130                 135                 140

Lys Glu Gln Gly Trp Ser Leu Phe Tyr Tyr Thr Thr Ser Trp Thr Val
145                 150                 155                 160

Gly Phe Tyr Leu Tyr Tyr Lys Ser Asp Tyr Phe Phe Asn Cys Asp His
                165                 170                 175

Ile Phe Ile Gly Trp Pro Asn Asn Lys Leu Asp Phe Tyr Phe Lys Ser
                180                 185                 190

Tyr Tyr Leu Ile Gln Met Ser Cys Trp Leu Gln Gln Ile Val Val Leu
            195                 200                 205

Asn Ile Glu Glu Arg Arg Lys Asp Tyr Val Gln Met Phe Ser His His
            210                 215                 220

Ile Ile Thr Cys Leu Leu Ile Ile Gly Ser Tyr Tyr Tyr Tyr Phe Leu
225                 230                 235                 240

Gln Ile Gly His Val Ile Leu Val Met Met Asp Ile Val Asp Val Phe
                245                 250                 255

Leu Ser Leu Ala Lys Met Leu Lys Tyr Cys Gly Tyr Ser Thr Leu Cys
            260                 265                 270

Asp Val Met Phe Phe Ile Phe Leu Val Ser Trp Ile Ala Ile Arg His
            275                 280                 285

Val Cys Tyr Asn Tyr Val Phe Trp His Thr Cys Thr Lys Ser Arg Asp
            290                 295                 300

Leu Met Asn Ala Asp Cys Ser Arg Tyr Ala Ile Tyr Gly Gly Pro Leu
305                 310                 315                 320

Asp Val Thr Pro Val Arg Cys Tyr Thr Asp Ser Thr Ile Arg Tyr Phe
                325                 330                 335

Ile Phe Leu Leu Gly Gly Leu Gln Ile Ile Thr Leu Ile Trp Met Tyr
                340                 345                 350

Leu Ile Leu Lys Val Phe Ile Gly Val Ile Thr Gly Lys Gly Ala Glu
            355                 360                 365

Asp Val Arg Ser Asp Asp Glu Glu Ser Ser
            370                 375

<210> SEQ ID NO 5
<211> LENGTH: 396
<212> TYPE: PRT
<213> ORGANISM: Pichia pastoris

<400> SEQUENCE: 5

Met Ser Gln Arg Glu Glu Thr Lys Asp Ala Ala Lys Lys Gln Ile Ala
1               5                   10                  15

Phe Ser Gly Ile Gly Ala Cys Gly Pro Pro Asn Phe Tyr Gly Thr Gln
            20                  25                  30

Asp Ala His Ala Arg Leu Glu Glu Asp Leu Ala Arg Phe Leu Gly Ala
        35                  40                  45

Glu Arg Ala Ile Leu Tyr Ser Gln Asp Phe Cys Thr Val Pro Ser Val
    50                  55                  60

Ile Ala Cys Phe Leu Lys Arg Gly Asp Ile Val Val Tyr Asp Ser Gly
65                  70                  75                  80

Ile Ala Leu Ala Thr Gln Lys Gly Ile Glu Leu Ser Arg Cys Thr Ala
                85                  90                  95
```

```
Tyr His Phe Asn His Asn Asp Met Asp Asn Leu Glu Lys Val Leu Ala
                100                 105                 110

Asp Leu Lys Pro Met Leu Asp Glu Gly Pro Leu Thr Arg Arg Phe Ile
            115                 120                 125

Ile Thr Glu Gly Leu Phe Gln Asn Phe Gly Asp Ser Pro Asp Leu Arg
130                 135                 140

Arg Ile Cys Glu Leu Lys Lys Lys Phe Lys Tyr Arg Leu Phe Leu Asp
145                 150                 155                 160

Glu Thr Leu Ser Ile Gly Val Leu Gly Ala Thr Gly Arg Gly Leu Pro
                165                 170                 175

Glu Leu Tyr Gly Ile Pro Arg Thr Asp Val Glu Val Thr Thr Gly Ala
            180                 185                 190

Leu Ser Tyr Ala Leu Gly Ser Ser Gly Gly Phe Cys Val Gly Glu Asn
        195                 200                 205

Ala Met Val His His Gln Leu Ile Ser Ser Ala Tyr Val Phe Ser
210                 215                 220

Ala Ala Ile Pro Pro Tyr Phe Ala Arg Val Ala Ser Val Ser Leu Arg
225                 230                 235                 240

Leu Leu Gln Glu Asp Ser Val Ser Arg Leu Gln Ser Ser Ile Asn
                245                 250                 255

Phe Leu Tyr Ser Lys Phe Lys Glu Cys Gln Lys Leu Lys Lys Leu Val
            260                 265                 270

Ile Ile Thr Ser Ser Asp Val Ser Pro Ile Leu His Leu Arg Leu His
                275                 280                 285

Arg Asp Leu Arg Ser Arg Leu Asp Leu Pro Val Ser Tyr Gly Gly Pro
290                 295                 300

Gly Ser Ala Met Glu Lys Ile Val Gln Arg Gly Asp Glu His Gly Tyr
305                 310                 315                 320

Phe Asp Glu Asn Tyr Asn Arg Glu Ser Gln Ile Leu Gln Gln Ile Val
                325                 330                 335

Asp Arg Val Leu Asn Asn His Asn Ile Leu Ile Thr Arg Cys Lys Arg
            340                 345                 350

Ile Leu His His Glu Lys Leu Pro Leu Pro Glu Leu Met Ile His
                355                 360                 365

Ile Asn Val Ala Phe Ser Glu Ser Glu Leu Ser Glu Ala Phe Glu Ala
370                 375                 380

Val Ser Ser Glu Ile Tyr Asn Val Leu Gln Gln Leu
385                 390                 395

<210> SEQ ID NO 6
<211> LENGTH: 561
<212> TYPE: PRT
<213> ORGANISM: Pichia pastoris

<400> SEQUENCE: 6

Met Ser Lys Thr Ile Pro Asp Ala Leu Ile Asp Asn Asp Ser Pro Gln
1               5                   10                  15

Glu Lys Ala Glu Lys Glu Phe Gly Ser Leu Thr Ser Lys Glu Trp Leu
            20                  25                  30

Phe Val Ser Lys His Asn Pro Gly Glu Pro Leu Pro Val Pro Ile Glu
        35                  40                  45

Asp Glu Pro Pro Tyr Phe Ile Leu Ile Ala Thr Tyr Leu Asn Tyr Leu
50                  55                  60
```

```
Ile Leu Ile Ile Ile Gly His Ile Arg Asp Phe Phe Gly Lys Leu Phe
 65                  70                  75                  80

His Pro Glu Leu Phe Arg Asp Val Met Val Lys Asp Gly Ile Ala Pro
                 85                  90                  95

Trp Tyr Ala Asn Phe Glu Ser Phe Tyr Thr Arg Arg Leu Lys Thr Arg
            100                 105                 110

Leu Asp Asp Cys Phe Ala Arg Pro Ile Cys Gly Val Pro Gly Arg Tyr
        115                 120                 125

Ile Lys Cys Tyr Asp Arg Thr Ser Asp Asp Tyr Asn Asn Thr Tyr Asn
130                 135                 140

Tyr Ser Gly Thr Val Thr Glu Arg Leu Asn Leu Ser Ser Tyr Asn Tyr
145                 150                 155                 160

Leu Gly Phe Ala Gln Ser Ser Gly Leu Cys Thr Ser Glu Ser Ile Lys
                165                 170                 175

Thr Val Glu Lys Tyr Gly Thr Asn Ser Ala Gly Pro Arg Val Ser Val
            180                 185                 190

Gly Thr Thr Asp Leu His Leu Glu Cys Glu Asp Val Ala Lys Phe
        195                 200                 205

Thr Gly Lys Asp Asn Ala Leu Val Phe Ser Met Gly Tyr Gly Thr Asn
210                 215                 220

Ala Asn Leu Phe Thr Ser Leu Val Asp Ser Lys Cys Cys Val Ile Ser
225                 230                 235                 240

Asp Ser Leu Asn His Gly Ser Ile Arg Thr Gly Val Arg Leu Ser Gly
                245                 250                 255

Ala Ser Val Lys Thr Phe Ala His Asn Asp Met Ala Ala Leu Glu Arg
            260                 265                 270

Thr Leu Arg Ser Val Ile Ser Gln Gly Gln Pro Lys Thr His Arg Pro
        275                 280                 285

Trp Lys Lys Ile Phe Val Ala Val Glu Gly Leu Tyr Ser Met Glu Gly
290                 295                 300

Thr Leu Cys Asn Leu Pro Lys Leu Val Glu Leu Arg Lys Arg Tyr Lys
305                 310                 315                 320

Phe Tyr Leu Phe Val Asp Glu Ala His Ser Ile Gly Ala Met Gly Pro
                325                 330                 335

Asn Gly Lys Gly Val Cys Asp Tyr Phe Gly Ile Ser Ser Ser Asn Ile
            340                 345                 350

Asp Ile Met Met Gly Thr Phe Thr Lys Ser Phe Gly Ala Thr Gly Gly
        355                 360                 365

Tyr Ile Ala Ala Asp Lys Ala Ile Ile Asp Arg Leu Lys Leu Asp Leu
370                 375                 380

Thr Thr Asn Thr Tyr Gly Glu Ser Met Ser Pro Ala Val Leu Thr Gln
385                 390                 395                 400

Ile Ile Thr Ser Leu Lys Ile Ile Asp Gly Gln Leu Asn Gly Asn Glu
                405                 410                 415

Gly Lys Glu Arg Leu Gln Arg Ile Ala Phe Asn Ser Arg Tyr Leu Arg
            420                 425                 430

Leu Gly Leu Lys Arg Leu Gly Phe Ile Val Tyr Gly Ala Asp Asp Ser
        435                 440                 445

Pro Val Ile Pro Leu Leu Leu Tyr Leu Pro Pro Lys Met Pro Ala Phe
450                 455                 460

Ser Arg Met Met Tyr Asp Arg Lys Val Ala Val Val Val Gly Tyr
465                 470                 475                 480
```

-continued

Pro Ala Thr Asp Ile Thr Ser Ser Arg Ile Arg Phe Cys Val Ser Ser
                485                 490                 495

Ser Leu Lys Lys Glu Asp Ile Asp Tyr Leu Leu Lys Cys Cys Asp Glu
            500                 505                 510

Ile Gly Asp Thr Leu Phe Leu Lys Phe Ser Thr Gly Ile Ala Gly Gly
        515                 520                 525

Glu Lys His Pro Gly Asp Tyr Lys Lys Gly Ile Ala Pro Arg Trp Thr
    530                 535                 540

Leu Glu Glu Val Leu Glu Lys Thr Pro Glu Asp Cys Lys Lys Ala Met
545                 550                 555                 560

Tyr

<210> SEQ ID NO 7
<211> LENGTH: 320
<212> TYPE: PRT
<213> ORGANISM: Pichia pastoris

<400> SEQUENCE: 7

Met Val Lys Leu Ile Val Asn Pro Arg Ser Glu Thr Leu Arg Gln Ile
1               5                   10                  15

Asn Val Asp Thr Thr Pro Asn Thr Arg Val Arg Asp Ile Val Val Ala
            20                  25                  30

Tyr Gly Lys Ala Asn Asn Ser Leu Ser Ser Ser Arg Ile Arg Phe Thr
        35                  40                  45

Lys Leu Glu Glu Asp Ala Val Ser Lys Lys Pro Lys His Val Thr Leu
    50                  55                  60

Asp Tyr Glu Lys Ser Leu Ala Gln Asn Gly Ile Val Phe Thr Asp Asp
65                  70                  75                  80

Ser Asp Ser Lys Glu Val Tyr Ala Lys Asp Leu Gly Pro Gln Ile Ser
                85                  90                  95

Trp Lys Leu Val Phe Leu Ile Glu Tyr Val Gly Pro Leu Ile Ile His
            100                 105                 110

Pro Leu Leu Tyr Tyr Gly Trp Phe Lys Pro Asp Tyr Asn Thr Leu Thr
        115                 120                 125

Gln Lys Val Ser Phe Ile Leu Val Met Leu His Phe Leu Lys Arg Glu
    130                 135                 140

Tyr Glu Thr Thr Phe Val His Leu Phe Ser Ser Asp Thr Met Pro Leu
145                 150                 155                 160

Phe Asn Val Phe Lys Asn Ser Ala His Tyr Trp Ile Leu Ser Gly Leu
                165                 170                 175

Ser Leu Ala Val Thr Ile Tyr Ala Pro Asp Ser Tyr Arg Asn Lys Phe
            180                 185                 190

Ala Pro Thr Trp Lys Gln Phe Phe His Val Ser Asp His Glu Asp
    195                 200                 205

Ser Thr Val Leu Ala Leu Ile Gly Leu Trp Val Phe Ala Glu Leu Ser
210                 215                 220

Asn Phe Ile Thr His Gln Lys Leu Ala Ser Leu Arg Ala Asp Gly Ser
225                 230                 235                 240

Arg Glu His Lys Ile Pro Tyr Gly Tyr Gly Phe Asn Leu Val Ser Phe
                245                 250                 255

Pro Asn Tyr Phe Phe Glu Ser Val Ala Trp Leu Ala Phe Ala Leu Leu
            260                 265                 270

Asn Asn Asn Trp Ser Ser Trp Val Phe Leu Thr Ile Ala Ser Ile Gln
        275                 280                 285

```
Met Tyr Ile Trp Ala Ala Lys Lys His Lys Arg Tyr Leu Lys Glu Phe
        290                 295                 300

Gly Asp Gln Tyr Pro Lys Asn Arg Lys Ala Met Ile Pro Phe Leu Leu
305                 310                 315                 320

<210> SEQ ID NO 8
<211> LENGTH: 150
<212> TYPE: PRT
<213> ORGANISM: Saccharomyces cerevisiae

<400> SEQUENCE: 8

Met Ser Gln Pro Thr Pro Ile Ile Thr Thr Lys Ser Ala Ala Lys Pro
1               5                   10                  15

Lys Pro Lys Ile Phe Asn Leu Phe Arg Val Cys Phe Ile Ser Leu Leu
            20                  25                  30

Leu Ile Ala Ala Val Glu Tyr Phe Lys Tyr Gly Thr Arg Ile Asn Tyr
        35                  40                  45

Glu Trp Phe His Cys Thr Pro Ile Lys Glu Pro Gln Ser Gly Ser Val
    50                  55                  60

Ile Lys Leu Trp Ala Arg Gly Gly Pro Ser Cys Asp Lys Arg Gly Glu
65                  70                  75                  80

Tyr Lys Thr Ile Val Lys Arg Ile Thr Arg Asp Tyr Glu Pro Asn Asp
                85                  90                  95

Glu His Leu Ser Phe Cys Ile Ile Glu Asn Asp Asn Val Pro Pro Val
            100                 105                 110

His Tyr Pro Ile His Glu Asp Lys Gly Glu Pro Gly Tyr Val Ala Tyr
        115                 120                 125

Val Gly Tyr Asp Thr Asp Ser Glu Leu Val Gln Glu Leu Cys Ala Asp
    130                 135                 140

Ser Thr Ile Tyr His Met
145                 150

<210> SEQ ID NO 9
<211> LENGTH: 80
<212> TYPE: PRT
<213> ORGANISM: Saccharomyces cerevisiae

<400> SEQUENCE: 9

Met Thr Gln His Lys Ser Ser Met Val Tyr Ile Pro Thr Thr Lys Glu
1               5                   10                  15

Ala Lys Arg Arg Asn Gly Lys Ser Glu Gly Ile Leu Asn Thr Ile Glu
            20                  25                  30

Glu Val Val Glu Lys Leu Tyr Trp Thr Tyr Tyr Ile His Leu Pro Phe
        35                  40                  45

Tyr Leu Met Ala Ser Phe Asp Ser Phe Phe Leu His Val Phe Phe Leu
    50                  55                  60

Thr Ile Phe Ser Leu Ser Phe Phe Gly Ile Leu Lys Tyr Cys Phe Leu
65                  70                  75                  80

<210> SEQ ID NO 10
<211> LENGTH: 775
<212> TYPE: PRT
<213> ORGANISM: Pichia pastoris

<400> SEQUENCE: 10

Met Gln Tyr Val Gly Arg Ala Ile Gly Ser Val Ser Lys Thr Trp Ser
1               5                   10                  15
```

```
Ser Ile Asn Pro Ala Thr Leu Ser Gly Ala Ile Asp Ile Ile Val Val
            20                  25                  30

Glu Gln Glu Asn Gly Asp Leu Ala Cys Ser Pro Phe His Val Arg Phe
        35                  40                  45

Gly Lys Phe Gln Leu Leu Arg Pro Ser Gln Lys Val Asp Phe Ile
50                  55                  60

Val Asn Gly Glu Lys Thr Asp Leu Pro Met Lys Leu Gly Asp Gly Gly
65                  70                  75                  80

Glu Ala Phe Phe Val Phe Glu Thr Asp Ala Ala Ile Pro Ser Glu Leu
                85                  90                  95

Gln Thr Ser Pro Val Ile Ser Pro Val Ser Ser Pro Glu Pro Ala Ser
            100                 105                 110

Pro Leu Ser Thr Pro Ser Arg Pro Asn Ser Glu Pro Asp Tyr Leu Glu
            115                 120                 125

Leu Gly Asp Gly Glu Ser Thr Thr Ser Glu Leu Glu Asn Phe Lys Leu
130                 135                 140

Asn Arg Tyr Pro Tyr Leu Ser Thr Glu Val Ser His Ser Asp Pro Gly
145                 150                 155                 160

Val Gly Ser Val Ser Ser Pro Glu Asn Thr Lys Ile Ile Gln Lys
            165                 170                 175

Ile Ser Arg Lys Leu Asn Thr Lys Asn Ile Pro Ser Lys Val Asp Asn
            180                 185                 190

Asn Gly Asn Leu Val Leu Asp Ile Gln Gly Tyr Lys Ser Asp Asp Leu
        195                 200                 205

Asp Asp Asn Ser Lys Ser Leu Lys Gln Leu Leu Ala Glu Leu Gly
210                 215                 220

Glu Asp Val Asp Leu Asp Lys Val Ile Glu Lys Asp His Glu Gly Asn
225                 230                 235                 240

Ile Met Ile Asn Gly Ala Ile Ser Leu Leu Ser Gly Glu Asp Leu
            245                 250                 255

Glu Ser Phe Pro Gln Thr Asp Asp Gln Ala Glu Ser Leu Lys Leu Asp
            260                 265                 270

Leu Glu Ser Asp Lys Ser Asp Ile Glu Ser Asp Thr Asn His Glu Leu
        275                 280                 285

Ser Arg Tyr Phe Lys Thr Leu Arg Leu Thr Ser Asp Gln Leu Lys Cys
        290                 295                 300

Leu Thr Leu Lys Lys Gly Ile Asn Glu Leu Lys Phe Ser Val Asn Lys
305                 310                 315                 320

Gly Lys Ser Val Val Thr Ala Asn Leu Tyr Phe Trp Asp Tyr Tyr Asp
                325                 330                 335

Pro Ile Val Ile Ser Asp Ile Asp Gly Thr Ile Thr Lys Ser Asp Ala
            340                 345                 350

Leu Gly His Val Phe Thr Met Ile Gly Arg Asp Trp Thr His Lys Gly
            355                 360                 365

Val Ala Lys Leu Phe Ser Asp Ile Lys Ser Asn Gly Tyr Asn Ile Met
            370                 375                 380

Tyr Leu Thr Ala Arg Ser Val Gly Gln Ala Asp Ser Thr Arg Tyr Tyr
385                 390                 395                 400

Leu Asn Asn Ile Glu Gln Gly Leu Arg Leu Pro Gln Gly Pro Val
            405                 410                 415

Ile Leu Ser Pro Asp Arg Thr Met Ala Ala Leu Arg Arg Glu Val Ile
            420                 425                 430
```

-continued

```
Leu Lys Lys Pro Glu Val Phe Lys Met Ala Cys Leu Asn Asp Ile Lys
        435                 440                 445

Lys Leu Tyr Leu Thr Asn Thr Lys Asp Leu Asn Pro Asn Thr Asp Ser
450                 455                 460

Ala Asp Phe Thr Asp Ile Asn Thr Asn Thr Leu Arg Ser Ser Ser Leu
465                 470                 475                 480

Thr Glu Asp Val Gln Thr Pro Phe Tyr Ala Gly Phe Gly Asn Arg Ile
                485                 490                 495

Thr Asp Ala Leu Ser Tyr Arg Ser Val Gly Ile Pro Ser Ser Arg Ile
                500                 505                 510

Phe Thr Ile Asn Pro Asp Gly Asp Val His Met Glu Leu Leu Glu Leu
        515                 520                 525

Ala Gly Tyr Arg Ser Ser Tyr Val His Ile Ser Glu Leu Val Asp His
    530                 535                 540

Phe Phe Pro Pro Val Asn Thr Glu Leu Phe Lys Ser Met Pro Ser Asp
545                 550                 555                 560

Thr Tyr Arg Asn Thr Ala Lys Phe Ser Asp Val Asn Tyr Trp Lys Glu
                565                 570                 575

Pro Leu Tyr Asn Phe Glu Glu Leu Ser Asp Glu Asp Ser Ser Glu Asp
                580                 585                 590

Glu Leu Arg Arg Arg Lys Glu Glu Arg Leu Gln Ser Ala Pro Arg
        595                 600                 605

Ser Pro Ile Leu Ala Ala Gly Ala Ser Phe Phe Lys Gly Ser Ser Ser
        610                 615                 620

Leu Leu Gly Ser Pro Glu Arg Met Thr Leu Ser Asp Pro Lys Pro Thr
625                 630                 635                 640

Glu Val Ala Pro Ser Thr Ile Lys Pro Pro Lys Ser Val Gly Ser Val
                645                 650                 655

Ser Ser Asp Glu Glu Lys Leu Lys Asp His Asp Asp Phe Ile Asp Val
                660                 665                 670

Asp His Glu Asp Glu Thr Leu Asp Asp Asp Asp Pro Phe Asp Tyr
        675                 680                 685

Asp Tyr Glu Tyr Glu Asp Glu Glu Glu Asn Asp Asp Val Asp Glu
    690                 695                 700

Val Asp Asp Gly Glu Glu Tyr Ser Asp Tyr Tyr Asp Glu Glu Asp
705                 710                 715                 720

Asp Tyr Asp Glu Glu Leu Asp His Thr Leu Glu Pro Asp Gln Lys Lys
                725                 730                 735

Glu Leu Asp Gln Thr Ala Glu Ala Asn Gln Leu Pro Pro Ser Gly Pro
            740                 745                 750

Asp Glu Met Glu Ser Lys Ser Phe Lys Lys Ala Ser Asp Leu Ile Ser
            755                 760                 765

Lys Met Arg Ile Asp Asp Ser
770                 775

<210> SEQ ID NO 11
<211> LENGTH: 313
<212> TYPE: PRT
<213> ORGANISM: Pichia pastoris

<400> SEQUENCE: 11

Met Lys Leu Ser Thr Asn Leu Ile Leu Ala Ile Ala Ala Ala Ser Ala
1               5                   10                  15

Val Val Ser Ala Ala Pro Val Ala Pro Glu Glu Ala Ala Asn His
                20                  25                  30
```

```
Leu His Lys Arg Ala Tyr Tyr Thr Asp Thr Thr Lys Thr His Thr Phe
        35                  40                  45

Thr Glu Val Val Thr Val Tyr Arg Thr Leu Lys Pro Gly Glu Ser Ile
50                  55                  60

Pro Thr Asp Ser Pro Ser His Gly Gly Lys Ser Thr Lys Lys Gly Lys
65                  70                  75                  80

Gly Ser Thr Thr His Ser Gly Ala Pro Gly Ala Thr Ser Gly Ala Pro
                85                  90                  95

Thr Asp Asp Thr Thr Ser Thr Ser Gly Ser Val Gly Leu Pro Thr Ser
            100                 105                 110

Ala Thr Ser Val Thr Ser Thr Ser Ser Ala Ser Thr Thr Ser Ser
        115                 120                 125

Gly Thr Ser Ala Thr Ser Thr Gly Thr Gly Thr Ser Thr Ser Thr Ser
        130                 135                 140

Thr Gly Thr Gly Thr Gly Thr Thr Gly Thr Gly Thr Thr Ser Ser Ser
145                 150                 155                 160

Thr Ser Ser Ser Ala Thr Ser Thr Pro Thr Gly Ser Ile Asp Ala Ile
                165                 170                 175

Ser Gln Thr Leu Leu Asp Thr His Asn Asp Lys Arg Ala Leu His Gly
        180                 185                 190

Val Pro Asp Leu Thr Trp Ser Thr Glu Leu Ala Asp Tyr Ala Gln Gly
        195                 200                 205

Tyr Ala Asp Ser Tyr Thr Cys Gly Ser Ser Leu Glu His Thr Gly Gly
        210                 215                 220

Pro Tyr Gly Glu Asn Leu Ala Ser Gly Tyr Ser Pro Ala Gly Ser Val
225                 230                 235                 240

Glu Ala Trp Tyr Asn Glu Ile Ser Asp Tyr Asp Phe Ser Asn Pro Gly
                245                 250                 255

Tyr Ser Ala Gly Thr Gly His Phe Thr Gln Val Val Trp Lys Ser Thr
            260                 265                 270

Thr Gln Leu Gly Cys Gly Tyr Lys Glu Cys Ser Thr Asp Arg Tyr Tyr
        275                 280                 285

Ile Ile Cys Glu Tyr Ala Pro Arg Gly Asn Ile Val Ser Ala Gly Tyr
        290                 295                 300

Phe Glu Asp Asn Val Leu Pro Pro Val
305                 310

<210> SEQ ID NO 12
<211> LENGTH: 515
<212> TYPE: PRT
<213> ORGANISM: Pichia pastoris

<400> SEQUENCE: 12

Met Ser Leu Val Gln Glu Leu Ile Gln Lys Ile Ser Ser Leu Glu Leu
1               5                   10                  15

Thr Leu Val Glu Lys Leu Ser Ile Leu Phe Val Ala Pro Phe Leu Leu
            20                  25                  30

Asn Ala Leu Trp Gln Phe Ile Tyr Ser Phe Arg Lys Asp Arg Val Pro
        35                  40                  45

Leu Val Phe His Trp Val Pro Trp Val Gly Ser Ala Val Thr Tyr Gly
        50                  55                  60

Met Gln Pro Tyr Glu Phe Phe Ala Asp Cys Gln Arg Lys Tyr Gly Asp
65                  70                  75                  80
```

```
Val Phe Ala Phe Val Leu Leu Gly Lys Val Met Thr Val Tyr Leu Gly
                85                  90                  95

Pro Lys Gly His Glu Phe Ile Leu Asn Ala Lys Leu Asn Asp Val Cys
            100                 105                 110

Ala Glu Asp Ala Tyr Lys His Leu Thr Thr Pro Val Phe Gly Glu Gly
            115                 120                 125

Val Ile Tyr Asp Cys Pro Asn Trp Lys Leu Met Asp Gln Lys Lys Phe
130                 135                 140

Val Lys Gly Ser Leu Thr Lys Glu Ser Phe Arg Ser Tyr Val Pro Lys
145                 150                 155                 160

Ile Arg Asp Glu Val Leu Asp Tyr Ile Asn Asn Asp Pro Asn Phe Met
                165                 170                 175

Gly Gly Asp Ser Lys Lys Thr Gly Lys Thr Asn Val Leu Asn Ser
            180                 185                 190

Gln Ser Glu Leu Thr Ile Leu Thr Ala Ser Arg Ser Leu Leu Gly Asp
            195                 200                 205

Asp Met Arg Lys Leu Leu Thr Lys Lys Trp Ala Lys Leu Phe Ser Asp
        210                 215                 220

Leu Asp Lys Gly Phe Thr Pro Leu Asn Phe Ile Phe Ser His Leu Pro
225                 230                 235                 240

Leu Pro Ser Tyr Trp Thr Arg Asp His Ala Gln Lys Thr Ile Ser Glu
                245                 250                 255

Thr Tyr Leu Ser Leu Ile Asn Lys Arg Arg Ala Thr Asn Asp Ile Gly
            260                 265                 270

Asp Arg Asp Leu Ile Asp Ser Leu Met Lys Ser Ser Thr Tyr Lys Asp
        275                 280                 285

Gly Ser Lys Met Thr Asp Glu Glu Ile Ser His Leu Leu Ile Gly Val
290                 295                 300

Leu Met Gly Gly Gln His Thr Ser Ala Ser Thr Ser Ser Trp Phe Leu
305                 310                 315                 320

Leu His Leu Gly Glu Lys Pro Glu Leu Gln Glu Glu Leu Phe Glu Glu
                325                 330                 335

Gln Glu Arg Val Leu Gln Gly Arg Glu Leu Thr Tyr Asp Asp Leu Ala
            340                 345                 350

Asn Met Pro Leu His Asn Gln Val Ile Lys Glu Thr Leu Arg Met His
        355                 360                 365

Met Pro Leu His Ser Ile Phe Arg Lys Val Thr Arg Pro Leu Pro Val
        370                 375                 380

Pro Asn Ser Lys Tyr Val Val Pro Lys Gly His Tyr Val Leu Val Ser
385                 390                 395                 400

Pro Gly Phe Ala Met Thr Asn Asp Ala Tyr Phe Pro Asn Ala Ser Asp
                405                 410                 415

Phe Gln Pro His Arg Trp Asp Glu Thr Val Glu Pro Val Ser Ala Asp
            420                 425                 430

Ala Lys Glu Thr Val Asp Tyr Gly Phe Gly Lys Val Ser Lys Gly Val
        435                 440                 445

Ser Ser Pro Tyr Leu Pro Phe Gly Gly Gly Arg His Arg Cys Ile Gly
450                 455                 460

Glu His Phe Ala Tyr Cys Gln Leu Gly Thr Ile Leu Asn Thr Phe Val
465                 470                 475                 480

Arg Thr Phe Lys Trp Lys Ala Val Val Pro Gln Pro Asp Tyr Thr Ser
                485                 490                 495
```

Met Val Thr Leu Pro Glu Pro Asn Leu Ser Thr Ile Thr Trp Glu Arg
            500                 505                 510

Arg Asp Asn
        515

<210> SEQ ID NO 13
<211> LENGTH: 986
<212> TYPE: PRT
<213> ORGANISM: Pichia pastoris

<400> SEQUENCE: 13

Met Leu Thr Gly Leu Ser Lys Ile Cys Ala His Arg Pro Ile His Thr
1               5                   10                  15

Ile Val Val Thr Ala Leu Leu Val Ser Leu Ala Tyr Leu Thr Ile Val
            20                  25                  30

Glu Glu Tyr Thr Ser Arg Ser Ser Leu Ser Asn Pro Phe Ile Ser Phe
            35                  40                  45

Tyr His Pro Pro Gly Asn Ser Asp Tyr Gln Asn Trp Ile Pro Val Asp
        50                  55                  60

Asp Ser Val Lys Leu Lys Ser Lys Ser Ala Gln His Leu Ser Val Cys
65                  70                  75                  80

Ala Leu Lys Phe Lys Arg Val Asn Gly His Gln Ile Pro Asp Leu Ala
                85                  90                  95

Gly Ser Phe Gln Ser Ala Asp Pro Thr Glu Ile Phe Val Gln Asp
            100                 105                 110

Phe Asp Lys Ser Phe Asp Tyr Phe Asp Ser Ile Ser Thr Ile Glu Gly
            115                 120                 125

Lys Asp Gly Ile Gln Trp Lys Val Arg His Pro Asn Arg Leu Gly Arg
        130                 135                 140

Tyr Ser Glu Tyr Phe Arg Ser Val Phe Ser Lys Thr Leu Arg Leu Val
145                 150                 155                 160

Gln Gly Ala Glu Pro Phe Asp Ile Val Leu Ile Ala Phe Ala Tyr Val
                165                 170                 175

Ala Met Trp Tyr Thr Phe Leu Gln Leu Tyr Tyr Glu Met Lys Thr Lys
            180                 185                 190

Ala Asn Ser Asn Phe Trp Leu Thr Phe Gly Ser Leu Ser Ser Gly
            195                 200                 205

Cys Ala Phe Val Phe Ala Leu Ala Val Thr Val Lys Val Tyr Gly Ile
        210                 215                 220

Lys Val Pro Leu Thr Ser Leu Thr Glu Gly Val Pro Phe Leu Val Ala
225                 230                 235                 240

Thr Ile Gly Phe Lys His Lys Val Ala Phe Thr Val Pro Ile Leu Gln
                245                 250                 255

Ala Ser Arg Ser Lys Lys Ala Lys Glu Ile Pro Asp Thr Ile Ile Ser
            260                 265                 270

Val Ile Glu Gln Thr Thr Gly Trp Pro Leu Ile Lys Asp His Leu Ile
        275                 280                 285

Met Ile Ser Ala Phe Leu Ala Cys Ser Phe Tyr Ala Pro Arg Met Glu
        290                 295                 300

Gly Leu Lys Asn Phe Cys Ile Leu Ser Ala Asn Ile Leu Thr Phe Asp
305                 310                 315                 320

Leu Ile Met Ile Phe Thr Phe Phe Thr Ala Val Leu Ser Leu Lys Ala
                325                 330                 335

Gln Ile Asn Lys Val His Glu Thr Thr Ala Leu Gln Gln Val Leu Glu
            340                 345                 350

```
Glu Asp Gly Ile Ala Glu Asp Val Ala Glu Arg Ile Ala Ala Ser Asn
        355                 360                 365
Arg Asn Met Phe Ser Arg Ser Thr Ser Val Val Ser Phe Lys Val Ile
    370                 375                 380
Met Ile Ala Gly Phe Leu Gly Phe His Leu Phe Val Leu Gly Thr Ser
385                 390                 395                 400
Trp Leu Tyr Asp Ser Asp Val Ser Ser Ser Ile Phe Gly Lys Ser
                405                 410                 415
Asn Val Ser Ala Leu Ser Lys Ala Ala Lys His Ile Pro Ile Gly
            420                 425                 430
Ser Glu Gly Thr Ile Val Thr Ile Met Pro Thr Arg Val Tyr Met Pro
        435                 440                 445
Val Asp Leu Leu Leu Lys Leu Glu Asp Phe Leu Asn Ile Phe Ser
        450                 455                 460
Lys Ile Ser Ala Ser Ile Thr Asp Pro Leu Ile Ser Lys Leu Leu Phe
465                 470                 475                 480
Ile Ile Thr Gly Ile Ser Ala Thr Ile Asn Val Tyr Leu Leu Asn Ala
                485                 490                 495
Ala Arg Phe His Ser Ser Arg Glu Ile Ala Val Ser Thr Ile Ala Lys
            500                 505                 510
Pro Gln Thr Pro Asp Val Val Pro Thr Val Glu Pro Leu Pro Asn Glu
        515                 520                 525
Asn Asp Thr Ser Ile Arg Pro Leu Glu Glu Met Val Ser Leu Leu Lys
    530                 535                 540
Glu Gly Lys Thr Arg Glu Leu Asn Asn Asp Glu Val Ser Ser Leu Val
545                 550                 555                 560
Val Gln Gly Lys Leu Pro Leu Tyr Ala Leu Glu Lys Gln Leu Val Asp
                565                 570                 575
Lys Thr Arg Ala Val Ile Val Arg Arg Lys Ala Ile Ala Ser Leu Ala
            580                 585                 590
Asp Ala Pro Val Leu Arg Thr Glu Lys Leu Pro Tyr Lys Asp Tyr Asp
        595                 600                 605
Tyr Asp Arg Val Phe Gly Ala Cys Cys Glu Asn Val Ile Gly Phe Met
    610                 615                 620
Pro Leu Pro Val Gly Val Ala Gly Pro Leu Ile Ile Asp Gly Lys Pro
625                 630                 635                 640
Tyr His Ile Pro Met Ala Thr Glu Gly Cys Leu Val Ala Ser Thr
                645                 650                 655
Met Arg Gly Cys Lys Ala Ile Asn Ser Gly Gly Gly Val Glu Thr Val
            660                 665                 670
Leu Thr Ala Asp Gly Met Thr Arg Gly Pro Cys Val Ser Phe Pro Ser
        675                 680                 685
Leu Ser Arg Ala Gly Ala Ala Lys Met Trp Leu Asp Ser Glu Glu Gly
    690                 695                 700
Gln Lys Thr Ile Lys Gly Ala Phe Asn Ser Thr Ser Arg Phe Ala Arg
705                 710                 715                 720
Leu Gln His Val Lys Thr Thr Leu Ala Gly Thr Leu Leu Phe Ile Arg
                725                 730                 735
Phe Lys Thr Thr Thr Gly Asp Ala Met Gly Met Asn Met Ile Ser Lys
            740                 745                 750
Gly Val Glu Tyr Ser Leu Lys Phe Met Ser Glu Cys Asp Trp Pro
        755                 760                 765
```

```
Asp Met Glu Val Ile Ser Val Ser Gly Asn Tyr Cys Thr Asp Lys Lys
770                 775                 780

Val Ala Ala Ile Asn Trp Ile Glu Gly Arg Gly Lys Ser Val Val Ala
785                 790                 795                 800

Glu Ala Arg Ile Pro Ala Asp Val Val Arg Ser Val Leu Lys Ser Asp
                805                 810                 815

Val Glu Ala Leu Val Glu Leu Asn Val Ser Lys Asn Leu Ile Gly Ser
                820                 825                 830

Ala Met Ala Gly Ser Ile Gly Gly Phe Asn Ala Gln Ala Ala Asn Leu
                835                 840                 845

Val Thr Ala Val Tyr Leu Ala Thr Gly Gln Asp Pro Ala Gln Asn Val
                850                 855                 860

Glu Ser Ser Asn Cys Ile Thr Leu Met Asn Lys Leu Pro Asn Gly Asp
865                 870                 875                 880

Leu Gln Ile Ser Val Ser Met Pro Ser Ile Glu Val Gly Thr Ile Gly
                885                 890                 895

Gly Gly Thr Val Leu Glu Pro Gln Gly Ser Met Leu Glu Leu Leu Gly
                900                 905                 910

Val Lys Gly Pro His Pro Thr Asn Pro Gly Ala Asn Ser Arg Gln Leu
                915                 920                 925

Ala Lys Ile Val Ala Ser Ala Val Leu Ala Ala Glu Leu Ser Leu Cys
                930                 935                 940

Ser Ala Leu Ala Ala Gly His Leu Val Gln Ser His Met Thr His Asn
945                 950                 955                 960

Arg Lys Gln Ala Pro Val Lys Glu Val Asn Gly Thr Ala Ala Arg Leu
                965                 970                 975

Ala Glu Gln Ser Lys Ile Cys Ile Lys Ser
                980                 985

<210> SEQ ID NO 14
<211> LENGTH: 471
<212> TYPE: PRT
<213> ORGANISM: Pichia pastoris

<400> SEQUENCE: 14

Met Thr Pro Asp Val Val Pro Thr Val Glu Pro Leu Pro Asn Glu Asn
1               5                   10                  15

Asp Thr Ser Ile Arg Pro Leu Glu Glu Met Val Ser Leu Leu Lys Glu
                20                  25                  30

Gly Lys Thr Arg Glu Leu Asn Asn Asp Glu Val Ser Ser Leu Val Val
            35                  40                  45

Gln Gly Lys Leu Pro Leu Tyr Ala Leu Glu Lys Gln Leu Val Asp Lys
        50                  55                  60

Thr Arg Ala Val Ile Val Arg Lys Ala Ile Ala Ser Leu Ala Asp
65                  70                  75                  80

Ala Pro Val Leu Arg Thr Glu Lys Leu Pro Tyr Lys Asp Tyr Asp Tyr
                85                  90                  95

Asp Arg Val Phe Gly Ala Cys Cys Glu Asn Val Ile Gly Phe Met Pro
                100                 105                 110

Leu Pro Val Gly Val Ala Gly Pro Leu Ile Ile Asp Gly Lys Pro Tyr
                115                 120                 125

His Ile Pro Met Ala Thr Thr Glu Gly Cys Leu Val Ala Ser Thr Met
        130                 135                 140

Arg Gly Cys Lys Ala Ile Asn Ser Gly Gly Gly Val Glu Thr Val Leu
145                 150                 155                 160
```

```
Thr Ala Asp Gly Met Thr Arg Gly Pro Cys Val Ser Phe Pro Ser Leu
                165                 170                 175

Ser Arg Ala Gly Ala Ala Lys Met Trp Leu Asp Ser Glu Glu Gly Gln
            180                 185                 190

Lys Thr Ile Lys Gly Ala Phe Asn Ser Thr Ser Arg Phe Ala Arg Leu
        195                 200                 205

Gln His Val Lys Thr Thr Leu Ala Gly Thr Leu Leu Phe Ile Arg Phe
    210                 215                 220

Lys Thr Thr Thr Gly Asp Ala Met Gly Met Asn Met Ile Ser Lys Gly
225                 230                 235                 240

Val Glu Tyr Ser Leu Lys Phe Met Ser Glu Glu Cys Asp Trp Pro Asp
            245                 250                 255

Met Glu Val Ile Ser Val Ser Gly Asn Tyr Cys Thr Asp Lys Lys Val
        260                 265                 270

Ala Ala Ile Asn Trp Ile Glu Gly Arg Gly Lys Ser Val Val Ala Glu
    275                 280                 285

Ala Arg Ile Pro Ala Asp Val Val Arg Ser Val Leu Lys Ser Asp Val
290                 295                 300

Glu Ala Leu Val Glu Leu Asn Val Ser Lys Asn Leu Ile Gly Ser Ala
305                 310                 315                 320

Met Ala Gly Ser Ile Gly Gly Phe Asn Ala Gln Ala Ala Asn Leu Val
            325                 330                 335

Thr Ala Val Tyr Leu Ala Thr Gly Gln Asp Pro Ala Gln Asn Val Glu
        340                 345                 350

Ser Ser Asn Cys Ile Thr Leu Met Asn Lys Leu Pro Asn Gly Asp Leu
    355                 360                 365

Gln Ile Ser Val Ser Met Pro Ser Ile Glu Val Gly Thr Ile Gly Gly
    370                 375                 380

Gly Thr Val Leu Glu Pro Gln Gly Ser Met Leu Glu Leu Leu Gly Val
385                 390                 395                 400

Lys Gly Pro His Pro Thr Asn Pro Gly Ala Asn Ser Arg Gln Leu Ala
            405                 410                 415

Lys Ile Val Ala Ser Ala Val Leu Ala Ala Glu Leu Ser Leu Cys Ser
        420                 425                 430

Ala Leu Ala Ala Gly His Leu Val Gln Ser His Met Thr His Asn Arg
    435                 440                 445

Lys Gln Ala Pro Val Lys Glu Val Asn Gly Thr Ala Ala Arg Leu Ala
    450                 455                 460

Glu Gln Ser Lys Ile Cys Ile
465                 470

<210> SEQ ID NO 15
<211> LENGTH: 504
<212> TYPE: PRT
<213> ORGANISM: Pichia pastoris

<400> SEQUENCE: 15

Met Gly Ile Ser Ala Thr Ile Asn Val Tyr Leu Leu Asn Ala Ala Arg
1               5                   10                  15

Phe His Ser Ser Arg Glu Ile Ala Val Ser Thr Ile Ala Lys Pro Gln
            20                  25                  30

Thr Pro Asp Val Val Pro Thr Val Glu Pro Leu Pro Asn Glu Asn Asp
        35                  40                  45
```

-continued

```
Thr Ser Ile Arg Pro Leu Glu Glu Met Val Ser Leu Leu Lys Glu Gly
    50                  55                  60

Lys Thr Arg Glu Leu Asn Asn Asp Glu Val Ser Ser Leu Val Val Gln
 65                  70                  75                  80

Gly Lys Leu Pro Leu Tyr Ala Leu Glu Lys Gln Leu Val Asp Lys Thr
                 85                  90                  95

Arg Ala Val Ile Val Arg Arg Lys Ala Ile Ala Ser Leu Ala Asp Ala
            100                 105                 110

Pro Val Leu Arg Thr Glu Lys Leu Pro Tyr Lys Asp Tyr Asp Tyr Asp
        115                 120                 125

Arg Val Phe Gly Ala Cys Cys Glu Asn Val Ile Gly Phe Met Pro Leu
    130                 135                 140

Pro Val Gly Val Ala Gly Pro Leu Ile Ile Asp Gly Lys Pro Tyr His
145                 150                 155                 160

Ile Pro Met Ala Thr Thr Glu Gly Cys Leu Val Ala Ser Thr Met Arg
                165                 170                 175

Gly Cys Lys Ala Ile Asn Ser Gly Gly Val Glu Thr Val Leu Thr
            180                 185                 190

Ala Asp Gly Met Thr Arg Gly Pro Cys Val Ser Phe Pro Ser Leu Ser
        195                 200                 205

Arg Ala Gly Ala Ala Lys Met Trp Leu Asp Ser Glu Glu Gly Gln Lys
    210                 215                 220

Thr Ile Lys Gly Ala Phe Asn Ser Thr Ser Arg Phe Ala Arg Leu Gln
225                 230                 235                 240

His Val Lys Thr Thr Leu Ala Gly Thr Leu Leu Phe Ile Arg Phe Lys
                245                 250                 255

Thr Thr Thr Gly Asp Ala Met Gly Met Asn Met Ile Ser Lys Gly Val
            260                 265                 270

Glu Tyr Ser Leu Lys Phe Met Ser Glu Glu Cys Asp Trp Pro Asp Met
        275                 280                 285

Glu Val Ile Ser Val Ser Gly Asn Tyr Cys Thr Asp Lys Lys Val Ala
    290                 295                 300

Ala Ile Asn Trp Ile Glu Gly Arg Gly Lys Ser Val Val Ala Glu Ala
305                 310                 315                 320

Arg Ile Pro Ala Asp Val Val Arg Ser Val Leu Lys Ser Asp Val Glu
                325                 330                 335

Ala Leu Val Glu Leu Asn Val Ser Lys Asn Leu Ile Gly Ser Ala Met
            340                 345                 350

Ala Gly Ser Ile Gly Gly Phe Asn Ala Gln Ala Ala Asn Leu Val Thr
        355                 360                 365

Ala Val Tyr Leu Ala Thr Gly Gln Asp Pro Ala Gln Asn Val Glu Ser
    370                 375                 380

Ser Asn Cys Ile Thr Leu Met Asn Lys Leu Pro Asn Gly Asp Leu Gln
385                 390                 395                 400

Ile Ser Val Ser Met Pro Ser Ile Glu Val Gly Thr Ile Gly Gly Gly
                405                 410                 415

Thr Val Leu Glu Pro Gln Gly Ser Met Leu Glu Leu Leu Gly Val Lys
            420                 425                 430

Gly Pro His Pro Thr Asn Pro Gly Ala Asn Ser Arg Gln Leu Ala Lys
        435                 440                 445

Ile Val Ala Ser Ala Val Leu Ala Ala Glu Leu Ser Leu Cys Ser Ala
    450                 455                 460
```

```
Leu Ala Ala Gly His Leu Val Gln Ser His Met Thr His Asn Arg Lys
465                 470                 475                 480

Gln Ala Pro Val Lys Glu Val Asn Gly Thr Ala Ala Arg Leu Ala Glu
            485                 490                 495

Gln Ser Lys Ile Cys Ile Lys Ser
            500

<210> SEQ ID NO 16
<211> LENGTH: 460
<212> TYPE: PRT
<213> ORGANISM: Pichia pastoris

<400> SEQUENCE: 16

Met Pro Glu Lys Lys Asn Ser Arg Ser Ala Asp Glu Ala Leu Ser Phe
1               5                   10                  15

Leu Ala Lys Thr Asn Val Glu Arg Pro Met His Tyr Ser Lys Thr Gly
            20                  25                  30

Asn Ile Thr Pro Asp Thr Val Ser Ser Arg Glu Asp His Tyr Gln Asp
        35                  40                  45

Tyr Asp Asp Ser Gln Asp Asp Ile Ile Asn Asn Lys Leu Leu Gln Arg
50                  55                  60

Arg Gln Gly Gly Pro His Asn Lys Ile Glu Lys Gln Arg Arg Phe Ala
65                  70                  75                  80

Leu Leu Arg Ser Ser Leu Asn Arg Arg Leu Glu Thr Leu Val Ile Leu
                85                  90                  95

Trp His Thr Ile Thr Ile Pro Phe Leu Ala Ser Leu Phe Phe Val Leu
            100                 105                 110

Cys Thr Ile Pro Met Leu Trp Pro Leu Ile Ile Val Tyr Leu Val Tyr
        115                 120                 125

Phe Tyr Ile Asp Ala Asn Thr Pro Ser Asn Gly Lys Ser Ala Asp Arg
130                 135                 140

Arg Val Glu Trp Phe Arg Ser Leu His Ile Trp Lys His Phe Val Asn
145                 150                 155                 160

Tyr Tyr Pro Ile Ser Val Tyr Lys Thr Val Asp Leu Glu Pro Thr Phe
                165                 170                 175

Lys Thr Lys Lys Ile Glu Ile Ile Leu Pro Lys Tyr His Gln Val Thr
            180                 185                 190

Thr Tyr Leu Pro Ser Ser Val Arg Lys Tyr Ile Pro Thr His Arg Val
        195                 200                 205

Leu Ile Glu Lys Glu Ile Lys Thr Gly Pro Arg Tyr Ile Phe Gly Tyr
210                 215                 220

His Pro His Gly Val Val Ser Leu Gly Ile Thr Gly Ala Phe Gly Thr
225                 230                 235                 240

Asn Gly Cys Asn Ile Gly Glu Leu Leu Pro Gly Ile Arg Ile Tyr Leu
                245                 250                 255

Leu Thr Leu Ile Thr Gln Phe Lys Leu Pro Leu Leu Arg Asp Tyr Leu
            260                 265                 270

Met Ala Leu Gly Ile Ser Ser Val Ser Lys Arg Asn Val Thr Ala Leu
        275                 280                 285

Ile Lys Arg Asn Gln Ser Val Cys Ile Val Ile Gly Gly Ala Ser Glu
290                 295                 300

Ser Leu Leu Ser Lys Pro His Thr Ile Asp Ile Val Leu Lys Lys Arg
305                 310                 315                 320

Lys Gly Phe Val Lys Val Ala Leu Glu Leu Gly Asp Thr Glu Leu Val
                325                 330                 335
```

Pro Val Phe Gly Phe Gly Glu Asn Thr Ala Tyr Asn Val Phe Asp Pro
            340                 345                 350

Ser Val Ser Gly Lys Ser Cys Ser Val Leu Asn Tyr Val Arg Lys Gln
            355                 360                 365

Met Cys Gly Phe Gln Leu Trp Leu Lys Gln His Phe Gly Phe Thr Phe
            370                 375                 380

Pro Phe Phe His Ala Arg Gly Val Phe Asn His Asp Phe Gly Leu Leu
385                 390                 395                 400

Pro Tyr Arg Lys Pro Ile Asn Leu Val Ile Gly Arg Pro Ile Pro Val
            405                 410                 415

Pro Tyr Ile His Ser Pro Thr Gln Glu Gln Ile Asp His Tyr His Ser
            420                 425                 430

Leu Tyr Val Glu Glu Leu Lys Arg Val Phe Glu Gln Asn Lys Glu Arg
            435                 440                 445

Phe Asn Ala Gly Ser Leu Glu Leu Arg Ile Val Glu
            450                 455                 460

<210> SEQ ID NO 17
<211> LENGTH: 652
<212> TYPE: PRT
<213> ORGANISM: Pichia pastoris

<400> SEQUENCE: 17

Met Gln Leu Arg Lys Arg Gly Asn Glu Arg Ser Arg Leu Glu Ser His
1               5                   10                  15

Ile Gly Asp Ser Asp Thr Val Ile Asp Leu Asp Asp Ser Ser Val Asn
            20                  25                  30

Asp Thr Leu Pro Asp Glu Asp Asn Ile Ala Lys Pro Arg Lys Ala Ser
            35                  40                  45

Thr His Arg Arg Pro Ser Leu Arg Lys Ile His Ser Ala Glu Thr Val
        50                  55                  60

Arg Arg Phe Tyr Glu Ser Lys Asn Val Ile Phe Ile Phe Gly Ala Phe
65              70                  75                  80

Ile Gly Ile Ala Val Ala Leu Tyr Phe Gly Ala Thr Ser Ser Glu Tyr
            85                  90                  95

Pro Ile Pro Asp Ile Asp Gln Leu Val Asn Phe Asp Ser Leu Ser Thr
            100                 105                 110

Tyr Phe Asp Asp Trp Lys Asp Val Leu Pro Lys Ser Leu Gln Ser Ile
            115                 120                 125

Val Glu Ser Thr Gln Phe Asn Gln Asn Ser Lys Ile Leu Ser Ser Glu
            130                 135                 140

Ser Phe Ala Val Gly Lys Gln Leu Lys Ser Lys Ser Met Ile Glu Ala
145                 150                 155                 160

Asn His Ser Ile Val Leu Val Pro Gly Val Ile Ser Thr Gly Leu Glu
            165                 170                 175

Ser Trp Gly Leu Glu Gly Thr Pro Asp Cys Pro Ser Glu Gly His Phe
            180                 185                 190

Arg Lys Arg Leu Trp Gly Ser Phe Tyr Met Leu Arg Thr Met Phe Leu
            195                 200                 205

Asp Lys Ala Cys Trp Leu Lys His Ile Met Leu Asp Thr Thr Thr Gly
            210                 215                 220

Leu Asp Pro Pro Gly Ile Ser Leu Arg Ala Ala Gln Gly Phe Glu Ala
225                 230                 235                 240

```
Ala Asp Phe Phe Ile Ala Gly Tyr Trp Ile Trp Asn Lys Ile Leu Gln
                245                 250                 255

Asn Leu Ala Val Ile Gly Tyr Asn Pro Asn Asn Met Val Ser Ala Ala
            260                 265                 270

Tyr Asp Trp Arg Leu Ala Phe Leu Asp Leu Glu Leu Arg Asp Ala Tyr
        275                 280                 285

Phe Ser Lys Leu Lys Gly Phe Val Glu Leu Gln Lys His Gln Ser Gly
    290                 295                 300

Lys Lys Ser Val Leu Val Gly His Ser Met Gly Ser Gln Val Ile Tyr
305                 310                 315                 320

Tyr Phe Met Lys Trp Val Glu Ala Asp Gly Tyr Gly Asn Gly Gly Pro
                325                 330                 335

Asn Trp Val Asn Asp His Val Asp Ser Phe Val Asp Ile Ser Gly Cys
            340                 345                 350

Met Leu Gly Thr Pro Lys Ala Ile Pro Ala Leu Leu Ser Gly Glu Met
        355                 360                 365

Lys Asp Thr Val Gln Leu Asn Ala Leu Ala Val Glu Gly Leu Glu Lys
    370                 375                 380

Phe Leu Ser Arg Arg Glu Arg Ala Asp Met Ile Arg Ser Phe Gly Gly
385                 390                 395                 400

Ile Ala Ser Met Ile Pro Lys Gly Gly Asp Leu Ile Trp Gly Asn Leu
                405                 410                 415

Glu Ser Ser Pro Asp Asp Ala Thr Ser Ile Gly Asp Leu Gly Asn Asp
            420                 425                 430

Thr Tyr Gly Asn Phe Ile Arg Phe Lys Glu Pro Val Gly Lys Tyr Ser
        435                 440                 445

Gln Lys Asn Leu Thr Val Thr Asp Ser Ile Gln Phe Leu Met Glu Gln
    450                 455                 460

Thr Pro Ala Trp Phe Gln Asp Arg Met Leu Arg Ala Tyr Ser Tyr Gly
465                 470                 475                 480

Phe Thr Asn Ser Ala Lys Gln Leu Lys Lys Asn Asn Lys Asp His Thr
                485                 490                 495

Lys Trp Ser Asn Pro Leu Glu Ala Ser Leu Pro Asn Ala Pro Asp Leu
            500                 505                 510

Lys Val Phe Cys Phe Tyr Gly Phe Gly Asn Pro Thr Glu Arg Ala Tyr
        515                 520                 525

Tyr Tyr Arg Glu Glu Val Asp Pro Ala Lys Thr Lys Leu Asn Val Thr
    530                 535                 540

Ile Glu Lys Asn Tyr Asp Ser Val Leu Met Ala Asp Gly Asp Gly Thr
545                 550                 555                 560

Val Ser Leu Met Thr His Ser Met Cys His Ile Trp Lys Gln Ala Asn
                565                 570                 575

Ser Val Tyr Asn Pro Gly Asn Ser Lys Val Lys Ile Val Glu Ile Asp
            580                 585                 590

His Glu Pro Asp Arg Phe Asp Ile Arg Gly Gly Ala Lys Thr Ala Glu
        595                 600                 605

His Val Asp Ile Leu Gly Ser Ala Glu Leu Asn Glu Leu Val Leu Leu
    610                 615                 620

Val Ala Ala Gly Lys Gly Asp Gln Ile Lys Glu Lys Ile Val Ser Asn
625                 630                 635                 640

Leu Lys Glu Ile Val Asp Asn Leu Glu Leu Asp Leu
                645                 650
```

<210> SEQ ID NO 18
<211> LENGTH: 678
<212> TYPE: PRT
<213> ORGANISM: Pichia pastoris

<400> SEQUENCE: 18

```
Met Leu Ser Leu Lys Pro Ser Trp Leu Thr Leu Ala Ala Leu Met Tyr
 1               5                  10                  15

Ala Met Leu Leu Val Val Pro Phe Ala Lys Pro Val Arg Ala Asp
            20                  25                  30

Asp Val Glu Ser Tyr Gly Thr Val Ile Gly Ile Asp Leu Gly Thr Thr
            35                  40                  45

Tyr Ser Cys Val Gly Val Met Lys Ser Gly Arg Val Glu Ile Leu Ala
        50                  55                  60

Asn Asp Gln Gly Asn Arg Ile Thr Pro Ser Tyr Val Ser Phe Thr Glu
65                  70                  75                  80

Asp Glu Arg Leu Val Gly Asp Ala Ala Lys Asn Leu Ala Ala Ser Asn
                85                  90                  95

Pro Lys Asn Thr Ile Phe Asp Ile Lys Arg Leu Ile Gly Met Lys Tyr
            100                 105                 110

Asp Ala Pro Glu Val Gln Arg Asp Leu Lys Arg Leu Pro Tyr Thr Val
        115                 120                 125

Lys Ser Lys Asn Gly Gln Pro Val Val Ser Val Glu Tyr Lys Gly Glu
    130                 135                 140

Glu Lys Ser Phe Thr Pro Glu Glu Ile Ser Ala Met Val Leu Gly Lys
145                 150                 155                 160

Met Lys Leu Ile Ala Glu Asp Tyr Leu Gly Lys Lys Val Thr His Ala
                165                 170                 175

Val Val Thr Val Pro Ala Tyr Phe Asn Asp Ala Gln Arg Gln Ala Thr
            180                 185                 190

Lys Asp Ala Gly Leu Ile Ala Gly Leu Thr Val Leu Arg Ile Val Asn
        195                 200                 205

Glu Pro Thr Ala Ala Ala Leu Ala Tyr Gly Leu Asp Lys Thr Gly Glu
    210                 215                 220

Glu Arg Gln Ile Ile Val Tyr Asp Leu Gly Gly Gly Thr Phe Asp Val
225                 230                 235                 240

Ser Leu Leu Ser Ile Glu Gly Gly Ala Phe Glu Val Leu Ala Thr Ala
                245                 250                 255

Gly Asp Thr His Leu Gly Gly Glu Asp Phe Asp Tyr Arg Val Val Arg
            260                 265                 270

His Phe Val Lys Ile Phe Lys Lys Lys His Asn Ile Asp Ile Ser Asn
        275                 280                 285

Asn Asp Lys Ala Leu Gly Lys Leu Arg Glu Val Glu Lys Ala Lys
    290                 295                 300

Arg Thr Leu Ser Ser Gln Met Thr Thr Arg Ile Glu Ile Asp Ser Phe
305                 310                 315                 320

Val Asp Gly Ile Asp Phe Ser Glu Gln Leu Ser Arg Ala Lys Phe Glu
                325                 330                 335

Glu Ile Asn Ile Glu Leu Phe Lys Lys Thr Leu Lys Pro Val Glu Gln
            340                 345                 350

Val Leu Lys Asp Ala Gly Val Lys Lys Ser Glu Ile Asp Asp Ile Val
        355                 360                 365

Leu Val Gly Gly Ser Thr Arg Ile Pro Lys Val Gln Gln Leu Leu Glu
    370                 375                 380
```

Asp Tyr Phe Asp Gly Lys Lys Ala Ser Lys Gly Ile Asn Pro Asp Glu
385                 390                 395                 400

Ala Val Ala Tyr Gly Ala Ala Val Gln Ala Gly Val Leu Ser Gly Glu
            405                 410                 415

Glu Gly Val Asp Asp Ile Val Leu Leu Asp Val Asn Pro Leu Thr Leu
            420                 425                 430

Gly Ile Glu Thr Thr Gly Gly Val Met Thr Thr Leu Ile Asn Arg Asn
            435                 440                 445

Thr Ala Ile Pro Thr Lys Lys Ser Gln Ile Phe Ser Thr Ala Ala Asp
        450                 455                 460

Asn Gln Pro Thr Val Leu Ile Gln Val Tyr Glu Gly Glu Arg Ala Leu
465                 470                 475                 480

Ala Lys Asp Asn Asn Leu Leu Gly Lys Phe Glu Leu Thr Gly Ile Pro
                485                 490                 495

Pro Ala Pro Arg Gly Thr Pro Gln Val Glu Val Thr Phe Val Leu Asp
            500                 505                 510

Ala Asn Gly Ile Leu Lys Val Ser Ala Thr Asp Lys Gly Thr Gly Lys
            515                 520                 525

Ser Glu Ser Ile Thr Ile Asn Asn Asp Arg Gly Arg Leu Ser Lys Glu
            530                 535                 540

Glu Val Asp Arg Met Val Glu Ala Glu Lys Tyr Ala Ala Glu Asp
545                 550                 555                 560

Ala Ala Leu Arg Glu Lys Ile Glu Ala Arg Asn Ala Leu Glu Asn Tyr
                565                 570                 575

Ala His Ser Leu Arg Asn Gln Val Thr Asp Asp Ser Glu Thr Gly Leu
            580                 585                 590

Gly Ser Lys Leu Asp Glu Asp Lys Glu Thr Leu Thr Asp Ala Ile
            595                 600                 605

Lys Asp Thr Leu Glu Phe Leu Glu Asp Asn Phe Asp Thr Ala Thr Lys
610                 615                 620

Glu Glu Leu Asp Glu Gln Arg Glu Lys Leu Ser Lys Ile Ala Tyr Pro
625                 630                 635                 640

Ile Thr Ser Lys Leu Tyr Gly Ala Pro Glu Gly Thr Pro Pro Gly
                645                 650                 655

Gly Gln Gly Phe Asp Asp Asp Gly Asp Phe Asp Tyr Asp Tyr Asp
            660                 665                 670

Tyr Asp His Asp Glu Leu
        675

<210> SEQ ID NO 19
<211> LENGTH: 993
<212> TYPE: DNA
<213> ORGANISM: Pichia pastoris

<400> SEQUENCE: 19
atgagtgaca ttaatactct gtcgcagaag attccgtcgt atgttcaata cggtattccc        60
agtattgatc atccttttgg aatccgttta tggccaattt tcagtcattt ctttgaagcg       120
gttgttggat acccggctga agatttccgc tttattcagg tctgactac catggccaat       180 ctaaaagacg ccctcggtgt tattgctgtt tattactttg tgattttttgg tggacaatgg     240 ttgatgagga ccctgaacgc tcgtcctttc aagttgaatt tcttgtttca attgcacaat     300
ttggttttga ccggggcgtc gtttaccttg ttgattga tcgtggaaca gttaatccca       360
ggtatttatc gccatggaat attttgggct atttgccaca aggattcttt caccaacgaa     420

```
cttgtcacgc tatattacct gaactacttg atcaagtacg tggagttgat cgataccgtg      480 ttttttggtcc tgaaacgcaa aaagttactt ttcttgcaca cttaccacca tggtgccact     540
gcattactat gctacaccca gctactcgga cacactgccg tcgaatgggt cccaattgcc      600
ctgaatctgg ctgttcacgt cgtccttgtac tggtactact tcctctctgc acgtggaatt    660
cgtgtatggt ggaagcaatg ggtgaccaga ttccaaatta ttcagttctt gatcgaccta     720
gggtttgtct actttgctac ctatacccttc tacgctgaca aatacttccc cgagctaccc   780
aacatgggaa catgttatgg gactgaggaa gctgctgctt tcggatactt gatcctcaca     840
tcgtatttgg tcctattcat tctcttttac attcgtgtct acaagtccgg gcccacaaca     900
agcaagggga aatcaaaggc agctgctact accggtcaaa aaactgagac tgcctcccct    960
tctggcaaaa gcactagtgt ccgtcgtgcc taa                                   993

<210> SEQ ID NO 20
<211> LENGTH: 1005
<212> TYPE: DNA
<213> ORGANISM: Pichia pastoris

<400> SEQUENCE: 20
atgtccattc tctcatttga taagcccttt ggcatcgaac tatggcccat tttcgatact      60
tttgcctcta aagccaccca cggtgctttt gttccttccg agtttgagtt tgttgctgga    120
aaactgcctt tatccactct ggaaccagta ttgtacagca ttgccgcgta ctactttatc    180
gtcttcggtg gctattattt tattaagaag ctggagctaa agccactagt tttaaatgcg    240
ttgttttctg ctcacaactt gttttttaact actgcttctt tggtgctgtt aactttgatg    300
gttgaacagc tcgttcctat tatttaccac catggacttt tctatgctat ttgcaacact    360
agggcttgga ctcaagagct tgtcactttg tactacctga attacctgat caagttcgta    420
gagtttattg acacattctt tttggttgtc aaacagaaaa agctgacatt tttacacact    480
taccaccacg gtgctactgc tttgctatgt tacactcagt tggttggtgt cacttccatc    540
tcttgggtcc caatctccct gaatctgggt gtccacgttg tcatgtactg gtattacttt    600
ctggcttcga gaggtatccg tgtatggtgg aaggaatggg tcactagatt tcaaattatg    660 caattatt tggatcttgg atttgtttat tttgccagtt accaaaagtt tgcctacact      720
tatttcaagg acgttctgcc atactgtggt gactgtgctg gaaccatggt agccgctgtg    780
tctggttgtg ccattctgtc gtcctacttg gtccttttca ttgccttcta cattgaagtc    840
tacagaaaac aaggtaaaaa gtccagatac gttaaaaagg tcagaggtgg tgttgctgcc    900
aaggtcaacg agtatgttct tttggaagac aaacagttgg catccggtgc ttcctctcgt    960
tccagctccc ctgtgaccag aaatttgcgc tctcgcaagg cctga                    1005

<210> SEQ ID NO 21
<211> LENGTH: 1212
<212> TYPE: DNA
<213> ORGANISM: Pichia pastoris

<400> SEQUENCE: 21
atgtctaaag aggaaaagac aagacgtcga agagcgtcat ccattggaaa cataaaccta      60
ggtgacaatg cagttccttc tttgactacc cgaaagtcga atgctcagca gagaaagtct    120
agctccgccc gtattaattt aatcaacaag aagggaagtt ccgattgggg tttagttaaa    180
aaaattggac tttccttggt cgaactgagc tcgcgtcaca catggttgcc attttttggtt    240
```

-continued

| | |
|---|---|
| tctttggttg ccatacatgg ctcgtatctg ttatctaata accacactcc atccaatcca | 300 |
| ttgcacaagt tcgttgatct ttcatataaa atcgaaggaa ctaaccctcc catgtatggc | 360 |
| aaaggatgga aagacttctg ctttgtgttt tacttcatga ttttcttcag tttctaccgt | 420 |
| gaatttttga tgcaagcgtt actgaaacct tggccagta agttgggtat cacaagagag | 480 |
| tctaaagtca gaagattcat ggaacagtct tattcaatgt gctactatgg attttctggg | 540 |
| cccttgggtc tatatatcat ggcaggtatg cccttgtggt acttcaacac gacagaattc | 600 |
| tatattactt accctcacaa aagtcatgaa tatctgttca agtactatta tttgggtcaa | 660 |
| gccgctttct ggtctcaaca agctgttgtc ttgatgctac aattggaaaa gccgagaaaa | 720 |
| gatttcaagg agctggttat tcaccacatt atcaccattg cactgattta ctgtagttac | 780 |
| agatttcatt tcacttggat ggggcttgca gtctacatta ccatggacat ctctgacttc | 840 |
| ttcctggctc tttccaagac cctgaactat gttgattcag cttacactgg tcccgcgttc | 900 |
| atgttctttg tgggtgtctg gttcacttg cgccattggc tcaatgtcaa gatcctttgg | 960 |
| tctgtattga ctgaattccg taccgtaggt ccatttgaat tgaactggat cacacagcaa | 1020 |
| tacaaatgtt ggatttcaca accaattgta ttttcattga tttttgcctt gcagctggtg | 1080 |
| aatctgtact ggtttgtgtt aattctccgg attttgtacc gtcacatctt tttagatgtt | 1140 |
| accaaagacg aaagatccga cgatgaaagc gaagaagaag cccaagtaga accctccaag | 1200 |
| aaggaagaat ag | 1212 |

<210> SEQ ID NO 22
<211> LENGTH: 1137
<212> TYPE: DNA
<213> ORGANISM: Pichia pastoris

<400> SEQUENCE: 22

| | |
|---|---|
| atgggtgttg aaacatcttc ctctggaact caacatttca gtgatgacgg ttgtgtatct | 60 |
| tcaaggaagc caaatgctac tgtaagcttt gagaagcctg agcgtgctaa cgagctgaag | 120 |
| aatcacaaaa tctataaaaa gtccaaggct tcatggttac agagaaatca aattttacta | 180 |
| gcatcttcat tgttgaacgc gttgttcatc ttaaagcaaa ttccctcatt tcaatcactc | 240 |
| gttaataaat tctttcattt acagtacaag aacttagatg gtacttatga tattggtaaa | 300 |
| gacgactatt ttttcgttat ttactggata atcaacttga ctattattcg cagtgtcttg | 360 |
| atggattggg tcctagaacc cttggcaatt aagatagttg ggattaacaa tagaaaagct | 420 |
| cttaccagat ttaaagaaca gggttggtct ttattctact acaccacgtc atggactgtg | 480 |
| ggcttctatt tatactacaa gtccgactat ttttcaatt gtgatcatat tttcatcggc | 540 |
| tggcccaaca ataagctgga tttctacttc aaatcttact acttgattca atgtcatgt | 600 |
| tggctccagc agatcgttgt tttgaacata gaggagagaa gaaaagatta tgttcaaatg | 660 |
| ttctcgcatc atataataac ctgtttgctg attattggct cttactacta ttactttttta | 720 |
| cagattggac acgtcatttt ggttatgatg acattgttg acgttttct cagtcttgcc | 780 |
| aaaatgttaa atactgtggg ttacagcact ctctgcgacg tgatgttttt catattcttg | 840 |
| gtttcatgga tagctataag acacgtgtgt tacaactacg tgttctggca cacatgcacc | 900 |
| aagtctaggg atcaatgaa cgcagattgt tccaggtacg caatctacgg aggtcccttg | 960 |
| gacgttactc cagtacgatg ctatacagat agtaccatta gatacttcat tttccttctt | 1020 |
| ggaggtctcc aaattatcac actaatctgg atgtaccta ttctaaaagt tttcataggg | 1080 |
| gtaataacgg gcaaaggtgc tgaagacgtt agaagtgatg atgaggagag ttcttga | 1137 |

<210> SEQ ID NO 23
<211> LENGTH: 1191
<212> TYPE: DNA
<213> ORGANISM: Pichia pastoris

<400> SEQUENCE: 23

| | |
|---|---|
| atgagccaac gtgaagaaac aaaagatgct gcaaagaaac agatcgcctt ttcgggaatt | 60 |
| ggagcctgcg gtcctccaaa cttctatggt acacaggatg ctcacgctag attggaagaa | 120 |
| gatctagccc gatttcttgg tgctgaacgt gccatattgt attcccagga tttctgtact | 180 |
| gtgccgtcag ttatagcatg ttttttgaaa agaggtgata ttgttgtgta tgactctggt | 240 |
| attgctttgg caacccaaaa gggaatcgaa ttatccagat gtaccgccta ccatttcaac | 300 |
| cataatgaca tggataacct ggagaaagtg ttagctgatc tgaagcccat gttagatgaa | 360 |
| ggacctttaa ctaggagatt tattatcaca gaaggtcttt ttcaaaactt tggagactct | 420 |
| ccagacttgc gtcgtatatg tgagctgaag aaaaagttca gtacagact gttcttagat | 480 |
| gaaactcttt caattggtgt tctaggtgct actggtagag gattgccaga attatacgga | 540 |
| atccctcgca cagacgttga ggtgaccacc ggcgctttat cctacgccct gggttcttct | 600 |
| ggaggattct gcgtcggtga aaacgccatg gtacatcacc agctaatttc ctctagtgcc | 660 |
| tatgtgtttt ctgcagctat tccacccttat tttgccagag ttgcatcggt atctcttcga | 720 |
| ttactccaag aagatgactc cgtgtcaaga ttacaatcca gtattaattt cctttactca | 780 |
| aagtttaaag aatgccagaa actcaaaaag ctggtaataa tcacttcatc tgacgtatct | 840 |
| ccaatcctac atctacgatt gcatcgtgac ttgagaagca gactcgatct tccggtgagt | 900 |
| tatggtggtc ccggatctgc tatggagaaa atagtacaga ggggagatga acacggttac | 960 |
| ttcgacgaaa attacaacag ggagtctcag atcttacaac aaattgtaga cagagtttta | 1020 |
| aacaaccata atatcctaat aacgagatgt aagaggatac ttcaccatga aaagctacca | 1080 |
| ttactgcctg agcttatgat ccatattaat gttgcatttt cggaatctga gctttcagaa | 1140 |
| gcatttgagg ccgtctcctc tgagatttac aatgttttgc aacagctttg a | 1191 |

<210> SEQ ID NO 24
<211> LENGTH: 1686
<212> TYPE: DNA
<213> ORGANISM: Pichia pastoris

<400> SEQUENCE: 24

| | |
|---|---|
| atgtcaaaaa ctatcccaga tgctctcata gacaatgatt caccacaaga gaaggccgag | 60 |
| aaagaatttg ggtccttgac cagtaaagaa tggctctttg tctctaagca taaccctggc | 120 |
| gagccgcttc cagttcccat cgaggacgaa cctccatatt tcatcctgat tgcaacatac | 180 |
| cttaattacc ttattttgat cataataggc catattagag acttctttgg gaagttgttt | 240 |
| caccctgaac tattcagaga tgtgatggtg aaagatggta ttgctccatg gtatgccaat | 300 |
| tttgaaagtt tctacacgcg tcgtttgaaa acaagattag atgactgttt tgcaaggccc | 360 |
| atatgtggag ttcccggtag gtacatcaaa tgttacgaca gaaccagtga cgattacaac | 420 |
| aatacctata attattccgg caccgtcaca gagcgcttga atttgagttc atacaactat | 480 |
| ttagggttcg cacaatcctc tggtctgtgc acctcagaaa gtatcaagac ggtggagaag | 540 |
| tatggtacca acagtgctgg tcctcgagtt agtgtgggaa ctactgatct ccatcttgaa | 600 |
| tgtgaggacg tcgttgccaa atttactggc aaggacaatg ctttggtatt ttccatgggt | 660 |

```
tatgggacca atgcaaatct cttcacctct ttggtggact ctaagtgttg tgttatctca      720
gattctttaa accacggatc tatcaggaca ggtgttcgtt tgtctggcgc ctcagtcaaa      780
acttttgctc acaacgacat ggcagcgctg aaagaactt tgagaagtgt catttcccaa      840
ggtcagccaa agactcatag accctggaag aagattttg ttgctgtaga gggactttat      900
tccatggaag gaacccttg taatttgcca aaactggtag aattgcgtaa gcgttacaag      960
ttttatttat ttgttgacga ggcacattct attggtgcta tgggacccaa tggtaagggt     1020
gtttgtgact attttggcat tcttcttcc aatattgata ttatgatggg tacttttacc     1080
aaatcatttg gagccacagg cggttacatc gctgccgaca aagccatcat agacagattg     1140
aagttagatc tcacaacaaa tacttatgga gaatcaatgt cacctgctgt gctcacacaa     1200
atcattactt ctttgaaaat tatagatgga caactcaatg gtaatgaagg taaagagagg     1260
ctacaaagga ttgccttcaa ttctaggtat ctgcgattag gactaaagcg attaggattt     1320
attgtttatg gtgctgatga ttctcctgtt atccccctt tactgtatct tcccccaag     1380 atgcctgcat ttagccgaat gatgtacgat agaaaggttg ctgtcgttgt tgtgggatat     1440
cctgcaacgg ataacgtc ttctcgtatt cgattctgcg tttcctcttc tttgaagaag     1500
gaggatatag attatttgct caaatgttgt gatgagatag gagatacttt gttttgaag     1560 ttcagcacag ggattgctgg tggtgagaag caccgggag actataagaa gggcattgct     1620
cctaggtgga cattggagga ggttctggag aagacaccgg aggattgcaa gaaagccatg     1680
tactaa                                                               1686

<210> SEQ ID NO 25
<211> LENGTH: 962
<212> TYPE: DNA
<213> ORGANISM: Pichia pastoris

<400> SEQUENCE: 25
atggttaaac tcattgttaa tccaaggtct gagaccctga gacaaatcaa cgtagacact       60 accccaata caagagtcag agacattgtg gtagcttacg gaaaggcaaa taacagttta     120
tccagctcca gaatcagatt cactaaactg gaagaagacg cagtttccaa gaaaccaaag     180
catgtcactc tggactacga gaaatcctta gctcaaatg ggatagtctt cacagatgat     240
tcagattcca agaagtcta tgcgaaagat ttgggacccc agatcagttg gaaattagtg     300
ttcctgatcg aatacgtggg cccgctgatt attcatccat tgctctatta cggctggttc     360
aaacctgact ataacactct tacacagaaa gtttctttca ttttggtgat gctgcacttc     420
ctgaaacgtg aatacgaaac aacttttgtg cacctgtttt catctgatac aatgcctctt     480
ttcaacgttt tcaagaactc agctcattat tggattctta gtggattgag ccttgctgtc     540
actatttatg ctccggattc ataccgaaat aagtttgcac ccacttggaa acagttttt     600 tccatgtatc tgaccatgaa gactccacag ttctagcact gattggactg tgggtatttg     660
ctgaattgtc caacttcatc actcaccaga aattggccag tctcagagcc gatggctcca     720
gagaacataa aattccctat ggatatggct tcaacctggt ctctttcccc aactatttct     780
ttgaatctgt agcttggttg gcatttgccc ttctcaacaa taactggtca tcttgggtgt     840
tccttaccat tgcctccatt cagatgtata tttgggccgc taagaaacac aaaagatatc     900
tcaaggagtt tggggaccaa tatcccaaga acaggaaagc aatgattcca ttcctttgt     960 ag                                                                    962
```

<210> SEQ ID NO 26
<211> LENGTH: 453
<212> TYPE: DNA
<213> ORGANISM: Saccharomyces cerevisiae

<400> SEQUENCE: 26

```
atgtctcaac ccactcccat cataactaca aaatcagctg ctaagccaaa accaaaaatt      60
tttaatttat tccgcgtttg cttcatttca ttattgctga tcgctgcggt tgaatacttc     120
aagtatggta caagaattaa ctatgaatgg ttccattgta ccccaatcaa agaaccccag     180
tctggctcag taatcaagct ttgggcacgt ggtgggccaa gttgtgacaa agaggcgaa      240
tataaaacta tagtaaagag aatcactaga gattatgaac caaatgatga acatctctcg     300
ttctgtatca tcgagaatga taatgttcca cccgtccact acccaattca cgaagataaa     360
ggtgaacctg gctacgtagc ttatgtcggg tacgacacag actctgagct ggttcaagaa     420
ctatgtgctg attccacaat ttatcacatg tga                                  453
```

<210> SEQ ID NO 27
<211> LENGTH: 243
<212> TYPE: DNA
<213> ORGANISM: Saccharomyces cerevisiae

<400> SEQUENCE: 27

```
atgacacaac ataaaagctc gatggtgtac atacccacca ctaaggaagc taaaagacgt      60
aatgggaaat cagaaggcat actaaatact attgaagaag tggtggaaaa gctttattgg     120
acctactaca tacatttacc cttttatttta atggcctctt ttgattcatt cttcctccat     180
gttttttttc tcacaatttt cagtttgagt ttcttcggta tactaaagta ttgcttcctt     240
tga                                                                    243
```

<210> SEQ ID NO 28
<211> LENGTH: 2328
<212> TYPE: DNA
<213> ORGANISM: Pichia pastoris

<400> SEQUENCE: 28

```
atgcagtacg taggtagagc cattggatca gtatccaaaa cctggtcgtc cattaacccg      60
gccacactga gtggtgctat tgatatcatc gtggtggaac aagaaaatgg tgatctggct     120
tgctctccct tccatgttcg gtttggaaag tttcaattat tgaggccttc ccaaaagaaa     180
gtggatttca tcgtcaatgg agaaaagaca gacttaccaa tgaaactggg cgatgggggc     240
gaagctttct ttgtgtttga aaccgatgct gccatcccga gtgagcttca aacttccccc     300
gtcatctcac ctgtatccag cccagaacca gcctctccac tgagtactcc ttccagacca     360
aactctgaac cagattattt agaattaggg gatggagaat ctacaaccag tgaattagag     420
aacttcaagt taaatcgata tccctatttta tcaactgagg tatcgcattc agatcctggt     480
gttgggtctg tgagctcaag tcctgagaat acgaagatta ttcaaaagat ctctcggaaa     540
ctcaatacga aaaatattcc ttccaaggtt gataataacg gaaatcttgt attggatata     600
caaggttaca aaagtgatga tctagacgac aattccaaat cttttgaaaca gttgttattg     660
gctgaactcg gagaagatgt agatttggac aaggttattg aaaaagatca cgaaggaaac     720
attatgatca atggtgccat atctttgttg agcggagaag atgatctgga atcatttcct     780
cagaccgacg accaagctga gagtctcaaa ttggatctgg agtcagataa atctgacatt     840
gaatcagaca caaatcatga attgtctcgc tacttcaaaa cgctaagact tacatcagat     900
```

```
caattgaaat gtcttacact gaagaaggga attaacgagc tgaaattcag tgtcaacaag      960
ggcaaatctg tggtgacggc aaatctatac ttctgggact attatgaccc catagtcata     1020
tcggatatag atggaaccat tactaaatct gatgccttag ccatgtatt taccatgatt      1080
ggccgtgatt ggactcacaa aggtgtagcc aaattatttt cagatatcaa atccaatgga     1140
tacaatatca tgtatttgac tgcaaggtct gttggtcaag ccgattcgac ccgctactat     1200
ttaaacaaca ttgaacaaga aggcttgagg cttcctcaag ggccggtgat cctttctccg     1260
gatcgcacaa tggccgcttt acgaagagag gtaattttga agaaacctga ggtgttcaag     1320
atggcatgtt taaacgacat aaagaaactg tatctcacca ataccaaaga cctaaatccg     1380
aacacagatt ctgcagattt cacggatatc aatacgaaca ctttgagatc ttcaagtctt     1440
acagaggatg tacaaacgcc attttacgcc ggttttggta atagaattac cgatgctttg     1500
tcctataggt cagtagggat accatcatca agaattttta ccataaaccc agacggtgat     1560
gttcacatgg agctactcga attggctggg tatagaagtt cttatgtaca tattagtgag     1620
ctggtagatc atttctttcc accagtgaac actgaactat ttaagtcgat gccttctgat     1680
acctatcgga cacggcaaa gttctctgat gtcaattatt ggaaagagcc tttgtacaat      1740
tttgaggagc tcagtgatga agattctagt gaagatgagc taagaagaag aaaggaggag     1800
gaacgtttac agtctgctcc tcgtagtcca atattggcag caggagcatc gttttcaaa      1860
ggaagtagta gccttttagg ttcaccagaa cggatgactt tgagtgaccc aaagccaact     1920
gaagttgccc ctagcacaat caaaccccca aaatcagttg ttctgtatc atccgatgaa      1980
gaaaagctga agatcatga tgatttcatt gacgttgatc acgaagatga aaccttggat      2040
gatgatgacg atcccttga ctacgattac gagtatgaag atgaagaaga ggaaaatgac      2100
gacgtagatg aagttgatga tggggaagag tattcagatg attattatga cgaagaagac     2160
gactacgatg aagaattaga tcatacttta gaaccagacc aaaagaaaga actggaccaa     2220
acagctgaag ccaaccagtt acccccttca ggacccgatg aaatggaatc aaaatctttc     2280
aagaaagcca gtgatttaat aagcaaaatg agaatcgatg acagctga                  2328

<210> SEQ ID NO 29
<211> LENGTH: 942
<212> TYPE: DNA
<213> ORGANISM: Pichia pastoris

<400> SEQUENCE: 29
atgaagctct ccaccaattt gattctagct attgcagcag cttccgccgt tgtctcagct      60
gctccagttg ctccagccga agaggcagca aaccacttgc acaagcgtgc ttactacacc     120
gacacaacca agactcacac tttcactgag gttgttactg tctaccgaac tttgaaaccg     180
ggcgaaagta tcccaactga ctctccaagc cacggtggta aaagtactaa aaagggtaag     240
ggtagtacca ctcactctgg tgctccagga gctacctctg tgctccaac tgacgacacc      300
acttcgacta gtggctcagt agggttacca actagcgcaa cttcagttac ctcttctacc     360
tcctctgcaa gtacaacaag cagtggaact tcagccacta gcactggtac cggtactagc     420
actagcacta gcactggtac tggtactggt actacaggca caggaaccac tagttccagc     480
actagctctt ctgctacttc gactccaacc ggttctatcg acgctatcag ccagacactt     540
ctggatactc acaatgataa gcgtgctttg cacggcgtcc cagacctac ttggtctacc      600
gaactcgctg actacgccca aggttacgcc gattcataca cttgtggctc ttcattagaa     660
cacacaggtg gaccatacgg tgaaaatttg gcctctggat actctcctgc tggcagtgta     720
```

```
gaagcatggt acaacgagat cagcgactac gatttctcta acccaggtta ttctgctggt    780
accggtcact tcacccaagt tgtctggaaa tcaactacac agctgggctg tggatacaag    840
gagtgcagta ccgacagata ctacatcatc tgcgaatacg cacctcgtgg aaatattgtt    900
tctgccggct acttcgaaga caacgtcctg cctcctgttt ga                      942
```

<210> SEQ ID NO 30
<211> LENGTH: 1548
<212> TYPE: DNA
<213> ORGANISM: Pichia pastoris

<400> SEQUENCE: 30

```
atgagtctgg tccaggagtt gattcaaaag ataagctctt ggagctcac cttggtggaa     60 aagctttcca tcctgttcgt agctcccttc ttgttgaacg cgctatggca gtttatctac    120
agtttcagaa aggacagagt tcctttggta ttccactggg ttccatgggt aggctcagca    180
gtcacatatg gaatgcaacc atatgaattt tttgcagact gtcaaagaaa atacggagac    240
gtgtttgcct ttgttttgtt gggtaaagtt atgacagtgt acctcggacc aaaaggccat    300
gagtttattt taaatgctaa actaaacgac gtttgtgctg aagatgccta caagcacctg    360
accactcctg tatttggtga aggtgttatt tacgattgtc ccaactggaa gttgatggac    420
cagaagaagt ttgttaaagg atctttaacc aaggagtcct tcagatctta tgtccctaag    480
attagagatg aagtcctgga ttacatcaat aatgaccca acttcatggg aggtgattct    540
aaaaagaaaa ctggaaagac caatgtcctg aactctcagt ccgagcttac gatcttgacc    600
gcttccagat ctctactggg agatgatatg agaaaactac tgactaagaa atgggctaaa    660
ctgtttagtg acctagacaa aggatttact cctttaaact tcatttttctc tcatcttcct    720 ctaccaagtt actggactcg tgatcatgct caaaagacca tttctgagac ttatttatct    780
ttgattaaca agagaagagc tacaaacgac attggtgaca gagatttgat cgattcatta    840
atgaaatctt ctacatacaa agatggtagc aagatgaccg acgaggagat ttcccacttg    900
ttaatcggag ttcttatggg tggccagcac acttctgcct ccacttcatc gtggtttttg    960
ttgcatctcg gagagaaacc agagctgcag gaggaattat ttgaagaaca ggaaagggta   1020
cttcaagggc gtgagttgac ttatgacgat cttgctaata tgcctttaca caatcaagtc   1080
atcaaggaaa ctttgcgcat gcacatgcct ctacactcaa tctttagaaa ggtcactcgt   1140
cctcttcccg ttcctaactc aaagtatgtg gttcctaagg tcattatgt attggtttca   1200 cctggatttg ccatgaccaa cgatgcgtac ttcccaaacg ctagtgactt ccagccacac   1260
agatgggatg aaactgttga accagtctca gctgacgcaa aggaaactgt tgactacgga   1320
tttggtaaag tctccaaagg tgtttcttct ccttacttac catttggagg aggaagacat   1380
agatgtattg gcgaacattt tgcgtactgt cagttaggaa ccatcttgaa cacattcgtt   1440
agaaccttca gtggaaggc cgtagtccct cagccggact atacctcaat ggttactctt   1500
cctgaaccta atttgtctac tattacatgg gaaagacgcg ataattag                1548
```

<210> SEQ ID NO 31
<211> LENGTH: 2961
<212> TYPE: DNA
<213> ORGANISM: Pichia pastoris

<400> SEQUENCE: 31

```
atgcttactg ggttgtccaa gatatgtgcg catagaccaa tccataccat agtggtgacc    60
gctctcttag tttccttagc atacctaacc attgtggagg agtacacatc gagatcttca   120
ttatccaatc cttttatatc gttttaccac ccaccaggaa acagtgatta ccaaaattgg   180
attccagtgg atgactctgt gaagctcaaa agcaagtcag cccagcatct ctctgtatgc   240
gctttgaagt ttaaagggt taatggacat cagattccg atctggcagg aagttttcag    300
agcgcagacc caactgaaat atttgtcgtt caggattttg acaaatcatt tgactatttt   360
gattcaattt caaccattga gggtaaggat ggcatccaat ggaaagtcag acaccccaat   420
aggttgggac gttattctga gtacttcaga tctgtttttt caaaaacttt gagactggtt   480
cagggtgctg aaccattcga cattgtgctt attgcttttg cttacgttgc tatgtggtac   540
acatttttgc agctctatta tgaaatgaaa acaaaggcca actctaactt ttggctgact   600
ttcggctctc tgctgtcttc aggttgtgca tttgtgtttg cattggccgt cactgtaaaa   660
gtatacggta tcaaggttcc actcacatct ttaactgaag gtgtcccatt tttggtagct   720
accattggtt tcaaacacaa agttgcattc actgttccta ttctccaagc ttcccgttca   780
aaaaaagcca agaaattcc tgacaccatt atttcagtga ttgaacaaac cacagggtgg   840
cctctgatta aggatcatct cattatgatt tccgccttct tagcatgttc tttttatgcc   900
ccccgtatgg aaggactcaa aaacttttgc attctctccg ctaatatctt aacgtttgac   960
cttataatga ttttcacatt ttttaccgct gtattatctt taaaagctca gattaataag  1020
gttcacgaaa caactgcttt gcagcaagtt ctggaggaag atggaattgc tgaagatgtt  1080
gctgaacgca ttgctgcttc aaaccgaaat atgttttccc gtagtaccag cgtcgtcagc  1140
ttcaaagtga taatgatcgc tgggttcctt ggattccatt tatttgtgtt gggaacttca  1200
tggctctatg actctgacgt ttcaagctct ctatatttg gtaagagcaa tgtatctgcc   1260
ttatccaaag ctgctgccaa acatattcct attggatccg aaggaactat tgtgaccatt  1320
atgcctacga gggtttacat gcctgttgat ttacttctaa agttggaaga tgattttctg  1380
aacattttt ccaagatatc ggctagcata actgatcctt tgattagcaa acttcttttc   1440
ataattaccg gaataagtgc cacaatcaac gtttacttgt tgaatgctgc tcgattccac  1500
tcgtctagag aaattgctgt ctctacaatt gcaaagcctc aaacgccaga cgttgttccc  1560
acagtagaac cgcttccaaa tgaaaatgac acaagcattc gaccattgga ggagatggtt  1620
tcattgctga aggaaggtaa aacacgagag ctgaacaatg atgaggtatc atctctcgtt  1680
gttcaaggaa aacttcccct tgtacgcccta gaaaaacaac ttgttgataa gacccgcgca  1740
gttattgtaa gaaggaaggc aattgcttcc ttagcagatg ctccggtctt gagaaccgaa  1800
aagctgcctt acaaagatta tgattatgac cgtgtatttg gcgcttgttg tgagaatgtt  1860
atcggattca tgcccttacc agtcggcgtt gctggtccct tgatcattga cggtaaacct  1920
tatcacattc ccatggctac tactgaaggc tgcttagtag cctcaaccat gagaggttgt  1980
aaagctatca attctggagg cggtgtagaa actgttctga cagccgacgg aatgacaaga  2040
ggaccatgcg tttctttccc atctctttct cgtgcaggtg cagctaagat gtggctagat  2100
agtgaagaag ggcaaaagac cattaagggt gcgtttaact ccacctctag atttgcccgt  2160
ttgcagcatg ttaagacaac ccttgctggt acattattgt tcatccgatt caagactact  2220
actggtgatg cgatgggtat gaacatgatt tctaagggtg tggagtattc actaaagttt  2280
```

```
atgtcggaag aatgtgactg gcctgacatg gaagttattt ctgtttcagg taattactgt    2340
acagacaaaa aagttgctgc aatcaactgg atcgaaggtc gtggtaagtc tgtcgttgct    2400
gaagctcgta ttccagccga tgttgtcaga agcgttctga agtccgatgt tgaggcattg    2460
gtagaattga atgttagcaa gaacttgatt ggatccgcaa tggcaggatc aattggtggt    2520
ttcaacgcac aagctgccaa tctagttaca gcagtatact tagctacagg acaggatcca    2580
gcccagaatg tcgaaagttc caactgtatt accttgatga acaagctccc aaatggagat    2640
ttacaaattt cagtctctat gccatctatc gaagttggaa ccattggtgg aggaaccgtt    2700
ttggaacctc aaggatcaat gttgaaacta ttaggagtta aaggtcctca cccaactaat    2760
ccaggtgcaa actcaaggca gttggctaag atcgttgctt ctgctgtctt ggctgcagag    2820
ctgtccttgt gctctgccct tgcagctggt cacttagtcc aaagtcatat gacccataac    2880
agaaagcaag ctccagtcaa ggaggtaaac ggcactgccg ctaggctagc ggaacaatct    2940
aagatttgca ttaaatcttg a                                              2961

<210> SEQ ID NO 32
<211> LENGTH: 1422
<212> TYPE: DNA
<213> ORGANISM: Pichia pastoris

<400> SEQUENCE: 32
atgacgccag acgttgttcc cacagtagaa ccgcttccaa atgaaaatga cacaagcatt      60
cgaccattgg aggagatggt ttcattgctg aaggaaggta aaacacgaga gctgaacaat     120
gatgaggtat catctctcgt tgttcaagga aaacttccct tgtacgccct agaaaaacaa     180
cttgttgata agaccecgcgc agttattgta agaaggaagg caattgcttc cttagcagat     240
gctccggtct tgagaaccga aaagctgcct tacaaagatt atgattatga ccgtgtattt     300
ggcgcttgtt gtgagaatgt tatcggattc atgcccttac cagtcggcgt tgctggtccc     360
ttgatcattg acggtaaacc ttatcacatt cccatggcta ctactgaagg ctgcttagta     420
gcctcaacca tgagaggttg taaagctatc aattctggag gcggtgtaga aactgttctg     480
acagccgacg gaatgacaag aggaccatgc gtttctttcc catctctttc tcgtgcaggt     540
gcagctaaga tgtggctaga tagtgaagaa gggcaaaaga ccattaaggg tgcgtttaac     600
tccacctcta gatttgcccg tttgcagcat gttaagacaa cccttgctgg tacattattg     660
ttcatccgat tcaagactac tactggtgat gcgatgggta tgaacatgat ttctaagggt     720
gtggagtatt cactaaagtt tatgtcggaa aatgtgact ggcctgacat ggaagttatt     780
tctgtttcag gtaattactg tacagacaaa aaagttgctg caatcaactg gatcgaaggt     840
cgtggtaagt ctgtcgttgc tgaagctcgt attccagccg atgttgtcag aagcgttctg     900
aagtccgatg ttgaggcatt ggtagaattg aatgttagca gaacttgat tggatccgca     960 atggcaggat caattggtgg tttcaacgca caagctgcca atctagttac agcagtatac    1020
ttagctacag gacaggatcc agcccagaat gtcgaaagtt ccaactgtat taccttgatg    1080
aacaagctcc caaatggaga tttacaaatt tcagtctcta tgccatctat cgaagttgga    1140
accattggtg gaggaaccgt tttggaacct caaggatcaa tgttgaaact attaggagtt    1200
aaaggtcctc acccaactaa tccaggtgca aactcaaggc agttggctaa gatcgttgct    1260
tctgctgtct tggctgcaga gctgtccttg tgctctgccc ttgcagctgg tcacttagtc    1320
caaagtcata tgacccataa cagaaagcaa gctccagtca ggaggtaaa cggcactgcc    1380 gctaggctag cggaacaatc taagatttgc attaaatctt ga                      1422
```

<210> SEQ ID NO 33
<211> LENGTH: 1515
<212> TYPE: DNA
<213> ORGANISM: Pichia pastoris

<400> SEQUENCE: 33

| | | |
|---|---|---|
| atgggaataa gtgccacaat caacgtttac ttgttgaatg ctgctcgatt ccactcgtct | 60 |
| agagaaattg ctgtctctac aattgcaaag cctcaaacgc cagacgttgt tcccacagta | 120 |
| gaaccgcttc caaatgaaaa tgacacaagc attcgaccat ggaggagat ggtttcattg | 180 |
| ctgaaggaag gtaaaacacg agagctgaac aatgatgagg tatcatctct cgttgttcaa | 240 |
| ggaaaacttc ccttgtacgc cctagaaaaa caacttgttg ataagacccg cgcagttatt | 300 |
| gtaagaagga aggcaattgc ttccttagca gatgctccgg tcttgagaac cgaaaagctg | 360 |
| ccttacaaag attatgatta tgaccgtgta tttggcgctt gttgtgagaa tgttatcgga | 420 |
| ttcatgccct taccagtcgg cgttgctggt cccttgatca ttgacggtaa accttatcac | 480 |
| attcccatgg ctactactga aggctgctta gtagcctcaa ccatgagagg ttgtaaagct | 540 |
| atcaattctg gaggcggtgt agaaactgtt ctgacagccg acggaatgac aagaggacca | 600 |
| tgcgtttctt tcccatctct ttctcgtgca ggtgcagcta agatgtggct agatagtgaa | 660 |
| gaagggcaaa agaccattaa gggtgcgttt aactccacct ctagatttgc ccgtttgcag | 720 |
| catgttaaga caacccttgc tggtacatta ttgttcatcc gattcaagac tactactggt | 780 |
| gatgcgatgg gtatgaacat gatttctaag ggtgtggagt attcactaaa gtttatgtcg | 840 |
| gaagaatgtg actggcctga catggaagtt atttctgttt caggtaatta ctgtacagac | 900 |
| aaaaaagttg ctgcaatcaa ctggatcgaa ggtcgtggta agtctgtcgt tgctgaagct | 960 |
| cgtattccag ccgatgttgt cagaagcgtt ctgaagtccg atgttgaggc attggtagaa | 1020 |
| ttgaatgtta gcaagaactt gattggatcc gcaatggcag atcaattgg tggtttcaac | 1080 |
| gcacaagctg ccaatctagt tacagcagta tacttagcta caggacagga tccagcccag | 1140 |
| aatgtcgaaa gttccaactg tattaccttg atgaacaagc tcccaaatgg agatttacaa | 1200 |
| atttcagtct ctatgccatc tatcgaagtt ggaaccattg tggaggaac cgttttggaa | 1260 |
| cctcaaggat caatgttgga actattagga gttaaaggtc ctcacccaac taatccaggt | 1320 |
| gcaaactcaa ggcagttggc taagatcgtt gcttctgctg tcttggctgc agagctgtcc | 1380 |
| ttgtgctctg cccttgcagc tggtcactta gtccaaagtc atatgaccca taacagaaag | 1440 |
| caagctccag tcaaggaggt aaacggcact gccgctaggc tagcggaaca atctaagatt | 1500 |
| tgcattaaat cttga | 1515 |

<210> SEQ ID NO 34
<211> LENGTH: 1383
<212> TYPE: DNA
<213> ORGANISM: Pichia pastoris

<400> SEQUENCE: 34

| | | |
|---|---|---|
| atgcctgaaa agaagaacag tcgttccgct gacgaagctc ttagctttct tgctaaaacg | 60 |
| aacgtagagc gcccgatgca ttactctaag acagggaaca taacgcccga cacggtatct | 120 |
| tcaagagaag atcactacca agattacgac gactcacaag atgacattat aaataacaaa | 180 |
| ctattacaaa gaagcaggg tgggccacac aacaagatag agaagcaaag gaggtttgct | 240 |
| ttgttgagga gttccctaaa caggagattg gaaactctag taatattgtg gcatactatc | 300 |

| | |
|---|---|
| acgattccat tttttagcatc actattttttc gttctgtgta caattcccat gttgtggcct | 360 |
| cttataatag tttacttggt ttattttttac atcgatgcca atactccaag caatggaaag | 420 |
| tctgctgacc gaagagtgga atggttcaga agtttgcata tttggaaaca ttttgtcaat | 480 |
| tattacccta tatctgtgta caaaactgtt gacctggaac cgacgttcaa gactaagaag | 540 |
| attgaaatta ttcttccgaa gtatcaccaa gtaaccactt atttgccaag ttctgttaga | 600 |
| aagtacatac cgacacacag agttctcata gaaaaggaga tcaaaacagg gccaagatac | 660 |
| atatttggtt atcaccctca tggggtagtt tccctgggga tcactggagc ttttggcacc | 720 |
| aatggttgta acattggcga gttactacca ggaatcagaa tatatttatt aaccctcatc | 780 |
| actcaattca aacttcctct attgagagat tacttaatgg cattgggtat ttcttctgtt | 840 |
| tcgaaacgta atgtgactgc actgataaaa cgaaatcagt ctgtctgtat tgtcattgga | 900 |
| ggtgcttcgg agtccctatt atccaaacca catactattg atattgtcct gaaaaaaagg | 960 |
| aaaggctttg tgaaagtcgc actagagctg ggtgacactg agttagttcc agtatttggt | 1020 |
| tttggagaaa acactgccta taatgttttt gacccaagtg tatctggcaa gtcttgctct | 1080 |
| gtcctaaatt acgtgcggaa gcaaatgtgt gggtttcaat tatggttaaa acaacacttt | 1140 |
| ggctttacct ttccattttt tcatgctagg ggtgttttca atcacgactt tggccttcta | 1200 |
| ccatatcgga aacctatcaa cttggtcatc ggtagaccca tcccggttcc ttacattcat | 1260 |
| tcaccaaccc aagaacagat tgaccattac cattccctat atgtcgaaga actgaaacga | 1320 |
| gttttttgagc agaataagga gaggtttaat gctggatcct tggagctacg aattgtcgag | 1380 |
| tga | 1383 |

<210> SEQ ID NO 35
<211> LENGTH: 1959
<212> TYPE: DNA
<213> ORGANISM: Pichia pastoris

<400> SEQUENCE: 35

| | |
|---|---|
| atgcaactac ggaaaagagg aaacgagaga tccagacttg aatcgcacat cggcgattcg | 60 |
| gacacggtta ttgacttgga tgactcttca gtaaacgaca cgcttccgga tgaagacaac | 120 |
| atcgctaaac caagaaaagc gtcaacgcac agaagaccat cacttcgaaa aatccacagc | 180 |
| gctgagactg tccgtcgttt ctatgagtca aagaatgtaa ttttttatttt tggagccttc | 240 |
| ataggaatcg ctgttgcttt gtactttgga gctaccagtt ctgagtaccc tattccagac | 300 |
| atagatcaac tggtcaactt tgactctctt tccacctatt ttgacgattg gaaggatgtc | 360 |
| ttaccaaagt cccttcaaag tattgttgag agtactcagt tcaatcagaa ttctaagata | 420 |
| ttgagctctg aatcatttgc agtaggtaag caattgaaga gtaagtcaat gattgaagct | 480 |
| aatcattcca ttgttcttgt tcctggtgtg atcagcaccg ggctggaaag ttggggcttg | 540 |
| gaaggaactc ctgactgccc ctccgaaggt cattttagaa aacgtctatg gggatcattt | 600 |
| tacatgttgc ggacaatgtt tttggataag gcgtgttggc tgaaacatat tatgctagat | 660 |
| acaacaacgg gattagaccc tccaggaata agcctcagag cagctcaggg gtttgaagct | 720 |
| gctgatttct ttatagcagg ttactggatt tggaataaaa tccttcagaa cttggcagtt | 780 |
| attggatata atccaaacaa catggtgagc gctgcttatg attggagact tgcttttctg | 840 |
| gatttagaat tacgggatgc atactttttca aaattaaaag gtttcgttga acttcaaaag | 900 |
| catcagagtg ggaaaaaatc ggttttggta ggtcattcaa tggggtcaca agtgatttac | 960 |
| tatttttatga agtgggttga agctgacgga tacggaaacg gaggccctaa ctgggtgaat | 1020 |

-continued

```
gatcatgtag attcttttgt ggacatatcc ggctgtatgc tgggtactcc taaggctata      1080
cctgctcttt tatccggaga aatgaaggat acagttcaat aaacgccct cgccgtggag      1140 ggcttagaaa agtttctgtc tagaagagaa cgtgctgata tgatccgttc ttttggtgga      1200
atagccagca tgattcccaa aggcggagat ctaatctggg gaaatctcga gagttctcct      1260
gatgacgcca cgtcaattgg agatttggga acgacactt atggtaattt cattaggttc       1320
aaggagccgg tggggaagta ctcccaaaag aacttaacgg tgactgatag tattcagttt      1380
ttgatggagc agactcccgc ctggttccaa gacaggatgt gagggctta ctcttatggg       1440 ttcaccaatt ctgctaagca gctgaaaaaa aataataaag atcatacaaa atggtccaat      1500
ccccttgagg catcacttcc aaatgcacct gatctgaaag tgttttgctt ttatgggttt      1560
ggaaatccta cagaaagagc ttactactac cgagaagaag ttgatccggc taagaccaaa      1620
ttgaacgtca ctattgaaaa gaactatgat tcggttctta tggcagatgg tgacggtacg      1680
gtcagtctaa tgactcactc aatgtgccac atatggaagc aagctaatag tgtttacaac      1740
ccaggaaata gcaaggtcaa gattgttgag attgatcatg aacctgatcg gtttgacatt      1800
cgaggaggtg ccaaaactgc tgaacatgta gacattctgg gatctgcaga gttaaacgag      1860
ctagtgttac tggtggccgc tggaaaggga gaccaaatta aggaaaagat tgttagtaat      1920
ctgaaggaaa tagttgataa tcttgaacta gatctttaa                            1959
```

<210> SEQ ID NO 36
<211> LENGTH: 2037
<212> TYPE: DNA
<213> ORGANISM: Pichia pastoris

<400> SEQUENCE: 36

```
atgctgtcgt taaaccatc ttggctgact ttggcggcat taatgtatgc catgctattg       60
gtcgtagtgc catttgctaa acctgttaga gctgacgatg tcgaatctta tggaacagtg      120
attggtatcg atttgggtac cacgtactct tgtgtcggtg tgatgaagtc gggtcgtgta      180
gaaattcttg ctaatgacca aggtaacaga atcactcctt cctacgttag tttcactgaa      240
gacgagagac tggttggtga tgctgctaag aacttagctg cttctaaccc aaaaaacacc      300
atctttgata ttaagagatt gatcggtatg aagtatgatg ccccagaggt ccaaagagac      360
ttgaagcgtc ttccttacac tgtcaagagc aagaacggcc aacctgtcgt ttctgtcgag      420
tacaagggtg aggagaagtc tttcactcct gaggagattt ccgccatggt cttgggtaag      480
atgaagttga tcgctgagga ctacttagga agaaagtca ctcatgctgt cgttaccgtt       540
ccagcctact tcaacgacgc tcaacgtcaa gccactaagg atgccggtct catcgccggt      600
ttgactgttc tgagaattgt gaacgagcct accgccgctg cccttgctta cggtttggac      660
aagactggtg aggaaagaca gatcatcgtc tacgacttgg gtggaggaac cttcgatgtt      720
tctctgcttt ctattgaggg tggtgctttc gaggttcttg ctaccgccgg tgacacccac      780
ttgggtggta aggactttga ctacagagtt gttcgccact tcgttaagat tttcaagaag      840
aagcataaca ttgacatcag caacaatgat aaggctttag gtaagctgaa gagagaggtc      900
gaaaaggcca agcgtacttt gtcttcccag atgactacca gaattgagat tgactctttc      960
gtcgacggta tcgacttctc tgagcaactg tctagagcta agtttgagga gatcaacatt      1020
gaattattca agaagacact gaaaccagtt gaacaagtcc tcaaagacgc tggtgtcaag      1080
aaatctgaaa ttgatgacat tgtcttggtt ggtggttcta ccagaattcc aaaggttcaa      1140
```

```
caattattgg aggattactt tgacggaaag aaggcttcta agggaattaa cccagatgaa    1200
gctgtcgcat acggtgctgc tgttcaggct ggtgttttgt ctggtgagga aggtgtcgat    1260
gacatcgtct tgcttgatgt gaaccccta actctgggta tcgagactac tggtggcgtt    1320
atgactacct taatcaacag aaacactgct atcccaacta agaaatctca aattttctcc    1380
actgctgctg acaaccagcc aactgtgttg attcaagttt atgagggtga gagagccttg    1440
gctaaggaca caacttgct tggtaaattc gagctgactg gtattccacc agctccaaga    1500
ggtactcctc aagttgaggt tacttttgtt ttagacgcta acggaatttt gaaggtctct    1560
gccaccgata agggaactgg aaaatccgag tccatcacca tcaacaatga tcgtggtaga    1620
ttgtccaagg aggaggttga ccgtatggtt gaagaggccg agaagtacgc cgctgaggat    1680
gctgcactaa gagaaaagat tgaggctaga aacgctctgg agaactacgc tcattccctt    1740
aggaaccaag ttactgatga ctctgaaacc gggcttggtt ctaaattgga cgaggacgac    1800
aaagagacat tgacagatgc catcaaagat accctagagt tcttggaaga caacttcgac    1860
accgcaacca aggaagaatt agacgaacaa agagaaaagc tttccaagat tgcttaccca    1920
atcacttcta agctatacgg tgctccagag ggtggtactc cacctggtgg tcaaggtttt    1980
gacgatgatg atggagactt tgactacgac tatgactatg atcatgatga gttgtag      2037
```

<210> SEQ ID NO 37
<211> LENGTH: 312
<212> TYPE: PRT
<213> ORGANISM: Pichia pastoris

<400> SEQUENCE: 37

```
Met Arg Phe Pro Ser Ile Phe Thr Ala Val Leu Phe Ala Ala Ser Ser
1               5                   10                  15

Ala Leu Ala Ala Pro Val Asn Thr Thr Thr Glu Asp Glu Thr Ala Gln
            20                  25                  30

Ile Pro Ala Glu Ala Val Ile Gly Tyr Ser Asp Leu Glu Gly Asp Phe
        35                  40                  45

Asp Val Ala Val Leu Pro Phe Ser Asn Ser Thr Asn Asn Gly Leu Leu
    50                  55                  60

Phe Ile Asn Thr Thr Ile Ala Ser Ile Ala Ala Lys Glu Glu Gly Val
65                  70                  75                  80

Ser Leu Glu Lys Arg Glu Val Gln Leu Val Gln Ser Gly Gly Gly Leu
                85                  90                  95

Val Gln Pro Gly Gly Ser Leu Arg Leu Ser Cys Ala Ala Ser Gly Phe
            100                 105                 110

Thr Phe Ser His Tyr Trp Met Ser Trp Val Arg Gln Ala Pro Gly Lys
        115                 120                 125

Gly Leu Glu Trp Val Ala Asn Ile Glu Gln Asp Gly Ser Glu Lys Tyr
    130                 135                 140

Tyr Val Asp Ser Val Lys Gly Arg Phe Thr Ile Ser Arg Asp Asn Ala
145                 150                 155                 160

Lys Asn Ser Leu Tyr Leu Gln Met Asn Ser Leu Arg Ala Glu Asp Thr
                165                 170                 175

Ala Val Tyr Phe Cys Ala Arg Asp Leu Glu Gly Leu His Gly Asp Gly
            180                 185                 190

Tyr Phe Asp Leu Trp Gly Arg Gly Thr Leu Val Thr Val Ser Ser Ala
        195                 200                 205

Ser Thr Lys Gly Pro Ser Val Phe Pro Leu Ala Pro Cys Ser Arg Ser
    210                 215                 220
```

```
Thr Ser Glu Ser Thr Ala Ala Leu Gly Cys Leu Val Lys Asp Tyr Phe
225                 230                 235                 240

Pro Glu Pro Val Thr Val Ser Trp Asn Ser Gly Ala Leu Thr Ser Gly
            245                 250                 255

Val His Thr Phe Pro Ala Val Leu Gln Ser Ser Gly Leu Tyr Ser Leu
            260                 265                 270

Ser Ser Val Val Thr Val Pro Ser Ser Ser Leu Gly Thr Lys Thr Tyr
        275                 280                 285

Thr Cys Asn Val Asp His Lys Pro Ser Asn Thr Lys Val Asp Lys Arg
    290                 295                 300

Val Glu Ser Lys Tyr Gly Pro Pro
305                 310

<210> SEQ ID NO 38
<211> LENGTH: 299
<212> TYPE: PRT
<213> ORGANISM: Pichia pastoris

<400> SEQUENCE: 38

Met Arg Phe Pro Ser Ile Phe Thr Ala Val Leu Phe Ala Ala Ser Ser
1               5                   10                  15

Ala Leu Ala Ala Pro Val Asn Thr Thr Thr Glu Asp Glu Thr Ala Gln
            20                  25                  30

Ile Pro Ala Glu Ala Val Ile Gly Tyr Ser Asp Leu Glu Gly Asp Phe
        35                  40                  45

Asp Val Ala Val Leu Pro Phe Ser Asn Ser Thr Asn Asn Gly Leu Leu
    50                  55                  60

Phe Ile Asn Thr Thr Ile Ala Ser Ile Ala Ala Lys Glu Glu Gly Val
65                  70                  75                  80

Ser Leu Glu Lys Arg Ala Ile Gln Leu Thr Gln Ser Pro Ser Ser Leu
                85                  90                  95

Ser Ala Ser Val Gly Asp Arg Val Ile Leu Thr Cys Arg Ala Ser Gln
            100                 105                 110

Gly Val Ser Ser Ala Leu Ala Trp Tyr Gln Gln Lys Pro Gly Lys Ala
        115                 120                 125

Pro Lys Leu Leu Ile Tyr Asp Ala Ser Ser Leu Glu Ser Gly Val Pro
    130                 135                 140

Ser Arg Phe Ser Gly Ser Gly Ser Gly Pro Asp Phe Thr Leu Thr Ile
145                 150                 155                 160

Ser Ser Leu Gln Pro Glu Asp Phe Ala Thr Tyr Phe Cys Gln Gln Phe
                165                 170                 175

Asn Ser Tyr Pro Leu Thr Phe Gly Gly Gly Thr Lys Leu Glu Ile Lys
            180                 185                 190

Arg Thr Val Ala Ala Pro Ser Val Phe Ile Phe Pro Pro Ser Asp Glu
        195                 200                 205

Gln Leu Lys Ser Gly Thr Ala Ser Val Val Cys Leu Leu Asn Asn Phe
    210                 215                 220

Tyr Pro Arg Glu Ala Lys Val Gln Trp Lys Val Asp Asn Ala Leu Gln
225                 230                 235                 240

Ser Gly Asn Ser Gln Glu Ser Val Thr Glu Gln Asp Ser Lys Asp Ser
                245                 250                 255

Thr Tyr Ser Leu Ser Ser Thr Leu Thr Leu Ser Lys Ala Asp Tyr Glu
            260                 265                 270
```

Lys His Lys Val Tyr Ala Cys Glu Val Thr His Gln Gly Leu Ser Ser
            275                 280                 285

Pro Val Thr Lys Ser Phe Asn Arg Gly Glu Cys
    290                 295

<210> SEQ ID NO 39
<211> LENGTH: 303
<212> TYPE: PRT
<213> ORGANISM: Pichia pastoris

<400> SEQUENCE: 39

Met Arg Phe Pro Ser Ile Phe Thr Ala Val Leu Phe Ala Ala Ser Ser
1               5                   10                  15

Ala Leu Ala Ala Pro Val Asn Thr Thr Thr Glu Asp Glu Thr Ala Gln
            20                  25                  30

Ile Pro Ala Glu Ala Val Ile Gly Tyr Ser Asp Leu Glu Gly Asp Phe
        35                  40                  45

Asp Val Ala Val Leu Pro Phe Ser Asn Ser Thr Asn Asn Gly Leu Leu
    50                  55                  60

Phe Ile Asn Thr Thr Ile Ala Ser Ile Ala Ala Lys Glu Glu Gly Val
65                  70                  75                  80

Ser Leu Glu Lys Arg Asp Val Gln Leu Gln Glu Ser Gly Pro Ser Leu
                85                  90                  95

Val Lys Pro Ser Gln Thr Leu Ser Leu Thr Cys Ser Val Thr Gly Asp
            100                 105                 110

Ser Ile Thr Ser Asp Tyr Trp Ser Trp Ile Arg Lys Phe Pro Gly Asn
        115                 120                 125

Arg Leu Glu Tyr Met Gly Tyr Val Ser Tyr Ser Gly Ser Thr Tyr Tyr
    130                 135                 140

Asn Pro Ser Leu Lys Ser Arg Ile Ser Ile Thr Arg Asp Thr Ser Lys
145                 150                 155                 160

Asn Gln Tyr Tyr Leu Asp Leu Asn Ser Val Thr Thr Glu Asp Thr Ala
                165                 170                 175

Thr Tyr Tyr Cys Ala Asn Trp Asp Gly Asp Tyr Trp Gly Gln Gly Thr
            180                 185                 190

Leu Val Thr Val Ser Ser Ala Ser Thr Lys Gly Pro Ser Val Phe Pro
        195                 200                 205

Leu Ala Pro Ser Ser Lys Ser Thr Ser Gly Gly Thr Ala Ala Leu Gly
    210                 215                 220

Cys Leu Val Lys Asp Tyr Phe Pro Glu Pro Val Thr Val Ser Trp Asn
225                 230                 235                 240

Ser Gly Ala Leu Thr Ser Gly Val His Thr Phe Pro Ala Val Leu Gln
                245                 250                 255

Ser Ser Gly Leu Tyr Ser Leu Ser Ser Val Val Thr Val Pro Ser Ser
            260                 265                 270

Ser Leu Gly Thr Gln Thr Tyr Ile Cys Asn Val Asn His Lys Pro Ser
        275                 280                 285

Asn Thr Lys Val Asp Lys Arg Val Glu Pro Lys Ser Cys Asp Lys
    290                 295                 300

<210> SEQ ID NO 40
<211> LENGTH: 299
<212> TYPE: PRT
<213> ORGANISM: Pichia pastoris

<400> SEQUENCE: 40

| Met | Arg | Phe | Pro | Ser | Ile | Phe | Thr | Ala | Val | Leu | Phe | Ala | Ala | Ser | Ser |
|---|---|---|---|---|---|---|---|---|---|---|---|---|---|---|---|
| 1 | | | | 5 | | | | | 10 | | | | | 15 | |

| Ala | Leu | Ala | Ala | Pro | Val | Asn | Thr | Thr | Thr | Glu | Asp | Glu | Thr | Ala | Gln |
|---|---|---|---|---|---|---|---|---|---|---|---|---|---|---|---|
| | | | 20 | | | | | 25 | | | | | 30 | | |

| Ile | Pro | Ala | Glu | Ala | Val | Ile | Gly | Tyr | Ser | Asp | Leu | Glu | Gly | Asp | Phe |
|---|---|---|---|---|---|---|---|---|---|---|---|---|---|---|---|
| | | 35 | | | | | 40 | | | | | 45 | | | |

| Asp | Val | Ala | Val | Leu | Pro | Phe | Ser | Asn | Ser | Thr | Asn | Asn | Gly | Leu | Leu |
|---|---|---|---|---|---|---|---|---|---|---|---|---|---|---|---|
| | 50 | | | | | 55 | | | | | 60 | | | | |

| Phe | Ile | Asn | Thr | Thr | Ile | Ala | Ser | Ile | Ala | Ala | Lys | Glu | Glu | Gly | Val |
|---|---|---|---|---|---|---|---|---|---|---|---|---|---|---|---|
| 65 | | | | | 70 | | | | | 75 | | | | | 80 |

| Ser | Leu | Glu | Lys | Arg | Asp | Ile | Val | Leu | Thr | Gln | Ser | Pro | Ala | Thr | Leu |
|---|---|---|---|---|---|---|---|---|---|---|---|---|---|---|---|
| | | | | 85 | | | | | 90 | | | | | 95 | |

| Ser | Val | Thr | Pro | Gly | Asn | Ser | Val | Ser | Leu | Ser | Cys | Arg | Ala | Ser | Gln |
|---|---|---|---|---|---|---|---|---|---|---|---|---|---|---|---|
| | | | 100 | | | | | 105 | | | | | 110 | | |

| Ser | Ile | Gly | Asn | Asn | Leu | His | Trp | Tyr | Gln | Gln | Lys | Ser | His | Glu | Ser |
|---|---|---|---|---|---|---|---|---|---|---|---|---|---|---|---|
| | | 115 | | | | | 120 | | | | | 125 | | | |

| Pro | Arg | Leu | Leu | Ile | Lys | Tyr | Ala | Ser | Gln | Ser | Ile | Ser | Gly | Ile | Pro |
|---|---|---|---|---|---|---|---|---|---|---|---|---|---|---|---|
| | 130 | | | | | 135 | | | | | 140 | | | | |

| Ser | Arg | Phe | Ser | Gly | Ser | Gly | Ser | Gly | Thr | Asp | Phe | Thr | Leu | Ser | Ile |
|---|---|---|---|---|---|---|---|---|---|---|---|---|---|---|---|
| 145 | | | | | 150 | | | | | 155 | | | | | 160 |

| Asn | Ser | Val | Glu | Thr | Glu | Asp | Phe | Gly | Met | Tyr | Phe | Cys | Gln | Gln | Ser |
|---|---|---|---|---|---|---|---|---|---|---|---|---|---|---|---|
| | | | | 165 | | | | | 170 | | | | | 175 | |

| Asn | Ser | Trp | Pro | Tyr | Thr | Phe | Gly | Gly | Gly | Thr | Lys | Leu | Glu | Ile | Lys |
|---|---|---|---|---|---|---|---|---|---|---|---|---|---|---|---|
| | | | 180 | | | | | 185 | | | | | 190 | | |

| Arg | Thr | Val | Ala | Ala | Pro | Ser | Val | Phe | Ile | Phe | Pro | Pro | Ser | Asp | Glu |
|---|---|---|---|---|---|---|---|---|---|---|---|---|---|---|---|
| | | 195 | | | | | 200 | | | | | 205 | | | |

| Gln | Leu | Lys | Ser | Gly | Thr | Ala | Ser | Val | Val | Cys | Leu | Leu | Asn | Asn | Phe |
|---|---|---|---|---|---|---|---|---|---|---|---|---|---|---|---|
| | 210 | | | | | 215 | | | | | 220 | | | | |

| Tyr | Pro | Arg | Glu | Ala | Lys | Val | Gln | Trp | Lys | Val | Asp | Asn | Ala | Leu | Gln |
|---|---|---|---|---|---|---|---|---|---|---|---|---|---|---|---|
| 225 | | | | | 230 | | | | | 235 | | | | | 240 |

| Ser | Gly | Asn | Ser | Gln | Glu | Ser | Val | Thr | Glu | Gln | Asp | Ser | Lys | Asp | Ser |
|---|---|---|---|---|---|---|---|---|---|---|---|---|---|---|---|
| | | | | 245 | | | | | 250 | | | | | 255 | |

| Thr | Tyr | Ser | Leu | Ser | Ser | Thr | Leu | Thr | Leu | Ser | Lys | Ala | Asp | Tyr | Glu |
|---|---|---|---|---|---|---|---|---|---|---|---|---|---|---|---|
| | | | 260 | | | | | 265 | | | | | 270 | | |

| Lys | His | Lys | Val | Tyr | Ala | Cys | Glu | Val | Thr | His | Gln | Gly | Leu | Ser | Ser |
|---|---|---|---|---|---|---|---|---|---|---|---|---|---|---|---|
| | | 275 | | | | | 280 | | | | | 285 | | | |

| Pro | Val | Thr | Lys | Ser | Phe | Asn | Arg | Gly | Glu | Cys |
|---|---|---|---|---|---|---|---|---|---|---|
| | 290 | | | | | 295 | | | | |

<210> SEQ ID NO 41
<211> LENGTH: 939
<212> TYPE: DNA
<213> ORGANISM: Pichia pastoris

<400> SEQUENCE: 41

```
atgagattcc catctatttt caccgctgtc ttgttcgctg cctcctctgc attggctgcc        60
cctgttaaca ctaccactga agacgagact gctcaaattc cagctgaagc agttatcggt       120
tactctgacc ttgagggtga tttcgacgtc gctgttttgc ctttctctaa ctccactaac       180
aacggtttgt tgttcattaa caccactatc gcttccattg ctgctaagga gagggtgtc        240
tctctcgaga agagagaggt ccaattggtc caatctggtg gaggattggt tcaaccaggt       300
ggatctctga gattgtcttg tgctgcttct ggtttcacct tctctcacta ctggatgtca       360
```

```
tgggttagac aagctcctgg taagggtttg gaatgggttg ctaacatcga gcaagatgga    420
tcagagaagt actacgttga ctctgttaag ggaagattca ctatttcccg tgataacgcc    480
aagaactcct tgtacctgca aatgaactcc cttagagctg aggatactgc tgtctacttc    540
tgtgctagag acttggaagg tttgcatggt gatggttact tcgacttatg gggtagaggt    600
actcttgtca ccgtttcatc tgcctctacc aaaggacctt ctgtgttccc attagctcca    660
tgttccagat ccacctccga atctactgca gctttgggtt gtttggtgaa ggactacttt    720
cctgaaccag tgactgtctc ttggaactct ggtgctttga cttctggtgt tcacaccttt    780
cctgcagttt tgcagtcatc tggtctgtac tctctgtcct cagttgtcac tgttccttcc    840
tcatctcttg gtaccaagac ctacacttgc aacgttgacc ataagccatc aataccaag     900 gttgacaaga gagttgagtc caagtatggt ccaccttaa                           939

<210> SEQ ID NO 42
<211> LENGTH: 900
<212> TYPE: DNA
<213> ORGANISM: Pichia pastoris

<400> SEQUENCE: 42
atgagattcc catctatttt caccgctgtc ttgttcgctg cctcctctgc attggctgcc     60
cctgttaaca ctaccactga agacgagact gctcaaattc agctgaagc agttatcggt    120 tactctgacc ttgagggtga tttcgacgtc gctgttttgc ctttctctaa ctccactaac    180
aacggtttgt tgttcattaa caccactatc gcttccattg ctgctaagga gagggtgtc    240 tctctcgaga agagagctat ccagttgact caatcaccat cctctttgtc tgcttctgtt    300
ggtgatagag tcatcctgac ttgtcgtgca ctctcaaggtg tttcctcagc tttagcttgg    360
taccaacaaa agccaggtaa agctccaaag ttgctgatct acgacgcttc atcccttgaa    420
tctggtgttc cttcacgttt ctctggatct ggatcaggtc ctgatttcac tctgactatc    480
tcatcccttc aaccagaaga ctttgctacc tacttctgtc aacagttcaa ctcttaccct    540
ttgacctttg gaggtggaac taagttggag atcaagagaa ctgttgctgc accatcagtg    600
ttcatctttc ctccatctga tgagcaactg aagtctggta ctgcatctgt tgtctgctta    660
ctgaacaact tctacccaag agaagctaag gtccaatgga aggttgacaa tgccttgcaa    720
tctggtaact ctcaagagtc tgttactgag caagactcta aggactctac ttactccctt    780
tcttccacct tgactttgtc taaggctgat tacgagaagc acaaggtta cgcttgtgag    840 gttactcacc aaggttttgtc ttctcctgtt accaagtctt tcaacagagg tgaatgctaa    900

<210> SEQ ID NO 43
<211> LENGTH: 915
<212> TYPE: DNA
<213> ORGANISM: Pichia pastoris

<400> SEQUENCE: 43
atgagattcc catctatttt caccgctgtc ttgttcgctg cctcctctgc attggctgcc     60
cctgttaaca ctaccactga agacgagact gctcaaattc agctgaagc agttatcggt    120 tactctgacc ttgagggtga tttcgacgtc gctgttttgc ctttctctaa ctccactaac    180
aacggtttgt tgttcattaa caccactatc gcttccattg ctgctaagga gagggtgtc    240 tctctcgaga agagagacgt tcaattgcaa gaatctggtc catccttggt taagccatcc    300
cagactttgt ccttgacttg ttccgttact ggtgactcca tcacttctga ctactggtcc    360
```

```
tggatcagaa agttcccagg taacagattg agtacatgg gttacgtttc ttactccggt    420
tccacttact acaacccatc cttgaagtcc agaatctcca tcactagaga cacttccaag    480
aaccagtact acttggactt gaactccgtt actactgagg acactgctac ttactactgt    540
gctaactggg acggtgacta ttggggtcaa ggtactttgg ttactgtttc ctccgcttcc    600
actaagggtc catctgtttt tccattggct ccatcctcca agtctacttc aggtggtact    660
gctgctttgg gttgtttggt taaggactac ttcccagagc cagttactgt ttcttggaac    720
tccggtgctt tgacttccgg tgttcacact ttcccagctg tcttgcaatc ctccggtctg    780
tactccttgt cctccgttgt tactgttcct tcttcctcct gggtactca aacttacatc    840 tgtaacgtta accacaagcc atccaacact aaggttgaca agagagttga gccaaagtcc    900
tgtgacaagt aatag                                                     915

<210> SEQ ID NO 44
<211> LENGTH: 903
<212> TYPE: DNA
<213> ORGANISM: Pichia pastoris

<400> SEQUENCE: 44
atgagattcc catctatttt caccgctgtc ttgttcgctg cctcctctgc attggctgcc     60
cctgttaaca ctaccactga agacgagact gctcaaattc agctgaagc agttatcggt    120 tactctgacc ttgagggtga tttcgacgtc gctgttttgc cttctctaa ctccactaac    180 aacggtttgt tgttcattaa caccactatc gcttccattg ctgctaagga gagggtgtc    240 tctctcgaga gagagacat cgttttgact caatccccag ctactttgtc cgttactcca    300
ggtaactccg tttccttgtc ctgtagagct tcccagtcca tcggtaacaa cttgcactgg    360
tatcagcaga gtctcacga gtccccaaga ctgttgatca agtacgcttc ccaatccatc    420
tccggtatcc catctagatt ctctggttct ggttccggta ctgacttcac tttgtccatc    480
aactccgttg agactgagga cttcggtatg tacttctgtc agcaatccaa ctcctggcca    540
tacacttttg gtggtggtac taagttggag atcaagagaa ctgttgctgc tccatccgtt    600
ttcatcttcc caccatctga cgagcagttg aagtctggta ctgcttccgt tgtttgttg    660 ttgaacaact tctacccaag agaagctaag gttcagtgga aggttgacaa cgccttgcaa    720
tccggtaact cccaagagtc cgttactgaa caagactcca aggactctac ttactccttg    780
tcctccactt tgacttttgc caaggctgac tacgagaagc acaaggttta cgcttgtgag    840
gttactcacc agggtttgtc ctccccagtt actaagtcct tcaacagagg tgagtgttaa    900
tag                                                                  903

<210> SEQ ID NO 45
<211> LENGTH: 85
<212> TYPE: PRT
<213> ORGANISM: Saccharomyces cerevisae

<400> SEQUENCE: 45

Met Arg Phe Pro Ser Ile Phe Thr Ala Val Leu Phe Ala Ala Ser Ser
1               5                   10                  15

Ala Leu Ala Ala Pro Val Asn Thr Thr Thr Glu Asp Glu Thr Ala Gln
            20                  25                  30

Ile Pro Ala Glu Ala Val Ile Gly Tyr Ser Asp Leu Glu Gly Asp Phe
        35                  40                  45

Asp Val Ala Val Leu Pro Phe Ser Asn Ser Thr Asn Asn Gly Leu Leu
    50                  55                  60
```

```
Phe Ile Asn Thr Thr Ile Ala Ser Ile Ala Ala Lys Glu Glu Gly Val
 65                  70                  75                  80

Ser Leu Glu Lys Arg
                85

<210> SEQ ID NO 46
<211> LENGTH: 255
<212> TYPE: DNA
<213> ORGANISM: Saccharomyces cerevisae

<400> SEQUENCE: 46
atgagattcc catctatttt caccgctgtc ttgttcgctg cctcctctgc attggctgcc      60
cctgttaaca ctaccactga agacgagact gctcaaattc agctgaagc agttatcggt     120 tactctgacc ttgagggtga tttcgacgtc gctgttttgc ctttctctaa ctccactaac    180
aacggtttgt tgttcattaa caccactatc gcttccattg ctgctaagga gagggtgtc    240 tctctcgaga agaga                                                       255

<210> SEQ ID NO 47
<211> LENGTH: 40
<212> TYPE: DNA
<213> ORGANISM: Artificial sequence
<220> FEATURE:
<223> OTHER INFORMATION: oligonucleotide for nucleic acid amplification

<400> SEQUENCE: 47
ctcgcctgca ggaccatgag tgacattaat actctgtcgc                             40

<210> SEQ ID NO 48
<211> LENGTH: 37
<212> TYPE: DNA
<213> ORGANISM: Artificial sequence
<220> FEATURE:
<223> OTHER INFORMATION: oligonucleotide for nucleic acid amplification

<400> SEQUENCE: 48
acggccgagg cggccagtta ggcacgacgg acactag                                37

<210> SEQ ID NO 49
<211> LENGTH: 35
<212> TYPE: DNA
<213> ORGANISM: Artificial sequence
<220> FEATURE:
<223> OTHER INFORMATION: oligonucleotide for nucleic acid amplification

<400> SEQUENCE: 49
tctacctgca ggaacgatgt ccattctctc atttg                                  35

<210> SEQ ID NO 50
<211> LENGTH: 42
<212> TYPE: DNA
<213> ORGANISM: Artificial sequence
<220> FEATURE:
<223> OTHER INFORMATION: oligonucleotide for nucleic acid amplification

<400> SEQUENCE: 50
tatggccgag gcggcctcag gccttgcgag agcgcaaatt tc                           42

<210> SEQ ID NO 51
<211> LENGTH: 37
<212> TYPE: DNA
<213> ORGANISM: Artificial sequence
<220> FEATURE:
```

```
<223> OTHER INFORMATION: oligonucleotide for nucleic acid amplification

<400> SEQUENCE: 51
atacctgcag gacaatgtct aaagaggaaa agacaag                              37

<210> SEQ ID NO 52
<211> LENGTH: 36
<212> TYPE: DNA
<213> ORGANISM: Artificial sequence
<220> FEATURE:
<223> OTHER INFORMATION: oligonucleotide for nucleic acid amplification

<400> SEQUENCE: 52
attggccgag gcggccctat tcttccttct tggagg                               36

<210> SEQ ID NO 53
<211> LENGTH: 34
<212> TYPE: DNA
<213> ORGANISM: Artificial sequence
<220> FEATURE:
<223> OTHER INFORMATION: oligonucleotide for nucleic acid amplification

<400> SEQUENCE: 53
atacctgcag gacaatgggt gttgaaacat cttc                                 34

<210> SEQ ID NO 54
<211> LENGTH: 37
<212> TYPE: DNA
<213> ORGANISM: Artificial sequence
<220> FEATURE:
<223> OTHER INFORMATION: oligonucleotide for nucleic acid amplification

<400> SEQUENCE: 54
attggccgag gcggcctcaa gaactctcct catcatc                              37

<210> SEQ ID NO 55
<211> LENGTH: 30
<212> TYPE: DNA
<213> ORGANISM: Artificial sequence
<220> FEATURE:
<223> OTHER INFORMATION: oligonucleotide for nucleic acid amplification

<400> SEQUENCE: 55
atacctgcag gacaatgagc caacgtgaag                                      30

<210> SEQ ID NO 56
<211> LENGTH: 34
<212> TYPE: DNA
<213> ORGANISM: Artificial sequence
<220> FEATURE:
<223> OTHER INFORMATION: oligonucleotide for nucleic acid amplification

<400> SEQUENCE: 56
attggccgag gcggcctcaa agctgttgca aaac                                 34

<210> SEQ ID NO 57
<211> LENGTH: 36
<212> TYPE: DNA
<213> ORGANISM: Artificial sequence
<220> FEATURE:
<223> OTHER INFORMATION: oligonucleotide for nucleic acid amplification

<400> SEQUENCE: 57
atacctgcag gacaatgtca aaaactatcc cagatg                               36
```

<210> SEQ ID NO 58
<211> LENGTH: 36
<212> TYPE: DNA
<213> ORGANISM: Artificial sequence
<220> FEATURE:
<223> OTHER INFORMATION: oligonucleotide for nucleic acid amplification

<400> SEQUENCE: 58
attggccgag gcggccttag tacatggctt tcttgc                         36

<210> SEQ ID NO 59
<211> LENGTH: 33
<212> TYPE: DNA
<213> ORGANISM: Artificial sequence
<220> FEATURE:
<223> OTHER INFORMATION: oligonucleotide for nucleic acid amplification

<400> SEQUENCE: 59
ataccctgca ggcaccaatg gttaaactca ttg                            33

<210> SEQ ID NO 60
<211> LENGTH: 31
<212> TYPE: DNA
<213> ORGANISM: Artificial sequence
<220> FEATURE:
<223> OTHER INFORMATION: oligonucleotide for nucleic acid amplification

<400> SEQUENCE: 60
ataggccgag gcggccctac aaaaggaatg g                              31

<210> SEQ ID NO 61
<211> LENGTH: 30
<212> TYPE: DNA
<213> ORGANISM: Artificial sequence
<220> FEATURE:
<223> OTHER INFORMATION: oligonucleotide for nucleic acid amplification

<400> SEQUENCE: 61
ttccctgcag gaccatgtct caacccactc                                30

<210> SEQ ID NO 62
<211> LENGTH: 34
<212> TYPE: DNA
<213> ORGANISM: Artificial sequence
<220> FEATURE:
<223> OTHER INFORMATION: oligonucleotide for nucleic acid amplification

<400> SEQUENCE: 62
acggccgagg cggcctcaca tgtgataaat tgtg                           34

<210> SEQ ID NO 63
<211> LENGTH: 39
<212> TYPE: DNA
<213> ORGANISM: Artificial sequence
<220> FEATURE:
<223> OTHER INFORMATION: oligonucleotide for nucleic acid amplification

<400> SEQUENCE: 63
ttccctgcag ggaaatgaca caacataaaa gctcgatgg                      39

<210> SEQ ID NO 64
<211> LENGTH: 36
<212> TYPE: DNA
<213> ORGANISM: Artificial sequence
<220> FEATURE:
<223> OTHER INFORMATION: oligonucleotide for nucleic acid amplification

<400> SEQUENCE: 64
acggccgagg cggcctcaaa ggaagcaata ctttag                              36

<210> SEQ ID NO 65
<211> LENGTH: 31
<212> TYPE: DNA
<213> ORGANISM: Artificial sequence
<220> FEATURE:
<223> OTHER INFORMATION: oligonucleotide for nucleic acid amplification

<400> SEQUENCE: 65
ttccctgcag gaccatgcag tacgtaggta g                                   31

<210> SEQ ID NO 66
<211> LENGTH: 33
<212> TYPE: DNA
<213> ORGANISM: Artificial sequence
<220> FEATURE:
<223> OTHER INFORMATION: oligonucleotide for nucleic acid amplification

<400> SEQUENCE: 66
tatggccgag gcggcctcag ctgtcatcga ttc                                 33

<210> SEQ ID NO 67
<211> LENGTH: 19
<212> TYPE: DNA
<213> ORGANISM: Artificial sequence
<220> FEATURE:
<223> OTHER INFORMATION: oligonucleotide for nucleic acid amplification

<400> SEQUENCE: 67
gaagctctcc accaatttg                                                 19

<210> SEQ ID NO 68
<211> LENGTH: 20
<212> TYPE: DNA
<213> ORGANISM: Artificial sequence
<220> FEATURE:
<223> OTHER INFORMATION: oligonucleotide for nucleic acid amplification

<400> SEQUENCE: 68
cgtcaaacag gaggcaggac                                                20

<210> SEQ ID NO 69
<211> LENGTH: 31
<212> TYPE: DNA
<213> ORGANISM: Artificial sequence
<220> FEATURE:
<223> OTHER INFORMATION: oligonucleotide for nucleic acid amplification

<400> SEQUENCE: 69
tctcctgcag gcaaacatga gtctggtcca g                                   31

<210> SEQ ID NO 70
<211> LENGTH: 36
<212> TYPE: DNA
<213> ORGANISM: Artificial sequence
<220> FEATURE:
<223> OTHER INFORMATION: oligonucleotide for nucleic acid amplification

<400> SEQUENCE: 70
tatggccgag gcggccaact aattatcgcg tctttc                              36

<210> SEQ ID NO 71
<211> LENGTH: 31

```
<212> TYPE: DNA
<213> ORGANISM: Artificial sequence
<220> FEATURE:
<223> OTHER INFORMATION: oligonucleotide for nucleic acid amplification

<400> SEQUENCE: 71
ttccctgcag gacgatgctt actgggttgt c                                31

<210> SEQ ID NO 72
<211> LENGTH: 37
<212> TYPE: DNA
<213> ORGANISM: Artificial sequence
<220> FEATURE:
<223> OTHER INFORMATION: oligonucleotide for nucleic acid amplification

<400> SEQUENCE: 72
aggccgaggc ggcctcaaga tttaatgcaa atcttag                           37

<210> SEQ ID NO 73
<211> LENGTH: 35
<212> TYPE: DNA
<213> ORGANISM: Artificial sequence
<220> FEATURE:
<223> OTHER INFORMATION: oligonucleotide for nucleic acid amplification

<400> SEQUENCE: 73
taccctgcag gacgatggga ataagtgcca caatc                             35

<210> SEQ ID NO 74
<211> LENGTH: 37
<212> TYPE: DNA
<213> ORGANISM: Artificial sequence
<220> FEATURE:
<223> OTHER INFORMATION: oligonucleotide for nucleic acid amplification

<400> SEQUENCE: 74
aggccgaggc ggcctcaaga tttaatgcaa atcttag                           37

<210> SEQ ID NO 75
<211> LENGTH: 34
<212> TYPE: DNA
<213> ORGANISM: Artificial sequence
<220> FEATURE:
<223> OTHER INFORMATION: oligonucleotide for nucleic acid amplification

<400> SEQUENCE: 75
ttccctgcag gacgatgacg ccagacgttg ttcc                              34

<210> SEQ ID NO 76
<211> LENGTH: 37
<212> TYPE: DNA
<213> ORGANISM: Artificial sequence
<220> FEATURE:
<223> OTHER INFORMATION: oligonucleotide for nucleic acid amplification

<400> SEQUENCE: 76
aggccgaggc ggcctcaaga tttaatgcaa atcttag                           37

<210> SEQ ID NO 77
<211> LENGTH: 34
<212> TYPE: DNA
<213> ORGANISM: Artificial sequence
<220> FEATURE:
<223> OTHER INFORMATION: oligonucleotide for nucleic acid amplification
```

-continued

```
<400> SEQUENCE: 77
atacctgcag gacaatgctg tcgttaaaac catc                              34

<210> SEQ ID NO 78
<211> LENGTH: 40
<212> TYPE: DNA
<213> ORGANISM: Artificial sequence
<220> FEATURE:
<223> OTHER INFORMATION: oligonucleotide for nucleic acid amplification

<400> SEQUENCE: 78
ataggccgag gcggccctac aactcatcat gatcatagtc                        40

<210> SEQ ID NO 79
<211> LENGTH: 38
<212> TYPE: DNA
<213> ORGANISM: Artificial sequence
<220> FEATURE:
<223> OTHER INFORMATION: oligonucleotide for nucleic acid amplification

<400> SEQUENCE: 79
agatatagtt ctgttttatt ccattagagg aggatccg                          38

<210> SEQ ID NO 80
<211> LENGTH: 40
<212> TYPE: DNA
<213> ORGANISM: Artificial sequence
<220> FEATURE:
<223> OTHER INFORMATION: oligonucleotide for nucleic acid amplification

<400> SEQUENCE: 80
gttgtcgacc tgcagcgtac tagatactgg cacataacac                        40

<210> SEQ ID NO 81
<211> LENGTH: 40
<212> TYPE: DNA
<213> ORGANISM: Artificial sequence
<220> FEATURE:
<223> OTHER INFORMATION: oligonucleotide for nucleic acid amplification

<400> SEQUENCE: 81
gtgttatgtg ccagtatcta gtacgctgca ggtcgacaac                        40

<210> SEQ ID NO 82
<211> LENGTH: 24
<212> TYPE: DNA
<213> ORGANISM: Artificial sequence
<220> FEATURE:
<223> OTHER INFORMATION: oligonucleotide for nucleic acid amplification

<400> SEQUENCE: 82
cggtgagaat ggcaaaagct tatg                                         24

<210> SEQ ID NO 83
<211> LENGTH: 21
<212> TYPE: DNA
<213> ORGANISM: Artificial sequence
<220> FEATURE:
<223> OTHER INFORMATION: oligonucleotide for nucleic acid amplification

<400> SEQUENCE: 83
aagcccgatg cgccagagtt g                                            21

<210> SEQ ID NO 84
```

```
<211> LENGTH: 40
<212> TYPE: DNA
<213> ORGANISM: Artificial sequence
<220> FEATURE:
<223> OTHER INFORMATION: oligonucleotide for nucleic acid amplification

<400> SEQUENCE: 84
acctcctttg cttctctatc agtggatctg atatcaccta                              40

<210> SEQ ID NO 85
<211> LENGTH: 40
<212> TYPE: DNA
<213> ORGANISM: Artificial sequence
<220> FEATURE:
<223> OTHER INFORMATION: oligonucleotide for nucleic acid amplification

<400> SEQUENCE: 85
taggtgatat cagatccact gatagagaag caaaggaggt                              40

<210> SEQ ID NO 86
<211> LENGTH: 23
<212> TYPE: DNA
<213> ORGANISM: Artificial sequence
<220> FEATURE:
<223> OTHER INFORMATION: oligonucleotide for nucleic acid amplification

<400> SEQUENCE: 86
actaactcag tgtcacccag ctc                                                23

<210> SEQ ID NO 87
<211> LENGTH: 21
<212> TYPE: DNA
<213> ORGANISM: Artificial sequence
<220> FEATURE:
<223> OTHER INFORMATION: oligonucleotide for nucleic acid amplification

<400> SEQUENCE: 87
tcttgccatc ctatggaact g                                                  21

<210> SEQ ID NO 88
<211> LENGTH: 19
<212> TYPE: DNA
<213> ORGANISM: Artificial sequence
<220> FEATURE:
<223> OTHER INFORMATION: oligonucleotide for nucleic acid amplification

<400> SEQUENCE: 88
acagagcaag acttgccag                                                     19

<210> SEQ ID NO 89
<211> LENGTH: 24
<212> TYPE: DNA
<213> ORGANISM: Artificial sequence
<220> FEATURE:
<223> OTHER INFORMATION: oligonucleotide for nucleic acid amplification

<400> SEQUENCE: 89
actctagctg ttgtccgcca gttc                                               24

<210> SEQ ID NO 90
<211> LENGTH: 40
<212> TYPE: DNA
<213> ORGANISM: Artificial sequence
<220> FEATURE:
<223> OTHER INFORMATION: oligonucleotide for nucleic acid amplification
```

```
<400> SEQUENCE: 90
gttgtcgacc tgcagcgtac tatcaattgt gaacataatg                              40

<210> SEQ ID NO 91
<211> LENGTH: 40
<212> TYPE: DNA
<213> ORGANISM: Artificial sequence
<220> FEATURE:
<223> OTHER INFORMATION: oligonucleotide for nucleic acid amplification

<400> SEQUENCE: 91
cattatgttc acaattgata gtacgctgca ggtcgacaac                              40

<210> SEQ ID NO 92
<211> LENGTH: 24
<212> TYPE: DNA
<213> ORGANISM: Artificial sequence
<220> FEATURE:
<223> OTHER INFORMATION: oligonucleotide for nucleic acid amplification

<400> SEQUENCE: 92
cggtgagaat ggcaaaagct tatg                                              24

<210> SEQ ID NO 93
<211> LENGTH: 21
<212> TYPE: DNA
<213> ORGANISM: Artificial sequence
<220> FEATURE:
<223> OTHER INFORMATION: oligonucleotide for nucleic acid amplification

<400> SEQUENCE: 93
aagcccgatg cgccagagtt g                                                 21

<210> SEQ ID NO 94
<211> LENGTH: 39
<212> TYPE: DNA
<213> ORGANISM: Artificial sequence
<220> FEATURE:
<223> OTHER INFORMATION: oligonucleotide for nucleic acid amplification

<400> SEQUENCE: 94
gactcataga aacgacggaa gtggatctga tatcaccta                              39

<210> SEQ ID NO 95
<211> LENGTH: 39
<212> TYPE: DNA
<213> ORGANISM: Artificial sequence
<220> FEATURE:
<223> OTHER INFORMATION: oligonucleotide for nucleic acid amplification

<400> SEQUENCE: 95
taggtgatat cagatccact tccgtcgttt ctatgagtc                              39

<210> SEQ ID NO 96
<211> LENGTH: 22
<212> TYPE: DNA
<213> ORGANISM: Artificial sequence
<220> FEATURE:
<223> OTHER INFORMATION: oligonucleotide for nucleic acid amplification

<400> SEQUENCE: 96
attcacccag ttagggcctc cg                                                22

<210> SEQ ID NO 97
```

<211> LENGTH: 21
<212> TYPE: DNA
<213> ORGANISM: Artificial sequence
<220> FEATURE:
<223> OTHER INFORMATION: oligonucleotide for nucleic acid amplification

<400> SEQUENCE: 97
tcttgccatc ctatggaact g                                              21

<210> SEQ ID NO 98
<211> LENGTH: 20
<212> TYPE: DNA
<213> ORGANISM: Artificial sequence
<220> FEATURE:
<223> OTHER INFORMATION: oligonucleotide for nucleic acid amplification

<400> SEQUENCE: 98
taggagtacc cagcatacag                                                20

<210> SEQ ID NO 99
<211> LENGTH: 33
<212> TYPE: DNA
<213> ORGANISM: Artificial sequence
<220> FEATURE:
<223> OTHER INFORMATION: oligonucleotide for nucleic acid amplification

<400> SEQUENCE: 99
actacctgca ggcgaaacga tgagattccc atc                                 33

<210> SEQ ID NO 100
<211> LENGTH: 44
<212> TYPE: DNA
<213> ORGANISM: Artificial sequence
<220> FEATURE:
<223> OTHER INFORMATION: oligonucleotide for nucleic acid amplification

<400> SEQUENCE: 100
tcatggccga ggcggcccta ttacttgtca caggactttg gctc                     44

<210> SEQ ID NO 101
<211> LENGTH: 39
<212> TYPE: DNA
<213> ORGANISM: Artificial sequence
<220> FEATURE:
<223> OTHER INFORMATION: oligonucleotide for nucleic acid amplification

<400> SEQUENCE: 101
ctatggccga ggcggcccta ttaacactca cctctgttg                           39

<210> SEQ ID NO 102
<211> LENGTH: 39
<212> TYPE: DNA
<213> ORGANISM: Artificial sequence
<220> FEATURE:
<223> OTHER INFORMATION: oligonucleotide for nucleic acid amplification

<400> SEQUENCE: 102
tatcggccga ggcggcccta ttacttacct ggggacaag                           39

<210> SEQ ID NO 103
<211> LENGTH: 39
<212> TYPE: DNA
<213> ORGANISM: Artificial sequence
<220> FEATURE:
<223> OTHER INFORMATION: oligonucleotide for nucleic acid amplification -continued

```
<400> SEQUENCE: 103
ctatggccga ggcggcccta ttaacactca cctctgttg                                39
```